United States Patent
Myette et al.

(10) Patent No.: US 11,136,385 B2
(45) Date of Patent: Oct. 5, 2021

(54) METHODS OF TREATING IGA NEPHROPATHY BY ADMINISTERING AN ANTI-APRIL (A PROLIFERATION-INDUCING LIGAND) ANTIBODY MOLECULE

(71) Applicant: VISTERRA, INC., Waltham, MA (US)

(72) Inventors: James R. Myette, Waltham, MA (US); Zachary Holmes Shriver, Winchester, MA (US); Karthik Viswanathan, Acton, MA (US); Andrew M. Wollacott, Milton, MA (US); Hedy Adari-Hall, Sudbury, MA (US); Boopathy Ramakrishnan, Braintree, MA (US); Gregory Babcock, Marlborough, MA (US)

(73) Assignee: VISTERRA, INC., Waltham, MA (US)

( * ) Notice: Subject to any disclaimer, the term of this patent is extended or adjusted under 35 U.S.C. 154(b) by 0 days.

(21) Appl. No.: 17/074,857

(22) Filed: Oct. 20, 2020

(65) Prior Publication Data
US 2021/0032324 A1 Feb. 4, 2021

Related U.S. Application Data

(62) Division of application No. 16/912,085, filed on Jun. 25, 2020, now Pat. No. 10,981,982, which is a division of application No. 16/456,810, filed on Jun. 28, 2019, now abandoned, which is a division of application No. 16/212,957, filed on Dec. 7, 2018, now Pat. No. 10,385,123, which is a division of application No. 15/360,145, filed on Nov. 23, 2016, now abandoned.

(60) Provisional application No. 62/422,848, filed on Nov. 16, 2016, provisional application No. 62/399,087, filed on Sep. 23, 2016, provisional application No. 62/313,684, filed on Mar. 25, 2016, provisional application No. 62/259,897, filed on Nov. 25, 2015.

(51) Int. Cl.
| | | |
|---|---|---|
| *C07K 16/24* | (2006.01) | |
| *A61K 39/395* | (2006.01) | |
| *A61K 45/06* | (2006.01) | |
| *C07K 16/28* | (2006.01) | |
| *A61K 39/00* | (2006.01) | |

(52) U.S. Cl.
CPC ........ *C07K 16/241* (2013.01); *A61K 39/3955* (2013.01); *A61K 45/06* (2013.01); *C07K 16/2875* (2013.01); *A61K 2039/505* (2013.01); *A61K 2039/54* (2013.01); *C07K 2317/14* (2013.01); *C07K 2317/24* (2013.01); *C07K 2317/33* (2013.01); *C07K 2317/34* (2013.01); *C07K 2317/52* (2013.01); *C07K 2317/56* (2013.01); *C07K 2317/76* (2013.01); *C07K 2317/92* (2013.01); *C07K 2317/94* (2013.01)

(58) Field of Classification Search
CPC .............. C07K 16/241; C07K 16/2875; C07K 2317/14; C07K 2317/24; C07K 2317/33; C07K 2317/34; C07K 2317/52; C07K 2317/56; C07K 2317/76; C07K 2317/92; C07K 2317/94; A61K 39/3955; A61K 45/06; A61K 2039/505; A61K 2039/54; A61P 9/00; A61P 7/00; A61P 43/00; A61P 37/02; A61P 37/06; A61P 35/00; A61P 35/02; A61P 29/00; A61P 19/02; A61P 17/00; A61P 13/12; A61P 1/16; A61P 1/00
See application file for complete search history.

(56) References Cited

U.S. PATENT DOCUMENTS

| | | |
|---|---|---|
| 7,189,820 B2 | 3/2007 | Ruben |
| 8,105,603 B2 | 1/2012 | Kelley et al. |
| 8,895,705 B2 | 11/2014 | Medema et al. |
| 9,000,128 B2 | 4/2015 | Medema et al. |
| 9,969,808 B2 | 5/2018 | van Eenennaam et al. |
| 10,107,821 B2 | 10/2018 | van Eenennaam et al. |
| 10,377,830 B2 | 8/2019 | van Eenennaam et al. |
| 10,385,123 B2 | 8/2019 | Myette et al. |
| 2002/0081296 A1 | 6/2002 | Theill et al. |
| 2003/0059862 A1 | 3/2003 | Ruben |
| 2003/0082175 A1 | 5/2003 | Schneider et al. |
| 2006/0073146 A1 | 4/2006 | Ashkenazi et al. |
| 2007/0160603 A1 | 7/2007 | Ruben |
| 2008/0260737 A1 | 10/2008 | Ponce et al. |
| 2012/0195909 A1 | 8/2012 | Medema et al. |
| 2012/0201823 A1 | 8/2012 | Janatpour et al. |
| 2013/0156769 A1 | 6/2013 | Kufer et al. |
| 2013/0273064 A1 | 10/2013 | Medema et al. |
| 2013/0295103 A1 | 11/2013 | Medema et al. |
| 2013/0302353 A1 | 11/2013 | Medema et al. |
| 2014/0161828 A1 | 6/2014 | Armitage et al. |

(Continued)

FOREIGN PATENT DOCUMENTS

| | | |
|---|---|---|
| EP | 1255558 B1 | 6/2006 |
| EP | 1666052 B1 | 6/2011 |

(Continued)

OTHER PUBLICATIONS

[No Author Listed] Purified anti-mouse CD256 (APRIL) Antibody-BioLegend, Version 5 Revised (2015) retrieved from biolegend.com/en-us/products/purified-anti-mouse-cd256-april-antibody-6360.

(Continued)

*Primary Examiner* — Robert S Landsman
(74) *Attorney, Agent, or Firm* — Lando & Anastasi, LLP

(57) ABSTRACT

Antibody molecules that specifically bind to APRIL are disclosed. The antibody molecules can be used to treat, prevent, and/or diagnose disorders, such as IgA nephropathy.

38 Claims, 43 Drawing Sheets
Specification includes a Sequence Listing.

(56) References Cited

U.S. PATENT DOCUMENTS

| | | | |
|---|---|---|---|
| 2016/0202267 | A1 | 7/2016 | Van Eenennaam et al. |
| 2016/0264674 | A1 | 9/2016 | van Eenennaam et al. |
| 2017/0145086 | A1 | 5/2017 | Myette et al. |
| 2017/0369582 | A1 | 12/2017 | Huard et al. |
| 2018/0258176 | A1 | 9/2018 | van Eenennaam et al. |
| 2019/0092851 | A1 | 3/2019 | Myette et al. |
| 2019/0330326 | A1 | 10/2019 | Myette et al. |
| 2020/0079859 | A1 | 3/2020 | van Eenennaam et al. |

FOREIGN PATENT DOCUMENTS

| | | | |
|---|---|---|---|
| EP | 2403528 | B1 | 4/2016 |
| EP | 3103476 | A2 | 12/2016 |
| JP | 2004537290 | A | 12/2004 |
| JP | 2011500073 | A | 1/2011 |
| JP | 2011501945 | A | 1/2011 |
| JP | 2011502126 | A | 1/2011 |
| JP | 2011523037 | A | 8/2011 |
| JP | 2012519198 | A | 8/2012 |
| JP | 5062606 | B2 | 10/2012 |
| JP | 2013512258 | A | 4/2013 |
| JP | 2013541522 | A | 11/2013 |
| JP | 2014523408 | A | 9/2014 |
| RU | 2013151455 | A | 5/2015 |
| WO | 1999012965 | A2 | 3/1999 |
| WO | 200160397 | A1 | 8/2001 |
| WO | 2002094192 | A2 | 11/2002 |
| WO | 2005075511 | A1 | 8/2005 |
| WO | 2007039489 | A1 | 4/2007 |
| WO | 2010100056 | A2 | 9/2010 |
| WO | 2011047121 | A1 | 4/2011 |
| WO | 2012163805 | A1 | 12/2012 |
| WO | 2014151680 | A1 | 9/2014 |
| WO | 2015034364 | A1 | 3/2015 |
| WO | 2015069865 | A1 | 5/2015 |
| WO | 2016110587 | A1 | 7/2016 |
| WO | 2016113368 | A1 | 7/2016 |
| WO | 2017091683 | A1 | 6/2017 |

OTHER PUBLICATIONS

Anonymous "(MAB5860) Human APRIL/TNFSF13 Antibody—R&D Systems—CiteAb" (2014) Retrieved from the internet Feb. 1, 2017, www.citeab.com/antibodies/699338-mab5860-human-april-tnfsf13-antibody.

Colman, PM, "Effects of amino acid sequence changes on antibody-antigen interactions," Research in Immunology, Elsevier, NY, 145(1):33-36, 1994.

Dulos et al., "Development of a first in class APRIL fully blocking antibody BION-1301 for the treatment of multiple myeloma," Abstract from the American Association for Cancer Research Annual Meeting, Apr. 1-5, 2017, 2 pages.

Gao et al., "In Vitro and In Vivo Evaluation of a Humanized Anti-APRIL Antibody," Current Molecular Medicine (2013) vol. 13, pp. 464-465.

Guadagnoli et al., "Development and characterization of APRIL antagonistic monoclonal antibodies for treatment of B-cell lymphomas," Blood (2011) vol. 117, No. 25, pp. 6856-6865.

Hahne et al., "APRIL, a New Ligand of the Tumor Necrosis Factor Family Stimulates Tumor Cell Growth," J Exp Med (1998) vol. 188, No. 6, pp. 1185-1190.

Huard et al., "Selective APRIL Blockade Delays Systemic Lupus Erythematosus in Mouse," PLOS ONE (2012) vol. 7, No. 2, e31837.

International Search Report and Written Opinion for International Application No. PCT/US2016/063518 dated Mar. 1, 2017.

Kim et al., "Pathogenic Role of a Proliferation-Inducing Ligand (APRIL) in Murine IgA Nephropathy," PLOS One (2015) vol. 10, No. 9, Article e0137044, 13 pages.

Lin et al., "A First in Class APRIL Fully Blocking Antibody Targets Novel Immune Regulation of APRIL in Multiple Myeloma: Further Therapeutic Implication," Blood (2017) vol. 130, p. 499. Abstract Only.

Mariuzza et al., "The Structural Basis of Antigen-Antibody Recognition," Ann Rev Biophys Biophys Chem (1987) vol. 16, pp. 139-159.

McConnell et al., "An intergrated approach to extreme thermostabilization and affinity maturation of an antibody," Protein Engineering, Design & Selection (2013) vol. 26, No. 2, 13 pages.

Myette et al., "A Proliferation Inducing Ligand (APRIL) targeted antibody is a safe and effective treatment of murine IgA nephropathy," Kidney International (2019) 16 pages.

Osorio et al., "Selective regulation of axonal growth from developing hippocampal neurons by tumor necrosis factor superfamily member APRIL," Molecular and Cellular Neuroscience (2014) vol. 59, pp. 24-36.

Paul, WE. Fundamental Immunology, 3rd ed. Raven Press, NY, Chap. 9, pp. 292-295, 1993.

Rudikoff S. et al., "Single Amino Acid Substation Altering Antigen-Binding Specificity." Proc. Natl. Acad. Sci. USA (1982) 79:1979-1983.

Ryan et al., "Targeting of BAFF and APRIL for autoimmunity and oncology," Adv Exp Med Biol (2009) vol. 647, pp. 52-63.

Safdari et al., "Antibody humanization methods—a review and update," Biotechnology and Genetic Engineering Reviews (2013) vol. 29, No. 2, pp. 175-186.

Search Report and Written Opinion issued in Chilean Patent Application No. 201801372, dated May 4, 2020.

Search Report and Written Opinion issued in Chilean Patent Application No. 201901642, dated May 11, 2020.

Search Report and Written Opinion issued in Singapore Application No. 11201804309P, dated Jan. 2, 2020, 13 pages.

Selvaskandan et al., "New strategies and perspectives on managing IgA nephropathy," Clinical and Experimental Nephrology (2019) vol. 23, pp. 577-588.

Vajdos et al., "Comprehensive Functional Maps of the Antigen-Binding Site of an anti-ErbB2 Antibody Obtained With Shotgun Scanning Mutagenesis," J Mol Biol (2002) vol. 320, No. 2, pp. 415-428.

Wollacott et al., "Structural prediction of antibody-APRIL complexes by computational docking constrained by antigen saturation mutagenesis library data," J Mol Recognition (2019) Article e2778, 12 pages.

Benjun Du et al., "Preparation of Polyclonal Antibody Against sAPRIL and Analysis of Function in Suppressing sAPRIL-Mediated Lymphocyte Proliferation", Chinese Journal of Experimental Hematolog, vol. 19, No. 4, pp. 1019-1022 (2011).

| Clone ID | Mouse ID | preliminary Isotype ID | Immunization scheme (prime-boost) | APRIL Binding (ELISA, A$_{450}$) | | % Receptor Blocking | |
|---|---|---|---|---|---|---|---|
| | | | | Human APRIL | Mouse APRIL | Human APRIL | Mouse APRIL |
| 01-001 | B-001-R | IgG1 | (H-H-H-H) | 0.75 | 0.09 | 82.0 | <10 |
| 01-002 | B-001-R | IgG1 | (H-H-H-H) | 0.94 | 1.67 | 91.4 | <10 |
| 01-019 | B-001-R | IgG1 | (H-H-H-H) | 0.74 | 0.08 | 94.4 | <10 |
| 01-035 | B-001-R | | (H-H-H-H) | 0.46 | 0.08 | 62.7 | <10 |
| 01-037 | B-001-R | IgG1 | (H-H-H-H) | 0.98 | 0.12 | 93.8 | <10 |
| 01-056 | B-001-R | | (H-H-H-H) | 1.43 | 0.64 | 93.5 | <10 |
| 01-059 | B-001-R | IgG1 | (H-H-H-H) | 0.97 | 0.13 | 92.7 | <10 |
| 01-062 | B-001-R | | (H-H-H-H) | 2.02 | 0.19 | 62.3 | <10 |
| 01-063 | B-001-R | | (H-H-H-H) | 2.15 | 0.58 | 61.3 | <10 |
| 01-064 | B-001-R | IgG1 | (H-H-H-H) | 2.12 | 0.71 | 12.8 | <10 |
| 01-077 | B-001-R | IgG1 | (H-H-H-H) | 1.08 | 0.08 | 16.4 | <10 |
| 01-079 | B-001-R | | (H-H-H-H) | 0.33 | 0.07 | 12.1 | <10 |
| 01-081 | B-001-R | IgG2b | (H-H-H-H) | 1.55 | 0.28 | 93.9 | <10 |
| 01-086 | B-001-R | IgG2b | (H-H-H-H) | 1.88 | 0.67 | 70.7 | <10 |
| 01-089 | B-001-R | IgG1 | (H-H-H-H) | 1.06 | 0.15 | 94.6 | <10 |
| 01-093 | B-001-R | | (H-H-H-H) | 0.49 | 0.08 | 14.5 | <10 |
| 01-097 | B-001-R | | (H-H-H-H) | 2.43 | 1.30 | 13.1 | <10 |
| 01-099 | B-001-R | | (H-H-H-H) | 2.45 | 0.47 | 12.1 | <10 |
| 01-100 | B-001-R | | (H-H-H-H) | 2.20 | 0.27 | 16.2 | <10 |
| 01-101 | B-001-R | IgG2b | (H-H-H-H) | 1.12 | 0.37 | 50.1 | <10 |
| 01-102 | B-001-R | | (H-H-H-H) | 1.87 | 0.70 | 22.5 | <10 |
| 01-103 | B-001-R | | (H-H-H-H) | 2.43 | 2.02 | 14.9 | <10 |
| 01-104 | B-001-R | IgG1 | (H-H-H-H) | 1.86 | 2.33 | 20.6 | <10 |
| 01-105 | B-001-R | IgG2b | (H-H-H-H) | 1.34 | 0.51 | 79.3 | 14.7 |
| 01-107 | B-001-R | | (H-H-H-H) | 2.20 | 0.30 | 46.6 | <10 |
| 01-109 | B-001-R | IgG1 | (H-H-H-H) | 1.14 | 0.13 | 93.4 | <10 |
| 01-110 | B-001-R | | (H-H-H-H) | 1.34 | 0.13 | 14.3 | <10 |
| 01-111 | B-001-R | IgG2a | (H-H-H-H) | 2.50 | 1.31 | 13.0 | <10 |
| 01-114 | B-001-R | IgG1 | (H-H-H-H) | 1.26 | 0.14 | 92.0 | <10 |
| 01-115 | B-001-R | IgG2a | (H-H-H-H) | 1.66 | 0.22 | 71.7 | <10 |
| 01-117 | B-001-R | IgG1 | (H-H-H-H) | 0.89 | 0.94 | 93.4 | <10 |
| 01-118 | B-001-R | | (H-H-H-H) | 1.55 | 0.85 | 93.6 | <10 |

FIG. 1A

| Clone ID | Mouse ID | preliminary Isotype ID | Immunization scheme (prime-boost) | APRIL Binding (ELISA, A$_{450}$) | | % Blocking | Receptor |
| --- | --- | --- | --- | --- | --- | --- | --- |
| | | | | Human APRIL | Mouse APRIL | Human APRIL | Mouse APRIL |
| 01-119 | B-001-R | IgG2a | (H-H-H-H) | 1.17 | 0.43 | 94.5 | <10 |
| 01-120 | B-001-R | IgG2a | (H-H-H-H) | 1.98 | 0.26 | 74.6 | <10 |
| 01-121 | B-001-R | IgG2a | (H-H-H-H) | 2.02 | 0.31 | 88.1 | <10 |
| 01-123 | B-001-R | | (H-H-H-H) | 0.75 | 0.12 | 11.7 | <10 |
| 01-124 | B-001-R | IgG1 | (H-H-H-H) | 1.53 | 0.21 | 94.6 | <10 |
| 01-125 | B-001-R | IgG2a | (H-H-H-H) | 1.97 | 0.15 | 14.6 | <10 |
| 01-126 | B-001-R | | (H-H-H-H) | 1.93 | 0.22 | 14.8 | <10 |
| 01-128 | B-001-R | | (H-H-H-H) | 1.65 | 0.19 | 21.8 | <10 |
| 01-133 | B-001-R | IgG1 | (H-H-H-H) | 2.25 | 0.37 | 20.1 | <10 |
| 01-135 | B-001-R | IgG3 | (H-H-H-H) | 2.39 | 0.74 | 57.5 | <10 |
| 01-136 | B-001-R | IgG2b | (H-H-H-H) | 2.42 | 0.40 | 18.1 | 15.9 |
| 01-137 | B-001-R | | (H-H-H-H) | 2.16 | 0.19 | 12.8 | <10 |
| 01-140 | B-001-R | | (H-H-H-H) | 1.96 | 0.26 | 74.3 | <10 |
| 01-143 | B-001-R | IgG2b | (H-H-H-H) | 2.33 | 0.34 | <10 | 54.9 |
| 01-144 | B-001-R | IgG2a | (H-H-H-H) | 2.36 | 0.52 | <10 | 12.1 |
| 01-147 | B-001-R | | (H-H-H-H) | 1.57 | 0.49 | 74.3 | <10 |
| 01-148 | B-001-R | IgG1 | (H-H-H-H) | 2.38 | 0.78 | 94.2 | <10 |
| 01-152 | B-001-R | IgG1 | (H-H-H-H) | 2.37 | 0.38 | 92.5 | <10 |
| 01-153 | B-001-R | | (H-H-H-H) | 1.29 | 0.21 | 92.8 | <10 |
| 01-154 | B-001-R | IgG1 | (H-H-H-H) | 2.52 | 0.70 | 29.6 | <10 |
| 02-009 | B-002-L | IgM | (M-M-M-H-M) | 3.04 | 0.06 | 96.4 | 19.2 |
| 02-011 | B-002-L | IgG1 | (M-M-M-H-M) | 0.21 | 0.07 | 15.1 | <10 |
| 02-016 | B-002-L | IgM | (M-M-M-H-M) | 0.06 | 0.18 | 18.8 | 26.5 |
| 02-024 | B-002-L | IgM | (M-M-M-H-M) | 1.64 | 0.06 | 23.1 | <10 |
| 02-029 | B-002-L | IgM | (M-M-M-H-M) | 1.88 | 0.06 | 12.5 | <10 |
| 02-033 | B-002-L | IgM | (M-M-M-H-M) | 2.40 | 0.22 | 25.9 | 29.1 |
| 02-046 | B-002-L | IgM | (M-M-M-H-M) | 2.80 | 0.09 | 82.0 | <10 |
| 02-069 | B-002-L | IgM | (M-M-M-H-M) | 1.47 | 1.60 | <10 | 17.1 |
| 02-075 | B-002-L | IgG1 | (M-M-M-H-M) | 0.06 | 0.78 | 5.2 | 30.2 |
| 02-086 | B-002-L | IgG2a | (M-M-M-H-M) | 2.49 | 0.11 | <10 | 26.9 |
| 02-111 | B-003-O | IgG1 | (H-H-H-M-H) | 2.98 | 2.17 | 80.1 | 67.6 |
| 02-115 | B-003-O | IgM | (H-H-H-M-H) | 0.07 | 0.39 | 25.1 | 40.0 |

FIG. 1B

| Clone ID | Binding (approximate EC$_{50}$) ng/mL | | Receptor Blocking (approximate IC$_{50}$) ng/mL | |
| --- | --- | --- | --- | --- |
| | Human APRIL | Mouse APRIL | Human APRIL | Mouse APRIL |
| 01-002 | 10.1 | 46.6 | 4.2 | >10000 |
| 01-019 | 16 | >10000 | 25.2 | -- |
| 01-062 | 51.8 | 314.8 | 36.3 | -- |
| 01-081 | 22 | -- | 13 | -- |
| 01-105 | 16 | >10000 | 512 | >10000 |
| 01-115 | 50 | -- | 62 | -- |
| 01-117 | 23.3 | 2203 | 23.4 | -- |
| 01-119 | 31 | 3974 | 28 | -- |
| 01-135 | 113 | >10000 | 315 | -- |
| 01-144 | 100 | >10000 | >10000 | -- |
| 02-111 | 35 | 706 | 932 | 2530 |
| 0201 | 10.4 | -- | 204 | -- |
| 1313 | 15.9 | -- | 69.5 | -- |
| Apry-1-1 | -- | 70.5 | -- | 15.1 |

FIG. 3

| Ab | EC$_{50}$ (ng/mL) | EC$_{50}$ (nM) | R$^2$ |
|---|---|---|---|
| 2218 | 12.64 | 0.085 | 1.00 |
| 2419 | 16.62 | 0.112 | 1.00 |
| 2621 | 14.31 | 0.097 | 0.99 |
| 2922 | 71.33 | 0.482 | 0.99 |
| 3125 | 281.5 | 1.902 | 0.99 |
| 3530 | 58.05 | 0.392 | 1.00 |
| 3525 | 53.45 | 0.361 | 1.00 |
| 1313 | 18.24 | 0.123 | 0.99 |
| 0201 | 118.2 | 0.799 | 0.99 |
| Aprily-5 | 968.9 | 6.547 | 0.99 |
| Apry-1-1 | -- | -- | 0.39 |

FIG. 6

| Ab | TACI-Fc IC$_{50}$ (nM) | R$^2$ | % Inhibition | BCMA-Fc IC$_{50}$ (nM) | R$^2$ | % Inhibition |
| --- | --- | --- | --- | --- | --- | --- |
| 2218 | 0.74 | 1.00 | 91 | 0.22 | 1.00 | 100 |
| 3530 | 4.95 | 1.00 | 81 | 0.68 | 0.99 | 35 |
| 3525 | 4.05 | 1.00 | 86 | 0.85 | 0.99 | 48 |
| 2419 | 0.74 | 1.00 | 99 | 0.22 | 1.00 | 100 |
| 2621 | 1.00 | 0.99 | 79 | -- | 0.10 | 0 |
| 2922 | 31.64 | 1.00 | 97 | 21.96 | 1.00 | 97 |
| 3125 | 112.97 | 1.00 | 52 | -- | 0.99 | <10 |
| 3327 | 3.16 | 1.00 | 89 | 2.35 | 1.00 | 99 |
| 0201 | 2.85 | 1.00 | 99 | 3.14 | 1.00 | 99 |
| 1313 | 0.95 | 1.00 | 96 | 0.55 | 0.99 | 99 |
| Aprily-5 | NA | 0.54 | 0 | -- | 0.39 | 0 |

FIG. 9

```
Human   1 MPASSPFLLAPKGPPGNMGGPVREPALSVALWLSWGAALGAVACAMALLT  50
          ||||:   |||  |:|||| ||||||||||||.|||||: ||| |:|||:
Mouse   1 MPASS------PGHMGGSVREPALSVALWLSWGAVLGAVTCAVALLI     41

Human  51 QQTELQSLRREVSRLQGTGGPSQNGEGYPWQSLPEQSSDALEAWENGERS 100
          ||||||||||||||||:|||||:|:||||||||:|:..|.:||||:|||:
Mouse  42 QQTELQSLRREVSRLQRSGGPSQKQGERPWQSLWEQSPDVLEAWKDGAKS  91

Human 101 RKRRAVLTQKQKKQHSVLHLVPINATSKDDSDVTEVMWQPALRRGRGLQA 150
          :|:||||||||:|:|||||||||:|:||||||||||||||:|:|||||:|
Mouse  92 RRRRAVLTQKHKKKHSVLHLVPVNITSKADSDVTEVMWQPVLRRGRGLEA 141

Human 151 QGYGVRIQDAGVYLLLYSQVLFQDVTFTMGQVVSREGQGRQETLFRCIRSM 200
          ||:|||:.|:|||||||||||.||||||||||||||||.|::||||||||
Mouse 142 QGDIVRVWDTGIYLLLYSQVLFHDVTFTMGQVVSREGQGRRETLFRCIRSM 191

Human 201 PSHPDRAYNSCYSAGVFHLHQGDILSVIIPRARAKLNLSPHGTFLGFVKL 250
          ||.|||||||||||||||||||||:::|:|||||:|.|||||||||||||
Mouse 192 PSDPDRAYNSCYSAGVFHLHQGDIITVKIPRANAKLSLSPHGTFLGFVKL 241
```

FIG. 13

| Antibody ID | IC$_{50}$ (pM) | R$^2$ |
|---|---|---|
| 2218 | 5.0 | 0.994 |
| 2419 | 8.7 | 0.995 |
| 1313 | 6.1 | 0.986 |
| 3530 | 48.9 | 0.997 |
| 3631 | 16.6 | 0.998 |
| 3732 | 7.2 | 0.997 |
| 3833 | 17.5 | 0.995 |
| 3934 | 10.1 | 0.989 |
| 4035 | 5.1 | 0.994 |
| 4237 | 12.6 | 0.996 |
| 4338 | 9.2 | 0.993 |
| 4540 | 12.9 | 0.997 |

FIG. 17

| TACI-Fc | | | | BCMA-Fc | | |
|---|---|---|---|---|---|---|
| Ab | IC$_{50}$ (nM) | R$^2$ | % Inhibition | IC$_{50}$ (nM) | R$^2$ | % Inhibition |
| 3833 | 2.25 | 1.00 | 72 | 2.70 | 1.00 | 96 |
| 4540 | 1.01 | 0.93 | 65 | 0.66 | 1.00 | 98 |
| 4035 | 0.44 | 1.00 | 100 | 0.16 | 1.00 | 99 |
| 4237 | 0.90 | 1.00 | 95 | 0.56 | 1.00 | 93 |
| 2419 | 1.44 | 1.00 | 97 | 0.27 | 1.00 | 100 |
| 2218 | 0.98 | 0.89 | 40 | 0.31 | 1.00 | 99 |
| 3530 | 2.90 | 0.99 | 89 | 0.48 | 0.99 | 37 |
| 3631 | 0.27 | 0.98 | 63 | 0.48 | 1.00 | 100 |
| 3732 | -- | -- | -- | 0.22 | 1.00 | 100 |
| 3934 | 2.43 | 0.99 | 96 | 0.21 | 1.00 | 98 |
| 4338 | 0.71 | 0.99 | 97 | 0.07 | 1.00 | 99 |
| 1313 | 1.55 | 0.90 | 69 | 1.29 | 1.00 | 98 |

FIG. 20

| Antibody ID | EC$_{50}$ (pM) |
|---|---|
| 4035 | 1.06 |
| 4035-062 | 1.28 |
| 2419 | 1.76 |
| 2419-1306 | 3.00 |
| 2419-1406 | 3.34 |
| 2419-0205 | 2.26 |
| 2419-0806 | 2.31 |
| 2419-1310 | 2.19 |
| 2419-1305 | 2.41 |

FIG. 29A

| Antibody ID | APRIL Binding EC$_{50}$ (pM) | |
|---|---|---|
| | Human APRIL | Mouse APRIL |
| 4504 | 1.39 | 1.51 |
| 4504-063 | 2.06 | 1.56 |

FIG. 29B

| Antibody ID | EC$_{50}$ (pM) |
|---|---|
| 2419-1406 | 38.4 |
| 4035-062 | 13.5 |
| Hu TACI-Fc | 102.6 |

|  | TACI | | BCMA | |
| --- | --- | --- | --- | --- |
| Antibody ID | IC$_{50}$ (nM) | Relative Activity | IC$_{50}$ (nM) | Relative Activity |
| 2419-0205 | 0.31 | 1.12 | 0.17 | 0.71 |
| 2419-0406 | 0.33 | 1.20 | 0.25 | 1.05 |
| 2419-0806 | 0.32 | 1.17 | 0.21 | 0.89 |
| 2419-1305 | 0.29 | 1.06 | 0.15 | 0.62 |
| 2419-1306 | 0.28 | 1.03 | 0.17 | 0.72 |
| 2419-1310 | 0.30 | 1.09 | 0.27 | 1.14 |
| 2419-1406 | 0.24 | 0.88 | 0.11 | 0.47 |
| 2419 | 0.28 | 1.00 | 0.24 | 1.00 |
| 4035 | 0.24 | 0.85 | 0.12 | 0.49 |
| 4035-062 | 0.26 | 0.93 | 0.10 | 0.41 |
| 4540 | 0.40 | 1.45 | 0.67 | 2.85 |
| 4540-033 | 0.35 | 1.26 | 3.68 | 15.57 |
| 4540-063 | 0.67 | 2.43 | 1.92 | 8.11 |
| 1313 | 0.33 | 1.20 | 0.97 | 4.10 |

FIG. 33

| Antibody ID | ~$IC_{50}$ (nM) | |
|---|---|---|
| | TACI | BCMA |
| 2419 | 0.87 | 0.42 |
| 2419-0205 | 0.81 | 0.32 |
| 2419-1306 | 0.66 | 0.30 |
| 4035 | 1.07 | 0.43 |
| 4035-062 | 1.02 | 0.38 |
| 4540 | 2.25 | 0.81 |
| 4540-063 | 7.19 | 1.04 |
| Negative Ab Control | -- | -- |

FIG. 35

APRIL TRIMER

| Antibody ID | Tm (°C) |
|---|---|
| 4035-062 | 71.2 |
| 2419-1406 | 73.7 |

| Antibody ID | Cmax (µg/mL) | Half-Life (hrs.) | AUC (hr*µg/ml) |
|---|---|---|---|
| 2419-1406 | 101 | 183 | 10600 |
| 4035-062 | 72 | 282 | 7788 |

SEQUENCE LISTING

```
<160> NUMBER OF SEQ ID NOS: 346

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ser Ile Thr Ser Gly Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Tyr Asp Gly Tyr
1               5
```

```
1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Tyr Asp Tyr Glu Asp Trp Tyr Phe Gly Val
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Glu Ser Val Ser Ile Ile Gly Thr Asn Ser Ile His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Ala Ser Asn Leu Glu Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Ser Arg Lys Ile Pro Tyr Thr
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Gly Tyr Tyr Trp Asn
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 8

Tyr Ile Ser Tyr Asp Gly Tyr Asn Asn Tyr Asn Pro Ser Leu Lys Asn
1               5                   10                  15

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Lys Leu Glu Trp
            35                  40                  45

Met Gly Tyr Ile Ser Tyr Asp Gly Tyr Asn Asn Tyr Asn Pro Ser Leu
        50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asn Tyr Tyr Asp Tyr Glu Asp Trp Tyr Phe Gly Val Trp Gly Thr
            100                 105                 110

Gly Thr Thr Val Thr Val Ser Ser
        115                 120

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Val Leu Thr Gln Ser Pro Ala Ser Leu Ala Met Ser Leu Gly
1               5                   10                  15

Lys Arg Ala Thr Ile Ser Cys Arg Ala Ser Glu Ser Val Ser Ile Ile
                20                  25                  30

Gly Thr Asn Ser Ile His Trp Tyr Gln Gln Lys Pro Gly Gln Pro Pro
            35                  40                  45

Lys Leu Leu Ile Tyr His Ala Ser Asn Leu Glu Thr Gly Val Pro Ala
        50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Ile Tyr Tyr Cys Leu Gln Ser Arg
                85                  90                  95

Lys Ile Pro Tyr Thr Phe Gly Gly Gly Thr Lys Leu Glu Ile Lys
            100                 105                 110

<210> SEQ ID NO 11
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 11

Gly Tyr Thr Phe Thr Asp Tyr
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Pro Leu Arg Gly Ser
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Gly Ala Tyr Tyr Ser Asn Ala Phe Asp Tyr
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Glu Ser Val Asp Asn Asp Gly Ile Arg Phe Met His
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ala Ser Asn Leu Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Ser Asn Lys Asp Pro Tyr Thr
1               5
```

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Asp Tyr Thr Ile His
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Trp Ile Tyr Pro Leu Arg Gly Ser Ile Asn Tyr Asn Glu Lys Phe Lys
1               5                   10                  15

Asp

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Gln Val Gln Leu Gln Gln Ser Gly Ala Glu Leu Val Lys Pro Gly Ala
1               5                   10                  15

Ser Val Arg Leu Ser Cys Glu Ala Ser Gly Tyr Thr Phe Thr Asp Tyr
                20                  25                  30

Thr Ile His Trp Val Lys Gln Arg Ser Gly Gln Gly Leu Glu Trp Ile
            35                  40                  45

Gly Trp Ile Tyr Pro Leu Arg Gly Ser Ile Asn Tyr Asn Glu Lys Phe
        50                  55                  60

Lys Asp Lys Ala Thr Leu Thr Ala Asp Lys Ser Ser Ser Thr Val Tyr
65                  70                  75                  80

Leu Glu Leu Gly Arg Leu Thr Ser Lys Asp Ser Ala Val Tyr Phe Cys
                85                  90                  95

Ala Arg His Gly Ala Tyr Tyr Ser Asn Ala Phe Asp Tyr Trp Gly Gln
            100                 105                 110

Gly Thr Thr Leu Thr Val Ser Ser
        115                 120

<210> SEQ ID NO 20
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

Asn Ile Val Met Thr Gln Ser Pro Ala Ser Leu Ala Val Ser Leu Gly
1               5                   10                  15

```
Gln Arg Ala Thr Ile Ser Cys Arg Ala Ser Glu Ser Val Asp Asn Asp
            20                  25                  30

Gly Ile Arg Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Tyr Thr Phe Gly Gly Gly Thr Lys Leu Glu Leu Lys
            100                 105                 110

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Thr Phe Thr Ser Tyr
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Ile Gly Asn Gly Tyr
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Tyr Pro Trp Phe Thr Tyr
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ala Ser Glu Asn Ile Tyr Ser Tyr Leu Ala
1               5                   10

<210> SEQ ID NO 25
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 25

Asn Ala Lys Thr Leu Ala Glu
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln His His Tyr Asp Thr Pro Phe Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Tyr Gly Ile Asn
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Ile Tyr Ile Gly Asn Gly Tyr Ala Glu Tyr Asn Glu Arg Phe Lys
1               5                   10                  15

Gly

<210> SEQ ID NO 29
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Gln Gln Ser Gly Ala Glu Leu Val Arg Pro Gly Ser
1               5                   10                  15

Ser Val Lys Met Ser Cys Lys Thr Ser Gly Tyr Thr Phe Thr Ser Tyr
                20                  25                  30

Gly Ile Asn Trp Val Lys Gln Arg Pro Gly Gln Gly Leu Glu Trp Ile
            35                  40                  45

Gly Tyr Ile Tyr Ile Gly Asn Gly Tyr Ala Glu Tyr Asn Glu Arg Phe
        50                  55                  60

Lys Gly Lys Ala Thr Leu Thr Ser Asp Thr Ser Ser Ser Thr Ala Tyr
65                  70                  75                  80
```

```
Met Gln Leu Ser Ser Leu Thr Ser Glu Asp Ser Ala Ile Tyr Phe Cys
                85                  90                  95

Ala Leu Tyr Tyr Pro Trp Phe Thr Tyr Trp Gly Gln Gly Thr Leu Val
            100                 105                 110

Thr Val Ser Ala
        115
```

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Asp Ile Gln Met Thr Gln Ser Pro Ala Ser Leu Ser Ala Ser Val Gly
1               5                   10                  15

Asp Ser Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His His Tyr Asp Thr Pro Phe
                85                  90                  95

Thr Phe Gly Gly Gly Thr Lys Leu Glu Ile Lys
            100                 105
```

<210> SEQ ID NO 31

<400> SEQUENCE: 31

000

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Tyr Pro Arg Asp Ser Ser
1               5
```

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Glu Gly Tyr Asp Tyr Asp Lys Arg Gly Phe Asp Tyr
1               5                   10
```

<210> SEQ ID NO 34
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Ala Ser Gln Ser Val Ser Phe Ala Gly Thr Asn Leu Met His
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ala Ser Asn Leu Glu Pro
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Ser Arg Glu Tyr Pro Trp Thr
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Tyr Asp Val Phe
1               5

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Ile Tyr Pro Arg Asp Ser Ser Thr Lys Tyr Asn Glu Lys Phe Lys
1               5                   10                  15

Gly

<210> SEQ ID NO 39
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39
```

```
Gln Val Gln Leu His Gln Ser Gly Pro Glu Leu Val Lys Pro Gly Ala
1               5                   10                  15

Ser Val Lys Leu Ser Cys Lys Thr Ser Gly Tyr Thr Phe Thr Ser Tyr
            20                  25                  30

Asp Val Phe Trp Val Lys Gln Arg Pro Gly Gln Gly Leu Glu Trp Ile
        35                  40                  45

Gly Trp Ile Tyr Pro Arg Asp Ser Ser Thr Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Met Glu Leu His Ser Leu Thr Ser Glu Asp Ser Ala Val Tyr Phe Cys
                85                  90                  95

Ala Lys Glu Gly Tyr Asp Tyr Asp Lys Arg Gly Phe Asp Tyr Trp Gly
            100                 105                 110

Gln Gly Thr Thr Leu Thr Val Ser Ser
            115                 120

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Val Leu Thr Gln Ser Pro Ala Ser Leu Ala Val Ser Leu Gly
1               5                   10                  15

Gln Arg Ala Ile Ile Ser Cys Lys Ala Ser Gln Ser Val Ser Phe Ala
            20                  25                  30

Gly Thr Asn Leu Met His Trp Tyr Gln Gln Arg Pro Gly Gln Gln Pro
        35                  40                  45

Lys Leu Leu Ile Tyr Arg Ala Ser Asn Leu Glu Pro Gly Val Pro Thr
    50                  55                  60

Arg Phe Ser Gly Ser Gly Ser Arg Thr Asp Phe Thr Leu Asn Ile His
65                  70                  75                  80

Pro Val Glu Glu Asp Asp Ala Ala Thr Tyr Tyr Cys Gln Gln Ser Arg
                85                  90                  95

Glu Tyr Pro Trp Thr Phe Gly Gly Gly Thr Lys Leu Glu Ile Lys
            100                 105                 110

<210> SEQ ID NO 41

<400> SEQUENCE: 41

000

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Pro Glu Thr Gly Gly
1               5
```

```
<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Asn Asp Gly Asp Tyr
1               5

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Ser Ser Gln Ser Leu Leu Tyr Ser Asn Gly Lys Thr Tyr Leu Asn
1               5                   10                  15

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Val Ser Lys Leu Asp Pro
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Gln Gly Thr Tyr Tyr Pro Tyr Thr
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Tyr Glu Met His
1               5

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

```
Ala Ile Asp Pro Glu Thr Gly Gly Thr Ala Tyr Asn Gln Arg Phe Lys
1               5                   10                  15

Gly
```

<210> SEQ ID NO 49
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Pro Val His Gly Leu Glu Trp Ile
            35                  40                  45

Gly Ala Ile Asp Pro Glu Thr Gly Gly Thr Ala Tyr Asn Gln Arg Phe
        50                  55                  60

Lys Gly Lys Ala Ile Leu Thr Thr Asp Lys Ser Ser Ile Thr Ala Tyr
65                  70                  75                  80

Met Glu Leu Arg Ser Leu Thr Ser Glu Asp Ser Ala Val Tyr Tyr Cys
                85                  90                  95

Thr Arg Trp Asn Asp Gly Asp Tyr Trp Gly Gln Gly Thr Thr Leu Thr
            100                 105                 110

Val Ser Ser
        115
```

<210> SEQ ID NO 50
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Asp Val Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
                20                  25                  30

Asn Gly Lys Thr Tyr Leu Asn Trp Phe Gln Gln Arg Pro Gly Gln Ser
            35                  40                  45

Pro Lys Arg Leu Met Tyr Gln Val Ser Lys Leu Asp Pro Gly Ile Pro
        50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Leu Tyr Tyr Cys Leu Gln Gly
                85                  90                  95

Thr Tyr Tyr Pro Tyr Thr Phe Gly Gly Gly Thr Lys Leu Glu Ile Lys
            100                 105                 110
```

<210> SEQ ID NO 51
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 51

Gly Tyr Ser Phe Thr Gly Tyr
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asn Pro Tyr Asn Gly Asp
1               5

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Gly Asp Gly Tyr Tyr Trp Tyr Phe Asp Val
1               5                   10

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala Ser Glu Ser Val Asp Asn Tyr Gly Ile Ser Phe Met Asn
1               5                   10                  15

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Ala Ser Asn Gln Gly Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Ser Lys Glu Val Pro Arg Thr
1               5
```

```
<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Tyr Phe Met Asn
1               5

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ile Asn Pro Tyr Asn Gly Asp Thr Phe Tyr Asn Gln Lys Phe Lys
1               5                   10                  15

Gly

<210> SEQ ID NO 59
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Gly Tyr
                20                  25                  30

Phe Met Asn Trp Val Lys Gln Ser His Gly Lys Ser Leu Glu Trp Ile
            35                  40                  45

Gly Arg Ile Asn Pro Tyr Asn Gly Asp Thr Phe Tyr Asn Gln Lys Phe
        50                  55                  60

Lys Gly Lys Ala Thr Leu Thr Val Asp Lys Ser Ser Ser Thr Ala His
65                  70                  75                  80

Met Glu Leu Arg Ser Leu Thr Ser Glu Asp Ser Ala Leu Tyr Tyr Cys
                85                  90                  95

Ala Ser Glu Gly Asp Gly Tyr Tyr Trp Tyr Phe Asp Val Trp Gly Ala
            100                 105                 110

Gly Thr Thr Val Thr Val Ser Ser
        115                 120

<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
```

```
                20                  25                  30
Gly Ile Ser Phe Met Asn Trp Phe Gln Gln Lys Pro Gly Gln Pro Pro
            35                  40                  45

Lys Leu Leu Ile Tyr Ala Ala Ser Asn Gln Gly Ser Gly Val Pro Ala
        50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Arg Thr Phe Gly Gly Gly Thr Lys Leu Glu Ile Lys
            100                 105                 110

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Tyr Thr Phe Thr Asp His
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Pro Asp Thr Gly Asp
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Trp Thr Gly Gly Asp Tyr
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp His Glu Met His
1               5

<210> SEQ ID NO 65
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 65

Val Ile Asp Pro Asp Thr Gly Asp Thr Thr Tyr Asn Gln Lys Phe Lys
1               5                   10                  15

Gly

<210> SEQ ID NO 66
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Asp His
            20                  25                  30

Glu Met His Trp Val Arg Gln Thr Pro Val His Gly Leu Glu Trp Ile
        35                  40                  45

Gly Val Ile Asp Pro Asp Thr Gly Asp Thr Thr Tyr Asn Gln Lys Phe
    50                  55                  60

Lys Gly Lys Ala Thr Leu Thr Ala Asp Lys Ser Ser Thr Ala Tyr
65                  70                  75                  80

Met Asp Leu Arg Ser Leu Thr Ser Glu Asp Ser Ala Val Phe Tyr Cys
                85                  90                  95

Thr Arg Trp Thr Gly Gly Asp Tyr Trp Gly His Gly Thr Thr Leu Thr
            100                 105                 110

Val Ser Ser
        115

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Ser Ser Gln Ser Leu Leu Tyr Ser Asp Gly Lys Thr Tyr Leu Asn
1               5                   10                  15

<210> SEQ ID NO 68

<400> SEQUENCE: 68

000

<210> SEQ ID NO 69

<400> SEQUENCE: 69

000

<210> SEQ ID NO 70
<211> LENGTH: 112
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 70

Asp Ala Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Phe Gln Gln Arg Pro Gly Gln Ser
        35                  40                  45

Pro Lys Arg Leu Met Tyr Gln Val Ser Lys Leu Asp Pro Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Val Tyr Tyr Cys Leu Gln Gly
                85                  90                  95

Thr Tyr Tyr Pro Tyr Thr Phe Gly Ser Gly Thr Lys Leu Glu Ile Lys
            100                 105                 110

<210> SEQ ID NO 71
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
gatgtacagc ttcaggagtc aggacctggc ctcgtgaaac cttctcagtc tctgtctctc      60
acctgctctg tcactggcta ctccatcacc agtggttatt actggaactg gatccggcag     120
tttccaggaa acaaactgga atggatgggc tacataagct acgatggtta caataactac     180
aacccatctc tcaaaaatcg aatctccatc actcgtgaca catctaagaa ccagttttc      240 ctgaagttga attctgtgac tactgaggac acagccacat attactgtgc aaactactat     300
gattacgaag actggtactt cggtgtctgg ggcacaggga ccacggtcac cgtctcctca     360

<210> SEQ ID NO 72
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 72
gacattgtgc tgacccaatc tccagcttct ttggctatgt ctctagggaa gagggccacc      60
atctcctgca gagccagcga aagtgtcagt attattggta ctaattcaat acactggtac     120
caacagaaac caggacagcc acccaaactc ctcatctatc atgcatccaa cctagaaact     180
ggagtccctg ccaggttcag tggcagtggg tctagaacag acttcaccct caccattgat     240
cctgtggagg aagatgatgt tgcaatctat tactgtctgc aaagtaggaa gattccgtac     300
acgttcggag gggggaccaa gctggaaata aaa                                  333

<210> SEQ ID NO 73
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

| caggtccagc tgcagcagtc tggagctgag ctggtgaaac ccggggcatc agtgaggctg | 60 |
| tcctgcgagg cttctggcta caccttcacg gactatacta tacactgggt aaagcagagg | 120 |
| tctggacagg gtcttgagtg gattggatgg atttaccctc taagaggtag tataaactac | 180 |
| aatgagaaat tcaaggacaa ggccacattg actgcggaca aatcctccag cacagtctat | 240 |
| ttggagcttg gtagattgac atctaaggac tctgcggtct atttctgtgc aagacacgga | 300 |
| gcctactata gtaacgcctt tgactactgg ggccaaggca ccactctcac agtctcctca | 360 |

<210> SEQ ID NO 74
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

| aacattgtaa tgacccaatc tccagcttca ttggctgtgt ctctaggtca gagggccacc | 60 |
| atctcctgca gagccagcga gagtgttgat aatgatggca ttagatttat gcactggtac | 120 |
| cagcagaaac caggacagcc acccaaactc ctcatctatc gtgcatccaa cctagaatct | 180 |
| gggatccctg ccaggttcag tggcagtggg tctaggacag acttcaccct cactattaat | 240 |
| cctgtggaga ctgatgatgt tgcaacctat tactgtcagc aaagtaataa ggatccgtac | 300 |
| acgttcggag gggggaccaa gctggagctg aaa | 333 |

<210> SEQ ID NO 75
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

| gaggtccagc ttcagcagtc tggagctgag ctggtgaggc ctgggtcctc agtgaagatg | 60 |
| tcctgcaaga cttctggata tactttcaca agctacggta aaactgggt gaagcagagg | 120 |
| cctggacagg gcctggaatg gattggatat atttatattg gaaatggtta tgctgagtac | 180 |
| aatgagaggt tcaagggcaa ggccacactg acttcagaca catcctccag cacagcctac | 240 |
| atgcagctca gcagcctgac atctgaggac tctgcaatct atttctgtgc actatactat | 300 |
| ccctggttta cttactgggg ccaggggact ctggtcactg tctctgca | 348 |

<210> SEQ ID NO 76
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

| gacatccaga tgactcagtc tccagcctcc ctttctgcat ctgtgggaga ttctgtcacc | 60 |
| atcacatgtc gagcaagtga gaatatttac agttatttag catggtatca gcagaaacag | 120 |
| ggaaaatctc ctcagctcct ggtctataat gcaaaaacct agctgaagg tgtgccatca | 180 |

| | |
|---|---|
| aggttcagtg gcagtggatc aggcacacag ttttctctga agatcaacag cctgcagcct | 240 |
| gaagattttg ggaattatta ctgtcaacat cattatgata ctccgttcac gttcggaggg | 300 |
| gggaccaagc tggaaataaa a | 321 |

<210> SEQ ID NO 77
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

| | |
|---|---|
| caggttcagc tgcaccagtc tggacctgag ctggtgaagc ctggggcttc agtgaagttg | 60 |
| tcctgcaaga cttctggcta caccttcaca agctacgatg tcttctgggt gaagcagagg | 120 |
| cctggacagg gacttgagtg gattggatgg atttatccta gagatagtag tactaaatac | 180 |
| aatgagaagt tcaagggcaa ggccacattg actgtagaca catcctccag cacagcatac | 240 |
| atggagctcc acagcctgac atctgaggac tctgcggtct atttctgtgc aaaagagggg | 300 |
| tatgattatg caagaggggg ctttgactac tggggccaag gcaccactct cacagtctcc | 360 |
| tca | 363 |

<210> SEQ ID NO 78
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

| | |
|---|---|
| gacattgtgc tgacccaatc tccagcttct ttggctgtgt ctctagggca gagggccatc | 60 |
| atctcctgca aggccagcca agtgtcagt tttgctggta ctaatttaat gcactggtac | 120 |
| caacagagac cagggcagca acccaaactc ctcatctatc gtgcatccaa cctagaacct | 180 |
| ggggttccta ccaggtttag tggcagtggg tctaggacag acttcaccct caatatccat | 240 |
| cctgtggagg aagatgatgc tgcaacctat tactgtcagc aaagtaggga atatccgtgg | 300 |
| acgttcggtg gaggcaccaa gctggaaatc aaa | 333 |

<210> SEQ ID NO 79
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

| | |
|---|---|
| caggttcaac tgcagcagtc tggggctgag ctggtgaggc ctggggcttc agtgacgctg | 60 |
| tcctgcaagg cttcgggcta cactttact gactatgaaa tgcactgggt gaagcagaca | 120 |
| cctgtgcatg gcctggaatg gattggagct attgatcctg aaactggtgg tactgcctac | 180 |
| aatcagaggt tcaagggcaa ggccatactg actacagaca atcctccat cacagcctac | 240 |
| atggagctcc gcagcctgac atctgaggac tctgccgtct attactgtac aagatggaat | 300 |
| gatggcgact actggggcca aggcaccact ctcacagtct cctca | 345 |

<210> SEQ ID NO 80

```
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
gatgttgtga tgacccagac tccactgtct ttgtcggtta ccattggaca accagcctcc    60
atttcttgca agtcaagtca gagcctctta tacagtaatg gaaagacata tttgaattgg   120
tttcaacaga ggcctggcca gtctccaaag cgcctaatgt atcaggtgtc caaactggac   180
cctggcatcc ctgacaggtt cagtggcagt ggatcagaaa cagattttac acttaaaatc   240
agcagagtgg aggctgaaga tttgggactt tattactgct tgcaaggtac atattatccg   300
tacacgttcg gagggggac caagctggaa ataaaa                              336

<210> SEQ ID NO 81
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
gaggtccagc tgcagcagtc tggacctgag ctggtgaagc ctggggcttc agtgaagatg    60
tcctgcaagg cttctggtta ctcctttact ggctacttta tgaactgggt gaagcagagc   120 catgaaaga gccttgagtg gattggacgt attaatcctt acaatggtga tactttctac    180
aaccagaagt tcaagggcaa ggccacattg actgtagaca atcctctag cacagcccac    240 atggagctcc ggagcctgac atctgaggac tctgcactct attattgtgc aagcgaaggt    300
gatggttact actggtactt cgatgtctgg ggcgcaggga ccacggtcac cgtctcctca    360

<210> SEQ ID NO 82
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
gacattgtgc tgacccaatc tccagcttct ttggctgtgt ctctagggca gagggccacc    60
atctcctgca gagccagcga aagtgttgat aattatggca ttagttttat gaactggttc   120
caacagaaac caggacagcc acccaaactc ctcatctatg ctgcatccaa ccaaggatcc   180
ggggtccctg ccaggtttag tggcagtggg tctgggacag acttcagcct caacatccat   240
cctatggagg aggatgatac tgcaatgtat ttctgtcagc aaagtaagga ggttcctcgg   300
acgttcggtg aggcaccaa gctggaaatc aaa                                333

<210> SEQ ID NO 83
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
caggttcaac tgcagcagtc tggggctgag ctggtgaggc ctggggcttc agtgaagctg    60
```
tcctgcaagg cttcgggcta cacatttact gaccatgaaa tgcactgggt gagacagaca    120
cctgtgcatg gcctggaatg gattggagtt attgatcctg acactggtga tactacctac    180
aatcagaaat tcaagggcaa ggccacactg actgcagaca atcctccag cacagcctac     240 atggacctcc gcagcctgac atctgaggac tctgccgtct tttactgtac acggtggact    300
gggggggact actggggcca tggcaccact ctcacagtct cctca                    345

```
<210> SEQ ID NO 84
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
```
gatgctgtga tgacccagac tccactgtct ttgtcggtta ccattggaca accagcctct    60
atctcttgca agtcgagtca gagcctctta tatagtgatg gaaagacata tttgaattgg    120
ttccaacaga ggccaggcca gtctccaaag cgcctaatgt atcaggtgtc caaactggac    180
cctggcatcc ctgacaggtt cagtggcagt ggatcagaga cagattttac acttaaaatc    240
agcagagtgg aggctgagga tttgggagtt tattactgct tgcaaggtac atattatccg    300
tatacgttcg gatcggggac caagctggaa ataaaa                              336

```
<210> SEQ ID NO 85
<211> LENGTH: 250
<212> TYPE: PRT
<213> ORGANISM: Homo sapiens

<400> SEQUENCE: 85
```

Met Pro Ala Ser Ser Pro Phe Leu Leu Ala Pro Lys Gly Pro Pro Gly
 1               5                  10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr

```
                    195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 86
<211> LENGTH: 234
<212> TYPE: PRT
<213> ORGANISM: Homo sapiens

<400> SEQUENCE: 86

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
                20                  25                  30

Leu Ser Trp Gly Ala Ala Leu Gly Ala Val Ala Cys Ala Met Ala Leu
            35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
                100                 105                 110

Asn Asp Ser Asp Val Thr Glu Val Met Trp Gln Pro Ala Leu Arg Arg
            115                 120                 125

Gly Arg Gly Leu Gln Ala Gln Gly Tyr Gly Val Arg Ile Gln Asp Ala
    130                 135                 140

Gly Val Tyr Leu Leu Tyr Ser Gln Val Leu Phe Gln Asp Val Thr Phe
145                 150                 155                 160

Thr Met Gly Gln Val Val Ser Arg Glu Gly Gln Gly Arg Gln Glu Thr
                165                 170                 175

Leu Phe Arg Cys Ile Arg Ser Met Pro Ser His Pro Asp Arg Ala Tyr
            180                 185                 190

Asn Ser Cys Tyr Ser Ala Gly Val Phe His Leu His Gln Gly Asp Ile
    195                 200                 205

Leu Ser Val Ile Ile Pro Arg Ala Arg Ala Lys Leu Asn Leu Ser Pro
210                 215                 220

His Gly Thr Phe Leu Gly Phe Val Lys Leu
225                 230

<210> SEQ ID NO 87
<211> LENGTH: 247
<212> TYPE: PRT
<213> ORGANISM: Homo sapiens

<400> SEQUENCE: 87

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
                20                  25                  30

Leu Ser Trp Gly Ala Ala Leu Gly Ala Val Ala Cys Ala Met Ala Leu
```

```
                35                  40                  45
Leu Thr Gln Gln Thr Glu Leu Gln Ser Leu Arg Arg Glu Val Ser Arg
 50                  55                  60
Leu Gln Gly Thr Gly Gly Pro Ser Gln Asn Gly Glu Gly Tyr Pro Trp
 65                  70                  75                  80
Gln Ser Leu Pro Glu Gln Ser Ser Asp Ala Leu Glu Ala Trp Glu Asn
                 85                  90                  95
Gly Glu Arg Ser Arg Lys Arg Ala Val Leu Thr Gln Lys Gln Lys
                100                 105                 110
Lys Gln His Ser Val Leu His Leu Val Pro Ile Asn Ala Thr Ser Lys
                115                 120                 125
Asp Asp Ser Asp Val Thr Glu Val Met Trp Gln Pro Ala Leu Arg Arg
130                 135                 140
Gly Arg Gly Leu Gln Ala Gln Gly Tyr Gly Val Arg Ile Gln Asp Ala
145                 150                 155                 160
Gly Val Tyr Leu Leu Tyr Ser Gln Val Leu Phe Gln Asp Val Thr Phe
                165                 170                 175
Thr Met Gly Gln Val Val Ser Arg Glu Gly Gln Gly Arg Gln Glu Thr
                180                 185                 190
Leu Phe Arg Cys Ile Arg Ser Met Pro Ser His Pro Asp Arg Ala Tyr
                195                 200                 205
Asn Ser Cys Tyr Ser Ala Gly Val Phe His Leu His Gln Gly Asp Ile
                210                 215                 220
Leu Ser Val Ile Ile Pro Arg Ala Arg Ala Lys Leu Asn Leu Ser Pro
225                 230                 235                 240
His Gly Thr Phe Leu Gly Leu
                245

<210> SEQ ID NO 88
<211> LENGTH: 222
<212> TYPE: PRT
<213> ORGANISM: Homo sapiens

<400> SEQUENCE: 88

Met Pro Ala Ser Ser Pro Phe Leu Leu Ala Pro Lys Gly Pro Pro Gly
 1               5                  10                  15
Asn Met Gly Gly Pro Val Arg Glu Pro Ala Leu Ser Val Ala Leu Trp
                20                  25                  30
Leu Ser Trp Gly Ala Ala Leu Gly Ala Val Ala Cys Ala Met Ala Leu
                35                  40                  45
Leu Thr Gln Gln Thr Glu Leu Gln Ser Leu Arg Arg Glu Val Ser Arg
 50                  55                  60
Leu Gln Gly Thr Gly Gly Pro Ser Gln Asn Gly Glu Gly Tyr Pro Trp
 65                  70                  75                  80
Gln Ser Leu Pro Glu Gln His Ser Val Leu His Leu Val Pro Ile Asn
                 85                  90                  95
Ala Thr Ser Lys Asp Asp Ser Asp Val Thr Glu Val Met Trp Gln Pro
                100                 105                 110
Ala Leu Arg Arg Gly Arg Gly Leu Gln Ala Gln Gly Tyr Gly Val Arg
                115                 120                 125
Ile Gln Asp Ala Gly Val Tyr Leu Leu Tyr Ser Gln Val Leu Phe Gln
                130                 135                 140
Asp Val Thr Phe Thr Met Gly Gln Val Val Ser Arg Glu Gly Gln Gly
145                 150                 155                 160
```

```
Arg Gln Glu Thr Leu Phe Arg Cys Ile Arg Ser Met Pro Ser His Pro
                165                 170                 175

Asp Arg Ala Tyr Asn Ser Cys Tyr Ser Ala Gly Val Phe His Leu His
            180                 185                 190

Gln Gly Asp Ile Leu Ser Val Ile Ile Pro Arg Ala Arg Ala Lys Leu
        195                 200                 205

Asn Leu Ser Pro His Gly Thr Phe Leu Gly Phe Val Lys Leu
    210                 215                 220

<210> SEQ ID NO 89
<211> LENGTH: 330
<212> TYPE: PRT
<213> ORGANISM: Homo sapiens

<400> SEQUENCE: 89

Met Ala Ala Arg Arg Ser Gln Arg Arg Gly Arg Gly Glu Pro
1               5                   10                  15

Gly Thr Ala Leu Leu Val Pro Leu Ala Leu Gly Leu Gly Leu Ala Leu
                20                  25                  30

Ala Cys Leu Gly Leu Leu Leu Ala Val Val Ser Leu Gly Ser Arg Ala
                35                  40                  45

Ser Leu Ser Ala Gln Glu Pro Ala Gln Glu Glu Leu Val Ala Glu Glu
        50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
                100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
        130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Ser Ser Asp Ala Leu Glu Ala Trp Glu Asn
                165                 170                 175

Gly Glu Arg Ser Arg Lys Arg Ala Val Leu Thr Gln Lys Gln Lys
            180                 185                 190

Lys Gln His Ser Val Leu His Leu Val Pro Ile Asn Ala Thr Ser Lys
        195                 200                 205

Asp Asp Ser Asp Val Thr Glu Val Met Trp Gln Pro Ala Leu Arg Arg
    210                 215                 220

Gly Arg Gly Leu Gln Ala Gln Gly Tyr Gly Val Arg Ile Gln Asp Ala
225                 230                 235                 240

Gly Val Tyr Leu Leu Tyr Ser Gln Val Leu Phe Gln Asp Val Thr Phe
                245                 250                 255

Thr Met Gly Gln Val Val Ser Arg Glu Gly Gln Gly Arg Gln Glu Thr
            260                 265                 270

Leu Phe Arg Cys Ile Arg Ser Met Pro Ser His Pro Asp Arg Ala Tyr
        275                 280                 285

Asn Ser Cys Tyr Ser Ala Gly Val Phe His Leu His Gln Gly Asp Ile
    290                 295                 300

Leu Ser Val Ile Ile Pro Arg Ala Arg Ala Lys Leu Asn Leu Ser Pro
305                 310                 315                 320
```

```
His Gly Thr Phe Leu Gly Phe Val Lys Leu
            325                 330

<210> SEQ ID NO 90
<211> LENGTH: 205
<212> TYPE: PRT
<213> ORGANISM: Homo sapiens

<400> SEQUENCE: 90

Met Gly Gly Pro Val Arg Glu Pro Ala Leu Ser Val Ala Leu Trp Leu
1               5                   10                  15

Ser Trp Gly Ala Ala Leu Gly Ala Val Ala Cys Ala Met Ala Leu Leu
            20                  25                  30

Thr Gln Gln Thr Glu Leu Gln Ser Leu Arg Arg Glu Val Ser Arg Leu
        35                  40                  45

Gln Gly Thr Gly Gly Pro Ser Gln Asn Gly Glu Gly Tyr Pro Trp Gln
    50                  55                  60

Ser Leu Pro Glu Gln His Ser Val Leu His Leu Val Pro Ile Asn Ala
65                  70                  75                  80

Thr Ser Lys Asp Asp Ser Asp Val Thr Glu Val Met Trp Gln Pro Ala
                85                  90                  95

Leu Arg Arg Gly Arg Gly Leu Gln Ala Gln Gly Tyr Gly Val Arg Ile
            100                 105                 110

Gln Asp Ala Gly Val Tyr Leu Leu Tyr Ser Gln Val Leu Phe Gln Asp
        115                 120                 125

Val Thr Phe Thr Met Gly Gln Val Val Ser Arg Glu Gly Gln Gly Arg
    130                 135                 140

Gln Glu Thr Leu Phe Arg Cys Ile Arg Ser Met Pro Ser His Pro Asp
145                 150                 155                 160

Arg Ala Tyr Asn Ser Cys Tyr Ser Ala Gly Val Phe His Leu His Gln
                165                 170                 175

Gly Asp Ile Leu Ser Val Ile Ile Pro Arg Ala Arg Ala Lys Leu Asn
            180                 185                 190

Leu Ser Pro His Gly Thr Phe Leu Gly Phe Val Lys Leu
        195                 200                 205

<210> SEQ ID NO 91
<211> LENGTH: 241
<212> TYPE: PRT
<213> ORGANISM: Mus musculus

<400> SEQUENCE: 91

Met Pro Ala Ser Ser Pro Gly His Met Gly Gly Ser Val Arg Glu Pro
1               5                   10                  15

Ala Leu Ser Val Ala Leu Trp Leu Ser Trp Gly Ala Val Leu Gly Ala
            20                  25                  30

Val Thr Cys Ala Val Ala Leu Leu Ile Gln Gln Thr Glu Leu Gln Ser
        35                  40                  45

Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Glu Gln Ser Pro Asp
65                  70                  75                  80

Val Leu Glu Ala Trp Lys Asp Gly Ala Lys Ser Arg Arg Arg Arg Ala
                85                  90                  95

Val Leu Thr Gln Lys His Lys Lys Lys His Ser Val Leu His Leu Val
            100                 105                 110
```

```
Pro Val Asn Ile Thr Ser Lys Ala Asp Ser Asp Val Thr Glu Val Met
        115                 120                 125

Trp Gln Pro Val Leu Arg Arg Gly Arg Gly Leu Glu Ala Gln Gly Asp
    130                 135                 140

Ile Val Arg Val Trp Asp Thr Gly Ile Tyr Leu Leu Tyr Ser Gln Val
145                 150                 155                 160

Leu Phe His Asp Val Thr Phe Thr Met Gly Gln Val Val Ser Arg Glu
                165                 170                 175

Gly Gln Gly Arg Arg Glu Thr Leu Phe Arg Cys Ile Arg Ser Met Pro
            180                 185                 190

Ser Asp Pro Asp Arg Ala Tyr Asn Ser Cys Tyr Ser Ala Gly Val Phe
        195                 200                 205

His Leu His Gln Gly Asp Ile Ile Thr Val Lys Ile Pro Arg Ala Asn
    210                 215                 220

Ala Lys Leu Ser Leu Ser Pro His Gly Thr Phe Leu Gly Phe Val Lys
225                 230                 235                 240

Leu

<210> SEQ ID NO 92
<211> LENGTH: 240
<212> TYPE: PRT
<213> ORGANISM: Mus musculus

<400> SEQUENCE: 92

Met Pro Ala Ser Ser Pro Gly His Met Gly Gly Ser Val Arg Glu Pro
1               5                   10                  15

Ala Leu Ser Val Ala Leu Trp Leu Ser Trp Gly Ala Val Leu Gly Ala
            20                  25                  30

Val Thr Cys Ala Val Ala Leu Leu Ile Gln Gln Thr Glu Leu Gln Ser
        35                  40                  45

Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Glu Gln Ser Pro Asp
65                  70                  75                  80

Val Leu Glu Ala Trp Lys Asp Gly Ala Lys Ser Arg Arg Arg Arg Ala
                85                  90                  95

Val Leu Thr Gln Lys His Lys Lys Lys His Ser Val Leu His Leu Val
            100                 105                 110

Pro Val Asn Ile Thr Ser Lys Asp Ser Asp Val Thr Glu Val Met Trp
        115                 120                 125

Gln Pro Val Leu Arg Arg Gly Arg Gly Leu Glu Ala Gln Gly Asp Ile
    130                 135                 140

Val Arg Val Trp Asp Thr Gly Ile Tyr Leu Leu Tyr Ser Gln Val Leu
145                 150                 155                 160

Phe His Asp Val Thr Phe Thr Met Gly Gln Val Val Ser Arg Glu Gly
                165                 170                 175

Gln Gly Arg Arg Glu Thr Leu Phe Arg Cys Ile Arg Ser Met Pro Ser
            180                 185                 190

Asp Pro Asp Arg Ala Tyr Asn Ser Cys Tyr Ser Ala Gly Val Phe His
        195                 200                 205

Leu His Gln Gly Asp Ile Ile Thr Val Lys Ile Pro Arg Ala Asn Ala
    210                 215                 220

Lys Leu Ser Leu Ser Pro His Gly Thr Phe Leu Gly Phe Val Lys Leu
225                 230                 235                 240
```

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Phe Ser Leu Thr Ile Tyr
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp Ser Asp Gly Ser
1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asn Trp Val Asp Gln Ala Trp Phe Ala Tyr
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ala Ser Lys Asn Ile Tyr Ser Tyr Leu Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Ala Lys Thr Leu Pro Glu
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln His His Tyr Gly Thr Pro Leu Thr
1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Tyr Asp Val His
1               5

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Val Ile Trp Ser Asp Gly Ser Thr Asp Tyr Asn Ala Ala Phe Ile Ser
1               5                   10                  15

<210> SEQ ID NO 101
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ile Tyr
            20                  25                  30

Asp Val His Trp Val Arg Gln Ser Pro Gly Lys Gly Leu Glu Trp Leu
        35                  40                  45

Gly Val Ile Trp Ser Asp Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asn Trp Val Asp Gln Ala Trp Phe Ala Tyr Trp Gly Gln Gly Thr
            100                 105                 110

Leu Val Thr Val Ser Ala
        115

<210> SEQ ID NO 102
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Asp Ile Gln Met Thr Gln Ser Pro Ala Ser Leu Ser Ala Ser Val Gly
1               5                   10                  15

Glu Thr Ile Thr Ile Thr Cys Arg Ala Ser Lys Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Pro Glu Gly Val Pro Ser Arg Phe Ser Gly
50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Tyr Gly Thr Pro Leu
                85                  90                  95

Thr Phe Gly Ala Gly Thr Lys Leu Glu Leu Lys
            100                 105

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Tyr Ile Phe Thr Asp Tyr
1               5

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Tyr Pro Gly Ser Gly Asn
1               5

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu Ser Asn Tyr Val Gly Tyr Tyr Ala Met Asp Tyr
1               5                   10

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Ser Ser Gln Ser Val Val Asn Ser Asn Gly Asn Thr Tyr Leu Glu
1               5                   10                  15
```

```
<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Lys Val Ser Asn Arg Phe Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Phe Gln Gly Ser His Val Pro Trp Thr
1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Tyr Thr Ile Asn
1               5

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Trp Ile Tyr Pro Gly Ser Gly Asn Arg Lys Tyr Asn Asp Lys Phe Lys
1               5                   10                  15

Gly

<210> SEQ ID NO 111
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Gln Gln Ser Gly Pro Glu Leu Val Lys Pro Gly Ala
1               5                   10                  15

Ser Val Lys Leu Ser Cys Lys Ala Ala Gly Tyr Ile Phe Thr Asp Tyr
            20                  25                  30

Thr Ile Asn Trp Val Lys Gln Ser Pro Gly Gln Gly Leu Glu Trp Ile
        35                  40                  45

Gly Trp Ile Tyr Pro Gly Ser Gly Asn Arg Lys Tyr Asn Asp Lys Phe
    50                  55                  60
```

```
Lys Gly Lys Ala Thr Met Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Glu Ser Asn Tyr Val Gly Tyr Tyr Ala Met Asp Tyr Trp Gly
            100                 105                 110

Gln Gly Thr Ser Val Thr Val Ser Ser
        115                 120
```

<210> SEQ ID NO 112
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Val Val Asn Ser
            20                  25                  30

Asn Gly Asn Thr Tyr Leu Glu Trp Tyr Leu Gln Lys Pro Gly Gln Ser
         35                 40                  45

Pro Asn Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
            100                 105                 110
```

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

```
Gly Tyr Thr Phe Thr Asn Tyr
 1               5
```

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

```
Tyr Pro Gly Gly Ile Gly Gly Gly Tyr
 1               5
```

<210> SEQ ID NO 115
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 115

Ser Glu Thr Gly Arg Ala Met Asp Tyr
1               5

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Ala Ser Gln Asp Ile Asn Lys Tyr Ile Ala
1               5                   10

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Tyr Thr Ser Thr Leu Lys Pro
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Gln Tyr Asp Asn Leu Asn Thr
1               5

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asn Tyr Trp Ile Gly
1               5

<210> SEQ ID NO 120
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Ile Tyr Pro Gly Gly Ile Gly Gly Gly Tyr Thr Lys Tyr Asn Glu
1               5                   10                  15

Lys Phe Lys Gly
```

20

<210> SEQ ID NO 121
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile Tyr Pro Gly Gly Ile Gly Gly Tyr Thr Lys Tyr Asn
    50                  55                  60

Glu Lys Phe Lys Gly Lys Ala Thr Leu Thr Ala Asp Thr Ser Ser Ser
65                  70                  75                  80

Thr Ala Tyr Met Gln Leu Gly Ser Leu Thr Ser Glu Asp Ser Ala Ile
                85                  90                  95

Tyr Phe Cys Ser Arg Ser Glu Thr Gly Arg Ala Met Asp Tyr Trp Gly
            100                 105                 110

Gln Gly Thr Ser Val Thr Val Ser Ser
        115                 120

<210> SEQ ID NO 122
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Lys Pro Gly Ile Pro Ser Arg Phe Ser Gly
    50                  55                  60

Ser Gly Ser Gly Arg Asp Tyr Ser Phe Ser Ile Ser Asp Leu Glu Pro
65                  70                  75                  80

Glu Asp Ile Ala Thr Tyr Tyr Cys Leu Gln Tyr Asp Asn Leu Asn Thr
                85                  90                  95

Phe Gly Gly Gly Thr Lys Leu Glu Ile Lys
            100                 105

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Gly Tyr Ser Phe Thr Asp Tyr
1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asp Pro Ser Asn Gly Gly
1               5

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Asp Asn Tyr Gly Ser Gly Thr Met Asp Tyr
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Lys Ala Ser Gln Asn Val Gly Thr Asp Val Ser
1               5                   10

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Trp Ala Ser Asn Arg Phe Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Gln Tyr Ser Ile Tyr Pro Leu Thr
1               5

<210> SEQ ID NO 129
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 129

Asp Tyr Asn Ile Tyr
1               5

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Tyr Ile Asp Pro Ser Asn Gly Gly Pro Gly Tyr Asn Gln Lys Phe Arg
1               5                   10                  15

Gly

<210> SEQ ID NO 131
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
                20                  25                  30

Asn Ile Tyr Trp Val Lys Gln Ser His Gly Lys Ser Leu Glu Trp Ile
            35                  40                  45

Gly Tyr Ile Asp Pro Ser Asn Gly Gly Pro Gly Tyr Asn Gln Lys Phe
    50                  55                  60

Arg Gly Lys Ala Thr Leu Thr Val Asp Lys Ser Ser Ser Thr Ala Phe
65                  70                  75                  80

Leu His Leu Asn Ser Leu Thr Ser Glu Asp Ser Ala Val Tyr Tyr Cys
                85                  90                  95

Ala Arg Arg Asp Asn Tyr Gly Ser Gly Thr Met Asp Tyr Trp Gly Gln
            100                 105                 110

Gly Thr Ser Val Thr Val Ser Ser
        115                 120

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Asp
                20                  25                  30

Val Ser Trp Tyr Gln Gln Lys Pro Gly Lys Ser Pro Lys Pro Leu Ile
            35                  40                  45
```

```
Tyr Trp Ala Ser Asn Arg Phe Thr Gly Val Pro Asp Arg Phe Ile Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Glu Gln Tyr Ser Ile Tyr Pro Leu
                85                  90                  95

Thr Phe Gly Ala Gly Thr Lys Leu Glu Leu Lys
            100                 105

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Tyr Ser Phe Thr Asp Asp
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Pro Leu Asn Gly Gly
1               5

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Asp Asn Tyr Ala Thr Gly Thr Met Asp Tyr
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys Ala Ser Lys Asn Val Gly Thr Asp Val Ser
1               5                   10

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137
```

```
Glu Gln Tyr Ser Ser Tyr Pro Leu Thr
1               5
```

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

```
Asp Asp Asn Met Tyr
1               5
```

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

```
Tyr Ile Asp Pro Leu Asn Gly Gly Thr Gly Tyr Asn Gln Lys Phe Lys
1               5                   10                  15

Gly
```

<210> SEQ ID NO 140
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

```
Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Asp
            20                  25                  30

Asn Met Tyr Trp Val Lys Gln Ser His Gly Lys Ser Leu Glu Trp Ile
        35                  40                  45

Gly Tyr Ile Asp Pro Leu Asn Gly Gly Thr Gly Tyr Asn Gln Lys Phe
    50                  55                  60

Lys Gly Lys Ala Thr Leu Thr Val Asp Lys Ser Ser Ser Thr Ala Phe
65                  70                  75                  80

Leu His Leu Asn Ser Leu Thr Ser Glu Asp Ser Ala Val Tyr Tyr Cys
                85                  90                  95

Ala Arg Arg Asp Asn Tyr Ala Thr Gly Thr Met Asp Tyr Trp Gly Gln
            100                 105                 110

Gly Thr Ser Val Thr Val Ser Ser
        115                 120
```

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Asp Ile Val Met Thr Gln Ser Gln Lys Phe Met Ser Thr Ser Val Gly
1               5                   10                  15

Asp Arg Val Ser Ile Thr Cys Lys Ala Ser Lys Asn Val Gly Thr Asp
            20                  25                  30

Val Ser Trp Tyr Gln Gln Lys Pro Gly Lys Ser Pro Lys Pro Leu Ile
        35                  40                  45

Tyr Trp Ala Ser Asn Arg Phe Thr Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105
```

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

```
Tyr Pro Ile Asn Gly Tyr
1               5
```

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

```
Asp Ser Asn Tyr Val Gly Trp Tyr Phe Asp Val
1               5                   10
```

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

```
Arg Ser Ser Gln Ser Leu Val His Ser Asn Gly Asn Thr Tyr Leu His
1               5                   10                  15
```

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

```
Ser Gln Ser Thr His Val Pro Arg Thr
1               5
```

```
<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Arg Ala Ser Lys Ser Val Ser Thr Ser Gly Tyr Ser Tyr Met His
1               5                   10                  15

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Phe Thr Ser Asp Leu Glu Pro
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln His Ser Arg Glu Leu Pro Tyr Pro
1               5

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asp Tyr Asn Met Asp
1               5

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Ile Tyr Pro Ile Asn Gly Tyr Thr Gly Tyr Asn Gln Arg Phe Lys
1               5                   10                  15

Asn

<210> SEQ ID NO 151
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 151

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asn Ile Tyr Pro Ile Asn Gly Tyr Thr Gly Tyr Asn Gln Arg Phe
50                  55                  60

Lys Asn Lys Ala Thr Leu Thr Val Asp Lys Ser Ser Thr Ala Tyr
65                  70                  75                  80

Met Glu Leu His Ser Leu Thr Ser Glu Asp Ser Ala Val Tyr Tyr Cys
            85                  90                  95

Ala Arg Asp Ser Asn Tyr Val Gly Trp Tyr Phe Asp Val Trp Gly Ala
                100                 105                 110

Gly Thr Thr Val Thr Val Ser Ser
            115                 120

<210> SEQ ID NO 152
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Phe Lys Ile
65                  70                  75                  80

Ser Arg Val Glu Ala Glu Asp Leu Gly Val Tyr Phe Cys Ser Gln Ser
            85                  90                  95

Thr His Val Pro Arg Thr Phe Gly Gly Gly Thr Lys Leu Glu Ile Lys
                100                 105                 110

<210> SEQ ID NO 153
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Val Leu Thr Gln Ser Pro Ala Ser Leu Thr Val Ser Leu Gly
1               5                   10                  15

Gln Arg Ala Thr Phe Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45
```

```
Lys Leu Leu Ile Tyr Phe Thr Ser Asp Leu Glu Pro Gly Val Pro Ala
        50                  55                  60

Arg Phe Thr Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                85                  90                  95

Glu Leu Pro Tyr Pro Phe Gly Gly Gly Thr Lys Leu Glu Ile Lys
                100                 105                 110

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Tyr Thr Phe Ala Asp Tyr
 1               5

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Phe Pro Gly Ser Gly Ser
 1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Asp Ser Gly Arg Ala Met Asp Tyr
 1               5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Tyr Thr Ser Thr Leu Gln Ser
 1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158
```

```
Leu Gln Tyr Asp Asn Leu Leu Thr
1               5
```

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

```
Asp Tyr Tyr Ile Asn
1               5
```

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

```
Trp Ile Phe Pro Gly Ser Gly Ser Thr Tyr Tyr Asn Glu Lys Phe Lys
1               5                   10                  15

Gly
```

<210> SEQ ID NO 161
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ala Asp Tyr
            20                  25                  30

Tyr Ile Asn Trp Val Lys Gln Arg Pro Gly Gln Gly Leu Glu Trp Ile
        35                  40                  45

Gly Trp Ile Phe Pro Gly Ser Gly Ser Thr Tyr Tyr Asn Glu Lys Phe
    50                  55                  60

Lys Gly Lys Ala Thr Leu Thr Val Asp Lys Ser Ser Ser Thr Ala Tyr
65                  70                  75                  80

Met Leu Leu Ser Ser Leu Thr Ser Glu Asp Ser Ala Val Tyr Phe Cys
                85                  90                  95

Ala Arg Gly Asp Ser Gly Arg Ala Met Asp Tyr Trp Gly Gln Gly Thr
            100                 105                 110

Ser Val Thr Val Ser Ser
        115
```

<210> SEQ ID NO 162
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
            35                  40                  45

His Tyr Thr Ser Thr Leu Gln Ser Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Asn Ala Thr Tyr Tyr Cys Leu Gln Tyr Asp Asn Leu Leu Thr
                85                  90                  95

Phe Gly Ala Gly Thr Lys Leu Glu Leu Lys
            100                 105
```

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

```
Gly Phe Ser Leu Thr Asp Tyr
1               5
```

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

```
Trp Asn Asp Gly Ser
1               5
```

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

```
Asn Trp Tyr Gly Gly Tyr Trp Phe Ala Tyr
1               5                   10
```

<210> SEQ ID NO 166
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

```
Arg Ser Ser Glu Asn Ile Tyr Ser Tyr Leu Ala
1               5                   10
```

<210> SEQ ID NO 167

<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asn Ala Asn Ala Leu Ala Glu
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gln His His Tyr Gly Thr Pro Phe Thr
1               5

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Tyr Asp Val His
1               5

<210> SEQ ID NO 170
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Val Ile Trp Asn Asp Gly Ser Thr Asp Tyr Asn Thr Ala Phe Ile Ser
1               5                   10                  15

<210> SEQ ID NO 171
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Ala His Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
                20                  25                  30

Asp Val His Trp Val Arg Gln Ser Pro Gly Lys Gly Leu Glu Trp Leu
            35                  40                  45

Gly Val Ile Trp Asn Asp Gly Ser Thr Asp Tyr Asn Thr Ala Phe Ile
        50                  55                  60

Ser Arg Leu Thr Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
            85                  90                  95

Arg Asn Trp Tyr Gly Gly Tyr Trp Phe Ala Tyr Trp Gly Gln Gly Thr
            100                 105                 110

Leu Val Thr Val Ser Ala
        115

<210> SEQ ID NO 172
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Asp Ile Gln Met Thr Gln Ser Pro Ala Ser Leu Ser Ala Ser Ala Gly
1               5                   10                  15

Glu Thr Val Thr Ile Thr Cys Arg Ser Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Asn Ala Leu Ala Glu Gly Val Pro Ser Arg Phe Ser Gly
    50                  55                  60

Ser Gly Ser Val Thr Gln Phe Ser Leu Lys Ile Asn Ser Leu Gln Pro
65                  70                  75                  80

Glu Asp Phe Gly Ser Tyr Tyr Cys Gln His Tyr Gly Thr Pro
                85                  90                  95

Thr Phe Gly Ser Gly Thr Lys Leu Glu Ile Lys
            100                 105

<210> SEQ ID NO 173
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173
caggtgcagc tgaaggagtc aggacctggc ctggtggcgc cctcacagag cctgtccatc      60
acctgcacag tctctggttt ctcattaacc atctatgatg tacactgggt tcgccagtct    120
ccaggaaagg gtctggagtg gctgggagtg atatggagtg atggaagcac agactataat    180
gcagctttca tatctagact gagcatcagc aaggacaact ccaagagcca gttttctttt    240
aaaatgaaca gtctgcaagc tgatgacaca gccatatact actgtgccag aaattgggtc    300
gaccaggcct ggtttgctta ctggggccaa gggactctgg tcactgtctc tgca          354

<210> SEQ ID NO 174
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 174
gacatccaga tgactcagtc tccagcctcc ctatctgcat ctgtgggaga aactatcacc      60
atcacatgtc gagcaagtaa gaatatttac agttatttag catggtatca gcagaaacag    120

```
ggaaaatctc ctcagctcct ggtctataat gcaaaaacct taccagaagg tgtgccatca    180
aggttcagtg gcagtggatc aggcacacag ttttctctga agatcaacag cctgcagcct    240
gaagattttg ggagttatta ctgtcaacat cattatggta ctccgctcac gttcggtgct    300
gggaccaagc tggagctgaa a                                              321
```

<210> SEQ ID NO 175
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175

```
caggtccaac tgcagcagtc tggacctgag ctggtgaagc ctggagcttc agtgaagctg    60
tcctgcaagg ctgctggcta catcttcact gactatacta taaactgggt gaagcagagt   120
cctggacaga gacttgagtg gattggatgg atttatcctg aagtggtaa tcgtaaatac    180 aatgacaagt tcaagggcaa ggccacaatg actgcagaca atcctccag cacagcctac    240 atgcagctca gcagcctgac ctctgaggat tctgcggtct atttctgtgc aagagagagt   300
aactacgtgg ggtactatgc tatggactat tggggtcaag gaacctcagt caccgtctcc   360
tca                                                                 363
```

<210> SEQ ID NO 176
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176

```
gatgttttga tgacccaaac tccactctcc ctgcctgtca gtcttggaga tcaagcctcc    60
atctcttgca gatctagtca gagcgttgta aatagtaatg aaacaccta tttagaatgg   120 tacctgcaga accaggcca gtctccaaat ctcctgatct acaaagtttc caatcgattt    180
tctggggtcc cagacaggtt cagtggcagt ggatcgggga cagatttcac actcaagatc    240
agcagagtgg aggctgagga tctgggagtt tattactgtt ttcaaggttc acatgttccg    300
tggacgttcg gtggaggcac caagctggaa atcaaa                              336
```

<210> SEQ ID NO 177
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177

```
caggtccagc tgcagcagtc tggagctgag ctggtaaggc ctggggcttc agtgaagatg    60
tcctgcaagg ctgctggata caccttcaca aactactgga taggttgggt aaagcagagg   120
cctggacatg gccttgagtg gattggagat atttaccctg aggtatagg aggtggttat    180 actaagtaca atgagaagtt caagggcaag gccacactga ctgcagacac atcctccagc    240
acagcctaca tgcagctcgg cagcctgaca tctgaggact ctgccatcta tttctgttca    300
agatcggaaa ctggacgggc tatggactac tggggtcaag gaacctcagt caccgtctcc    360
``` tca                                                                    363

<210> SEQ ID NO 178
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
gacatccaga tgacacagtc tccatcctca ctgtctgcat ctctgggagg caaagtcacc     60
atcacttgca aggcaagcca agacattaat aagtatatag cttggtacca acacaagcct    120
ggaaaaggtc ctaggctgct catacattac acatctacat taaagccagg catcccatca    180
aggttcagtg gaagtgggtc tgggagagat tattccttca gcatcagtga cctggagcct    240
gaagatattg caacttatta ttgtctacag tatgataatc tgaacacgtt cggagggggg    300
accaagctgg aaataaaa                                                  318

<210> SEQ ID NO 179
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
gagatccagc tgcagcagtc tggacctgag ctggtgaagc ctggggcttc agtgaaggtg     60
tcctgcaagg cttctggtta ttcattcact gactacaaca tctactgggt gaagcagagc    120
catggaaaga gccttgagtg gattggatat attgatcctt ccaatggtgg tcctggctac    180
aaccagaagt tcaggggcaa ggccacattg actgttgaca gtcctccag cacagccttc     240 ctgcatctca acagcctgac atctgaggac tctgcagtct attactgtgc aagaagggac    300
aactacggct cggggactat ggactactgg ggtcaaggaa cctcagtcac cgtctcctca    360

<210> SEQ ID NO 180
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
gacattgtga tgacccagtc tcaaaaattc atgtccacat cagtaggaga cagggtcagc     60
atcacctgta aggccagtca gaatgtgggt actgatgtat cctggtatca acagaaacca    120
gggaaatctc ctaaaccact gatttactgg gcatcaaacc ggttcactgg agtccctgat    180
cgcttcatag gtagtggatc tgggacagat ttcactctca ccatcagcaa tgtgcagtct    240
gaagacttgg cagattattt ctgtgagcaa tatagcatct atccgctcac gttcggtgct    300
gggaccaagc tggagctgaa a                                              321

<210> SEQ ID NO 181
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 181

| gagatccagc tgcagcagtc tggacctgag ctggtgaagc ctggggcgtc agtgaaggta | 60 |
| tcctgcaagg cttctggtta ctcattcact gacgacaaca tgtactgggt gaagcagagc | 120 |
| catggaaaga gccttgagtg gattggatat attgatcctc tcaatggtgg tactggctac | 180 |
| aaccagaaat tcaagggcaa ggccacactg actgttgaca gtcctccag cacagccttc | 240 |
| ctgcatctca acagcctgac atctgaggac tctgcagtct attactgtgc aagaagggac | 300 |
| aactacgcca cggggactat ggactactgg ggtcaaggaa cctcagtcac cgtctcctca | 360 |

<210> SEQ ID NO 182
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 182

| gacattgtga tgacccagtc tcaaaaattc atgtccacat cagtaggaga cagggtcagc | 60 |
| atcacctgca aggccagtaa gaatgtgggt actgatgtat cctggtatca acagaaacca | 120 |
| gggaaatctc ctaaaccact gatttactgg gcatcaaacc ggttcactgg agtccctgat | 180 |
| cgcttcacag gcagtggatc tgggacagat ttcactctca ccatcaacaa tgtgcagtct | 240 |
| gaagacttgg cagattattt ctgtgagcaa tatagcagct atccgctcac gttcggtgct | 300 |
| gggaccaagc tggagctgaa a | 321 |

<210> SEQ ID NO 183
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 183

| gaggtccagc tgcagcagtc tggccctgag ctggtgaagc ctggggcttc agtgaagata | 60 |
| tcctgcaagg cttctggata cacattcact gactacaaca tggactgggt gaagcagagc | 120 |
| catggaaaga gccttgagtg gattggaaat atttatccta tcaatggtta tactggctac | 180 |
| aaccagaggt tcaagaacaa ggccacattg actgtagaca gtcctccag cacagcctac | 240 |
| atggaactcc acagcctgac atctgaggac tctgcggtct attactgcgc aagagatagt | 300 |
| aactacgttg gctggtactt cgatgtctgg ggcgcaggga ccacggtcac cgtctcctca | 360 |

<210> SEQ ID NO 184
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 184

| gatgttgtga tgacccaaac tccactctcc ctgcctgtca gtcttggaga tcaagcctcc | 60 |
| atctcttgca gatctagtca gagccttgta cacagtaatg aaacaccta tttacattgg | 120 |
| tacctgcaga agccaggcca gtctccaaag ctcctgatct acaaagtttc caaccgattt | 180 |

```
tctggggtcc cagacaggtt cagtggcagt ggatcaggga cagatttcac attcaagatc    240
agcagagtgg aggctgagga tctgggagtt tatttctgct ctcaaagtac acatgttcct    300
cggacgttcg gtggaggcac caagctggaa atcaaa                              336

<210> SEQ ID NO 185
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
gacattgtgc tgacacagtc tcctgcttcc ttaactgtat ctctggggca gagggccacc    60
ttctcatgca gggccagcaa aagtgtcagt acatctggct atagttatat gcactggtac    120
caacagaaac caggacagcc acccaaactc ctcatctatt ttacatccga cctagaacct    180
ggggtccctg ccaggttcac tggcagtggg tctgggacag acttcaccct caacatccat    240
cctgtggagg aggaggatgc tgcaacctat tactgtcagc acagtaggga gcttccgtac    300
cccttcggag gggggaccaa gttggaaata aaa                                 333

<210> SEQ ID NO 186
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
caggtccagc tacagcagtc tggacctgag ctggtgaagc tgggggcttc agtgaagata    60
tcctgcaagg cttctggcta caccttcgct gactactata aaactgggt gaagcagagg    120 cctggacagg gacttgagtg gattggatgg atttttcctg gaagtggtag tacttactac    180
aatgagaagt tcaagggcaa ggccacactt actgtagaca atcctccag cacagcctac    240 atgttgctca gcagcctgac ctctgaggac tctgcggtct atttctgtgc aagaggggac    300
tccggtaggg ctatggacta ctggggtcaa ggaacctcag tcaccgtctc ctca          354

<210> SEQ ID NO 187
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
gacatccaga tgacacagtc tccatcctca ctgtctgcat ctctgggagg caaagtcacc    60
atcacttgca aggcaagcca agacattaac aaatatatag cttggtacca acacaagcct    120
ggaaaaggtc ctaggctgct catacattac acatctacat tacagtcagg catcccatca    180
aggttcagtg aagtgggtc tgggagagat tattccttca gcatcagcaa cctggagcct    240
gaagataatg caacttatta ttgtctacag tatgataatc ttctcacgtt cggtgctggg    300
accaagctgg agctgaaa                                                  318

<210> SEQ ID NO 188
<211> LENGTH: 354
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 188

```
caggcgcacc tgaaggagtc aggacctggc ctggtggcgc cctcacagag cctgtccatc      60
acctgcacag tctctggttt ctcattaacc gactatgatg tacactgggt tcgccagtct     120
ccaggaaagg gtctggagtg gctgggagtg atatggaatg atggaagcac agactataat     180
acagctttca tatctagact gaccatcagc aaggacaact ccaagagcca gttttctttt     240
aaaatgaaca gtctgcaagc tgatgacaca gccatatact actgtgccag aaattggtat     300
ggtggctact ggtttgctta ctggggccaa gggactctgg tcactgtctc tgca           354
```

<210> SEQ ID NO 189
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 189

```
gacatccaga tgactcagtc tccagcctcc ctatctgcat ctgcgggaga aactgtcacc      60
atcacatgtc gatcaagtga aaatatttac agttatttag catggtatca gcagaaacag     120
ggaaaatctc ctcagctcct agtctataat gcaaatgcct tagcagaagg tgtgccatcg     180
aggttcagtg gcagtggatc agtcacacag ttttctctga agatcaacag cctgcagcct     240
gaagattttg ggagttatta ctgtcaacat cattatggta ctccattcac gttcggctcg     300
gggacaaagt tggaaataaa a                                               321
```

<210> SEQ ID NO 190
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 190

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Ser Tyr Asp Gly Tyr Asn Asn Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Tyr Asp Tyr Glu Asp Trp Tyr Phe Gly Val Trp Gly Gln
            100                 105                 110

Gly Thr Met Val Thr Val Ser Ser
        115                 120
```

<210> SEQ ID NO 191

<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Ser Trp Ile Arg Gln His Pro Gly Lys Gly Leu Glu Trp
        35                  40                  45

Ile Gly Tyr Ile Ser Tyr Asp Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Tyr Asp Tyr Glu Asp Trp Tyr Phe Gly Val Trp Gly Gln
            100                 105                 110

Gly Thr Met Val Thr Val Ser Ser
        115                 120

<210> SEQ ID NO 192
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Ser Tyr Asp Gly Tyr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Tyr Asp Tyr Glu Asp Trp Tyr Phe Gly Val Trp Gly Gln
            100                 105                 110

Gly Thr Met Val Thr Val Ser Ser
        115                 120

<210> SEQ ID NO 193
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
            20                  25                  30

Tyr Tyr Trp Asn Trp Ile Arg Gln Pro Pro Gly Lys Gly Leu Glu Trp
            35                  40                  45

Ile Gly Tyr Ile Ser Tyr Asp Gly Tyr Asn Asn Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asn Tyr Tyr Asp Tyr Glu Asp Trp Tyr Phe Gly Val Trp Gly Gln
                100                 105                 110

Gly Thr Thr Val Thr Val Ser Ser
            115                 120

<210> SEQ ID NO 194
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gln Val Gln Leu Gln Gln Trp Gly Ala Gly Leu Val Lys Pro Ser Glu
1               5                   10                  15

Thr Leu Ser Leu Thr Cys Ala Val Tyr Gly Tyr Ser Ile Thr Ser Gly
            20                  25                  30

Tyr Tyr Trp Asn Trp Ile Arg Gln Pro Pro Gly Lys Gly Leu Glu Trp
            35                  40                  45

Ile Gly Tyr Ile Ser Tyr Asp Gly Tyr Asn Asn Tyr Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asn Tyr Tyr Asp Tyr Glu Asp Trp Tyr Phe Gly Val Trp Gly Gln
                100                 105                 110

Gly Thr Thr Val Thr Val Ser Ser
            115                 120

<210> SEQ ID NO 195
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln Pro Pro Gly Lys Gly Leu Glu Trp
            35                  40                  45

Ile Gly Tyr Ile Ser Tyr Asp Gly Tyr Asn Asn Tyr Asn Pro Ser Leu
    50                  55                  60

Lys Asn Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Asn Tyr Tyr Asp Tyr Glu Asp Trp Tyr Phe Gly Val Trp Gly Gln
            100                 105                 110

Gly Thr Thr Val Thr Val Ser Ser
            115                 120

<210> SEQ ID NO 196
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gln Val Gln Leu Gln Glu Ser Gly Pro Gly Leu Val Lys Pro Ser Glu
 1               5                  10                  15

Thr Leu Ser Leu Thr Cys Thr Val Ser Gly Tyr Ser Ile Thr Ser Gly
                 20                  25                  30

Tyr Tyr Trp Asn Trp Ile Arg Gln Pro Pro Gly Lys Gly Leu Glu Trp
             35                  40                  45

Ile Gly Tyr Ile Ser Tyr Asp Gly Tyr Asn Asn Tyr Asn Pro Ser Leu
    50                  55                  60

Lys Asn Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Asn Tyr Tyr Asp Tyr Glu Asp Trp Tyr Phe Gly Val Trp Gly Gln
            100                 105                 110

Gly Thr Thr Val Thr Val Ser Ser
            115                 120

<210> SEQ ID NO 197
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gln Val Gln Leu Gln Glu Ser Gly Pro Gly Leu Met Lys Pro Ser Glu
 1               5                  10                  15

Thr Leu Ser Leu Thr Cys Ser Val Ser Gly Tyr Ser Ile Thr Ser Gly
                 20                  25                  30

Tyr Tyr Trp Ser Trp Ile Arg Lys Pro Pro Gly Lys Gly Leu Glu Tyr
             35                  40                  45

Ile Gly Tyr Val Ser Tyr Asp Gly Ser Thr Tyr Tyr Asn Pro Ser Leu
    50                  55                  60

Lys Ser Arg Val Thr Ile Ser Val Asp Thr Ser Lys Asn Arg Phe Ser
 65                  70                  75                  80

Leu Lys Leu Asn Ser Val Thr Ala Ala Asp Thr Ala Val Tyr Tyr Cys
                 85                  90                  95

Ala Asn Tyr Tyr Asp Tyr Glu Asp Trp Tyr Phe Gly Tyr Trp Gly Gln
            100                 105                 110

Gly Ile Leu Val Thr Val Ser Ser
        115                 120

<210> SEQ ID NO 198
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gln Val Gln Leu Gln Glu Ser Gly Pro Gly Leu Met Lys Pro Ser Glu
1               5                   10                  15

Thr Leu Ser Leu Thr Cys Ser Val Ser Gly Tyr Ser Ile Thr Ser Gly
            20                  25                  30

Tyr Tyr Trp Asn Trp Ile Arg Lys Pro Pro Gly Lys Gly Leu Glu Trp
        35                  40                  45

Ile Gly Tyr Ile Ser Tyr Asp Gly Tyr Asn Asn Tyr Asn Pro Ser Leu
    50                  55                  60

Lys Ser Arg Val Thr Ile Ser Arg Asp Thr Ser Lys Asn Arg Phe Ser
65                  70                  75                  80

Leu Lys Leu Asn Ser Val Thr Ala Ala Asp Thr Ala Val Tyr Tyr Cys
                85                  90                  95

Ala Asn Tyr Tyr Asp Tyr Glu Asp Trp Tyr Phe Gly Val Trp Gly Gln
            100                 105                 110

Gly Ile Leu Val Thr Val Ser Ser
        115                 120

<210> SEQ ID NO 199
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Tyr Trp Asn Trp Ile Arg Gln Ala Pro Gly Lys Gly Leu Glu Trp
        35                  40                  45

Val Ala Ser Ile Ser Tyr Asp Gly Tyr Asn Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Asn Tyr Tyr Asp Tyr Glu Asp Trp Tyr Phe Gly Val Trp Gly Gln
            100                 105                 110

Gly Thr Leu Val Thr Val Ser Ser
        115                 120

<210> SEQ ID NO 200
<211> LENGTH: 120

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Tyr Trp Asn Trp Ile Arg Gln Ala Pro Gly Lys Gly Leu Glu Trp
        35                  40                  45

Val Ala Tyr Ile Ser Tyr Asp Gly Tyr Asn Asn Tyr Asn Pro Ser Val
    50                  55                  60

Lys Gly Arg Ile Thr Ile Ser Arg Asp Thr Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Asn Tyr Tyr Asp Tyr Glu Asp Trp Tyr Phe Gly Val Trp Gly Gln
            100                 105                 110

Gly Thr Leu Val Thr Val Ser Ser
        115                 120

<210> SEQ ID NO 201
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Ser Ile Thr Ser Gly
            20                  25                  30

Tyr Tyr Trp Asn Trp Val Arg Gln Ala Pro Gly Lys Gly Leu Glu Trp
        35                  40                  45

Val Ala Tyr Ile Ser Tyr Asp Gly Tyr Asn Asn Tyr Asn Pro Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Tyr Tyr Asp Tyr Glu Asp Trp Tyr Phe Gly Val Trp Gly Gln
            100                 105                 110

Gly Thr Met Val Thr Val Ser Ser
        115                 120

<210> SEQ ID NO 202
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Glu Ile Val Leu Thr Gln Ser Pro Ala Thr Leu Ser Leu Ser Pro Gly
```

```
            1               5                  10                 15
        Glu Arg Ala Thr Leu Ser Cys Arg Ala Ser Glu Ser Val Ser Ile Ile
                        20                 25                 30

Gly Thr Asn Ser Ile His Trp Tyr Gln Gln Lys Pro Gly Gln Ala Pro
                        35                 40                 45

Arg Leu Leu Ile Tyr His Ala Ser Asn Leu Glu Thr Gly Ile Pro Ala
                50                 55                 60

Arg Phe Ser Gly Ser Gly Pro Gly Thr Asp Phe Thr Leu Thr Ile Ser
        65                 70                 75                 80

Ser Leu Glu Pro Glu Asp Phe Ala Val Tyr Tyr Cys Leu Gln Ser Arg
                        85                 90                 95

Lys Ile Pro Tyr Thr Phe Gly Gln Gly Thr Lys Leu Glu Ile Lys
                        100                105                110
```

<210> SEQ ID NO 203
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

```
        Asp Ile Val Leu Thr Gln Ser Pro Ala Ser Leu Ala Val Ser Pro Gly
        1               5                  10                 15

Gln Arg Ala Thr Ile Thr Cys Arg Ala Ser Glu Ser Val Ser Ile Ile
                        20                 25                 30

Gly Thr Asn Ser Ile His Trp Tyr Gln Gln Lys Pro Gly Gln Pro Pro
                        35                 40                 45

Lys Leu Leu Ile Tyr His Ala Ser Asn Leu Glu Thr Gly Val Pro Ala
                50                 55                 60

Arg Phe Ser Gly Ser Gly Ser Gly Thr Asp Phe Thr Leu Thr Ile Asn
        65                 70                 75                 80

Pro Val Glu Ala Asn Asp Thr Ala Asn Tyr Tyr Cys Leu Gln Ser Arg
                        85                 90                 95

Lys Ile Pro Tyr Thr Phe Gly Gly Gly Thr Lys Leu Glu Ile Lys
                        100                105                110
```

<210> SEQ ID NO 204
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

```
        Glu Ile Val Met Thr Gln Ser Pro Ala Thr Leu Ser Val Ser Pro Gly
        1               5                  10                 15

Glu Arg Ala Thr Leu Ser Cys Arg Ala Ser Glu Ser Val Ser Ile Ile
                        20                 25                 30

Gly Thr Asn Ser Leu His Trp Tyr Gln Gln Lys Pro Gly Gln Ala Pro
                        35                 40                 45

Arg Leu Leu Ile Tyr His Ala Ser Gln Ser Ile Ser Gly Ile Pro Ala
                50                 55                 60

Arg Phe Ser Gly Ser Gly Ser Gly Thr Glu Phe Thr Leu Thr Ile Ser
        65                 70                 75                 80

Ser Leu Gln Ser Glu Asp Phe Ala Val Tyr Tyr Cys Gln Gln Ser Arg
```

-continued

```
                85                  90                  95

Lys Ile Pro Tyr Thr Phe Gly Gly Gly Thr Lys Val Glu Ile Lys
            100                 105                 110

<210> SEQ ID NO 205
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ile Ile
            20                  25                  30

Gly Thr Asn Ser Ile His Trp Tyr Gln Gln Lys Pro Gly Gln Ala Pro
        35                  40                  45

Arg Leu Leu Ile Tyr His Ala Ser Asn Leu Glu Thr Gly Ile Pro Ala
    50                  55                  60

Arg Phe Ser Gly Ser Gly Ser Arg Thr Glu Phe Thr Leu Thr Ile Ser
65                  70                  75                  80

Ser Leu Gln Ser Glu Asp Phe Ala Val Tyr Tyr Cys Leu Gln Ser Arg
                85                  90                  95

Lys Ile Pro Tyr Thr Phe Gly Gly Gly Thr Lys Val Glu Ile Lys
            100                 105                 110

<210> SEQ ID NO 206
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Ser Ile Ile
            20                  25                  30

Gly Thr Asn Ser Met Asn Trp Tyr Gln Gln Lys Pro Gly Lys Ala Pro
        35                  40                  45

Lys Leu Leu Ile Tyr His Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Leu Gln Ser Arg
                85                  90                  95

Lys Ile Pro Tyr Thr Phe Gly Gln Gly Thr Lys Val Glu Ile Lys
            100                 105                 110

<210> SEQ ID NO 207
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207
```

-continued

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Ser Ile Ile
            20                  25                  30

Gly Thr Asn Ser Met His Trp Tyr Gln Gln Lys Pro Gly Lys Ala Pro
        35                  40                  45

Lys Leu Leu Ile Tyr His Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Leu Gln Ser Arg
                85                  90                  95

Lys Ile Pro Tyr Thr Phe Gly Gln Gly Thr Lys Val Glu Ile Lys
            100                 105                 110
```

<210> SEQ ID NO 208
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Ser Ile Ile
            20                  25                  30

Gly Thr Asn Ser Met His Trp Tyr Gln Gln Lys Pro Gly Lys Ala Pro
        35                  40                  45

Lys Leu Leu Ile Tyr His Ala Ser Asn Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Leu Gln Ser Arg
                85                  90                  95

Lys Ile Pro Tyr Thr Phe Gly Gln Gly Thr Lys Val Glu Ile Lys
            100                 105                 110
```

<210> SEQ ID NO 209
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45

Gly Trp Ile Tyr Pro Leu Arg Gly Ser Ile Asn Tyr Asn Glu Lys Phe
    50                  55                  60

Lys Asp Arg Val Thr Ser Thr Arg Asp Thr Ser Ile Ser Thr Ala Tyr
65                  70                  75                  80
```

```
Met Glu Leu Ser Arg Leu Arg Ser Asp Asp Thr Val Tyr Tyr Cys
            85                  90                  95

Ala Arg His Gly Ala Tyr Tyr Ser Asn Ala Phe Asp Tyr Trp Gly Gln
            100                 105                 110

Gly Thr Leu Val Thr Val Ser Ser
        115                 120

<210> SEQ ID NO 210
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Ile Tyr Pro Leu Arg Gly Ser Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Tyr Tyr Cys
            85                  90                  95

Ala Arg His Gly Ala Tyr Tyr Ser Asn Ala Phe Asp Tyr Trp Gly Gln
            100                 105                 110

Gly Thr Leu Val Thr Val Ser Ser
        115                 120

<210> SEQ ID NO 211
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45

Gly Trp Ile Tyr Pro Leu Arg Gly Ser Ile Asn Tyr Asn Glu Lys Phe
    50                  55                  60

Lys Asp Arg Val Thr Met Thr Ala Asp Thr Ser Ser Ser Thr Ala Tyr
65                  70                  75                  80

Met Glu Leu Ser Arg Leu Arg Ser Asp Asp Thr Val Tyr Tyr Cys
            85                  90                  95

Ala Arg His Gly Ala Tyr Tyr Ser Asn Ala Phe Asp Tyr Trp Gly Gln
            100                 105                 110

Gly Thr Leu Val Thr Val Ser Ser
        115                 120
```

<210> SEQ ID NO 212
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Asp Tyr
            20                  25                  30

Thr Ile His Trp Val Arg Gln Ala Pro Gly Lys Gly Leu Glu Trp Met
        35                  40                  45

Gly Trp Ile Tyr Pro Leu Arg Gly Ser Ile Asn Tyr Asn Glu Lys Phe
    50                  55                  60

Lys Asp Arg Val Thr Met Thr Ala Asp Thr Ser Thr Asp Thr Ala Tyr
65                  70                  75                  80

Met Glu Leu Ser Ser Leu Arg Ser Lys Asp Thr Ala Val Tyr Tyr Cys
                85                  90                  95

Ala Arg His Gly Ala Tyr Tyr Ser Asn Ala Phe Asp Tyr Trp Gly Gln
            100                 105                 110

Gly Thr Leu Val Thr Val Ser Ser
        115                 120

<210> SEQ ID NO 213
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Asp Tyr
            20                  25                  30

Thr Met Tyr Trp Val Lys Gln Ala Pro Gly Gln Gly Leu Glu Trp Ile
        35                  40                  45

Gly Glu Ile Tyr Pro Leu Arg Gly Ser Ile Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Ala Tyr Tyr Ser Asn Ala Phe Asp Tyr Trp Gly Gln
            100                 105                 110

Gly Thr Leu Val Thr Val Ser Ser
        115                 120

<210> SEQ ID NO 214
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Asp Tyr
            20                  25                  30

Thr Met His Trp Val Lys Gln Ala Pro Gly Gln Gly Leu Glu Trp Ile
        35                  40                  45

Gly Glu Ile Tyr Pro Leu Arg Gly Ser Ile Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Ala Tyr Tyr Ser Asn Ala Phe Asp Tyr Trp Gly Gln
            100                 105                 110

Gly Thr Leu Val Thr Val Ser Ser
            115                 120

<210> SEQ ID NO 215
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Asp
            20                  25                  30

Gly Ile Arg Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Pro Gly Thr Asp Phe Thr Leu Thr Ile Ser
65                  70                  75                  80

Ser Leu Glu Pro Glu Asp Phe Ala Val Tyr Tyr Cys Gln Gln Ser Asn
                85                  90                  95

Lys Asp Pro Tyr Thr Phe Gly Gln Gly Thr Lys Leu Glu Ile Lys
            100                 105                 110

<210> SEQ ID NO 216
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Asp
            20                  25                  30

Gly Ile Arg Phe Met His Trp Tyr Gln Gln Lys Pro Gly Gln Ala Pro
        35                  40                  45

```
Arg Leu Leu Ile Tyr Arg Ala Ser Asn Leu Glu Ser Gly Ile Pro Ala
 50                  55                  60

Arg Phe Ser Gly Ser Gly Pro Gly Thr Asp Phe Thr Leu Thr Ile Ser
 65                  70                  75                  80

Ser Leu Glu Pro Glu Asp Val Ala Val Tyr Tyr Cys Gln Gln Ser Asn
                 85                  90                  95

Lys Asp Pro Tyr Thr Phe Gly Gln Gly Thr Lys Leu Glu Ile Lys
                100                 105                 110
```

<210> SEQ ID NO 217
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

```
Asp Ile Val Met Thr Gln Ser Pro Ala Ser Leu Ala Val Ser Leu Gly
 1               5                  10                  15

Glu Arg Ala Thr Ile Asn Cys Arg Ala Ser Glu Ser Val Asp Asn Asp
                 20                  25                  30

Gly Ile Arg Phe Met His Trp Tyr Gln Gln Lys Pro Gly Gln Pro Pro
             35                  40                  45

Lys Leu Leu Ile Tyr Arg Ala Ser Asn Leu Glu Ser Gly Val Pro Asp
 50                  55                  60

Arg Phe Ser Gly Ser Gly Ser Arg Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Lys Asp Pro Tyr Thr Phe Gly Gly Gly Thr Lys Val Glu Ile Lys
                100                 105                 110
```

<210> SEQ ID NO 218
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

```
Asp Ile Val Met Thr Gln Ser Pro Ala Ser Leu Ala Val Ser Leu Gly
 1               5                  10                  15

Glu Arg Ala Thr Ile Asn Cys Arg Ala Ser Glu Ser Val Asp Asn Asp
                 20                  25                  30

Gly Ile Arg Phe Met His Trp Tyr Gln Gln Lys Pro Gly Gln Pro Pro
             35                  40                  45

Lys Leu Leu Ile Tyr Arg Ala Ser Asn Leu Glu Ser Gly Val Pro Asp
 50                  55                  60

Arg Phe Ser Gly Ser Gly Ser Arg Thr Asp Phe Thr Leu Thr Ile Asn
 65                  70                  75                  80

Ser Leu Gln Ala Glu Asp Val Ala Val Tyr Tyr Cys Gln Gln Ser Asn
                 85                  90                  95

Lys Asp Pro Tyr Thr Phe Gly Gly Gly Thr Lys Val Glu Leu Lys
                100                 105                 110
```

<210> SEQ ID NO 219
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Asp Ile Val Leu Thr Gln Ser Pro Ala Thr Leu Ser Val Ser Pro Gly
1               5                   10                  15

Glu Arg Ala Thr Ile Ser Cys Arg Ala Ser Glu Ser Val Asp Asn Asp
            20                  25                  30

Gly Ile Arg Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 220
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Ile Tyr
            20                  25                  30

Asp Val His Trp Val Arg Gln Ala Pro Gly Lys Gly Leu Glu Trp Val
        35                  40                  45

Ala Val Ile Trp Ser Asp Gly Ser Thr Asp Tyr Asn Ala Ala Phe Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Trp Val Asp Gln Ala Trp Phe Ala Tyr Trp Gly Gln Gly Thr
            100                 105                 110

Leu Val Thr Val Ser Ser
        115

<210> SEQ ID NO 221
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Ile Tyr
```

```
                    20                  25                  30

Asp Val His Trp Val Arg Gln Ala Pro Gly Lys Gly Leu Glu Trp Val
            35                  40                  45

Gly Val Ile Trp Ser Asp Gly Ser Thr Asp Tyr Asn Ala Ala Phe Ile
        50                  55                  60

Ser Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Trp Val Asp Gln Ala Trp Phe Ala Tyr Trp Gly Gln Gly Thr
            100                 105                 110

Leu Val Thr Val Ser Ser
            115

<210> SEQ ID NO 222
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Ile Tyr
            20                  25                  30

Asp Val His Trp Val Arg Gln Ala Pro Gly Lys Gly Leu Glu Trp Val
            35                  40                  45

Ala Val Ile Trp Ser Asp Gly Ser Thr Asp Tyr Ala Asp Ser Val Lys
        50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Trp Val Asp Gln Ala Trp Phe Ala Tyr Trp Gly Gln Gly Thr
            100                 105                 110

Leu Val Thr Val Ser Ser
            115

<210> SEQ ID NO 223
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Ile Tyr
            20                  25                  30

Asp Val His Trp Val Arg Gln Ala Pro Gly Lys Gly Leu Glu Trp Val
            35                  40                  45

Gly Val Ile Trp Ser Asp Gly Ser Thr Asp Tyr Ala Asp Ser Val Lys
        50                  55                  60

Gly Arg Phe Thr Ile Ser Lys Asp Asn Ser Lys Asn Thr Val Tyr Leu
```

```
                65                  70                  75                  80
Gln Met Asn Ser Leu Arg Ala Glu Asp Thr Ala Val Tyr Tyr Cys Ala
                    85                  90                  95

Arg Asn Trp Val Asp Gln Ala Trp Phe Ala Tyr Trp Gly Gln Gly Thr
                100                 105                 110

Leu Val Thr Val Ser Ser
        115

<210> SEQ ID NO 224
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ile Tyr
                20                  25                  30

Asp Val His Trp Ile Arg Gln Pro Pro Gly Lys Gly Leu Glu Trp Ile
            35                  40                  45

Gly Val Ile Trp Ser Asp Gly Ser Thr Asp Tyr Asn Ala Ala Phe Ile
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asn Trp Val Asp Gln Ala Trp Phe Ala Tyr Trp Gly Gln Gly Thr
                100                 105                 110

Leu Val Thr Val Ser Ser
        115

<210> SEQ ID NO 225
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ile Tyr
                20                  25                  30

Asp Val His Trp Val Arg Gln Pro Pro Gly Lys Gly Leu Glu Trp Ile
            35                  40                  45

Gly Val Ile Trp Ser Asp Gly Ser Thr Asp Tyr Asn Pro Ser Leu Lys
        50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Trp Val Asp Gln Ala Trp Phe Ala Tyr Trp Gly Gln Gly Thr
                100                 105                 110

Leu Val Thr Val Ser Ser
```

<210> SEQ ID NO 226
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 226

Gln Val Gln Leu Gln Glu Ser Gly Pro Gly Leu Met Lys Pro Ser Glu
1               5                   10                  15

Thr Leu Ser Leu Thr Cys Ser Val Ser Gly Asp Ser Ile Thr Ile Tyr
            20                  25                  30

Asp Trp His Trp Ile Arg Gln Pro Pro Gly Lys Gly Leu Glu Trp Ile
        35                  40                  45

Gly Val Val Trp Ser Asp Gly Ser Thr Asp Tyr Asn Pro Ser Leu Lys
    50                  55                  60

Ser Arg Val Thr Ile Ser Val Asp Thr Ser Lys Asn Arg Phe Ser Leu
65                  70                  75                  80

Lys Leu Ser Ser Val Thr Ala Ala Asp Thr Ala Val Tyr Tyr Cys Ala
                85                  90                  95

Arg Asn Trp Val Asp Gln Ala Trp Phe Ala Tyr Trp Gly Gln Gly Thr
            100                 105                 110

Leu Val Thr Val Ser Ser
        115

<210> SEQ ID NO 227
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 227

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ile Tyr
            20                  25                  30

Asp Val His Trp Ile Arg Gln Pro Pro Gly Lys Gly Leu Glu Trp Ile
        35                  40                  45

Gly Val Ile Trp Ser Asp Gly Ser Thr Asp Tyr Asn Pro Ser Leu Lys
    50                  55                  60

Ser Arg Val Thr Ile Ser Lys Asp Asn Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asn Trp Val Asp Gln Ala Trp Phe Ala Tyr Trp Gly Gln Gly Thr
            100                 105                 110

Leu Val Thr Val Ser Ser
        115

<210> SEQ ID NO 228
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Pro Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gln Gly Thr Lys Leu Glu Ile Lys
            100                 105

<210> SEQ ID NO 229
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Lys Thr Leu Pro Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gln Gly Thr Lys Leu Glu Ile Lys
            100                 105

<210> SEQ ID NO 230
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Asn Ile Tyr Ser Tyr
            20                  25                  30

Leu Ala Trp Tyr Gln Gln Lys Pro Gly Gln Ala Pro Arg Leu Leu Ile
        35                  40                  45

Tyr Asn Ala Lys Thr Arg Ala Thr Gly Ile Pro Ala Arg Phe Ser Gly
50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His His Tyr Gly Thr Pro Leu
                 85                  90                  95

Thr Phe Gly Gln Gly Thr Lys Leu Glu Ile Lys
            100                 105

<210> SEQ ID NO 231
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Lys Asn Ile Tyr Ser Tyr
                 20                  25                  30

Leu Ala Trp Tyr Gln Gln Lys Pro Gly Gln Ala Pro Arg Leu Leu Val
             35                  40                  45

Tyr Asn Ala Lys Thr Leu Pro Glu Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His His Tyr Gly Thr Pro Leu
                 85                  90                  95

Thr Phe Gly Gln Gly Thr Lys Leu Glu Ile Lys
            100                 105

<210> SEQ ID NO 232
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Glu Ile Val Met Thr Gln Ser Pro Ala Thr Leu Ser Val Ser Pro Gly
  1               5                  10                  15

Glu Arg Ala Thr Leu Ser Cys Arg Ala Ser Lys Asn Ile Tyr Ser Tyr
                 20                  25                  30

Leu Ala Trp Tyr Gln Gln Lys Pro Gly Gln Ala Pro Arg Leu Leu Ile
             35                  40                  45

Tyr Asn Ala Lys Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln His His Tyr Gly Thr Pro Leu
                 85                  90                  95

Thr Phe Gly Gly Gly Thr Lys Val Glu Ile Lys
            100                 105

<210> SEQ ID NO 233
<211> LENGTH: 107
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 233

Asp Ile Gln Leu Thr Gln Ser Pro Ser Phe Leu Ser Ala Ser Val Gly
1               5                   10                  15

Asp Arg Val Thr Ile Thr Cys Arg Ala Ser Lys Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gly Gly Thr Lys Leu Glu Ile Lys
            100                 105

<210> SEQ ID NO 234
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Asp Ile Gln Leu Thr Gln Ser Pro Ser Phe Leu Ser Ala Ser Val Gly
1               5                   10                  15

Asp Arg Val Thr Ile Thr Cys Arg Ala Ser Lys Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gly Gly Thr Lys Leu Glu Ile Lys
            100                 105

<210> SEQ ID NO 235
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gln Leu Gln Leu Gln Glu Ser Gly Ser Gly Leu Val Lys Pro Ser Gln
1               5                   10                  15

Thr Leu Ser Leu Thr Cys Ala Val Ser Gly Phe Ser Leu Thr Asp Tyr
            20                  25                  30

Asp Val His Trp Val Arg Gln Pro Pro Gly Lys Gly Leu Glu Trp Ile
        35                  40                  45
```

```
Gly Val Ile Trp Asn Asp Gly Ser Thr Asp Tyr Asn Pro Ser Leu Ile
        50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Trp Tyr Gly Gly Tyr Trp Phe Ala Tyr Trp Gly Gln Gly Thr
                100                 105                 110

Leu Val Thr Val Ser Ser
            115
```

<210> SEQ ID NO 236
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

```
Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Thr Asp Tyr
                20                  25                  30

Asp Trp His Trp Val Arg Gln Pro Pro Gly Lys Gly Leu Glu Trp Ile
            35                  40                  45

Gly Val Ile Trp Asn Asp Gly Ser Thr Asp Tyr Asn Pro Ser Leu Ile
        50                  55                  60

Ser Arg Val Thr Ile Ser Val Asp Asn Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asn Trp Tyr Gly Gly Tyr Trp Phe Ala Tyr Trp Gly Gln Gly Thr
                100                 105                 110

Leu Val Thr Val Ser Ser
            115
```

<210> SEQ ID NO 237
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Thr Asp Tyr
                20                  25                  30

Asp Met His Trp Val Arg Gln Ala Pro Gly Lys Gly Leu Glu Trp Val
            35                  40                  45

Ala Val Ile Trp Asn Asp Gly Ser Thr Asp Tyr Ala Thr Ser Val Ile
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

Arg Asn Trp Tyr Gly Gly Tyr Trp Phe Ala Tyr Trp Gly Gln Gly Thr
            100                 105                 110

Leu Val Thr Val Ser Ser
        115

<210> SEQ ID NO 238
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Thr Asp Tyr
            20                  25                  30

Asp Met His Trp Val Arg Gln Ala Pro Gly Lys Gly Leu Glu Trp Val
        35                  40                  45

Gly Val Ile Trp Asn Asp Gly Ser Thr Asp Tyr Ala Thr Ser Val Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Trp Tyr Gly Gly Tyr Trp Phe Ala Tyr Trp Gly Gln Gly Thr
            100                 105                 110

Leu Val Thr Val Ser Ser
        115

<210> SEQ ID NO 239
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gln Val Gln Leu Gln Glu Ser Gly Pro Gly Leu Met Lys Pro Ser Glu
1               5                   10                  15

Thr Leu Ser Leu Thr Cys Ser Val Ser Gly Ser Ile Thr Asp Tyr
            20                  25                  30

Asp Trp His Trp Ile Arg Gln Pro Pro Gly Lys Gly Leu Glu Trp Ile
        35                  40                  45

Gly Val Val Trp Asn Asp Gly Ser Thr Asp Tyr Asn Pro Ser Leu Lys
    50                  55                  60

Ser Arg Val Thr Ile Ser Val Asp Thr Ser Lys Asn Arg Phe Ser Leu
65                  70                  75                  80

Lys Leu Asn Ser Val Thr Ala Ala Asp Thr Ala Val Tyr Tyr Cys Ala
                85                  90                  95

Arg Asn Trp Tyr Gly Gly Tyr Trp Phe Ala Tyr Trp Gly Gln Gly Ile
            100                 105                 110

Leu Val Thr Val Ser Ser
        115

<210> SEQ ID NO 240
<211> LENGTH: 118

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Asp Tyr
            20                  25                  30

Asp Val His Trp Ile Arg Gln Pro Pro Gly Lys Ala Leu Glu Trp Leu
        35                  40                  45

Ala Val Ile Trp Asn Asp Gly Ser Thr Asp Tyr Ser Pro Ser Leu Lys
    50                  55                  60

Ser Arg Leu Thr Ile Thr Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asn Trp Tyr Gly Gly Tyr Trp Phe Ala Tyr Trp Gly Gln Gly Thr
            100                 105                 110

Leu Val Thr Val Ser Ser
            115

<210> SEQ ID NO 241
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Asp Ile Gln Met Thr Gln Ser Pro Ser Leu Ser Ala Ser Val Gly
1               5                   10                  15

Asp Arg Val Thr Ile Thr Cys Arg Ser Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Asn Ala Leu Ala Glu Gly Val Pro Ser Arg Phe Ser Gly
    50                  55                  60

Ser Gly Ser Val Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Phe
                85                  90                  95

Thr Phe Gly Gln Gly Thr Lys Leu Glu Ile Lys
            100                 105

<210> SEQ ID NO 242
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Asp Ile Gln Met Thr Gln Ser Pro Ser Thr Leu Ser Ala Ser Val Gly
1               5                   10                  15

Asp Arg Val Thr Ile Thr Cys Arg Ser Ser Glu Asn Ile Tyr Ser Tyr

```
                    20                  25                  30

Leu Ala Trp Tyr Gln Gln Lys Pro Gly Lys Ala Pro Lys Leu Leu Val
            35                  40                  45

Tyr Asn Ala Asn Ala Leu Ala Glu Gly Val Pro Ser Arg Phe Ser Gly
        50                  55                  60

Ser Gly Ser Val Thr Glu Phe Thr Leu Thr Ile Ser Ser Leu Gln Pro
65                  70                  75                  80

Asp Asp Phe Ala Thr Tyr Tyr Cys Gln His His Tyr Gly Thr Pro Phe
                85                  90                  95

Thr Phe Gly Gln Gly Thr Lys Leu Glu Ile Lys
                100                 105

<210> SEQ ID NO 243
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Asn Ile Tyr Ser Tyr
            20                  25                  30

Leu Ala Trp Tyr Gln Gln Lys Pro Gly Gln Ala Pro Arg Leu Leu Ile
            35                  40                  45

Tyr Asn Ala Asn Ala Ser Ala Glu Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Tyr Gly Thr Pro Phe
                85                  90                  95

Thr Phe Gly Gly Gly Thr Lys Val Glu Ile Lys
                100                 105

<210> SEQ ID NO 244
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Leu
            35                  40                  45

Tyr Asn Ala Asn Arg Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln His His Tyr Gly Thr Pro Phe
                85                  90                  95

Thr Phe Gly Ser Gly Thr Lys Leu Glu Ile Lys
```

<210> SEQ ID NO 245
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Leu
        35                  40                  45

Tyr Asn Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Ser Tyr Tyr Cys Gln His His Tyr Gly Thr Pro Phe
                85                  90                  95

Thr Phe Gly Ser Gly Thr Lys Leu Glu Ile Lys
            100                 105

<210> SEQ ID NO 246
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Gly Trp Val Arg Gln Ala Pro Gly Gln Gly Leu Glu Trp Met
        35                  40                  45

Gly Asp Ile Tyr Pro Gly Gly Ile Gly Gly Tyr Thr Lys Tyr Asn
    50                  55                  60

Glu Lys Phe Lys Gly Arg Val Thr Met Thr Ala Asp Thr Ser Thr Ser
65                  70                  75                  80

Thr Ala Tyr Met Glu Leu Arg Ser Leu Arg Ser Asp Asp Thr Ala Val
                85                  90                  95

Tyr Tyr Cys Ser Arg Ser Glu Thr Gly Arg Ala Met Asp Tyr Trp Gly
            100                 105                 110

Gln Gly Thr Leu Val Thr Val Ser Ser
        115                 120

<210> SEQ ID NO 247
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Gly Trp Val Arg Gln Ala Pro Gly Gln Gly Leu Glu Trp Met
        35                  40                  45

Gly Asp Ile Tyr Pro Gly Gly Ile Gly Gly Tyr Thr Lys Tyr Ala
    50                  55                  60

Gln Lys Leu Gln Gly Arg Val Thr Met Thr Ala Asp Thr Ser Thr Ser
65              70                  75                  80

Thr Ala Tyr Met Glu Leu Arg Ser Leu Arg Ser Asp Asp Thr Ala Val
                85                  90                  95

Tyr Tyr Cys Ser Arg Ser Glu Thr Gly Arg Ala Met Asp Tyr Trp Gly
            100                 105                 110

Gln Gly Thr Leu Val Thr Val Ser Ser
        115                 120

<210> SEQ ID NO 248
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Gly Trp Val Arg Gln Ala Pro Gly Gln Gly Leu Glu Trp Met
        35                  40                  45

Gly Asp Ile Tyr Pro Gly Gly Ile Gly Gly Tyr Thr Lys Tyr Ala
    50                  55                  60

Gln Lys Phe Gln Gly Arg Val Thr Met Thr Ala Asp Thr Ser Thr Ser
65              70                  75                  80

Thr Ala Tyr Met Glu Leu Ser Ser Leu Arg Ser Glu Asp Thr Ala Val
                85                  90                  95

Tyr Tyr Cys Ser Arg Ser Glu Thr Gly Arg Ala Met Asp Tyr Trp Gly
            100                 105                 110

Gln Gly Thr Leu Val Thr Val Ser Ser
        115                 120

<210> SEQ ID NO 249
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Gly Trp Val Arg Gln Ala Pro Gly Gln Gly Leu Glu Trp Met
        35                  40                  45
```

```
Gly Asp Ile Tyr Pro Gly Gly Ile Gly Gly Tyr Thr Lys Tyr Asn
        50                  55                  60

Glu Lys Phe Lys Gly Arg Val Thr Met Thr Ala Asp Thr Ser Thr Ser
 65                  70                  75                  80

Thr Ala Tyr Met Glu Leu Ser Ser Leu Arg Ser Glu Asp Thr Ala Val
                85                  90                  95

Tyr Phe Cys Ser Arg Ser Glu Thr Gly Arg Ala Met Asp Tyr Trp Gly
            100                 105                 110

Gln Gly Thr Leu Val Thr Val Ser Ser
            115                 120

<210> SEQ ID NO 250
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gln Val Gln Leu Val Gln Ser Gly Ala Glu Leu Lys Arg Pro Gly Ala
 1               5                  10                  15

Ser Val Lys Val Ser Cys Lys Ala Ser Gly Tyr Thr Phe Thr Asn Tyr
                20                  25                  30

Trp Met Gly Trp Val Lys Gln Ala Pro Gly Gln Gly Leu Glu Trp Met
            35                  40                  45

Gly Asp Ile Tyr Pro Gly Gly Ile Gly Gly Tyr Thr Asn Tyr Ala
        50                  55                  60

Gln Lys Phe Lys Gly Lys Ala Thr Met Thr Ala Asp Thr Ser Ser Ser
 65                  70                  75                  80

Thr Ala Tyr Met Gln Leu Ser Arg Leu Arg Ser Glu Asp Thr Ala Val
                85                  90                  95

Tyr Tyr Cys Ser Arg Ser Glu Thr Gly Arg Ala Met Asp Tyr Trp Gly
            100                 105                 110

Gln Gly Thr Leu Val Thr Val Ser Ser
            115                 120

<210> SEQ ID NO 251
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asn Lys Tyr
                20                  25                  30

Leu Ala Trp Tyr Gln Gln Lys Pro Gly Lys Ala Pro Lys Leu Leu Ile
            35                  40                  45

His Tyr Thr Ser Thr Leu Lys Pro Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln Tyr Asp Asn Leu Asn Thr
                85                  90                  95
```

```
Phe Gly Gly Gly Thr Lys Leu Glu Ile Lys
            100                 105

<210> SEQ ID NO 252
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln Gln Lys Pro Gly Lys Ala Pro Lys Leu Leu Ile
        35                  40                  45

His Tyr Thr Ser Thr Leu Lys Pro Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Asn Thr
                85                  90                  95

Phe Gly Gly Gly Thr Lys Leu Glu Ile Lys
            100                 105

<210> SEQ ID NO 253
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Ala Trp Tyr Gln Gln Lys Pro Gly Lys Ala Pro Lys Leu Leu Ile
        35                  40                  45

Tyr Tyr Thr Ser Thr Leu Glu Thr Gly Val Pro Ser Arg Phe Ser Gly
    50                  55                  60

Ser Gly Ser Gly Thr Asp Phe Thr Phe Ser Ile Ser Ser Leu Gln Pro
65                  70                  75                  80

Glu Asp Ile Ala Thr Tyr Tyr Cys Leu Gln Tyr Asp Asn Leu Asn Thr
                85                  90                  95

Phe Gly Gly Gly Thr Lys Leu Glu Ile Lys
            100                 105

<210> SEQ ID NO 254
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asp Tyr
            20                  25                  30

Tyr Ile Asn Trp Val Arg Gln Ala Pro Gly Lys Gly Leu Glu Trp Met
        35                  40                  45

Gly Trp Ile Phe Pro Gly Ser Gly Ser Thr Tyr Tyr Asn Glu Lys Phe
    50                  55                  60

Lys Gly Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Asp Ser Gly Arg Ala Met Asp Tyr Trp Gly Gln Gly Thr
            100                 105                 110

Leu Val Thr Val Ser Ser
            115
```

<210> SEQ ID NO 255
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asp Tyr
            20                  25                  30

Tyr Met Asn Trp Val Arg Gln Ala Pro Gly Gln Gly Leu Glu Trp Met
        35                  40                  45

Gly Trp Ile Phe Pro Gly Ser Gly Ser Thr Tyr Tyr Ala Glu Lys Phe
    50                  55                  60

Lys Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Asp Ser Gly Arg Ala Met Asp Tyr Trp Gly Gln Gly Thr
            100                 105                 110

Leu Val Thr Val Ser Ser
            115
```

<210> SEQ ID NO 256
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asp Tyr
            20                  25                  30

Tyr Ile Asn Trp Val Arg Gln Ala Pro Gly Gln Gly Leu Glu Trp Met
        35                  40                  45
```

```
Gly Trp Ile Phe Pro Gly Ser Gly Ser Thr Tyr Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Asp Ser Gly Arg Ala Met Asp Tyr Trp Gly Gln Gly Thr
            100                 105                 110

Leu Val Thr Val Ser Ser
        115

<210> SEQ ID NO 257
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ala Asp Tyr
                20                  25                  30

Tyr Ile Asn Trp Val Arg Gln Ala Pro Gly Gln Gly Leu Glu Trp Met
            35                  40                  45

Gly Trp Ile Phe Pro Gly Ser Gly Ser Thr Tyr Tyr Ala Gln Lys Leu
 50                  55                  60

Gln Gly Arg Val Thr Met Thr Val Asp Lys Ser Ser Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Asp Ser Gly Arg Ala Met Asp Tyr Trp Gly Gln Gly Thr
            100                 105                 110

Leu Val Thr Val Ser Ser
        115

<210> SEQ ID NO 258
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Gln Val Gln Leu Val Gln Ser Gly Ala Glu Leu Lys Lys Pro Gly Ala
 1               5                  10                  15

Ser Val Lys Val Ser Cys Lys Ala Ser Gly Tyr Thr Phe Ala Asp Tyr
                20                  25                  30

Tyr Met Asn Trp Val Arg Gln Ala Pro Gly Gln Gly Leu Glu Trp Met
            35                  40                  45

Gly Trp Ile Phe Pro Gly Ser Gly Ser Thr Tyr Tyr Asn Gln Lys Phe
 50                  55                  60

Gln Gly Arg Val Thr Met Thr Val Asp Lys Ser Ser Ser Thr Ala Tyr
 65                  70                  75                  80

Met Glu Leu Ser Arg Leu Arg Ser Asp Asp Thr Ala Val Tyr Tyr Cys
                 85                  90                  95
```

Ala Arg Gly Asp Ser Gly Arg Ala Met Asp Tyr Trp Gly Gln Gly Thr
            100                 105                 110

Leu Val Thr Val Ser Ser
        115

<210> SEQ ID NO 259
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln Gln Lys Pro Gly Lys Ala Pro Lys Leu Leu Ile
        35                  40                  45

His Tyr Thr Ser Thr Leu Gln Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Thr
                85                  90                  95

Phe Gly Gln Gly Thr Lys Leu Glu Ile Lys
            100                 105

<210> SEQ ID NO 260
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln His Lys Pro Gly Lys Ala Pro Lys Leu Leu Ile
        35                  40                  45

His Tyr Thr Ser Thr Leu Gln Ser Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Leu Thr
                85                  90                  95

Phe Gly Gln Gly Thr Lys Leu Glu Ile Lys
            100                 105

<210> SEQ ID NO 261
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Ala Trp Tyr Gln His Lys Pro Gly Lys Ala Pro Lys Leu Leu Ile
        35                  40                  45

His Tyr Thr Ser Thr Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Thr
                85                  90                  95

Phe Gly Gly Gly Thr Lys Val Glu Ile Lys
            100                 105

<210> SEQ ID NO 262
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ile Tyr
            20                  25                  30

Asp Val His Trp Ile Arg Gln Pro Pro Gly Lys Gly Leu Glu Trp Ile
        35                  40                  45

Gly Val Ile Trp Ser Asp Gly Ser Thr Asp Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Trp Val Asp Gln Ala Trp Phe Ala Tyr Trp Gly Gln Gly Thr
            100                 105                 110

Leu Val Thr Val Ser Ser
        115

<210> SEQ ID NO 263
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ile Tyr
            20                  25                  30

Asp Trp His Trp Val Arg Gln Pro Pro Gly Lys Gly Leu Glu Trp Ile
        35                  40                  45

Gly Val Ile Trp Ser Asp Gly Ser Thr Asp Tyr Asn Pro Ser Leu Lys

```
            50                  55                  60
Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asn Trp Val Asp Gln Ala Trp Phe Ala Tyr Trp Gly Gln Gly Thr
            100                 105                 110

Leu Val Thr Val Ser Ser
        115

<210> SEQ ID NO 264
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Thr Ile Tyr
            20                  25                  30

Asp Trp His Trp Val Arg Gln Pro Pro Gly Lys Gly Leu Glu Trp Ile
        35                  40                  45

Gly Val Ile Trp Ser Asp Gly Ser Thr Asp Tyr Asn Pro Ser Leu Lys
    50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asn Trp Val Asp Gln Ala Trp Phe Ala Tyr Trp Gly Gln Gly Thr
            100                 105                 110

Leu Val Thr Val Ser Ser
        115

<210> SEQ ID NO 265
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Thr Ile Tyr
            20                  25                  30

Asp Trp His Trp Ile Arg Gln Pro Pro Gly Lys Gly Leu Glu Trp Ile
        35                  40                  45

Gly Val Ile Trp Ser Asp Gly Ser Thr Asp Tyr Asn Pro Ser Leu Lys
    50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asn Trp Val Asp Gln Ala Trp Phe Ala Tyr Trp Gly Gln Gly Thr
```

```
                    100                 105                 110
Leu Val Thr Val Ser Ser
        115

<210> SEQ ID NO 266
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Asp Tyr Ser Phe Thr Gly Tyr
1               5

<210> SEQ ID NO 267
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

His Pro Tyr Tyr Gly Gly
1               5

<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Glu Arg Ser Asn Phe His Ala Leu Asp Tyr
1               5                   10

<210> SEQ ID NO 269
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gly Tyr Asn Met Asn
1               5

<210> SEQ ID NO 270
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Asn Ile His Pro Tyr Tyr Gly Gly Thr Ser Phe Asn Gln Lys Phe Met
1               5                   10                  15

Gly

<210> SEQ ID NO 271
```

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Glu Ile Gln Leu Gln Gln Ser Gly Ala Glu Leu Val Lys Pro Gly Ala
1               5                   10                  15

Ser Val Lys Ile Ser Cys Lys Ala Ser Asp Tyr Ser Phe Thr Gly Tyr
            20                  25                  30

Asn Met Asn Trp Val Met Gln Ser His Gly Lys Ser Leu Glu Trp Ile
        35                  40                  45

Gly Asn Ile His Pro Tyr Tyr Gly Gly Thr Ser Phe Asn Gln Lys Phe
    50                  55                  60

Met Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Arg Ser Asn Phe His Ala Leu Asp Tyr Trp Gly Gln Gly
            100                 105                 110

Thr Ser Val Thr Val Ser Ser
        115

<210> SEQ ID NO 272
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Asp Ile Val Leu Thr Gln Ser Pro Ala Ser Leu Thr Val Ser Leu Gly
1               5                   10                  15

Gln Arg Ala Thr Phe Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Phe Thr Ser Asp Leu Glu Pro Gly Val Pro Ala
    50                  55                  60

Arg Phe Thr Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Pro Phe Gly Gly Gly Thr Lys Leu Glu Ile Lys
            100                 105                 110

<210> SEQ ID NO 273
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Val Ile Trp Ser Asp Gly Ser Thr Asp Tyr Asn Pro Ser Leu Lys Ser
1               5                   10                  15
```

```
<210> SEQ ID NO 274
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gln Ala Ser Gln Asp Ile Asn Lys Tyr Leu Ala
1               5                   10

<210> SEQ ID NO 275
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Tyr Thr Ser Thr Leu Glu Thr
1               5

<210> SEQ ID NO 276
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Asp Tyr Tyr Met Asn
1               5

<210> SEQ ID NO 277
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Trp Ile Phe Pro Gly Ser Gly Ser Thr Tyr Tyr Asn Gln Lys Phe Gln
1               5                   10                  15

Gly

<210> SEQ ID NO 278
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Trp Ile Phe Pro Gly Ser Gly Ser Thr Tyr Tyr Ala Gln Lys Leu Gln
1               5                   10                  15

Gly

<210> SEQ ID NO 279

<400> SEQUENCE: 279
```

<210> SEQ ID NO 280
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Arg Ala Ser Glu Ser Val Asp Asn Asp Gly Ile Arg Phe Leu His
1               5                   10                  15

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Arg Ala Ser Asn Arg Glu Thr
1               5

<210> SEQ ID NO 282
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Trp Ile Tyr Pro Leu Arg Gly Ser Ile Asn Tyr Ala Gln Lys Phe Gln
1               5                   10                  15

Gly

<210> SEQ ID NO 283
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Thr Ile His Trp Val Arg Gln Ala Thr Gly Gln Gly Leu Glu Trp Met
            35                  40                  45

Gly Trp Ile Tyr Pro Leu Arg Gly Ser Ile Asn Tyr Ala Gln Lys Phe
        50                  55                  60

Gln Gly Arg Val Thr Met Thr Ala Asn Lys Ser Ile Ser Thr Val Tyr
65                  70                  75                  80

Met Glu Leu Ser Ser Leu Arg Ser Glu Asp Thr Ala Val Tyr Phe Cys
                85                  90                  95

Ala Arg His Gly Ala Tyr Tyr Ser Asn Ala Phe Asp Tyr Trp Gly Gln
            100                 105                 110

Gly Thr Leu Val Thr Val Ser Ser
        115                 120

<210> SEQ ID NO 284
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 284

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Asp Asn Asp
            20                  25                  30

Gly Ile Arg Phe Leu His Trp Tyr Gln Gln Lys Pro Gly Gln Ala Pro
        35                  40                  45

Arg Leu Leu Ile Tyr Arg Ala Ser Asn Arg Glu Thr Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Ser Asn
                85                  90                  95

Lys Asp Pro Tyr Thr Phe Gly Gly Gly Thr Lys Val Glu Ile Lys
            100                 105                 110
```

<210> SEQ ID NO 285
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

```
Arg Ala Ser Thr Arg Ala Thr
1               5
```

<210> SEQ ID NO 286
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 286

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Asp Asn Asp
            20                  25                  30

Gly Ile Arg Phe Leu His Trp Tyr Gln Gln Lys Pro Gly Gln Ala Pro
        35                  40                  45

Arg Leu Leu Ile Tyr Arg Ala Ser Thr Arg Ala Thr Gly Ile Pro Ala
    50                  55                  60

Arg Phe Ser Gly Ser Gly Ser Arg Thr Glu Phe Thr Leu Thr Ile Ser
65                  70                  75                  80

Ser Leu Gln Ser Glu Asp Phe Ala Val Tyr Tyr Cys Gln Gln Ser Asn
                85                  90                  95

Lys Asp Pro Tyr Thr Phe Gly Gly Gly Thr Lys Val Glu Ile Lys
            100                 105                 110
```

<210> SEQ ID NO 287
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 287

Trp Ile Tyr Pro Leu Arg Gly Ser Ile Asn Tyr Ser Pro Ser Phe Gln
1               5                   10                  15
Gly

<210> SEQ ID NO 288
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 288

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Phe Thr Asp Tyr
            20                  25                  30

Thr Ile His Trp Val Arg Gln Met Pro Gly Lys Gly Leu Glu Trp Met
        35                  40                  45

Gly Trp Ile Tyr Pro Leu Arg Gly Ser Ile Asn Tyr Ser Pro Ser Phe
    50                  55                  60

Gln Gly Gln Val Thr Ile Ser Ala Asp Lys Ser Ile Ser Thr Val Tyr
65                  70                  75                  80

Leu Gln Trp Ser Ser Leu Lys Ala Ser Asp Thr Ala Met Tyr Phe Cys
                85                  90                  95

Ala Arg His Gly Ala Tyr Tyr Ser Asn Ala Phe Asp Tyr Trp Gly Gln
            100                 105                 110

Gly Thr Leu Val Thr Val Ser Ser
        115                 120

<210> SEQ ID NO 289
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 289

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45

Gly Trp Ile Tyr Pro Leu Arg Gly Ser Ile Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys

```
                    85                  90                  95

Ala Arg His Gly Ala Tyr Tyr Ser Asn Ala Phe Asp Tyr Trp Gly Gln
                100                 105                 110

Gly Thr Leu Val Thr Val Ser Ser
        115                 120

<210> SEQ ID NO 290
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Trp Ile Tyr Pro Leu Arg Gly Ser Ile Asn Tyr Ala Glu Lys Phe Lys
1               5                   10                  15

Gly

<210> SEQ ID NO 291
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45

Gly Trp Ile Tyr Pro Leu Arg Gly Ser Ile Asn Tyr Ala Glu Lys Phe
    50                  55                  60

Lys Gly Arg Val Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg His Gly Ala Tyr Tyr Ser Asn Ala Phe Asp Tyr Trp Gly Gln
                100                 105                 110

Gly Thr Leu Val Thr Val Ser Ser
        115                 120

<210> SEQ ID NO 292
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45
```

```
Gly Trp Ile Tyr Pro Leu Arg Gly Ser Ile Asn Tyr Ala Gln Lys Phe
        50                  55                  60

Gln Gly Arg Val Thr Met Thr Ala Asp Lys Ser Ile Ser Thr Val Tyr
65                  70                  75                  80

Met Glu Leu Ser Arg Leu Arg Ser Asp Asp Thr Ala Val Tyr Tyr Cys
                85                  90                  95

Ala Arg His Gly Ala Tyr Tyr Ser Asn Ala Phe Asp Tyr Trp Gly Gln
                100                 105                 110

Gly Thr Leu Val Thr Val Ser Ser
        115                 120

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Arg Ala Ser Thr Leu Glu Thr
1               5

<210> SEQ ID NO 294
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Thr Ile His Trp Val Arg Gln Ala Thr Gly Gln Gly Leu Glu Trp Met
            35                  40                  45

Gly Trp Ile Tyr Pro Leu Arg Gly Ser Ile Asn Tyr Ala Gln Lys Phe
        50                  55                  60

Gln Gly Arg Val Thr Met Thr Ala Asn Lys Ser Ser Ser Thr Val Tyr
65                  70                  75                  80

Met Glu Leu Ser Ser Leu Arg Ser Glu Asp Thr Ala Val Tyr Phe Cys
                85                  90                  95

Ala Arg His Gly Ala Tyr Tyr Ser Asn Ala Phe Asp Tyr Trp Gly Gln
                100                 105                 110

Gly Thr Leu Val Thr Val Ser Ser
        115                 120

<210> SEQ ID NO 295
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Asp Asn Asp
```

```
                    20                  25                  30

Gly Ile Arg Phe Leu His Trp Tyr Gln Gln Lys Pro Gly Gln Ala Pro
            35                  40                  45

Arg Leu Leu Ile Tyr Arg Ala Ser Thr Leu Glu Thr Gly Ile Pro Ala
        50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Ser Asn
                85                  90                  95

Lys Asp Pro Tyr Thr Phe Gly Gly Gly Thr Lys Val Glu Ile Lys
            100                 105                 110

<210> SEQ ID NO 296
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Thr Gly Gln Gly Leu Glu Trp Met
        35                  40                  45

Gly Trp Ile Tyr Pro Leu Arg Gly Ser Ile Asn Tyr Ala Gln Lys Phe
    50                  55                  60

Gln Gly Arg Val Thr Met Thr Ala Asp Lys Ser Ile Ser Thr Val Tyr
65                  70                  75                  80

Met Glu Leu Ser Ser Leu Arg Ser Glu Asp Thr Ala Val Tyr Phe Cys
                85                  90                  95

Ala Arg His Gly Ala Tyr Tyr Ser Asn Ala Phe Asp Tyr Trp Gly Gln
            100                 105                 110

Gly Thr Leu Val Thr Val Ser Ser
        115                 120

<210> SEQ ID NO 297
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297
gagatccagc tgcagcagtc tggagctgaa ctggtgaagc ctggggcttc agtgaagata      60
tcctgcaagg cttctgatta ctcattcact ggctacaaca tgaactgggt gatgcagagc     120
catggaaaga gccttgagtg gattggaaat attcatcctt actatggtgg tactagcttc     180
aatcagaagt tcatgggcaa ggccacattg actgcagaca atcttccag cacagcctac      240 atgcagctca cagcctgac atctgaagac tctgcagtct attactgtgc aagagagaga     300
agtaacttcc atgctctgga ctactggggt cagggaacct cagtcaccgt ctcctca       357

<210> SEQ ID NO 298
<211> LENGTH: 333
<212> TYPE: DNA
```

<213> ORGANISM: Artificial Sequence
<220> FEATURE:
<223> OTHER INFORMATION: Description of Artificial Sequence: Synthetic
    polynucleotide

<400> SEQUENCE: 298

```
gacattgtgc tgacacagtc tcctgcttcc ttaactgtat ctctggggca gagggccacc      60
ttctcatgca gggccagcaa agtgtcagt  acatctggct atagttatat gcactggtac     120
caacagaaac caggacagcc acccaaactc ctcatctatt ttacatccga cctagaacct    180
ggggtccctg ccaggttcac tggcagtggg tctgggacag acttcaccct caacatccat    240
cctgtggagg aggaggatgc tgcaacctat tactgtcagc acagtaggga gcttccgtac    300
cccttcggag gggggaccaa gttggaaata aaa                                  333
```

<210> SEQ ID NO 299
<211> LENGTH: 354
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 299

```
caggtacaac tccaggaatc cgggcctggg ctcgtcaaac caagcgaaac actctctctc      60
acctgcaccg tttctggggtt ttctcttact atctatgacg tacattgggt aaggcaacca   120
cccgggaagg ggctggagtg gatcggtgta atctggtcag atggatctac agactacaac    180
ccatccctta aaagcagggt gaccatttct aaggacactt ccaagaacca agtatccctt    240
aaattgtcct ctgtaaccgc agcagacacc gcagtttact actgcgcacg aaattgggtt    300
gaccaagcat ggtttgcata ttggggacag ggaactcttg tcactgtgtc ttca          354
```

<210> SEQ ID NO 300
<211> LENGTH: 321
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 300

```
gatattcaaa tgacccaatc cccctcatca ctttcagcat ctgtcggtga tcgggtcacc      60
attacttgca gagccagtaa gaatatctac agctacctgg cttggtatca gcaaaaacct    120
ggtaaggccc ctaaacttct cgtttacaat gctaagaccc ttcccgaggg agttccttcc    180
aggttttccg gtagcgggag tggaacagat ttcaccttga ctatttctag cttgcagccc    240
gaggatttcg ctacatacta ctgccagcat cactatggaa cccccctgac cttcggtcag    300
ggaaccaagc tcgagatcaa a                                               321
```

<210> SEQ ID NO 301
<211> LENGTH: 354
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 301

```
caagtccagc tcgtacagag cggggcagag ctgaagaagc ctggggcctc cgtcaaggtc      60
tcctgtaagg cttctggtta cacatttgcc gactactaca tgaactgggt acggcaagcc    120
```

```
ccaggtcaag ggctggaatg gatgggatgg attttccag ggagcggcag cacttactac      180
aaccagaaat ttcaaggtcg tgtgacaatg accgtggata aaagcagctc tacagcttac      240
atggagcttt cccgcttgag gtccgatgat actgccgtat attattgtgc ccgtggtgac      300
tcaggtaggg ccatggacta ttggggacag ggcaccctcg tgaccgtgtc cagc            354

<210> SEQ ID NO 302
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 302
gatatccaga tgacacaatc cccttcatcc ttgagcgcat cagttggcga cagggtcacc       60
ataacttgtc aggctagtca ggatattaac aagtacctgg cttggtatca acacaagcct      120
ggaaaggccc ccaaattgct gattcactac acctctacat tggaaactgg cgtacccagt      180
cgcttttctg ggagtggaag cggaactgat ttcactttca ctatatccag tcttcagcca      240
gaagatatcg caacttacta ttgtcttcag tatgataact tgcttacttt cggaggaggg      300
accaaagttg aaatcaag                                                    318

<210> SEQ ID NO 303
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 303
caggtgcagt tggtccaatc cggggctgag gtgaagaagc ctggggcctc tgttaaagtt       60
agttgcaagg catcaggcta caccttcgct gactactaca tcaactgggt tagacaggcc      120
cccgggcagg ggttggagtg gatggttgg attttccag gatcaggttc aacatattac      180
gcacaaaaac tgcaaggtag agtaaccatg acaactgata ctagcacctc cacagcctat      240
atggaactcc gctctctcag gagtgacgat acagccgttt attactgcgc ccgtggggat      300
tcaggccgtg caatggatta ctggggtcaa gggaccctcg tgaccgtaag ttca            354

<210> SEQ ID NO 304
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 304
caagttcagt tggtgcaaag cggggcagaa gtgaagaaac ctggtgcttc tgtgaaagtt       60
tcctgcaagg ccagcggcta cacctttact gattacacaa tacactgggt acggcaggca      120
actgggcaag gattggaatg gatgggtgg atatacccat gcgagggtc tataaactac       180 gcacagaaat ttcaaggtcg agtaacaatg acagccaaca aatcaataag caccgtttat      240
atggaactct catctctcag gagtgaggat accgccgtgt atttctgcgc acgacacggt      300
gcatattact caaacgcttt cgactattgg ggccagggca cccttgtgac tgttagtagc      360
```

```
<210> SEQ ID NO 305
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 305
gagatagtaa tgactcagtc tcccgctaca cttagtgtaa gcccagggga gcgagcaacc      60
ctcagttgca gagcatctga gagtgttgat aatgatggaa tacgttttct ccattggtat     120
caacaaaaac cagggcaggc ccccagattg ctgatctacc gtgcttccaa tcgcgagact     180
ggcattcctg cacgtttcag cggcagcggc tccggaaccg agtttacact tactattagc     240
tcactccagt ctgaagactt cgctgtgtat tactgtcagc aatccaacaa ggacccatac     300
actttcggag gcggcactaa ggttgagatc aaa                                  333

<210> SEQ ID NO 306
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 306
gagatagtta tgactcagtc tcccgccaca ctttcagtaa gtcccggtga acgcgccacc      60
ctgtcctgcc gtgcttccga atcagtggat aatgacggca ttaggttttt gcactggtac     120
caacaaaagc ccggacaggc ccccgcctg ctgatatatc gtgcatcaac acgagcaaca     180
gggatccccg ctcgatttag tggatccgga agcaggaccg aatttacact taccatttcc     240
tcacttcagt cagaagattt cgccgtttac tactgtcagc agtcaaataa ggatccttac     300
acatttgggg gcggtacaaa agtcgagatc aaa                                  333

<210> SEQ ID NO 307
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 307
gaggtccagt tggtccagtc aggagccgaa gtcaagaagc ctggggaaag cctgaaaata      60
agttgcaaag ctagtggata tacatttaca gattatacca ttcattgggt ccggcaaatg     120
ccaggaaaag gcttggagtg gatggggtgg atttatcccc tccgaggctc aataaattat     180
agtcctagtt ttcaggggca ggtaactatt agcgctgata aaagtatttc tacagtttat     240
ttgcagtgga gttcattgaa ggctagtgac accgctatgt atttctgcgc tagacatggt     300
gcatattatt caaatgcctt cgactattgg ggccagggca ccctcgtcac tgtgagttcc     360

<210> SEQ ID NO 308
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 308
```

```
caggtgcaac ttgttcagtc aggggctgaa gtaaagaagc caggctcatc agtcaaggta    60
tcatgcaaag catctggcta tacatttaca gattacacca ttcactgggt gaggcaagct   120
cccggtcaag gtctcgagtg gatggggtgg atataccctc tcagaggctc tataaattac   180
gctcagaaat ttcaagggag agttacaatt actgctgata aaagtaccag cactgcttat   240
atggagcttt cctcacttcg ttcagaggac accgccgttt acttttgtgc ccggcatggt   300
gcctattatt caaatgcctt cgattattgg gggcagggaa ctttggtcac agtttcatct   360
```

<210> SEQ ID NO 309
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 309

```
caagttcaac ttgtccaaag tggggctgaa gttaaaaaac ctggatcatc agtcaaggtt    60
tcatgcaaag ccagcggtta cacatttaca gactatacaa tacattgggt tcgacaggct   120
cccgggcaag ggctcgaatg gatgggatgg atttatcccc tcagggctc aattaactat   180 gctgagaaat ttaagggtcg tgtaacactc accgccgata aatccacctc aaccgtatat   240
atggagcttt cttctcttcg ctctgaagat accgccgtct atttctgcgc acgacacggg   300
gcatactatt ctaatgcttt tgactactgg ggacaaggga cacttgtgac cgttagtagc   360
```

<210> SEQ ID NO 310
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 310

```
caagtgcagt tggtccagag tggagcagag gtgaagaagc ctggtgcttc cgtcaaggtg    60
agttgcaagg catctggtta tactttcact gactacacaa ttcattgggt caggcaggcc   120
cctggacagg gactggaatg gatgggatgg atctatccac ttagaggatc aatcaactat   180
gctcaaaagt tccagggtcg tgtaacaatg accgcagaca aaagtatctc aactgtatac   240
atggaattgt cccgattgag gagcgacgac acagccgtat attattgtgc caggcacgga   300
gcctactaca gtaatgcctt cgactactgg gggcagggca cccttgttac cgtgtccagc   360
```

<210> SEQ ID NO 311
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 311

```
caagtgcagc tcgttcagtc tggcgcagaa gtgaagaagc caggagcttc cgttaaagtg    60
tcctgtaaag cctctggata tacattcaca gattatacaa ttcactgggt gagacaagca   120
accggtcaag gtctcgaatg gatgggctgg atataccccc tccgaggttc catcaactac   180
gctcaaaaat tccaaggacg agtcactatg acagcaaaca agagttcctc cactgtatat   240
atggaactct ctagtttgcg ctctgaagac accgccgtgt acttctgtgc caggcacggc   300
```

```
gcatactatt ctaatgcatt tgactattgg gggcagggca cattggtaac agttagttcc      360
```

<210> SEQ ID NO 312
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 312

```
gaaattgtaa tgacccagag ccccgccacc cttagtgtgt ccccaggcga gagggccact      60
ctttcttgcc gcgcaagcga atccgtagac aacgatggta taagattttt gcattggtat     120
cagcaaaagc caggccaggc accccggctt ctcatctaca gagctagcac cctcgaaact     180
ggaatccccg ctcgtttttc aggatctggt agcggaacag aatttacttt gacaattagt     240
agtttgcagt cagaggactt tgctgtctat tattgccagc agtctaataa agatccatac     300
accttcggcg agggaccaa agtagagatt aaa                                  333
```

<210> SEQ ID NO 313
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 313

```
caagttcagt tggtgcaaag cggggcagaa gtgaagaaac tggtgcttc tgtgaaagtt      60
tcctgcaagg ccagcggcta cacctttact gattacacaa tacactgggt acggcaggca    120
actgggcaag gattggaatg gatggggtgg atatacccat tgcgagggtc tataaactac    180
gcacagaaat ttcaaggtcg agtaacaatg acagccgaca aatcaataag caccgtttat    240
atggaactct catctctcag gagtgaggat accgccgtgt atttctgcgc acgacacggt    300
gcatattact caaacgcttt cgactattgg ggccagggca cccttgtgac tgttagtagc    360
```

<210> SEQ ID NO 314
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

```
Lys Ser Ser Gln Ser Val Asp Asn Asp Gly Ile Arg Phe Leu His
1               5                   10                  15
```

<210> SEQ ID NO 315
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

```
Arg Ala Ser Thr Arg Glu Ser
1               5
```

<210> SEQ ID NO 316
<211> LENGTH: 111

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Asn Asp
            20                  25                  30

Gly Ile Arg Phe Leu His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Lys Asp Pro Tyr Thr Phe Gly Gly Gly Thr Lys Val Glu Ile Lys
            100                 105                 110

<210> SEQ ID NO 317
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45

Gly Trp Ile Tyr Pro Leu Arg Gly Ser Ile Asn Tyr Ala Gln Lys Phe
    50                  55                  60

Gln Gly Arg Val Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg His Gly Ala Tyr Tyr Ser Asn Ala Phe Asp Tyr Trp Gly Gln
            100                 105                 110

Gly Thr Leu Val Thr Val Ser Ser
        115                 120

<210> SEQ ID NO 318
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 318
gacattgtaa tgacccagtc tcccgatagc ctcgctgtct cactcggaga acgcgcaacc      60
atcaactgca agtcctccca aagcgttgac aatgacggca ttaggttttt gcactggtac     120

```
cagcagaaac ccggtcaacc tcctaagttg ctcatttacc gagcatctac ccgcgagtca    180
ggagtacctg atcgcttttc cggtagcggt agtggaacag attttactct gaccattagt    240
tcactccagg cagaagatgt ggctgtctac tactgccaac agtcaaataa agacccttat    300
accttcggtg ggggtaccaa agtagagatc aaa                                 333

<210> SEQ ID NO 319
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 319
caggtgcagt tggtccagag cggggcagag gttaagaagc ctggggcctc agtaaaggta    60
tcctgcaagg cttctgggta caccttcaca gattacacta ttcattgggt gcgccaagca    120
cctggtcaag gccttgaatg gatgggatgg atttacccct tgcgagggag tattaattat    180
gcacagaagt tccagggaag ggttactctt accgccgaca gtccacatc aaccgtttac     240 atggagcttt cctctctcag gtccgaagac actgctgtat atttctgcgc tcggcatggg    300
gcttattaca gcaacgcctt cgattactgg ggtcaggta cattggtcac agtgtccagt     360

<210> SEQ ID NO 320
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
```

```
            195                 200                 205
Ala Leu Pro Ala Pro Ile Glu Lys Thr Ile Ser Lys Ala Lys Gly Gln
        210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro
                325

<210> SEQ ID NO 321
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

-continued

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 322
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 323
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
```

```
               275                 280                 285
Thr Val Asp Lys Ser Arg Trp Gln Gln Gly Asn Val Phe Ser Cys Ser
    290                 295                 300
Val Met His Glu Ala Leu His Asn His Tyr Thr Gln Lys Ser Leu Ser
305                 310                 315                 320
Leu Ser Pro

<210> SEQ ID NO 324
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Ser Thr Lys Gly Pro Ser Val Phe Pro Leu Ala Pro Cys Ser Arg Ser
1               5                   10                  15
Thr Ser Glu Ser Thr Ala Ala Leu Gly Cys Leu Val Lys Asp Tyr Phe
            20                  25                  30
Pro Glu Pro Val Thr Val Ser Trp Asn Ser Gly Ala Leu Thr Ser Gly
        35                  40                  45
Val His Thr Phe Pro Ala Val Leu Gln Ser Ser Gly Leu Tyr Ser Leu
    50                  55                  60
Ser Ser Val Val Thr Val Thr Ser Ser Asn Phe Gly Thr Gln Thr Tyr
65                  70                  75                  80
Thr Cys Asn Val Asp His Lys Pro Ser Asn Thr Lys Val Asp Lys Thr
                85                  90                  95
Val Glu Arg Lys Cys Cys Val Glu Cys Pro Pro Cys Pro Ala Pro Pro
            100                 105                 110
Val Ala Gly Pro Ser Val Phe Leu Phe Pro Pro Lys Pro Lys Asp Thr
        115                 120                 125
Leu Met Ile Ser Arg Thr Pro Glu Val Thr Cys Val Val Val Asp Val
    130                 135                 140
Ser His Glu Asp Pro Glu Val Gln Phe Asn Trp Tyr Val Asp Gly Met
145                 150                 155                 160
Glu Val His Asn Ala Lys Thr Lys Pro Arg Glu Glu Gln Phe Asn Ser
                165                 170                 175
Thr Phe Arg Val Val Ser Val Leu Thr Val Val His Gln Asp Trp Leu
            180                 185                 190
Asn Gly Lys Glu Tyr Lys Cys Lys Val Ser Asn Lys Gly Leu Pro Ala
        195                 200                 205
Pro Ile Glu Lys Thr Ile Ser Lys Thr Lys Gly Gln Pro Arg Glu Pro
    210                 215                 220
Gln Val Tyr Thr Leu Pro Pro Ser Arg Glu Glu Met Thr Lys Asn Gln
225                 230                 235                 240
Val Ser Leu Thr Cys Leu Val Lys Gly Phe Tyr Pro Ser Asp Ile Ala
                245                 250                 255
Val Glu Trp Glu Ser Asn Gly Gln Pro Glu Asn Asn Tyr Lys Thr Thr
            260                 265                 270
Pro Pro Met Leu Asp Ser Asp Gly Ser Phe Phe Leu Tyr Ser Lys Leu
        275                 280                 285
Thr Val Asp Lys Ser Arg Trp Gln Gln Gly Asn Val Phe Ser Cys Ser
    290                 295                 300
Val Met His Glu Ala Leu His Asn His Tyr Thr Gln Lys Ser Leu Ser
```

Leu Ser Pro

<210> SEQ ID NO 325
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

```
Ser Thr Lys Gly Pro Ser Val Phe Pro Leu Ala Pro Cys Ser Arg Ser
 1               5                  10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro
```

<210> SEQ ID NO 326

```
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ser
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro

<210> SEQ ID NO 327
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(2)
<223> OTHER INFORMATION: Ala or Ser
<220> FEATURE:
<221> NAME/KEY: MOD_RES
<222> LOCATION: (4)..(4)
<223> OTHER INFORMATION: Glu or Gln
<220> FEATURE:
<221> NAME/KEY: MOD_RES
<222> LOCATION: (14)..(14)
<223> OTHER INFORMATION: Met or Leu

<400> SEQUENCE: 327

Xaa Xaa Ser Xaa Ser Val Asp Asn Asp Gly Ile Arg Phe Xaa His
1               5                   10                  15

<210> SEQ ID NO 328
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asn or Thr
<220> FEATURE:
<221> NAME/KEY: MOD_RES
<222> LOCATION: (5)..(5)
<223> OTHER INFORMATION: Leu or Arg
<220> FEATURE:
<221> NAME/KEY: MOD_RES
<222> LOCATION: (6)..(6)
<223> OTHER INFORMATION: Glu or Ala
<220> FEATURE:
<221> NAME/KEY: MOD_RES
<222> LOCATION: (7)..(7)
<223> OTHER INFORMATION: Ser or Thr

<400> SEQUENCE: 328

Arg Ala Ser Xaa Xaa Xaa Xaa
1               5

<210> SEQ ID NO 329
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Asn, Ser or Ala
<220> FEATURE:
<221> NAME/KEY: MOD_RES
<222> LOCATION: (13)..(13)
<223> OTHER INFORMATION: Glu, Pro or Gln
<220> FEATURE:
<221> NAME/KEY: MOD_RES
<222> LOCATION: (14)..(14)
<223> OTHER INFORMATION: Lys or Ser
<220> FEATURE:
<221> NAME/KEY: MOD_RES
<222> LOCATION: (16)..(16)
<223> OTHER INFORMATION: Lys or Gln
<220> FEATURE:
<221> NAME/KEY: MOD_RES
<222> LOCATION: (17)..(17)
```

```
<223> OTHER INFORMATION: Asp or Gly

<400> SEQUENCE: 329

Trp Ile Tyr Pro Leu Arg Gly Ser Ile Asn Tyr Xaa Xaa Xaa Phe Xaa
1               5                   10                  15

Xaa

<210> SEQ ID NO 330
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Ile or Phe
<220> FEATURE:
<221> NAME/KEY: MISC_FEATURE
<222> LOCATION: (6)..(6)
<223> OTHER INFORMATION: May or may not be present
<220> FEATURE:
<221> NAME/KEY: MOD_RES
<222> LOCATION: (7)..(7)
<223> OTHER INFORMATION: Gly, Asp or Ser

<400> SEQUENCE: 330

Gly Tyr Xaa Xaa Thr Ser Xaa Tyr
1               5

<210> SEQ ID NO 331
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Tyr or not present
<220> FEATURE:
<221> NAME/KEY: MOD_RES
<222> LOCATION: (2)..(2)
<223> OTHER INFORMATION: Ser or Pro
<220> FEATURE:
<221> NAME/KEY: MOD_RES
<222> LOCATION: (3)..(3)
<223> OTHER INFORMATION: Tyr, Leu or Arg
<220> FEATURE:
<221> NAME/KEY: MOD_RES
<222> LOCATION: (4)..(4)
<223> OTHER INFORMATION: Asp, Asn or Arg
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Tyr, Asp or Ser

<400> SEQUENCE: 331

Xaa Xaa Xaa Xaa Xaa Xaa
1               5

<210> SEQ ID NO 332
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, Glu or His
<220> FEATURE:
<221> NAME/KEY: MISC_FEATURE
<222> LOCATION: (2)..(2)
<223> OTHER INFORMATION: May or may not be present
<220> FEATURE:
<221> NAME/KEY: MOD_RES
<222> LOCATION: (3)..(3)
<223> OTHER INFORMATION: Tyr, Asp or Ala
<220> FEATURE:
<221> NAME/KEY: MOD_RES
<222> LOCATION: (4)..(4)
<223> OTHER INFORMATION: Asp, Gly or Tyr
<220> FEATURE:
<221> NAME/KEY: MOD_RES
<222> LOCATION: (6)..(6)
<223> OTHER INFORMATION: Glu, Asp or absent
<220> FEATURE:
<221> NAME/KEY: MOD_RES
<222> LOCATION: (7)..(7)
<223> OTHER INFORMATION: Asp, Tyr, Ser or Lys
<220> FEATURE:
<221> NAME/KEY: MOD_RES
<222> LOCATION: (8)..(8)
<223> OTHER INFORMATION: Trp, Asn or Arg
<220> FEATURE:
<221> NAME/KEY: MOD_RES
<222> LOCATION: (9)..(9)
<223> OTHER INFORMATION: Tyr, Ala or Gly
<220> FEATURE:
<221> NAME/KEY: MOD_RES
<222> LOCATION: (11)..(11)
<223> OTHER INFORMATION: Gly or Asp
<220> FEATURE:
<221> NAME/KEY: MOD_RES
<222> LOCATION: (12)..(12)
<223> OTHER INFORMATION: Val or Tyr

<400> SEQUENCE: 332

Xaa Gly Xaa Xaa Tyr Xaa Xaa Xaa Xaa Phe Xaa Xaa
1               5                   10

<210> SEQ ID NO 333
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (4)..(4)
<223> OTHER INFORMATION: Glu or Gln
<220> FEATURE:
<221> NAME/KEY: MOD_RES
<222> LOCATION: (7)..(7)
<223> OTHER INFORMATION: Asp or Ser
<220> FEATURE:
<221> NAME/KEY: MOD_RES
<222> LOCATION: (8)..(8)
<223> OTHER INFORMATION: Asn, Phe or Ile
<220> FEATURE:
<221> NAME/KEY: MOD_RES
<222> LOCATION: (9)..(9)
```

```
<223> OTHER INFORMATION: Tyr, Ala, Ile or Asp
<220> FEATURE:
<221> NAME/KEY: MOD_RES
<222> LOCATION: (11)..(11)
<223> OTHER INFORMATION: Ile or Thr
<220> FEATURE:
<221> NAME/KEY: MOD_RES
<222> LOCATION: (12)..(12)
<223> OTHER INFORMATION: Ser, Asn or Arg
<220> FEATURE:
<221> NAME/KEY: MOD_RES
<222> LOCATION: (13)..(13)
<223> OTHER INFORMATION: Phe, Leu or Ser
<220> FEATURE:
<221> NAME/KEY: MOD_RES
<222> LOCATION: (14)..(14)
<223> OTHER INFORMATION: Met or Ile
<220> FEATURE:
<221> NAME/KEY: MOD_RES
<222> LOCATION: (15)..(15)
<223> OTHER INFORMATION: Asn or His

<400> SEQUENCE: 333

Xaa Ala Ser Xaa Ser Val Xaa Xaa Xaa Gly Xaa Xaa Xaa Xaa Xaa
1               5                   10                  15

<210> SEQ ID NO 334
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Arg or His
<220> FEATURE:
<221> NAME/KEY: MOD_RES
<222> LOCATION: (5)..(5)
<223> OTHER INFORMATION: Gln or Leu
<220> FEATURE:
<221> NAME/KEY: MOD_RES
<222> LOCATION: (6)..(6)
<223> OTHER INFORMATION: Gly or Glu
<220> FEATURE:
<221> NAME/KEY: MOD_RES
<222> LOCATION: (7)..(7)
<223> OTHER INFORMATION: Ser, Pro or Thr

<400> SEQUENCE: 334

Xaa Ala Ser Asn Xaa Xaa Xaa
1               5

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Leu
<220> FEATURE:
<221> NAME/KEY: MOD_RES
<222> LOCATION: (4)..(4)
<223> OTHER INFORMATION: Lys, Arg or Asn
<220> FEATURE:
<221> NAME/KEY: MOD_RES
<222> LOCATION: (5)..(5)
<223> OTHER INFORMATION: Glu or Lys
<220> FEATURE:
<221> NAME/KEY: MOD_RES
```

```
<222> LOCATION: (6)..(6)
<223> OTHER INFORMATION: Val, Tyr, Ile or Asp
<220> FEATURE:
<221> NAME/KEY: MOD_RES
<222> LOCATION: (8)..(8)
<223> OTHER INFORMATION: Arg, Trp or Tyr

<400> SEQUENCE: 335

Xaa Gln Ser Xaa Xaa Xaa Pro Xaa Thr
1               5

<210> SEQ ID NO 336
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: May or may not be absent
<220> FEATURE:
<221> NAME/KEY: MOD_RES
<222> LOCATION: (2)..(2)
<223> OTHER INFORMATION: Gly, Asp or Ser
<220> FEATURE:
<221> NAME/KEY: MOD_RES
<222> LOCATION: (4)..(4)
<223> OTHER INFORMATION: Tyr, Phe, Thr or Asp
<220> FEATURE:
<221> NAME/KEY: MOD_RES
<222> LOCATION: (5)..(5)
<223> OTHER INFORMATION: Trp, Met, Ile or Val
<220> FEATURE:
<221> NAME/KEY: MOD_RES
<222> LOCATION: (6)..(6)
<223> OTHER INFORMATION: Asn, His or Phe

<400> SEQUENCE: 336

Ser Xaa Tyr Xaa Xaa Xaa
1               5

<210> SEQ ID NO 337
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, Arg or Trp
<220> FEATURE:
<221> NAME/KEY: MOD_RES
<222> LOCATION: (3)..(3)
<223> OTHER INFORMATION: Asn, Tyr or not present
<220> FEATURE:
<221> NAME/KEY: MOD_RES
<222> LOCATION: (4)..(4)
<223> OTHER INFORMATION: Ser or Pro
<220> FEATURE:
<221> NAME/KEY: MOD_RES
<222> LOCATION: (5)..(5)
<223> OTHER INFORMATION: Tyr, Leu or Arg
<220> FEATURE:
<221> NAME/KEY: MOD_RES
<222> LOCATION: (6)..(6)
<223> OTHER INFORMATION: Asp, Asn or Arg
<220> FEATURE:
<221> NAME/KEY: MOD_RES
<222> LOCATION: (7)..(7)
<223> OTHER INFORMATION: Gly or Ser
<220> FEATURE:
```

```
<221> NAME/KEY: MOD_RES
<222> LOCATION: (8)..(8)
<223> OTHER INFORMATION: Tyr, Asp or Ser
<220> FEATURE:
<221> NAME/KEY: MOD_RES
<222> LOCATION: (9)..(9)
<223> OTHER INFORMATION: Asn, Thr or Ile
<220> FEATURE:
<221> NAME/KEY: MOD_RES
<222> LOCATION: (10)..(10)
<223> OTHER INFORMATION: Asn, Phe or Lys
<220> FEATURE:
<221> NAME/KEY: MOD_RES
<222> LOCATION: (13)..(13)
<223> OTHER INFORMATION: Pro, Gln or Glu
<220> FEATURE:
<221> NAME/KEY: MOD_RES
<222> LOCATION: (14)..(14)
<223> OTHER INFORMATION: Ser or Lys
<220> FEATURE:
<221> NAME/KEY: MOD_RES
<222> LOCATION: (15)..(15)
<223> OTHER INFORMATION: Leu or Phe
<220> FEATURE:
<221> NAME/KEY: MOD_RES
<222> LOCATION: (17)..(17)
<223> OTHER INFORMATION: Asn, Gly or Asp

<400> SEQUENCE: 337

Xaa Ile Xaa Xaa Xaa Xaa Xaa Xaa Xaa Xaa Tyr Asn Xaa Xaa Xaa Lys
1               5                   10                  15

Xaa

<210> SEQ ID NO 338
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Asp Asp Ser Asp
1

<210> SEQ ID NO 339
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Val Thr Phe Thr Met Gly Gln Val
1               5

<210> SEQ ID NO 340
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Met Pro Ser His
1

<210> SEQ ID NO 341
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Pro Arg Ala Arg
1

<210> SEQ ID NO 342
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ala or Pro
<220> FEATURE:
<221> NAME/KEY: MOD_RES
<222> LOCATION: (13)..(13)
<223> OTHER INFORMATION: Ala or Ser
<220> FEATURE:
<221> NAME/KEY: MOD_RES
<222> LOCATION: (14)..(14)
<223> OTHER INFORMATION: Phe or Leu
<220> FEATURE:
<221> NAME/KEY: MOD_RES
<222> LOCATION: (15)..(15)
<223> OTHER INFORMATION: Ile or Lys

<400> SEQUENCE: 342

Val Ile Trp Ser Asp Gly Ser Thr Asp Tyr Asn Xaa Xaa Xaa Xaa Ser
1               5                   10                  15

<210> SEQ ID NO 343
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ile or Met

<400> SEQUENCE: 343

Asp Tyr Tyr Xaa Asn
1               5

<210> SEQ ID NO 344
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Asn or Ala
<220> FEATURE:
<221> NAME/KEY: MOD_RES
<222> LOCATION: (13)..(13)
<223> OTHER INFORMATION: Glu or Gln
<220> FEATURE:
<221> NAME/KEY: MOD_RES
<222> LOCATION: (15)..(15)
```

```
<223> OTHER INFORMATION: Phe or Leu
<220> FEATURE:
<221> NAME/KEY: MOD_RES
<222> LOCATION: (16)..(16)
<223> OTHER INFORMATION: Lys or Gln

<400> SEQUENCE: 344

Trp Ile Phe Pro Gly Ser Gly Ser Thr Tyr Tyr Xaa Xaa Lys Xaa Xaa
1               5                   10                  15
Gly

<210> SEQ ID NO 345
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Gln

<400> SEQUENCE: 345

Xaa Ala Ser Gln Asp Ile Asn Lys Tyr Ile Ala
1               5                   10

<210> SEQ ID NO 346
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Gln or Glu
<220> FEATURE:
<221> NAME/KEY: MOD_RES
<222> LOCATION: (7)..(7)
<223> OTHER INFORMATION: Ser or Thr

<400> SEQUENCE: 346

Tyr Thr Ser Thr Leu Xaa Xaa
1               5
```

METHODS OF TREATING IGA NEPHROPATHY BY ADMINISTERING AN ANTI-APRIL (A PROLIFERATION-INDUCING LIGAND) ANTIBODY MOLECULE

CROSS REFERENCE TO RELATED APPLICATIONS

This application is a divisional application of U.S. patent application Ser. No. 16/912,085, filed Jun. 25, 2020, now U.S. Pat. No. 10,981,982, which is a divisional application of U.S. patent application Ser. No. 16/456,810, filed Jun. 28, 2019, now abandoned, which is a divisional application of U.S. patent application Ser. No. 16/212,957 filed Dec. 7, 2018, now U.S. Pat. No. 10,385,123, which is a divisional application of U.S. patent application Ser. No. 15/360,145, filed Nov. 23, 2016, now abandoned, which claims the benefit of U.S. Provisional Application No. 62/259,897, filed Nov. 25, 2015, U.S. Provisional Application No. 62/313,684, filed Mar. 25, 2016, U.S. Provisional Application No. 62/399,087, filed Sep. 23, 2016, and U.S. Provisional Application No. 62/422,848, filed Nov. 16, 2016. The contents of the aforementioned applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Nov. 21, 2016, is named P2029-700410_SL.txt and is 248,428 bytes in size.

BACKGROUND

IgA nephropathy is one of the most prevalent, chronic glomerular diseases worldwide. Conservative epidemiological estimates cite a global incidence of approximately 5-50 cases/million (children) and 10-40 cases/million (adults). This incidence of disease presents a regional bias with a higher prevalence in Asia and the Americas, with a particularly higher disease burden in Japan and regions of China. Biopsy confirmed cases of IgA nephropathy in Japan are projected at approximately 350,000. In the US, this projection is approximately 100,000—as such, it is the most frequently diagnosed 1° glomerular disease in adults. While a relatively indolent disease, IgA nephropathy leads to end stage renal disease (ESRD), i.e., renal failure in 20-50% of patients within a 20-30 year span. These numbers are likely grossly underreported given the need to confirm the disease by kidney biopsy, a protocol that is variably practiced in various clinical settings. The disease has a complex pathogenesis with genetic, epidemiological, and potentially environmental components to disease etiology, pathology, and progression. It likewise has a variable clinical presentation ranging from asymptomatic to end-stage renal failure (ESRD). IgA nephropathy is caused by the deposition of IgA, typically in the form of immune complexes in the mesangium of the kidney. There are currently no disease-specific treatments to address primary disease or progression.

There is a need for developing new approaches for treating, preventing and diagnosing IgA nephropathy and other disorders that share similar disease mechanisms.

SUMMARY

This disclosure provides, at least in part, antibody molecules that bind to APRIL, e.g., human and/or mouse APRIL, and that comprise one or more functional and structural properties disclosed herein. In an embodiment, the antibody molecule binds to and/or reduces (e.g., inhibits, blocks or neutralizes) one or more activities of APRIL. In an embodiment, the antibody molecule binds to a region in APRIL that interacts with TACI (e.g., the CRD2 domain of TACI). In an embodiment, the antibody molecule binds to one or more residues within a region of human APRIL as defined in any of Tables 3-4 or 7-8. While not wishing to be bound by theory, it is believed that in an embodiment, improved or optimal inhibition of APRIL activities can be achieved, by targeting certain region(s) on APRIL (e.g., the region(s) associated with the interactions between APRIL and the CDR2 domain of TACI). In an embodiment, the antibody molecule is selected from Table 1 or 5, or competes for binding to APRIL with an antibody molecule selected from Table 1 or 5. In an embodiment, the antibody molecule binds to the same or overlapping epitope as the epitope recognized by an antibody molecule selected from Table 1 or 5. In an embodiment, the antibody molecule comprises one or more heavy chain variable regions and/or one or more light chain variable regions described in Table 1 or 5. In an embodiment, the antibody molecule comprises one or more heavy chain CDRs and/or one or more light chain CDRs described in Table 1 or 5. In an embodiment, nucleic acid molecules encoding the antibody molecules, expression vectors, host cells, compositions (e.g., pharmaceutical compositions), kits, containers, and methods for making the antibody molecules, are also provided. The antibody molecules disclosed herein can be used (alone or in combination with other agents or therapeutic modalities) to treat, prevent and/or diagnose disorders associated with APRIL, such as IgA nephropathy.

Accordingly, in certain aspects, this disclosure provides an antibody molecule, e.g., an antibody molecule described herein, having one or more (e.g., 1, 2, 3, 4, 5, 6, 7, 8, 9, 10, 11, 12, 13, 14, 15, 16, 17, 18, 19, 20, 21, 22, or 23) of the following properties:

a) Binds to human APRIL with high affinity, e.g., with a dissociation constant ($K_D$) of less than about 100 nM, typically about 10 nM, and more typically, about 10-0.001 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM, b) Binds to mouse APRIL with high affinity, e.g., with a dissociation constant ($K_D$) of less than about 100 nM, typically about 10 nM, and more typically, about 10-0.001 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM, c) Does not bind to mouse APRIL, or binds mouse APRIL with low affinity, e.g., with a dissociation constant ($K_D$) of greater than about 500 nM, e.g., greater than about 1000 nM, d) Does not bind, or binds with low affinity, e.g., with a dissociation constant ($K_D$) of greater than about 500 nM, e.g., greater than about 1000 nM, to one or more (e.g., 2, 3, 4, 5, 6, 7, 8, or more) cytokines from the TNF superfamily (TNFSF) other than APRIL (e.g., TNFα, CD40 (TNFSF4), FasL (TNFSF6), TRAIL (TNFSF10), RANKL (TNFSF11), Tweak (TNFSF12), BAFF (TNFSF13B), or LIGHT (TNFSF14)), e) Binds to one or more (e.g., 2, 3, 4, 5, 6, 7, 8, 9, 10, 11, 12, 13, 14, 15, 16, 17, 18, 19, 20, 21, 22, 23, 24, 25, or all) residues within a region of APRIL as defined in Table 3, or binds specifically to an epitope on APRIL, e.g., an epitope comprising one or more (e.g., 2, 3, 4, 5, 6, 7, 8, 9, 10, 11, 12, 13, 14, 15, 16, 17, 18, 19, 20, 21, 22, 23, 24, 25, or all) residues described in Table 3, f) Binds to one or more (e.g., 2, 3, 4, 5, 6, 7, 8, 9, 10, or all) residues within a region of APRIL as defined in Table 4, or binds specifically to an epitope on APRIL, e.g., an epitope comprising one or more (e.g., 2, 3, 4, 5, 6, 7, 8, 9, 10, or all) residues described in Table 4, g) Binds to one or more (e.g., 2, 3, 4, 5, 6, 7, 8, 9, 10, 11, 12, 13, 14, 15, 16, 17, or all) residues within a region of APRIL as defined in Table 7, or binds specifically to an epitope on APRIL, e.g., an epitope comprising one or more (e.g., 2, 3, 4, 5, 6, 7, 8, 9, 10, 11, 12, 13, 14, 15, 16, 17, or all) residues described in Table 7, h) Binds to one or more (e.g., 2, 3, 4, 5, 6, 7, 8, 9, 10, 11, 12, 13, 14, 15, 16, 17, 18, 19, 20, 21, 22, 23, 24, 25, or all) residues within a region of APRIL as defined in Table 8, or binds specifically to an epitope on APRIL, e.g., an epitope comprising one or more (e.g., 2, 3, 4, 5, 6, 7, 8, 9, 10, 11, 12, 13, 14, 15, 16, 17, 18, 19, 20, 21, 22, 23, 24, 25, or all) residues described in Table 8, i) Binds specifically to an epitope on APRIL, e.g., the same, similar, or overlapping epitope as the epitope recognized by a monoclonal antibody described in Table 1 or 5, e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237, j) Reduces (e.g., inhibits, blocks, or neutralizes) one or more biological activities of APRIL (e.g., human APRIL, mouse APRIL, or both), in vitro, ex vivo, or in vivo, k) Reduces (e.g., inhibits, blocks, or neutralizes) binding of human APRIL to TACI, e.g., at an $IC_{50}$ of about 50 nM or less, typically about 0.01-50 nM, 0.1-25 nM, 0.1-10 nM, 0.5-5 nM, or 1-5 nM, e.g., less than about 40, 30, 20, 10, 5, 1, 0.5, 0.2, 0.1, 0.05, or 0.01 nM, e.g., as determined by a method described herein, l) Reduces (e.g., inhibits, blocks, or neutralizes) binding of mouse APRIL to TACI, e.g., at an $IC_{50}$ of about 100 nM or less, typically about 0.01-75 nM, 0.1-50 nM, 0.1-25 nM, 0.1-10 nM, 0.5-5 nM, or 1-5 nM, e.g., less than about 80, 60, 40, 20, 10, 5, 1, 0.5, 0.2, 0.1, 0.05, or 0.01 nM, e.g., as determined by a method described herein, m) Reduces (e.g., inhibits, blocks, or neutralizes) binding of human APRIL to BMCA, e.g., at an $IC_{50}$ of about 50 nM or less, typically about 0.01-50 nM, 0.1-25 nM, 0.1-10 nM, 0.5-5 nM, or 1-5 nM, e.g., less than about 40, 30, 20, 10, 5, 1, 0.5, 0.2, 0.1, 0.05, or 0.01 nM, e.g., as determined by a method described herein, n) Reduces (e.g., inhibits, blocks, or neutralizes) binding of mouse APRIL to BMCA, e.g., at an $IC_{50}$ of about 200 nM or less, typically about 0.01-200 nM, 0.1-150 nM, 0.1-100 nM, 0.1-50 nM, 0.1-25 nM, 0.1-10 nM, 0.5-5 nM, or 1-5 nM, e.g., less than about 150, 100, 50, 40, 30, 20, 10, 5, 1, 0.5, 0.2, 0.1, 0.05, or 0.01 nM, e.g., as determined by a method described herein, o) Shows the same or similar binding affinity or specificity, or both, as a monoclonal antibody described in Table 1 or 5, e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237, p) Shows the same or similar binding affinity or specificity, or both, as an antibody molecule comprising a heavy chain variable region and/or light chain variable region described in Table 1 or 5, e.g., a heavy chain variable region and/or light chain variable region of any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237, q) Shows the same or similar binding affinity or specificity, or both, as an antibody molecule comprising one or more (e.g., two or three) heavy chain CDRs and/or one or more (e.g., two or three) light chain CDRs described in Table 1 or 5, e.g., one or more (e.g., two or three) heavy chain CDRs and/or one or more (two or three) light chain CDRs of any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237, r) Shows the same or similar binding affinity or specificity, or both, as an antibody molecule comprising an amino acid sequence shown in Table 1 or 5, s) Shows the same or similar binding affinity or specificity, or both, as an antibody molecule comprising an amino acid sequence encoded by a nucleotide sequence shown in Table 2, t) Inhibits, e.g., competitively inhibits, the binding of a second antibody molecule to human APRIL, mouse APRIL, or both, wherein the second antibody molecule is an antibody molecule chosen from Table 1 or 5, e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237, u) Competes for binding with a second antibody molecule to human APRIL, mouse APRIL, or both, wherein the second antibody molecule is a monoclonal antibody chosen from Table 1 or 5, e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237, v) Has one or more biological properties of a monoclonal antibody chosen from Table 1 or 5, e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237, w) Has one or more structural properties of a monoclonal antibody chosen from Table 1 or 5, e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237, or x) Has one or more pharmacokinetic properties of a monoclonal antibody chosen from Table 1 or 5, e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237.

In an aspect, the disclosure features an anti-APRIL antibody molecule, which:

(i) binds, or substantially binds, to human APRIL;
(ii) binds, or substantially binds, to mouse APRIL;
(iii) inhibits, or substantially inhibits, binding of APRIL (e.g., human APRIL, mouse APRIL, or both) to TACI (e.g., human TACI, mouse TACI, or both); and
(iv) inhibits, or substantially inhibits, binding of APRIL (e.g., human APRIL, mouse APRIL, or both) to BCMA (e.g., human BCMA, mouse BCMA, or both).

In an embodiment, the antibody molecule is a synthetic antibody molecule. In an embodiment, the antibody molecule is an isolated antibody molecule.

In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule binds, or substantially binds, to mouse APRIL at an $EC_{50}$ of 100 nM or less, e.g., 80 nM or less, 60 nM or less, 40 nM or less, 20 nM or less, 10 nM or less, 9 nM or less 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 100 nM, e.g., between 0.001 nM and 50 nM, between 0.01 nM and 20 nM, between 0.1 nM and 10 nM, between 0.5 nM and 5 nM or between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule inhibits, or substantially inhibits, binding of APRIL (e.g., human APRIL, mouse APRIL, or both) to TACI (e.g., human TACI, mouse TACI, or both), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In an embodiment, the antibody molecule inhibits, or substantially inhibits, binding of APRIL (e.g., human APRIL, mouse APRIL, or both) to BCMA (e.g., human BCMA, mouse BCMA, or both), e.g., at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In an embodiment, the antibody molecule is an IgG antibody molecule, e.g., comprising a heavy chain constant region of IgG, e.g., chosen from IgG1, IgG2 (e.g., IgG2a), IgG3, or IgG4, e.g., IgG2 or IgG4. In an embodiment, the antibody molecule is an IgG1 antibody molecule, e.g., having an IgG1 constant region described herein. In another embodiment, the antibody molecule is an IgG2 antibody molecule e.g., having an IgG2 constant region described herein. In an embodiment, the antibody molecule comprises a light chain constant region of kappa or lambda light chain.

In an embodiment, the antibody molecule comprises an Fc region. In an embodiment, the Fc region comprises one or more mutations located at the interface between the CH2 and CH3 domains (e.g., to increase the binding affinity to neonatal receptor FcRn and/or the half-life of the antibody molecule). In an embodiment, the Fc region comprises one or more mutations, e.g., one or more (e.g., 2, 3, 4, 5, 6 or all) mutations chosen from T250Q, M252Y, S254T, T256E, M428L, H433K, N434F, or any combination thereof, of IgG1. In an embodiment, the Fc region comprises one or more mutations at positions 233-236 or 322 of human IgG1 or IgG2, or one or more substitutions at positions 327, 330 or 331 of human IgG4 (e.g., to reduce complement-dependent cytotoxicity (CDC)). In an embodiment, the Fc region comprises one or more (e.g., 2, 3, 4, 5, 6, 7 or all) mutations chosen from E233P, L234V, L235A, G236, K322A, A327G, A330S, P331S, or any combination thereof.

In an embodiment, the antibody molecule is a humanized antibody molecule, e.g., comprising one or more framework regions derived from human framework germline sequence. In an embodiment, the antibody molecule comprises a heavy chain variable region (VH) described in Table 1 or 5. In an embodiment, the antibody molecule comprises a light chain variable region (VL) described in Table 1 or 5. In an embodiment, the antibody molecule comprises a heavy chain variable region (VH) and a light chain variable region (VL) described in Table 1 or 5. In an embodiment, the antibody molecule comprises one, two, or three CDRs of a heavy chain variable region (VH) described in Table 1 or 5. In an embodiment, the antibody molecule comprises one, two, or three CDRs of a light chain variable region (VL) described in Table 1 or 5. In an embodiment, the antibody molecule comprises one, two, or three CDRs of a heavy chain variable region (VH) described in Table 1 or 5, and one, two, or three CDRs of a light chain variable region (VL) described in Table 1 or 5. In an embodiment, the antibody molecule comprises two heavy chain variable regions and two light chain variable regions. In an embodiment, the antibody molecule is a Fab, F(ab')2, Fv, Fd, or a single chain Fv fragment (scFv).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3530 (e.g., SEQ ID NO: 61); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3530 (e.g., SEQ ID NO: 62); or (ii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3530 (e.g., SEQ ID NO: 63).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3530 (e.g., SEQ ID NO: 67); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3530 (e.g., SEQ ID NO: 45); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3530 (e.g., SEQ ID NO: 46).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3530 (e.g., SEQ ID NO: 61); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3530 (e.g., SEQ ID NO: 62); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3530 (e.g., SEQ ID NO: 63), and
(ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3530 (e.g., SEQ ID NO: 67); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3530 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3530 (e.g., SEQ ID NO: 46).

In an embodiment, the antibody molecule comprises: (i) a VH comprising: an HCDR1 comprising the amino acid sequence of the HCDR1 of monoclonal antibody 3530 (e.g., SEQ ID NO: 61); an HCDR2 comprising the amino acid sequence of the HCDR2 of monoclonal antibody 3530 (e.g., SEQ ID NO: 62); and an HCDR3 comprising the amino acid sequence of the HCDR3 of monoclonal antibody 3530 (e.g., SEQ ID NO: 63), and (ii) a VL comprising: an LCDR1 comprising the amino acid sequence of the LCDR1 of monoclonal antibody 3530 (e.g., SEQ ID NO: 67); an LCDR2 comprising the amino acid sequence of the LCDR2 of monoclonal antibody 3530 (e.g., SEQ ID NO: 45); and an LCDR3 comprising the amino acid sequence of the LCDR3 of monoclonal antibody 3530 (e.g., SEQ ID NO: 46).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3530 (e.g., SEQ ID NO: 64); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3530 (e.g., SEQ ID NO: 65); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3530 (e.g., SEQ ID NO: 63).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3530 (e.g., SEQ ID NO: 67); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3530 (e.g., SEQ ID NO: 45); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3530 (e.g., SEQ ID NO: 46).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3530 (e.g., SEQ ID NO: 64); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3530 (e.g., SEQ ID NO: 65); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3530 (e.g., SEQ ID NO: 63), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3530 (e.g., SEQ ID NO: 67); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3530 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3530 (e.g., SEQ ID NO: 46).

In an embodiment, the antibody molecule comprises: (i) a VH comprising: an HCDR1 comprising the amino acid sequence of the HCDR1 of monoclonal antibody 3530 (e.g., SEQ ID NO: 64); an HCDR2 comprising the amino acid sequence of the HCDR2 of monoclonal antibody 3530 (e.g., SEQ ID NO: 65); and an HCDR3 comprising the amino acid sequence of the HCDR3 of monoclonal antibody 3530 (e.g., SEQ ID NO: 63), and (ii) a VL comprising: an LCDR1 comprising the amino acid sequence of the LCDR1 of monoclonal antibody 3530 (e.g., SEQ ID NO: 67); an LCDR2 comprising the amino acid sequence of the LCDR2 of monoclonal antibody 3530 (e.g., SEQ ID NO: 45); and an LCDR3 comprising the amino acid sequence of the LCDR3 of monoclonal antibody 3530 (e.g., SEQ ID NO: 46).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3530 (e.g., SEQ ID NO: 66). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3530 (e.g., SEQ ID NO: 70).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3530 (e.g., SEQ ID NO: 66); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3530 (e.g., SEQ ID NO: 70). In an embodiment, the antibody molecule comprises: (i) a VH comprising the amino acid sequence of the VH of monoclonal antibody 3530 (e.g., SEQ ID NO: 66); and (ii) a VL comprising the amino acid sequence of the VL of monoclonal antibody 3530 (e.g., SEQ ID NO: 70).

In an embodiment the antibody molecule is monoclonal antibody 3530. In an embodiment, the antibody molecule is a humanized monoclonal antibody 3530.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3525 (e.g., SEQ ID NO: 61); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3525 (e.g., SEQ ID NO: 62); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3525 (e.g., SEQ ID NO: 63).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3525 (e.g., SEQ ID NO: 44); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3525 (e.g., SEQ ID NO: 45); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3525 (e.g., SEQ ID NO: 46).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3525 (e.g., SEQ ID NO: 61); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3525 (e.g., SEQ ID NO: 62); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3525 (e.g., SEQ ID NO: 63), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3525 (e.g., SEQ ID NO: 44); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3525 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3525 (e.g., SEQ ID NO: 46).

In an embodiment, the antibody molecule comprises: (i) a VH comprising three heavy chain complementarity determining regions (HCDR1, HCDR2, and HCDR3), wherein the heavy chain variable region comprises: an HCDR1 comprises the amino acid sequence of the HCDR1 of monoclonal antibody 3525 (e.g., SEQ ID NO: 61); an HCDR2 comprising the amino acid sequence of the HCDR2 of monoclonal antibody 3525 (e.g., SEQ ID NO: 62); and an HCDR3 comprising the amino acid sequence of the HCDR3 of monoclonal antibody 3525 (e.g., SEQ ID NO: 63), and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of the LCDR1 of monoclonal antibody 3525 (e.g., SEQ ID NO: 44); an LCDR2 comprising the amino acid sequence of the LCDR2 of monoclonal antibody 3525 (e.g., SEQ ID NO: 45); and an LCDR3 comprising the amino acid sequence of the LCDR3 of monoclonal antibody 3525 (e.g., SEQ ID NO: 46).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3525 (e.g., SEQ ID NO: 64); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3525 (e.g., SEQ ID NO: 65); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3525 (e.g., SEQ ID NO: 63).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3525 (e.g., SEQ ID NO: 44); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3525 (e.g., SEQ ID NO: 45); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3525 (e.g., SEQ ID NO: 46).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3525 (e.g., SEQ ID NO: 64); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3525 (e.g., SEQ ID NO: 65); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3525 (e.g., SEQ ID NO: 63), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3525 (e.g., SEQ ID NO: 44); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3525 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3525 (e.g., SEQ ID NO: 46).

In an embodiment, the antibody molecule comprises: (i) a VH comprising: an HCDR1 comprises the amino acid sequence of the HCDR1 of monoclonal antibody 3525 (e.g., SEQ ID NO: 64); an HCDR2 comprising the amino acid sequence of the HCDR2 of monoclonal antibody 3525 (e.g., SEQ ID NO: 65); and an HCDR3 comprising the amino acid sequence of the HCDR3 of monoclonal antibody 3525 (e.g., SEQ ID NO: 63), and (ii) a VL comprising: an LCDR1 comprising the amino acid sequence of the LCDR1 of monoclonal antibody 3525 (e.g., SEQ ID NO: 44); an LCDR2 comprising the amino acid sequence of the LCDR2 of monoclonal antibody 3525 (e.g., SEQ ID NO: 45); and an LCDR3 comprising the amino acid sequence of the LCDR3 of monoclonal antibody 3525 (e.g., SEQ ID NO: 46).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3525 (e.g., SEQ ID NO: 66). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3525 (e.g., SEQ ID NO: 50).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3525 (e.g., SEQ ID NO: 66); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3525 (e.g., SEQ ID NO: 50). In an embodiment, the antibody molecule comprises: (i) a VH comprising the amino acid sequence of the VH of monoclonal antibody 3525 (e.g., SEQ ID NO: 66);

and (ii) a VL comprising the amino acid sequence of the VL of monoclonal antibody 3525 (e.g., SEQ ID NO: 50).

In an embodiment the antibody molecule is monoclonal antibody 3525. In an embodiment, the antibody molecule is a humanized monoclonal antibody 3525.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3833 (e.g., SEQ ID NO: 113); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3833 (e.g., SEQ ID NO: 114); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3833 (e.g., SEQ ID NO: 115).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3833 (e.g., SEQ ID NO: 116); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3833 (e.g., SEQ ID NO: 117); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3833 (e.g., SEQ ID NO: 118).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3833 (e.g., SEQ ID NO: 113); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3833 (e.g., SEQ ID NO: 114); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3833 (e.g., SEQ ID NO: 115), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3833 (e.g., SEQ ID NO: 116); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3833 (e.g., SEQ ID NO: 117); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3833 (e.g., SEQ ID NO: 118).

In an embodiment, the antibody molecule comprises: (i) a VH comprising three heavy chain complementarity determining regions (HCDR1, HCDR2, and HCDR3), wherein the heavy chain variable region comprises: an HCDR1 comprises the amino acid sequence of the HCDR1 of monoclonal antibody 3833 (e.g., SEQ ID NO: 113); an HCDR2 comprising the amino acid sequence of the HCDR2 of monoclonal antibody 3833 (e.g., SEQ ID NO: 114); and an HCDR3 comprising the amino acid sequence of the HCDR3 of monoclonal antibody 3833 (e.g., SEQ ID NO: 115), and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of the LCDR1 of monoclonal antibody 3833 (e.g., SEQ ID NO: 116); an LCDR2 comprising the amino acid sequence of the LCDR2 of monoclonal antibody 3833 (e.g., SEQ ID NO: 117); and an LCDR3 comprising the amino acid sequence of the LCDR3 of monoclonal antibody 3833 (e.g., SEQ ID NO: 118).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3833 (e.g., SEQ ID NO: 119); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3833 (e.g., SEQ ID NO: 120); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3833 (e.g., SEQ ID NO: 115).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3833 (e.g., SEQ ID NO: 116); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3833 (e.g., SEQ ID NO: 117); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3833 (e.g., SEQ ID NO: 118).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3833 (e.g., SEQ ID NO: 119); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3833 (e.g., SEQ ID NO: 120); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3833 (e.g., SEQ ID NO: 115), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3833 (e.g., SEQ ID NO: 116); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3833 (e.g., SEQ ID NO: 117); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3833 (e.g., SEQ ID NO: 118).

In an embodiment, the antibody molecule comprises: (i) a VH comprising: an HCDR1 comprises the amino acid sequence of the HCDR1 of monoclonal antibody 3833 (e.g., SEQ ID NO: 119); an HCDR2 comprising the amino acid sequence of the HCDR2 of monoclonal antibody 3833 (e.g., SEQ ID NO: 120); and an HCDR3 comprising the amino acid sequence of the HCDR3 of monoclonal antibody 3833 (e.g., SEQ ID NO: 115), and (ii) a VL comprising: an LCDR1 comprising the amino acid sequence of the LCDR1 of monoclonal antibody 3833 (e.g., SEQ ID NO: 116); an LCDR2 comprising the amino acid sequence of the LCDR2 of monoclonal antibody 3833 (e.g., SEQ ID NO: 117); and an LCDR3 comprising the amino acid sequence of the LCDR3 of monoclonal antibody 3833 (e.g., SEQ ID NO: 118).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3833 (e.g., SEQ ID NO: 121). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3833 (e.g., SEQ ID NO: 122).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3833 (e.g., SEQ ID NO: 122). In an embodiment, the antibody molecule comprises: (i) a VH comprising the amino acid sequence of the VH of monoclonal antibody 3833 (e.g., SEQ ID NO: 121); and (ii) a VL comprising the amino acid sequence of the VL of monoclonal antibody 3833 (e.g., SEQ ID NO: 122).

In an embodiment the antibody molecule is monoclonal antibody 3833. In an embodiment, monoclonal antibody 3833 is a humanized monoclonal antibody 3833. In an embodiment, the antibody molecule comprises a VH comprising the amino acid sequence of any of SEQ ID NO: 246-250, a VL comprising the amino acid sequence of any of SEQ ID NO: 251-253, or both.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3631 (e.g., SEQ ID NO: 123); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3631 (e.g., SEQ ID NO: 124); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3631 (e.g., SEQ ID NO: 125).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3631 (e.g., SEQ ID NO: 126); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3631 (e.g., SEQ ID NO: 127); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3631 (e.g., SEQ ID NO: 128).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3631 (e.g., SEQ ID NO: 123); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3631 (e.g., SEQ ID NO: 124); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3631 (e.g., SEQ ID NO: 125), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3631 (e.g., SEQ ID NO: 126); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3631 (e.g., SEQ ID NO: 127); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3631 (e.g., SEQ ID NO: 128).

In an embodiment, the antibody molecule comprises: (i) a VH comprising three heavy chain complementarity determining regions (HCDR1, HCDR2, and HCDR3), wherein the heavy chain variable region comprises: an HCDR1 comprises the amino acid sequence of the HCDR1 of monoclonal antibody 3631 (e.g., SEQ ID NO: 123); an HCDR2 comprising the amino acid sequence of the HCDR2 of monoclonal antibody 3631 (e.g., SEQ ID NO: 124); and an HCDR3 comprising the amino acid sequence of the HCDR3 of monoclonal antibody 3631 (e.g., SEQ ID NO: 125), and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of the LCDR1 of monoclonal antibody 3631 (e.g., SEQ ID NO: 126); an LCDR2 comprising the amino acid sequence of the LCDR2 of monoclonal antibody 3631 (e.g., SEQ ID NO: 127); and an LCDR3 comprising the amino acid sequence of the LCDR3 of monoclonal antibody 3631 (e.g., SEQ ID NO: 128).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3631 (e.g., SEQ ID NO: 129); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3631 (e.g., SEQ ID NO: 130); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3631 (e.g., SEQ ID NO: 125).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3631 (e.g., SEQ ID NO: 126); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3631 (e.g., SEQ ID NO: 127); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3631 (e.g., SEQ ID NO: 128).

In an embodiment, the antibody molecule comprises: (i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3631 (e.g., SEQ ID NO: 129); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3631 (e.g., SEQ ID NO: 130); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3631 (e.g., SEQ ID NO: 125), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3631 (e.g., SEQ ID NO: 126); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3631 (e.g., SEQ ID NO: 127); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3631 (e.g., SEQ ID NO: 128).

In an embodiment, the antibody molecule comprises: (i) a VH comprising: an HCDR1 comprises the amino acid sequence of the HCDR1 of monoclonal antibody 3631 (e.g., SEQ ID NO: 129); an HCDR2 comprising the amino acid sequence of the HCDR2 of monoclonal antibody 3631 (e.g., SEQ ID NO: 130); and an HCDR3 comprising the amino acid sequence of the HCDR3 of monoclonal antibody 3631 (e.g., SEQ ID NO: 125), and (ii) a VL comprising: an LCDR1 comprising the amino acid sequence of the LCDR1 of monoclonal antibody 3631 (e.g., SEQ ID NO: 126); an LCDR2 comprising the amino acid sequence of the LCDR2 of monoclonal antibody 3631 (e.g., SEQ ID NO: 127); and an LCDR3 comprising the amino acid sequence of the LCDR3 of monoclonal antibody 3631 (e.g., SEQ ID NO: 128).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3631 (e.g., SEQ ID NO: 131). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3631 (e.g., SEQ ID NO: 132).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3631 (e.g., SEQ ID NO: 131); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3631 (e.g., SEQ ID NO: 132). In an embodiment, the antibody molecule comprises: (i) a VH comprising the amino acid sequence of the VH of monoclonal antibody 3631 (e.g., SEQ ID NO: 131); and (ii) a VL comprising the amino acid sequence of the VL of monoclonal antibody 3631 (e.g., SEQ ID NO: 132).

In an embodiment the antibody molecule is monoclonal antibody 3631. In an embodiment, the antibody molecule is a humanized monoclonal antibody 3631.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3732 (e.g., SEQ ID NO: 133); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3732 (e.g., SEQ ID NO: 134); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3732 (e.g., SEQ ID NO: 135).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3732 (e.g., SEQ ID NO: 136); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3732 (e.g., SEQ ID NO: 127); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3732 (e.g., SEQ ID NO: 137).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3732 (e.g., SEQ ID NO: 133); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3732 (e.g., SEQ ID NO: 134); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3732 (e.g., SEQ ID NO: 135), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3732 (e.g., SEQ ID NO: 136); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3732 (e.g., SEQ ID NO: 127); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3732 (e.g., SEQ ID NO: 137).

In an embodiment, the antibody molecule comprises: (i) a VH comprising three heavy chain complementarity determining regions (HCDR1, HCDR2, and HCDR3), wherein the heavy chain variable region comprises: an HCDR1 comprises the amino acid sequence of the HCDR1 of monoclonal antibody 3732 (e.g., SEQ ID NO: 133); an HCDR2 comprising the amino acid sequence of the HCDR2 of monoclonal antibody 3732 (e.g., SEQ ID NO: 134); and an HCDR3 comprising the amino acid sequence of the HCDR3 of monoclonal antibody 3732 (e.g., SEQ ID NO: 135), and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of the LCDR1 of monoclonal antibody 3732 (e.g., SEQ ID NO: 136); an LCDR2 comprising the amino acid sequence of the LCDR2 of monoclonal antibody 3732 (e.g., SEQ ID NO: 127); and an LCDR3 comprising the amino acid sequence of the LCDR3 of monoclonal antibody 3732 (e.g., SEQ ID NO: 137).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3732 (e.g., SEQ ID NO: 138); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3732 (e.g., SEQ ID NO: 139); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3732 (e.g., SEQ ID NO: 135).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3732 (e.g., SEQ ID NO: 136); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3732 (e.g., SEQ ID NO: 127); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3732 (e.g., SEQ ID NO: 137).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3732 (e.g., SEQ ID NO: 138); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3732 (e.g., SEQ ID NO: 139); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3732 (e.g., SEQ ID NO: 135), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3732 (e.g., SEQ ID NO: 136); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3732 (e.g., SEQ ID NO: 127); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3732 (e.g., SEQ ID NO: 137).

In an embodiment, the antibody molecule comprises: (i) a VH comprising: an HCDR1 comprises the amino acid sequence of the HCDR1 of monoclonal antibody 3732 (e.g., SEQ ID NO: 138); an HCDR2 comprising the amino acid sequence of the HCDR2 of monoclonal antibody 3732 (e.g., SEQ ID NO: 139); and an HCDR3 comprising the amino acid sequence of the HCDR3 of monoclonal antibody 3732 (e.g., SEQ ID NO: 135), and (ii) a VL comprising: an LCDR1 comprising the amino acid sequence of the LCDR1 of monoclonal antibody 3732 (e.g., SEQ ID NO: 136); an LCDR2 comprising the amino acid sequence of the LCDR2 of monoclonal antibody 3732 (e.g., SEQ ID NO: 127); and an LCDR3 comprising the amino acid sequence of the LCDR3 of monoclonal antibody 3732 (e.g., SEQ ID NO: 137).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3732 (e.g., SEQ ID NO: 140). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3732 (e.g., SEQ ID NO: 141).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3732 (e.g., SEQ ID NO: 140); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3732 (e.g., SEQ ID NO: 141). In an embodiment, the antibody molecule comprises: (i) a VH comprising the amino acid sequence of the VH of monoclonal antibody 3732 (e.g., SEQ ID NO: 140); and (ii) a VL comprising the amino acid sequence of the VL of monoclonal antibody 3732 (e.g., SEQ ID NO: 141).

In an embodiment the antibody molecule is monoclonal antibody 3732. In an embodiment, monoclonal antibody 3732 is a humanized monoclonal antibody 3732.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540, 4540-063, or 4540-033 (e.g., SEQ ID NO: 154); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540, 4540-063, or 4540-033 (e.g., SEQ ID NO: 155); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540, 4540-063, or 4540-033 (e.g., SEQ ID NO: 156).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540, 4540-063, or 4540-033 (e.g., SEQ ID NO: 158).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540, 4540-063, or 4540-033 (e.g., SEQ ID NO: 154); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540, 4540-063, or 4540-033 (e.g., SEQ ID NO: 155); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540, 4540-063, or 4540-033 (e.g., SEQ ID NO: 156), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540, 4540-063, or 4540-033 (e.g., SEQ ID NO: 158).

In an embodiment, the antibody molecule comprises: (i) a VH comprising three heavy chain complementarity determining regions (HCDR1, HCDR2, and HCDR3), wherein the heavy chain variable region comprises: an HCDR1 comprises the amino acid sequence of the HCDR1 of monoclonal antibody 4540, 4540-063, or 4540-033 (e.g., SEQ ID NO: 154); an HCDR2 comprising the amino acid sequence of the HCDR2 of monoclonal antibody 4540, 4540-063, or 4540-033 (e.g., SEQ ID NO: 155); and an HCDR3 comprising the amino acid sequence of the HCDR3 of monoclonal antibody 4540, 4540-063, or 4540-033 (e.g., SEQ ID NO: 156), and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); an LCDR2 comprising the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); and an LCDR3 comprising the amino acid sequence of the LCDR3 of monoclonal antibody 4540, 4540-063, or 4540-033 (e.g., SEQ ID NO: 158).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540 (e.g., SEQ ID NO: 159), 4540-063 (e.g., SEQ ID NO: 276), or 4540-033 (e.g., SEQ ID NO: 159); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540 (e.g., SEQ ID NO: 160), 4540-063 (e.g., SEQ ID NO: 277), or 4540-033 (e.g., SEQ ID NO: 278); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540, 4540-063, or 4540-033 (e.g., SEQ ID NO: 156).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540, 4540-063, or 4540-033 (e.g., SEQ ID NO: 158).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540 (e.g., SEQ ID NO: 159), 4540-063 (e.g., SEQ ID NO: 276), or 4540-033 (e.g., SEQ ID NO: 159); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540 (e.g., SEQ ID NO: 160), 4540-063 (e.g., SEQ ID NO: 277), or 4540-033 (e.g., SEQ ID NO: 278); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540, 4540-063, or 4540-033 (e.g., SEQ ID NO: 156), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540, 4540-063, or 4540-033 (e.g., SEQ ID NO: 158).

In an embodiment, the antibody molecule comprises: (i) a VH comprising one, two, or all of the following: an HCDR1 comprising the amino acid sequence of the HCDR1 of monoclonal antibody 4540 (e.g., SEQ ID NO: 159), 4540-063 (e.g., SEQ ID NO: 276), or 4540-033 (e.g., SEQ ID NO: 159); an HCDR2 comprising the amino acid sequence of the HCDR2 of monoclonal antibody 4540 (e.g., SEQ ID NO: 160), 4540-063 (e.g., SEQ ID NO: 277), or 4540-033 (e.g., SEQ ID NO: 278); or an HCDR3 comprising the amino acid sequence of the HCDR3 of monoclonal antibody 4540, 4540-063, or 4540-033 (e.g., SEQ ID NO: 156), and (ii) a VL comprising one, two, or all of the following: an LCDR1 comprising the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); an LCDR2 comprising the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); or an LCDR3 comprising the amino acid sequence of the LCDR3 of monoclonal antibody 4540, 4540-063, or 4540-033 (e.g., SEQ ID NO: 158).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4540 (e.g., SEQ ID NO: 161), 4540-063 (e.g., SEQ ID NO: 258), or 4540-033 (e.g., SEQ ID NO: 256). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4540 (e.g., SEQ ID NO: 162), 4540-063 (e.g., SEQ ID NO: 261), or 4540-033 (e.g., SEQ ID NO: 261).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4540 (e.g., SEQ ID NO: 161), 4540-063 (e.g., SEQ ID NO: 258), or 4540-033 (e.g., SEQ ID NO: 256); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4540 (e.g., SEQ ID NO: 162), 4540-063 (e.g., SEQ ID NO: 261), or 4540-033 (e.g., SEQ ID NO: 261). In an embodiment, the antibody molecule comprises: (i) a VH comprising the amino acid sequence of the VH of monoclonal antibody 4540 (e.g., SEQ ID NO: 161), 4540-063 (e.g., SEQ ID NO: 258), or 4540-033 (e.g., SEQ ID NO: 256); and (ii) a VL comprising the amino acid sequence of the VL of monoclo-nal antibody 4540 (e.g., SEQ ID NO: 162), 4540-063 (e.g., SEQ ID NO: 261), or 4540-033 (e.g., SEQ ID NO: 261).

In an embodiment, the antibody molecule is monoclonal antibody 4540, 4540-063, or 4540-033. In an embodiment, monoclonal antibody 4540 is a humanized monoclonal antibody 4540 (e.g., antibodies 4540-063 or 4540-033). In an embodiment, the antibody molecule comprises a VH comprising the amino acid sequence of any of SEQ ID NO: 254-258, a VL comprising the amino acid sequence of any of SEQ ID NO: 259-261, or both.

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or more, residues within a region of human APRIL as defined in any of Tables 3-4 or 7-8.

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or more, residues within a region of human APRIL as defined in Table 3. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 3. In an embodiment, the antibody molecule binds, or substantially binds, to an epitope that overlaps an epitope that comprises or consists of all of the human APRIL residues from Table 3. In an embodiment, the antibody molecule binds, or substantially binds, to an epitope that comprises APRIL residues from two monomers, e.g., one or more residues from monomer A and monomer B as shown in Table 3.

In an embodiment, the antibody molecule binds, or substantially binds, to one or more, e.g., 2, 3, 4, 5, 6, 7, 8, 9, 10, or more, residues within a region of human APRIL as defined in Table 4. In an embodiment, the antibody molecule binds, or substantially binds, to an epitope that comprises or consists of one or more, e.g., 2, 3, 4, 5, 6, 7, 8, 9, 10, or all, of the human APRIL residues from Table 4. In an embodiment, the antibody molecule binds, or substantially binds, to an epitope that overlaps an epitope that comprises or consists of all of the human APRIL residues from Table 4. In an embodiment, the antibody molecule binds, or substantially binds, to an epitope that comprises one or more APRIL residues from the C-D loop (e.g., the loop connecting β-sheets C and D), the G-H loop (e.g., the loop connecting β-sheets G and H), or both.

In an embodiment, the antibody molecule binds, or substantially binds, to one or more, e.g., 2, 3, 4, 5, 6, 7, 8, 9, 10, 11, 12, 13, 14, 15, 16, 17, or all, residues within a region of human APRIL as defined in Table 7. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, or all, of the human APRIL residues from Table 7. In an embodiment, the antibody molecule binds, or substantially binds, to an epitope that overlaps an epitope that comprises or consists of all of the human APRIL residues from Table 7.

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or all, residues within a region of human APRIL as defined in Table 8. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 8. In an embodiment, the antibody molecule binds, or substantially binds, to an epitope that overlaps an epitope that comprises or consists of all of the human APRIL residues from Table 8.

In an embodiment, the antibody molecule binds, or substantially binds, to one or more (e.g., 2, 3, 4, 5, 6, 7, 8, 9, or all) residues of human APRIL from positions 105-114 and/or one or more (e.g., 2, 3, 4, 5, 6, 7, 8, 9, or all) residues of mouse APRIL from positions 96-105. In an embodiment, the antibody molecule does not bind, or does not substantially bind, to one, two or all of Asp129, Arg233, or His203 of human APRIL. In an embodiment, the epitope is a conformational epitope.

In an embodiment, binding of the antibody molecule to APRIL (e.g., human APRIL) inhibits, or substantially inhibits, the binding of the CRD2 domain of TACI (e.g., human TACI) to APRIL (e.g., human APRIL). In another embodiment, binding of the antibody molecule to human APRIL, inhibits, or substantially inhibits, the binding of human TACI, to one or more, e.g., 2, 3, 4, 5, 6, 7, 8, 9, 10, 11, 12, 13, 14, 15, 16, 17, 18, 19, 20, 21, 22, 23, 24, 25, or all, of the APRIL residues from Table 3. In yet another embodiment, binding of the antibody molecule to human APRIL, inhibits, or substantially inhibits, the binding of human TACI, to one or more, e.g., 2, 3, 4, 5, 6, 7, 8, 9, 10, or all, of the human APRIL residues from Table 4. In still another embodiment, binding of the antibody molecule to human APRIL, inhibits, or substantially inhibits, the binding of human TACI, to one or more, e.g., 2, 3, 4, 5, 6, 7, 8, 9, 10, 11, 12, 13, 14, 15, 16, 17, or all, of the human APRIL residues from Table 7. In still another embodiment, binding of the antibody molecule to human APRIL, inhibits, or substantially inhibits, the binding of human TACI, to one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 8. In another embodiment, binding of the antibody molecule to human APRIL inhibits, or substantially inhibits, the binding of human BCMA, to one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 8.

In an aspect, the disclosure features an antibody molecule that binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or more, residues within a region of human APRIL as defined in any of Tables 3-4 or 7-8.

In an embodiment, the anti-APRIL antibody molecule binds, or substantially binds, to an epitope that comprises or consists of one or more, e.g., 2, 3, 4, 5, 6, 7, 8, 9, 10, 11, 12, 13, 14, 15, 16, 17, 18, 19, 20, 21, 22, 23, 24, 25, or more, of the human APRIL residues from any of Tables 3-4 or 7-8. In an embodiment, the antibody molecule binds, or substantially binds, to a conformational epitope.

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or more, residues within a region of human APRIL as defined in Table 3. In an embodiment, the anti-APRIL antibody molecule binds, or substantially binds, to an epitope that comprises or consists of one or more (e.g., 2, 3, 4, 5, 6, 7, 8, 9, 10, 11, 12, 13, 14, 15, 16, 17, 18, 19, 20, 21, 22, 23, 24, 25, or all) of the human APRIL residues from Table 3. In an embodiment, the antibody molecule binds, or substantially binds, to an epitope that comprises APRIL residues from two monomers, e.g., one or more residues from monomer A and monomer B as shown in Table 3.

In an embodiment, the antibody molecule binds, or substantially binds, to one or more, e.g., 2, 3, 4, 5, 6, 7, 8, 9, 10, or all, residues within a region of human APRIL as defined in Table 4. In an embodiment, the epitope comprises consists of one or more, e.g., 2, 3, 4, 5, 6, 7, 8, 9, 10, or all of the APRIL residues from Table 4. In an embodiment, the epitope comprises or consists of one or more APRIL residues from the C-D loop (e.g., the loop connecting β-sheets C and D), the G-H loop (e.g., the loop connecting β-sheets G and H), or both.

In an embodiment, the antibody molecule binds, or substantially binds, to one or more, e.g., 2, 3, 4, 5, 6, 7, 8, 9, 10, 11, 12, 13, 14, 15, 16, 17, or all, residues within a region of human APRIL as defined in Table 7. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, or all, of the human APRIL residues from Table 7. In an embodiment, the antibody molecule binds, or substantially binds, to an epitope that overlaps an epitope that comprises or consists of all of the human APRIL residues from Table 7.

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or all, residues within a region of human APRIL as defined in Table 8. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 8. In an embodiment, the antibody molecule binds, or substantially binds, to an epitope that overlaps an epitope that comprises or consists of all of the human APRIL residues from Table 8.

In an embodiment, the antibody molecule binds, or substantially binds, to one or more (e.g., 2, 3, 4, 5, 6, 7, 8, 9, or all) residues of human APRIL from positions 105-114 and/or one or more (e.g., 2, 3, 4, 5, 6, 7, 8, 9, or all) residues of mouse APRIL from positions 96-105. In an embodiment, the antibody molecule does not bind, or does not substantially bind, to one, two or all of Asp129, Arg233, or His203 of human APRIL.

In an embodiment, the antibody molecule binds, or substantially binds, to an epitope that comprises or consists of one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or all) of human APRIL residues from Table 6.

In an embodiment, the antibody molecule binds, or substantially binds, to one or more (e.g., 2, 3, 4, 5, or all) of the amino acid residues of human APRIL chosen from V174, F176, Q190, R195, R206, or Y208. In an embodiment, the antibody molecule does not binds, or does not substantially bind, to one or more (e.g., 2, 3, or all) of the amino acid residues of human APRIL chosen from V181, S226, I228, or N237. In an embodiment, the antibody molecule binds, or substantially binds, to one or more (e.g., 2, 3, or all) of the amino acid residues of human APRIL chosen from F176, V181, Q190, or I228. In an embodiment, the antibody molecule does not bind, or does not substantially bind, to one or both of the amino acid residues of human APRIL chosen from Y208 or N237. In an embodiment, the antibody molecule binds, or substantially binds, to one or more (e.g., 2, or all) of the amino acid residues of human APRIL chosen from V174, R206, or Y208. In an embodiment, the antibody molecule does not bind, or does not substantially bind, to one or more (e.g., 2, 3, or all) of the amino acid residues of human APRIL chosen from F176, V181, Q190, or N237.

In an embodiment, the antibody molecule binds, or substantially binds, to human APRIL. In an embodiment, the antibody molecule binds, or substantially binds, to human APRIL and mouse APRIL. In an embodiment, the antibody molecule binds, or substantially binds to, human APRIL, but does not bind to mouse APRIL, or binds to mouse APRIL with low affinity.

In an embodiment, the antibody molecule binds, or substantially binds, to human APRIL at an $EC_{50}$ of 20 nM or less, e.g., 10 nM or less, 9 nM or less or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, e.g., between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule binds, or substantially binds, to mouse APRIL at an $EC_{50}$ of 100 nM or less, e.g., 80 nM or less, 60 nM or less, 40 nM or less, 20 nM or less, e.g., 10 nM or less, e.g., 9 nM or less 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 100 nM, e.g., between 0.001 nM and 50 nM, between 0.01 nM and 20 nM, between 0.1 nM and 20 nM, e.g., between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule does not bind to mouse APRIL, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL, mouse APRIL, or both) to TACI (e.g., human TACI, mouse TACI, or both). In an embodiment, the antibody molecule inhibits, or substantially inhibits, binding of APRIL (e.g., human APRIL, mouse APRIL, or both) to TACI (e.g., human TACI, mouse TACI, or both), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In an embodiment, binding of the antibody molecule to APRIL (e.g., human APRIL) inhibits, or substantially inhibits, the binding of the CRD2 domain of TACI (e.g., human TACI) to APRIL (e.g., human APRIL). In an embodiment, binding of the antibody molecule to human APRIL inhibits, or substantially inhibits, the binding of human TACI, to one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 3. In an embodiment, binding of the antibody molecule to human APRIL, inhibits, or substantially inhibits, the binding of human TACI to one or more, e.g., 2, 3, 4, 5, 6, 7, 8, 9, 10, or all, of the human APRIL residues from Table 4. In an embodiment, binding of the antibody molecule to human APRIL inhibits, or substantially inhibits, the binding of human TACI, to one or more, e.g., 2, 3, 4, 5, 6, 7, 8, 9, 10, 11, 12, 13, 14, 15, 16, 17, or all, of the human APRIL residues from Table 7. In an embodiment, binding of the antibody molecule to human APRIL inhibits, or substantially inhibits, the binding of human TACI, to one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 8. In another embodiment, binding of the antibody molecule to human APRIL inhibits, or substantially inhibits, the binding of human BCMA, to one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 8.

In an embodiment, the antibody molecule inhibits, or substantially inhibits, binding of APRIL (e.g., human APRIL, mouse APRIL, or both) to BCMA (e.g., human BCMA, mouse BCMA, or both). In an embodiment, the antibody molecule inhibits, or substantially inhibits, binding of APRIL (e.g., human APRIL, mouse APRIL, or both) to BCMA (e.g., human BCMA, mouse BCMA, or both), e.g., at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In an embodiment, the antibody molecule is a synthetic antibody molecule. In an embodiment, the antibody molecule is an isolated antibody molecule. In an embodiment, the antibody molecule is an IgG antibody molecule, e.g., comprising a heavy chain constant region of IgG, e.g., chosen from IgG1, IgG2 (e.g., IgG2a), IgG3, or IgG4, e.g., IgG2 or IgG4. In an embodiment, the antibody molecule is an IgG1 antibody molecule. In an embodiment, the antibody molecule is an IgG2 antibody molecule. In an embodiment, the antibody molecule comprises a light chain constant region of kappa or lambda light chain.

In an embodiment, the antibody molecule comprises an Fc region. In an embodiment, the Fc region comprises one or more mutations located at the interface between the CH2 and CH3 domains (e.g., to increase the binding affinity to neonatal receptor FcRn and/or the half-life of the antibody molecule). In an embodiment, the Fc region comprises one or more mutations, e.g., one or more (e.g., 2, 3, 4, 6 or all) mutations chosen from T250Q, M252Y, S254T, T256E, M428L, H433K, N434F, or any combination thereof, of IgG1. In an embodiment, the Fc region comprises one or more mutations at positions 233-236 or 322 of human IgG1 or IgG2, or one or more substitutions at positions 327, 330 or 331 of human IgG4 (e.g., to reduce complement-dependent cytotoxicity (CDC)). In an embodiment, the Fc region comprises one or more (e.g., 2, 3, 4, 6 7 or all) mutations chosen from E233P, L234V, L235A, G236, K322A, A327G, A330S, P331S, or any combination thereof.

In an embodiment, the antibody molecule is a humanized antibody molecule, e.g., as described in Table 1 or 5, e.g., comprising one or more framework regions derived from human framework germline sequence.

In an embodiment, the antibody molecule comprises two heavy chain variable regions and two light chain variable regions. In an embodiment, the antibody molecule is a Fab, F(ab')2, Fv, Fd, or a single chain Fv fragment (scFv).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2218 (e.g., SEQ ID NO: 1); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2218 (e.g., SEQ ID NO: 2); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2218 (e.g., SEQ ID NO: 3).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2218 (e.g., SEQ ID NO: 4); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2218 (e.g., SEQ ID NO: 5); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2218 (e.g., SEQ ID NO: 6).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2218 (e.g., SEQ ID NO: 1); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2218 (e.g., SEQ ID NO: 2); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2218 (e.g., SEQ ID NO: 3), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2218 (e.g., SEQ ID NO: 4); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2218 (e.g., SEQ ID NO: 5); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2218 (e.g., SEQ ID NO: 6).

In an embodiment, the antibody molecule comprises: (i) a VH comprising: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2218 (e.g., SEQ ID NO: 1); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2218 (e.g., SEQ ID NO: 2); and an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2218 (e.g., SEQ ID NO: 3), and (ii) a VL comprising: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2218 (e.g., SEQ ID NO: 4); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2218 (e.g., SEQ ID NO: 5); and an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2218 (e.g., SEQ ID NO: 6).

In an embodiment, the antibody molecule comprises a VH comprising one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2218 (e.g., SEQ ID NO: 7); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2218 (e.g., SEQ ID NO: 8); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2218 (e.g., SEQ ID NO: 3).

In an embodiment, the antibody molecule comprises a VL comprising one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2218 (e.g., SEQ ID NO: 4); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2218 (e.g., SEQ ID NO: 5); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2218 (e.g., SEQ ID NO: 6).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2218 (e.g., SEQ ID NO: 7); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2218 (e.g., SEQ ID NO: 8); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2218 (e.g., SEQ ID NO: 3), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2218 (e.g., SEQ ID NO: 4); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2218 (e.g., SEQ ID NO: 5); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2218 (e.g., SEQ ID NO: 6).

In an embodiment, the antibody molecule comprises: (i) a VH comprising: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2218 (e.g., SEQ ID NO: 7); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2218 (e.g., SEQ ID NO: 8); and an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2218 (e.g., SEQ ID NO: 3), and (ii) a VL comprising: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2218 (e.g., SEQ ID NO: 4); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2218 (e.g., SEQ ID NO: 5); and an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2218 (e.g., SEQ ID NO: 6).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2218 (e.g., SEQ ID NO: 9). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2218 (e.g., SEQ ID NO: 10).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2218 (e.g., SEQ ID NO: 9); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2218 (e.g., SEQ ID NO: 10). In an embodiment, the antibody molecule comprises: (i) a VH comprising the amino acid sequence of the VH of monoclonal antibody 2218 (e.g., SEQ ID NO: 9); and (ii) a VL comprising the amino acid sequence of the VL of monoclonal antibody 2218 (e.g., SEQ ID NO: 10).

In an embodiment the antibody molecule is monoclonal antibody 2218. In an embodiment, monoclonal antibody 2218 is a humanized monoclonal antibody 2218. In an embodiment, the antibody molecule comprises a VH comprising the amino acid sequence of any of SEQ ID NO: 190-201, a VL comprising the amino acid sequence of any of SEQ ID NO: 202-208, or both.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2419 (e.g., SEQ ID NO: 11) or a 2419-related antibody; (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2419 (e.g., SEQ ID NO: 12) or a 2419-related antibody; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2419 (e.g., SEQ ID NO: 13) or a 2419-related antibody.

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2419 (e.g., SEQ ID NO: 14) or a 2419-related antibody; (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2419 (e.g., SEQ ID NO: 15) or a 2419-related antibody; or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2419 (e.g., SEQ ID NO: 16) or a 2419-related antibody.

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2419 (e.g., SEQ ID NO: 11) or a 2419-related antibody; an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2419 (e.g., SEQ ID NO: 12) or a 2419-related antibody; or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2419 (e.g., SEQ ID NO: 13) or a 2419-related antibody, and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2419 (e.g., SEQ ID NO: 14) or a 2419-related antibody; an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2419 (e.g., SEQ ID NO: 15) or a 2419-related antibody; or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2419 (e.g., SEQ ID NO: 16) or a 2419-related antibody.

In an embodiment, the antibody molecule comprises: (i) a VH comprising: an HCDR1 comprising the amino acid sequence of the HCDR1 of monoclonal antibody 2419 (e.g., SEQ ID NO: 11) or a 2419-related antibody; an HCDR2 comprising the amino acid sequence of the HCDR2 of monoclonal antibody 2419 (e.g., SEQ ID NO: 12) or a 2419-related antibody; or an HCDR3 comprising the amino acid sequence of the HCDR3 of monoclonal antibody 2419 (e.g., SEQ ID NO: 13) or a 2419-related antibody, and (ii) a VL comprising: an LCDR1 comprising the amino acid sequence of the LCDR1 of monoclonal antibody 2419 (e.g., SEQ ID NO: 14) or a 2419-related antibody; an LCDR2 comprising the amino acid sequence of the LCDR2 of monoclonal antibody 2419 (e.g., SEQ ID NO: 15) or a 2419-related antibody; and an LCDR3 comprising the amino acid sequence of the LCDR3 of monoclonal antibody 2419 (e.g., SEQ ID NO: 16) or a 2419-related antibody.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2419 (e.g., SEQ ID NO: 17) or a 2419-related antibody; (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2419 (e.g., SEQ ID NO: 18) or a 2419-related antibody; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2419 (e.g., SEQ ID NO: 13) or a 2419-related antibody.

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2419 (e.g., SEQ ID NO: 14) or a 2419-related antibody; (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2419 (e.g., SEQ ID NO: 15) or a 2419-related antibody; or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2419 (e.g., SEQ ID NO: 16) or a 2419-related antibody.

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2419 (e.g., SEQ ID NO: 17) or a 2419-related antibody; an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2419 (e.g., SEQ ID NO: 18) or a 2419-related antibody; or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2419 (e.g., SEQ ID NO: 13) or a 2419-related antibody, and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2419 (e.g., SEQ ID NO: 14) or a 2419-related antibody; an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2419 (e.g., SEQ ID NO: 15) or a 2419-related antibody; or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2419 (e.g., SEQ ID NO: 16) or a 2419-related antibody.

In an embodiment, the antibody molecule comprises: (i) a VH comprising: an HCDR1 comprising the amino acid sequence of the HCDR1 of monoclonal antibody 2419 (e.g., SEQ ID NO: 17) or a 2419-related antibody; an HCDR2 comprising the amino acid sequence of the HCDR2 of monoclonal antibody 2419 (e.g., SEQ ID NO: 18) or a 2419-related antibody; or an HCDR3 comprising the amino acid sequence of the HCDR3 of monoclonal antibody 2419 (e.g., SEQ ID NO: 13) or a 2419-related antibody, and (ii) a VL comprising: an LCDR1 comprising the amino acid sequence of the LCDR1 of monoclonal antibody 2419 (e.g., SEQ ID NO: 14) or a 2419-related antibody; an LCDR2 comprising the amino acid sequence of the LCDR2 of monoclonal antibody 2419 (e.g., SEQ ID NO: 15) or a 2419-related antibody; and an LCDR3 comprising the amino acid sequence of the LCDR3 of monoclonal antibody 2419 (e.g., SEQ ID NO: 16) or a 2419-related antibody.

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2419 (e.g., SEQ ID NO: 19) or a 2419-related antibody. In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2419 (e.g., SEQ ID NO: 20) or a 2419-related antibody.

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2419 (e.g., SEQ ID NO: 19) or a 2419-related antibody; and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2419 (e.g., SEQ ID NO: 20) or a 2419-related antibody.

In an embodiment, the antibody molecule comprises: (i) a VH comprising the amino acid sequence of the VH of monoclonal antibody 2419 (e.g., SEQ ID NO: 19) or a 2419-related antibody; and (ii) a VL comprising the amino acid sequence of the VL of monoclonal antibody 2419 (e.g., SEQ ID NO: 20) or a 2419-related antibody.

In an embodiment the antibody molecule is monoclonal antibody 2419. In an embodiment, monoclonal antibody 2419 is a humanized monoclonal antibody 2419. In an embodiment, the antibody molecule is a 2419-related antibody molecule, e.g., any of antibodies 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, or 2419-1406, e.g., as disclosed in Table 1 or 5. In an embodiment, the antibody molecule comprises a VH comprising the amino acid sequence of any of SEQ ID NOS: 209-214, 283, 288, 289, 291, 292, 294, 296, or 317, a VL comprising the amino acid sequence of any of SEQ ID NOS: 215-219, 284, 286, 295, or 316, or both.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2922 (e.g., SEQ ID NO: 21); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2922 (e.g., SEQ ID NO: 32); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2922 (e.g., SEQ ID NO: 33).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2922 (e.g., SEQ ID NO: 34); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2922 (e.g., SEQ ID NO: 35); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2922 (e.g., SEQ ID NO: 36).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2922 (e.g., SEQ ID NO: 21); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2922 (e.g., SEQ ID NO: 32); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2922 (e.g., SEQ ID NO: 33), and
(ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2922 (e.g., SEQ ID NO: 34); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2922 (e.g., SEQ ID NO: 35); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2922 (e.g., SEQ ID NO: 36).

In an embodiment, the antibody molecule comprises: (i) a VH comprising: an HCDR1 comprising the amino acid sequence of the HCDR1 of monoclonal antibody 2922 (e.g., SEQ ID NO: 21); an HCDR2 comprising the amino acid sequence of the HCDR2 of monoclonal antibody 2922 (e.g., SEQ ID NO: 32); and an HCDR3 comprising the amino acid sequence of the HCDR3 of monoclonal antibody 2922 (e.g., SEQ ID NO: 33), and (ii) a VL comprising: an LCDR1 comprising the amino acid sequence of the LCDR1 of monoclonal antibody 2922 (e.g., SEQ ID NO: 34); an LCDR2 comprising the amino acid sequence of the LCDR2 of monoclonal antibody 2922 (e.g., SEQ ID NO: 35); and an LCDR3 comprising the amino acid sequence of the LCDR3 of monoclonal antibody 2922 (e.g., SEQ ID NO: 36).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2922 (e.g., SEQ ID NO: 37); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2922 (e.g., SEQ ID NO: 38); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2922 (e.g., SEQ ID NO: 33).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2922 (e.g., SEQ ID NO: 34); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2922 (e.g., SEQ ID NO: 35); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2922 (e.g., SEQ ID NO: 36).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2922 (e.g., SEQ ID NO: 37); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2922 (e.g., SEQ ID NO: 38); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2922 (e.g., SEQ ID NO: 33), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2922 (e.g., SEQ ID NO: 34); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2922 (e.g., SEQ ID NO: 35); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2922 (e.g., SEQ ID NO: 36).

In an embodiment, the antibody molecule comprises: (i) a VH comprising: an HCDR1 comprising the amino acid sequence of the HCDR1 of monoclonal antibody 2922 (e.g., SEQ ID NO: 37); an HCDR2 comprising the amino acid sequence of the HCDR2 of monoclonal antibody 2922 (e.g., SEQ ID NO: 38); and an HCDR3 comprising the amino acid sequence of the HCDR3 of monoclonal antibody 2922 (e.g., SEQ ID NO: 33), and (ii) a VL comprising: an LCDR1 comprising the amino acid sequence of the LCDR1 of monoclonal antibody 2922 (e.g., SEQ ID NO: 34); an LCDR2 comprising the amino acid sequence of the LCDR2 of monoclonal antibody 2922 (e.g., SEQ ID NO: 35); and an LCDR3 comprising the amino acid sequence of the LCDR3 of monoclonal antibody 2922 (e.g., SEQ ID NO: 36).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2922 (e.g., SEQ ID NO: 39). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2922 (e.g., SEQ ID NO: 40).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2922 (e.g., SEQ ID NO: 39); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2922 (e.g., SEQ ID NO: 40). In an embodiment, the antibody molecule comprises: (i) a VH comprising the amino acid sequence of the VH of monoclonal antibody 2922 (e.g., SEQ ID NO: 39); and (ii) a VL comprising the amino acid sequence of the VL of monoclonal antibody 2922 (e.g., SEQ ID NO: 40).

In an embodiment the antibody molecule is monoclonal antibody 2922. In an embodiment, the antibody molecule is a humanized monoclonal antibody 2922.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3327 (e.g., SEQ ID NO: 51); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3327 (e.g., SEQ ID NO: 52); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3327 (e.g., SEQ ID NO: 53).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3327 (e.g., SEQ ID NO: 54); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3327 (e.g., SEQ ID NO: 55); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3327 (e.g., SEQ ID NO: 56).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3327 (e.g., SEQ ID NO: 51); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3327 (e.g., SEQ ID NO: 52); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3327 (e.g., SEQ ID NO: 53), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3327 (e.g., SEQ ID NO: 54); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3327 (e.g., SEQ ID NO: 55); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3327 (e.g., SEQ ID NO: 56).

In an embodiment, the antibody molecule comprises: (i) a VH comprising: an HCDR1 comprising the amino acid sequence of the HCDR1 of monoclonal antibody 3327 (e.g., SEQ ID NO: 51); an HCDR2 comprising the amino acid sequence of the HCDR2 of monoclonal antibody 3327 (e.g., SEQ ID NO: 52); and an HCDR3 comprising the amino acid sequence of the HCDR3 of monoclonal antibody 3327 (e.g., SEQ ID NO: 53), and (ii) a VL comprising: an LCDR1 comprising the amino acid sequence of the LCDR1 of monoclonal antibody 3327 (e.g., SEQ ID NO: 54); an LCDR2 comprising the amino acid sequence of the LCDR2 of monoclonal antibody 3327 (e.g., SEQ ID NO: 55); and an LCDR3 comprising the amino acid sequence of the LCDR3 of monoclonal antibody 3327 (e.g., SEQ ID NO: 56).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3327 (e.g., SEQ ID NO: 57); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3327 (e.g., SEQ ID NO: 58); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3327 (e.g., SEQ ID NO: 53).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3327 (e.g., SEQ ID NO: 54); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3327 (e.g., SEQ ID NO: 55); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3327 (e.g., SEQ ID NO: 56).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3327 (e.g., SEQ ID NO: 57); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3327 (e.g., SEQ ID NO: 58); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3327 (e.g., SEQ ID NO: 53), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3327 (e.g., SEQ ID NO: 54); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3327 (e.g., SEQ ID NO: 55); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3327 (e.g., SEQ ID NO: 56).

In an embodiment, the antibody molecule comprises: (i) a VH comprising: an HCDR1 comprising the amino acid sequence of the HCDR1 of monoclonal antibody 3327 (e.g., SEQ ID NO: 57); an HCDR2 comprising the amino acid sequence of the HCDR2 of monoclonal antibody 3327 (e.g., SEQ ID NO: 58); and an HCDR3 comprising the amino acid sequence of the HCDR3 of monoclonal antibody 3327 (e.g., SEQ ID NO: 53), and (ii) a VL comprising: an LCDR1 comprising the amino acid sequence of the LCDR1 of monoclonal antibody 3327 (e.g., SEQ ID NO: 54); an LCDR2 comprising the amino acid sequence of the LCDR2 of monoclonal antibody 3327 (e.g., SEQ ID NO: 55); and an LCDR3 comprising the amino acid sequence of the LCDR3 of monoclonal antibody 3327 (e.g., SEQ ID NO: 56).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3327 (e.g., SEQ ID NO: 59). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3327 (e.g., SEQ ID NO: 60).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3327 (e.g., SEQ ID NO: 59); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3327 (e.g., SEQ ID NO: 60). In an embodiment, the antibody molecule comprises: (i) a VH comprising the amino acid sequence of the VH of monoclonal antibody 3327 (e.g., SEQ ID NO: 59); and (ii) a VL comprising the amino acid sequence of the VL of monoclonal antibody 3327 (e.g., SEQ ID NO: 60).

In an embodiment the antibody molecule is monoclonal antibody 3327. In an embodiment, the antibody molecule is a humanized monoclonal antibody 3327.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3530 (e.g., SEQ ID NO: 61); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3530 (e.g., SEQ ID NO: 62); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3530 (e.g., SEQ ID NO: 63).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3530 (e.g., SEQ ID NO: 67); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3530 (e.g., SEQ ID NO: 45); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3530 (e.g., SEQ ID NO: 46).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3530 (e.g., SEQ ID NO: 61); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3530 (e.g., SEQ ID NO: 62); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3530 (e.g., SEQ ID NO: 63), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3530 (e.g., SEQ ID NO: 67); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3530 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3530 (e.g., SEQ ID NO: 46).

In an embodiment, the antibody molecule comprises: (i) a VH comprising: an HCDR1 comprising the amino acid sequence of the HCDR1 of monoclonal antibody 3530 (e.g., SEQ ID NO: 61); an HCDR2 comprising the amino acid sequence of the HCDR2 of monoclonal antibody 3530 (e.g., SEQ ID NO: 62); and an HCDR3 comprising the amino acid sequence of the HCDR3 of monoclonal antibody 3530 (e.g., SEQ ID NO: 63), and (ii) a VL comprising: an LCDR1 comprising the amino acid sequence of the LCDR1 of monoclonal antibody 3530 (e.g., SEQ ID NO: 67); an LCDR2 comprising the amino acid sequence of the LCDR2 of monoclonal antibody 3530 (e.g., SEQ ID NO: 45); and an LCDR3 comprising the amino acid sequence of the LCDR3 of monoclonal antibody 3530 (e.g., SEQ ID NO: 46).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3530 (e.g., SEQ ID NO: 64); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3530 (e.g., SEQ ID NO: 65); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3530 (e.g., SEQ ID NO: 63).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3530 (e.g., SEQ ID NO: 67); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3530 (e.g., SEQ ID NO: 45); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3530 (e.g., SEQ ID NO: 46).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3530 (e.g., SEQ ID NO: 64); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3530 (e.g., SEQ ID NO: 65); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3530 (e.g., SEQ ID NO: 63), and
(ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3530 (e.g., SEQ ID NO: 67); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3530 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3530 (e.g., SEQ ID NO: 46).

In an embodiment, the antibody molecule comprises: (i) a VH comprising: an HCDR1 comprising the amino acid sequence of the HCDR1 of monoclonal antibody 3530 (e.g., SEQ ID NO: 64); an HCDR2 comprising the amino acid sequence of the HCDR2 of monoclonal antibody 3530 (e.g., SEQ ID NO: 65); and an HCDR3 comprising the amino acid sequence of the HCDR3 of monoclonal antibody 3530 (e.g., SEQ ID NO: 63), and (ii) a VL comprising: an LCDR1 comprising the amino acid sequence of the LCDR1 of monoclonal antibody 3530 (e.g., SEQ ID NO: 67); an LCDR2 comprising the amino acid sequence of the LCDR2 of monoclonal antibody 3530 (e.g., SEQ ID NO: 45); and an LCDR3 comprising the amino acid sequence of the LCDR3 of monoclonal antibody 3530 (e.g., SEQ ID NO: 46).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3530 (e.g., SEQ ID NO: 66). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3530 (e.g., SEQ ID NO: 70).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3530 (e.g., SEQ ID NO: 66); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3530 (e.g., SEQ ID NO: 70). In an embodiment, the antibody molecule comprises: (i) a VH comprising the amino acid sequence of the VH of monoclonal antibody 3530 (e.g., SEQ ID NO: 66); and (ii) a VL comprising the amino acid sequence of the VL of monoclonal antibody 3530 (e.g., SEQ ID NO: 70).

In an embodiment the antibody molecule is monoclonal antibody 3530. In an embodiment, the antibody molecule is a humanized monoclonal antibody 3530.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3525 (e.g., SEQ ID NO: 61); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3525 (e.g., SEQ ID NO: 62); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3525 (e.g., SEQ ID NO: 63).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3525 (e.g., SEQ ID NO: 44); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3525 (e.g., SEQ ID NO: 45); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3525 (e.g., SEQ ID NO: 46).

In an embodiment, the antibody molecule comprises:

(i) a VH comprising: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3525 (e.g., SEQ ID NO: 61); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3525 (e.g., SEQ ID NO: 62); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3525 (e.g., SEQ ID NO: 63), and (ii) a VL comprising: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3525 (e.g., SEQ ID NO: 44); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3525 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3525 (e.g., SEQ ID NO: 46).

In an embodiment, the antibody molecule comprises: (i) a VH comprising: an HCDR1 comprising the amino acid sequence of the HCDR1 of monoclonal antibody 3525 (e.g., SEQ ID NO: 61); an HCDR2 comprising the amino acid sequence of the HCDR2 of monoclonal antibody 3525 (e.g., SEQ ID NO: 62); and an HCDR3 comprising the amino acid sequence of the HCDR3 of monoclonal antibody 3525 (e.g., SEQ ID NO: 63), and (ii) a VL comprising: an LCDR1 comprising the amino acid sequence of the LCDR1 of monoclonal antibody 3525 (e.g., SEQ ID NO: 44); an LCDR2 comprising the amino acid sequence of the LCDR2 of monoclonal antibody 3525 (e.g., SEQ ID NO: 45); and an LCDR3 comprising the amino acid sequence of the LCDR3 of monoclonal antibody 3525 (e.g., SEQ ID NO: 46).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3525 (e.g., SEQ ID NO: 64); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3525 (e.g., SEQ ID NO: 65); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3525 (e.g., SEQ ID NO: 63).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3525 (e.g., SEQ ID NO: 44); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3525 (e.g., SEQ ID NO: 45); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3525 (e.g., SEQ ID NO: 46).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3525 (e.g., SEQ ID NO: 64); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3525 (e.g., SEQ ID NO: 65); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3525 (e.g., SEQ ID NO: 63), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3525 (e.g., SEQ ID NO: 44); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3525 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3525 (e.g., SEQ ID NO: 46).

In an embodiment, the antibody molecule comprises: (i) a VH comprising: an HCDR1 comprising the amino acid sequence of the HCDR1 of monoclonal antibody 3525 (e.g., SEQ ID NO: 64); an HCDR2 comprising the amino acid sequence of the HCDR2 of monoclonal antibody 3525 (e.g., SEQ ID NO: 65); and an HCDR3 comprising the amino acid sequence of the HCDR3 of monoclonal antibody 3525 (e.g., SEQ ID NO: 63), and (ii) a VL comprising: an LCDR1 comprising the amino acid sequence of the LCDR1 of monoclonal antibody 3525 (e.g., SEQ ID NO: 44); an LCDR2 comprising the amino acid sequence of the LCDR2 of monoclonal antibody 3525 (e.g., SEQ ID NO: 45); and an LCDR3 comprising the amino acid sequence of the LCDR3 of monoclonal antibody 3525 (e.g., SEQ ID NO: 46).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3525 (e.g., SEQ ID NO: 66). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3525 (e.g., SEQ ID NO: 50).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3525 (e.g., SEQ ID NO: 66); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3525 (e.g., SEQ ID NO: 50). In an embodiment, the antibody molecule comprises: (i) a VH comprising the amino acid sequence of the VH of monoclonal antibody 3525 (e.g., SEQ ID NO: 66); and (ii) a VL comprising the amino acid sequence of the VL of monoclonal antibody 3525 (e.g., SEQ ID NO: 50).

In an embodiment the antibody molecule is monoclonal antibody 3525. In an embodiment, the antibody molecule is a humanized monoclonal antibody 3525.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2621 (e.g., SEQ ID NO: 21); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2621 (e.g., SEQ ID NO: 22); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2621 (e.g., SEQ ID NO: 23).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2621 (e.g., SEQ ID NO: 24); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2621 (e.g., SEQ ID NO: 25); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2621 (e.g., SEQ ID NO: 26).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2621 (e.g., SEQ ID NO: 21); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2621 (e.g., SEQ ID NO: 22); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2621 (e.g., SEQ ID NO: 23), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2621 (e.g., SEQ ID NO: 24); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2621 (e.g., SEQ ID NO: 25); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2621 (e.g., SEQ ID NO: 26).

In an embodiment, the antibody molecule comprises: (i) a VH comprising: an HCDR1 comprising the amino acid sequence of the HCDR1 of monoclonal antibody 2621 (e.g., SEQ ID NO: 21); an HCDR2 comprising the amino acid sequence of the HCDR2 of monoclonal antibody 2621 (e.g., SEQ ID NO: 22); and an HCDR3 comprising the amino acid sequence of the HCDR3 of monoclonal antibody 2621 (e.g., SEQ ID NO: 23), and (ii) a VL comprising: an LCDR1 comprising the amino acid sequence of the LCDR1 of monoclonal antibody 2621 (e.g., SEQ ID NO: 24); an LCDR2 comprising the amino acid sequence of the LCDR2 of monoclonal antibody 2621 (e.g., SEQ ID NO: 25); and an LCDR3 comprising the amino acid sequence of the LCDR3 of monoclonal antibody 2621 (e.g., SEQ ID NO: 26).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2621 (e.g., SEQ ID NO: 27); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2621 (e.g., SEQ ID NO: 28); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2621 (e.g., SEQ ID NO: 23).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2621 (e.g., SEQ ID NO: 24); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2621 (e.g., SEQ ID NO: 25); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2621 (e.g., SEQ ID NO: 26).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2621 (e.g., SEQ ID NO: 27); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2621 (e.g., SEQ ID NO: 28); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2621 (e.g., SEQ ID NO: 23), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2621 (e.g., SEQ ID NO: 24); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2621 (e.g., SEQ ID NO: 25); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2621 (e.g., SEQ ID NO: 26).

In an embodiment, the antibody molecule comprises: (i) a VH comprising: an HCDR1 comprising the amino acid sequence of the HCDR1 of monoclonal antibody 2621 (e.g., SEQ ID NO: 27); an HCDR2 comprising the amino acid sequence of the HCDR2 of monoclonal antibody 2621 (e.g., SEQ ID NO: 28); and an HCDR3 comprising the amino acid sequence of the HCDR3 of monoclonal antibody 2621 (e.g., SEQ ID NO: 23), and (ii) a VL comprising: an LCDR1 comprising the amino acid sequence of the LCDR1 of monoclonal antibody 2621 (e.g., SEQ ID NO: 24); an LCDR2 comprising the amino acid sequence of the LCDR2 of monoclonal antibody 2621 (e.g., SEQ ID NO: 25); and an LCDR3 comprising the amino acid sequence of the LCDR3 of monoclonal antibody 2621 (e.g., SEQ ID NO: 26).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2621 (e.g., SEQ ID NO: 29). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2621 (e.g., SEQ ID NO: 30).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2621 (e.g., SEQ ID NO: 29); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2621 (e.g., SEQ ID NO: 30). In an embodiment, the antibody molecule comprises: (i) a VH comprising the amino acid sequence of the VH of monoclonal antibody 2621 (e.g., SEQ ID NO: 29); and (ii) a VL comprising the amino acid sequence of the VL of monoclonal antibody 2621 (e.g., SEQ ID NO: 30).

In an embodiment the antibody molecule is monoclonal antibody 2621. In an embodiment, the antibody molecule is a humanized monoclonal antibody 2621.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3125 (e.g., SEQ ID NO: 11); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3125 (e.g., SEQ ID NO: 42); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3125 (e.g., SEQ ID NO: 43).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3125 (e.g., SEQ ID NO: 44); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3125 (e.g., SEQ ID NO: 45); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3125 (e.g., SEQ ID NO: 46).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3125 (e.g., SEQ ID NO: 11); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3125 (e.g., SEQ ID NO: 42); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3125 (e.g., SEQ ID NO: 43), and
(ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3125 (e.g., SEQ ID NO: 44); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3125 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3125 (e.g., SEQ ID NO: 46).

In an embodiment, the antibody molecule comprises: (i) a VH comprising: an HCDR1 comprising the amino acid sequence of the HCDR1 of monoclonal antibody 3125 (e.g., SEQ ID NO: 11); an HCDR2 comprising the amino acid sequence of the HCDR2 of monoclonal antibody 3125 (e.g., SEQ ID NO: 42); and an HCDR3 comprising the amino acid sequence of the HCDR3 of monoclonal antibody 3125 (e.g., SEQ ID NO: 43), and (ii) a VL comprising: an LCDR1 comprising the amino acid sequence of the LCDR1 of monoclonal antibody 3125 (e.g., SEQ ID NO: 44); an LCDR2 comprising the amino acid sequence of the LCDR2 of monoclonal antibody 3125 (e.g., SEQ ID NO: 45); and an LCDR3 comprising the amino acid sequence of the LCDR3 of monoclonal antibody 3125 (e.g., SEQ ID NO: 46).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3125 (e.g., SEQ ID NO: 47); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3125 (e.g., SEQ ID NO: 48); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3125 (e.g., SEQ ID NO: 43).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3125 (e.g., SEQ ID NO: 44); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3125 (e.g., SEQ ID NO: 45); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3125 (e.g., SEQ ID NO: 46).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3125 (e.g., SEQ ID NO: 47); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3125 (e.g., SEQ ID NO: 48); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3125 (e.g., SEQ ID NO: 43), and
(ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3125 (e.g., SEQ ID NO: 44); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3125 (e.g., SEQ ID NO:45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3125 (e.g., SEQ ID NO: 46).

In an embodiment, the antibody molecule comprises: (i) a VH comprising: an HCDR1 comprising the amino acid sequence of the HCDR1 of monoclonal antibody 3125 (e.g., SEQ ID NO: 47); an HCDR2 comprising the amino acid sequence of the HCDR2 of monoclonal antibody 3125 (e.g., SEQ ID NO: 48); and an HCDR3 comprising the amino acid sequence of the HCDR3 of monoclonal antibody 3125 (e.g., SEQ ID NO: 43), and (ii) a VL comprising: an LCDR1 comprising the amino acid sequence of the LCDR1 of monoclonal antibody 3125 (e.g., SEQ ID NO: 44); an LCDR2 comprising the amino acid sequence of the LCDR2 of monoclonal antibody 3125 (e.g., SEQ ID NO: 45); and an LCDR3 comprising the amino acid sequence of the LCDR3 of monoclonal antibody 3125 (e.g., SEQ ID NO: 46).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3125 (e.g., SEQ ID NO: 49). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3125 (e.g., SEQ ID NO: 50).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3125 (e.g., SEQ ID NO: 49); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3125 (e.g., SEQ ID NO: 50). In an embodiment, the antibody molecule comprises: (i) a VH comprising the amino acid sequence of the VH of monoclonal antibody 3125 (e.g., SEQ ID NO: 49); and (ii) a VL comprising the amino acid sequence of the VL of monoclonal antibody 3125 (e.g., SEQ ID NO: 50).

In an embodiment the antibody molecule is monoclonal antibody 3125. In an embodiment, the antibody molecule is a humanized monoclonal antibody 3125.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4035 or 4035-062 (e.g., SEQ ID NO: 93); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4035 or 4035-062 (e.g., SEQ ID NO: 94); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4035 or 4035-062 (e.g., SEQ ID NO: 95).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4035 or 4035-062 (e.g., SEQ ID NO: 96); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4035 or 4035-062 (e.g., SEQ ID NO: 97); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4035 or 4035-062 (e.g., SEQ ID NO: 98).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4035 or 4035-062 (e.g., SEQ ID NO: 93); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4035 or 4035-062 (e.g., SEQ ID NO: 94); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4035 or 4035-062 (e.g., SEQ ID NO: 95), and
(ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4035 or 4035-062 (e.g., SEQ ID NO: 96); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4035 or 4035-062 (e.g., SEQ ID NO: 97); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4035 or 4035-062 (e.g., SEQ ID NO: 98).

In an embodiment, the antibody molecule comprises: (i) a VH comprising: an HCDR1 comprising the amino acid sequence of the HCDR1 of monoclonal antibody 4035 or 4035-062 (e.g., SEQ ID NO: 93); an HCDR2 comprising the amino acid sequence of the HCDR2 of monoclonal antibody 4035 or 4035-062 (e.g., SEQ ID NO: 94); and an HCDR3 comprising the amino acid sequence of the HCDR3 of monoclonal antibody 4035 or 4035-062 (e.g., SEQ ID NO: 95), and (ii) a VL comprising: an LCDR1 comprising the amino acid sequence of the LCDR1 of monoclonal antibody 4035 or 4035-062 (e.g., SEQ ID NO: 96); an LCDR2 comprising the amino acid sequence of the LCDR2 of monoclonal antibody 4035 or 4035-062 (e.g., SEQ ID NO: 97); and an LCDR3 comprising the amino acid sequence of the LCDR3 of monoclonal antibody 4035 or 4035-062 (e.g., SEQ ID NO: 98).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4035 or 4035-062 (e.g., SEQ ID NO: 99); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4035 (e.g., SEQ ID NO: 100) or 4035-062 (e.g., SEQ ID NO: 273); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4035 or 4035-062 (e.g., SEQ ID NO: 95).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4035 or 4035-062 (e.g., SEQ ID NO: 96); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4035 or 4035-062 (e.g., SEQ ID NO: 97); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4035 or 4035-062 (e.g., SEQ ID NO: 98).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4035 or 4035-062 (e.g., SEQ ID NO: 99); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4035 (e.g., SEQ ID NO: 100) or 4035-062 (e.g., SEQ ID NO: 273); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4035 or 4035-062 (e.g., SEQ ID NO: 95), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4035 or 4035-062 (e.g., SEQ ID NO: 96); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4035 or 4035-062 (e.g., SEQ ID NO: 97); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4035 or 4035-062 (e.g., SEQ ID NO: 98).

In an embodiment, the antibody molecule comprises: (i) a VH comprising: an HCDR1 comprising the amino acid sequence of the HCDR1 of monoclonal antibody 4035 or 4035-062 (e.g., SEQ ID NO: 99); an HCDR2 comprising the amino acid sequence of the HCDR2 of monoclonal antibody 4035 (e.g., SEQ ID NO: 100) or 4035-062 (e.g., SEQ ID NO: 273); and an HCDR3 comprising the amino acid sequence of the HCDR3 of monoclonal antibody 4035 or 4035-062 (e.g., SEQ ID NO: 95), and (ii) a VL comprising: an LCDR1 comprising the amino acid sequence of the LCDR1 of monoclonal antibody 4035 or 4035-062 (e.g., SEQ ID NO: 96); an LCDR2 comprising the amino acid sequence of the LCDR2 of monoclonal antibody 4035 or 4035-062 (e.g., SEQ ID NO: 97); and an LCDR3 comprising the amino acid sequence of the LCDR3 of monoclonal antibody 4035 or 4035-062 (e.g., SEQ ID NO: 98).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4035 (e.g., SEQ ID NO: 101) or 4035-062 (e.g., SEQ ID NO: 225). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4035 (e.g., SEQ ID NO: 102) or 4035-062 (e.g., SEQ ID NO: 229).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4035 (e.g., SEQ ID NO: 101) or 4035-062 (e.g., SEQ ID NO: 225); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4035 (e.g., SEQ ID NO: 102) or 4035-062 (e.g., SEQ ID NO: 229). In an embodiment, the antibody molecule comprises: (i) a VH comprising the amino acid sequence of the VH of monoclonal antibody 4035 (e.g., SEQ ID NO: 101) or 4035-062 (e.g., SEQ ID NO: 225); and (ii) a VL comprising the amino acid sequence of the VL of monoclonal antibody 4035 (e.g., SEQ ID NO: 102) or 4035-062 (e.g., SEQ ID NO: 229).

In an embodiment, the antibody molecule is monoclonal antibody 4035. In an embodiment, monoclonal antibody 4035 is a humanized monoclonal antibody 4035 (e.g., antibody 4035-062). In another embodiment, the antibody molecule is antibody 4035-062. In an embodiment, the antibody molecule comprises a VH comprising the amino acid sequence of any of SEQ ID NOS: 220-227 or 262-265, a VL comprising the amino acid sequence of any of SEQ ID NOS: 228-234, or both.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3934 (e.g., SEQ ID NO: 103); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3934 (e.g., SEQ ID NO: 104); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3934 (e.g., SEQ ID NO: 105).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3934 (e.g., SEQ ID NO: 106); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3934 (e.g., SEQ ID NO: 107); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3934 (e.g., SEQ ID NO: 108).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3934 (e.g., SEQ ID NO: 103); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3934 (e.g., SEQ ID NO: 104); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3934 (e.g., SEQ ID NO: 105), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3934 (e.g., SEQ ID NO: 106); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3934 (e.g., SEQ ID NO: 107); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3934 (e.g., SEQ ID NO: 108).

In an embodiment, the antibody molecule comprises: (i) a VH comprising: an HCDR1 comprising the amino acid sequence of the HCDR1 of monoclonal antibody 3934 (e.g., SEQ ID NO: 103); an HCDR2 comprising the amino acid sequence of the HCDR2 of monoclonal antibody 3934 (e.g., SEQ ID NO: 104); and an HCDR3 comprising the amino acid sequence of the HCDR3 of monoclonal antibody 3934 (e.g., SEQ ID NO: 105), and (ii) a VL comprising: an LCDR1 comprising the amino acid sequence of the LCDR1 of monoclonal antibody 3934 (e.g., SEQ ID NO: 106); an LCDR2 comprising the amino acid sequence of the LCDR2 of monoclonal antibody 3934 (e.g., SEQ ID NO: 107); and an LCDR3 comprising the amino acid sequence of the LCDR3 of monoclonal antibody 3934 (e.g., SEQ ID NO: 108).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3934 (e.g., SEQ ID NO: 109); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3934 (e.g., SEQ ID NO: 110); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3934 (e.g., SEQ ID NO: 105).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3934 (e.g., SEQ ID NO: 106); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3934 (e.g., SEQ ID NO: 107); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3934 (e.g., SEQ ID NO: 108).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3934 (e.g., SEQ ID NO: 109); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3934 (e.g., SEQ ID NO: 110); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3934 (e.g., SEQ ID NO: 105), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3934 (e.g., SEQ ID NO: 106); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3934 (e.g., SEQ ID NO: 107); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3934 (e.g., SEQ ID NO: 108).

In an embodiment, the antibody molecule comprises: (i) a VH comprising: an HCDR1 comprising the amino acid sequence of the HCDR1 of monoclonal antibody 3934 (e.g., SEQ ID NO: 109); an HCDR2 comprising the amino acid sequence of the HCDR2 of monoclonal antibody 3934 (e.g., SEQ ID NO: 110); and an HCDR3 comprising the amino acid sequence of the HCDR3 of monoclonal antibody 3934 (e.g., SEQ ID NO: 105), and (ii) a VL comprising: an LCDR1 comprising the amino acid sequence of the LCDR1 of monoclonal antibody 3934 (e.g., SEQ ID NO: 106); an LCDR2 comprising the amino acid sequence of the LCDR2 of monoclonal antibody 3934 (e.g., SEQ ID NO: 107); and an LCDR3 comprising the amino acid sequence of the LCDR3 of monoclonal antibody 3934 (e.g., SEQ ID NO: 108).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3934 (e.g., SEQ ID NO: 111). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3934 (e.g., SEQ ID NO: 112).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3934 (e.g., SEQ ID NO: 111); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3934 (e.g., SEQ ID NO: 112). In an embodiment, the antibody molecule comprises: (i) a VH comprising the amino acid sequence of the VH of monoclonal antibody 3934 (e.g., SEQ ID NO: 111); and (ii) a VL comprising the amino acid sequence of the VL of monoclonal antibody 3934 (e.g., SEQ ID NO: 112).

In an embodiment the antibody molecule is monoclonal antibody 3934. In an embodiment, the antibody molecule is a humanized monoclonal antibody 3934.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3833 (e.g., SEQ ID NO: 112); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3833 (e.g., SEQ ID NO: 113); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3833 (e.g., SEQ ID NO: 114).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3833 (e.g., SEQ ID NO: 115); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3833 (e.g., SEQ ID NO: 116); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3833 (e.g., SEQ ID NO: 117).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3833 (e.g., SEQ ID NO: 113); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3833 (e.g., SEQ ID NO: 114); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3833 (e.g., SEQ ID NO: 115), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3833 (e.g., SEQ ID NO: 116); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3833 (e.g., SEQ ID NO: 117); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3833 (e.g., SEQ ID NO: 118).

In an embodiment, the antibody molecule comprises: (i) a VH comprising: an HCDR1 comprising the amino acid sequence of the HCDR1 of monoclonal antibody 3833 (e.g., SEQ ID NO: 113); an HCDR2 comprising the amino acid sequence of the HCDR2 of monoclonal antibody 3833 (e.g., SEQ ID NO: 114); and an HCDR3 comprising the amino acid sequence of the HCDR3 of monoclonal antibody 3833 (e.g., SEQ ID NO: 115), and (ii) a VL comprising: an LCDR1 comprising the amino acid sequence of the LCDR1 of monoclonal antibody 3833 (e.g., SEQ ID NO: 116); an LCDR2 comprising the amino acid sequence of the LCDR2 of monoclonal antibody 3833 (e.g., SEQ ID NO: 117); and an LCDR3 comprising the amino acid sequence of the LCDR3 of monoclonal antibody 3833 (e.g., SEQ ID NO: 118).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3833 (e.g., SEQ ID NO: 119); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3833 (e.g., SEQ ID NO: 120); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3833 (e.g., SEQ ID NO: 115).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3833 (e.g., SEQ ID NO: 116); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3833 (e.g., SEQ ID NO: 117); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3833 (e.g., SEQ ID NO: 118).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3833 (e.g., SEQ ID NO: 119); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3833 (e.g., SEQ ID NO: 120); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3833 (e.g., SEQ ID NO: 115), and
(ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3833 (e.g., SEQ ID NO: 116); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3833 (e.g., SEQ ID NO: 117); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3833 (e.g., SEQ ID NO: 118).

In an embodiment, the antibody molecule comprises: (i) a VH comprising: an HCDR1 comprising the amino acid sequence of the HCDR1 of monoclonal antibody 3833 (e.g., SEQ ID NO: 119); an HCDR2 comprising the amino acid sequence of the HCDR2 of monoclonal antibody 3833 (e.g., SEQ ID NO: 120); and an HCDR3 comprising the amino acid sequence of the HCDR3 of monoclonal antibody 3833 (e.g., SEQ ID NO: 115), and (ii) a VL comprising: an LCDR1 comprising the amino acid sequence of the LCDR1 of monoclonal antibody 3833 (e.g., SEQ ID NO: 116); an LCDR2 comprising the amino acid sequence of the LCDR2 of monoclonal antibody 3833 (e.g., SEQ ID NO: 117); and an LCDR3 comprising the amino acid sequence of the LCDR3 of monoclonal antibody 3833 (e.g., SEQ ID NO: 118).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3833 (e.g., SEQ ID NO: 121). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3833 (e.g., SEQ ID NO: 122).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3833 (e.g., SEQ ID NO: 121); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3833 (e.g., SEQ ID NO: 122). In an embodiment, the antibody molecule comprises: (i) a VH comprising the amino acid sequence of the VH of monoclonal antibody 3833 (e.g., SEQ ID NO: 121); and (ii) a VL comprising the amino acid sequence of the VL of monoclonal antibody 3833 (e.g., SEQ ID NO: 122).

In an embodiment the antibody molecule is monoclonal antibody 3833. In an embodiment, monoclonal antibody 3833 is a humanized monoclonal antibody 3833. In an embodiment, the antibody molecule comprises a VH comprising the amino acid sequence of any of SEQ ID NO: 246-250, a VL comprising the amino acid sequence of any of SEQ ID NO: 251-253, or both.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3631 (e.g., SEQ ID NO: 123); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3631 (e.g., SEQ ID NO: 124); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3631 (e.g., SEQ ID NO: 125).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3631 (e.g., SEQ ID NO: 126); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3631 (e.g., SEQ ID NO: 127); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3631 (e.g., SEQ ID NO: 128).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3631 (e.g., SEQ ID NO: 123); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3631 (e.g., SEQ ID NO: 124); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3631 (e.g., SEQ ID NO: 125), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3631 (e.g., SEQ ID NO: 126); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3631 (e.g., SEQ ID NO: 127); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3631 (e.g., SEQ ID NO: 128).

In an embodiment, the antibody molecule comprises: (i) a VH comprising: an HCDR1 comprising the amino acid sequence of the HCDR1 of monoclonal antibody 3631 (e.g., SEQ ID NO: 123); an HCDR2 comprising the amino acid sequence of the HCDR2 of monoclonal antibody 3631 (e.g., SEQ ID NO: 124); and an HCDR3 comprising the amino acid sequence of the HCDR3 of monoclonal antibody 3631 (e.g., SEQ ID NO: 125), and (ii) a VL comprising: an LCDR1 comprising the amino acid sequence of the LCDR1 of monoclonal antibody 3631 (e.g., SEQ ID NO: 126); an LCDR2 comprising the amino acid sequence of the LCDR2 of monoclonal antibody 3631 (e.g., SEQ ID NO: 127); and an LCDR3 comprising the amino acid sequence of the LCDR3 of monoclonal antibody 3631 (e.g., SEQ ID NO: 128).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3631 (e.g., SEQ ID NO: 129); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3631 (e.g., SEQ ID NO: 130); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3631 (e.g., SEQ ID NO: 125).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3631 (e.g., SEQ ID NO: 126); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3631 (e.g., SEQ ID NO: 127); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3631 (e.g., SEQ ID NO: 128).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3631 (e.g., SEQ ID NO: 129); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3631 (e.g., SEQ ID NO: 130); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3631 (e.g., SEQ ID NO: 125), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3631 (e.g., SEQ ID NO: 126); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3631 (e.g., SEQ ID NO:45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3631 (e.g., SEQ ID NO: 128).

In an embodiment, the antibody molecule comprises: (i) a VH comprising: an HCDR1 comprising the amino acid sequence of the HCDR1 of monoclonal antibody 3631 (e.g., SEQ ID NO: 129); an HCDR2 comprising the amino acid sequence of the HCDR2 of monoclonal antibody 3631 (e.g., SEQ ID NO: 130); and an HCDR3 comprising the amino acid sequence of the HCDR3 of monoclonal antibody 3631 (e.g., SEQ ID NO: 125), and (ii) a VL comprising: an LCDR1 comprising the amino acid sequence of the LCDR1 of monoclonal antibody 3631 (e.g., SEQ ID NO: 126); an LCDR2 comprising the amino acid sequence of the LCDR2 of monoclonal antibody 3631 (e.g., SEQ ID NO: 127); and an LCDR3 comprising the amino acid sequence of the LCDR3 of monoclonal antibody 3631 (e.g., SEQ ID NO: 128).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3631 (e.g., SEQ ID NO: 131). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3631 (e.g., SEQ ID NO: 132).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3631 (e.g., SEQ ID NO: 131); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3631 (e.g., SEQ ID NO: 132). In an embodiment, the antibody molecule comprises: (i) a VH comprising the amino acid sequence of the VH of monoclonal antibody 3631 (e.g., SEQ ID NO: 131); and (ii) a VL comprising the amino acid sequence of the VL of monoclonal antibody 3631 (e.g., SEQ ID NO: 132).

In an embodiment the antibody molecule is monoclonal antibody 3631. In an embodiment, the antibody molecule is a humanized monoclonal antibody 3631.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3732 (e.g., SEQ ID NO: 133); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3732 (e.g., SEQ ID NO: 134); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3732 (e.g., SEQ ID NO: 135).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3732 (e.g., SEQ ID NO: 136); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3732 (e.g., SEQ ID NO: 127); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3732 (e.g., SEQ ID NO: 137).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3732 (e.g., SEQ ID NO: 133); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3732 (e.g., SEQ ID NO: 134); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3732 (e.g., SEQ ID NO: 135), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3732 (e.g., SEQ ID NO: 136); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3732 (e.g., SEQ ID NO: 127); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3732 (e.g., SEQ ID NO: 137).

In an embodiment, the antibody molecule comprises: (i) a VH comprising: an HCDR1 comprising the amino acid sequence of the HCDR1 of monoclonal antibody 3732 (e.g., SEQ ID NO: 133); an HCDR2 comprising the amino acid sequence of the HCDR2 of monoclonal antibody 3732 (e.g., SEQ ID NO: 134); and an HCDR3 comprising the amino acid sequence of the HCDR3 of monoclonal antibody 3732 (e.g., SEQ ID NO: 135), and (ii) a VL comprising: an LCDR1 comprising the amino acid sequence of the LCDR1 of monoclonal antibody 3732 (e.g., SEQ ID NO: 136); an LCDR2 comprising the amino acid sequence of the LCDR2 of monoclonal antibody 3732 (e.g., SEQ ID NO: 127); and an LCDR3 comprising the amino acid sequence of the LCDR3 of monoclonal antibody 3732 (e.g., SEQ ID NO: 137).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3732 (e.g., SEQ ID NO: 138); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3732 (e.g., SEQ ID NO: 139); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3732 (e.g., SEQ ID NO: 135).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3732 (e.g., SEQ ID NO: 136); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3732 (e.g., SEQ ID NO: 127); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3732 (e.g., SEQ ID NO: 137).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3732 (e.g., SEQ ID NO: 138); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3732 (e.g., SEQ ID NO: 139); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3732 (e.g., SEQ ID NO: 135), and
(ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3732 (e.g., SEQ ID NO: 136); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3732 (e.g., SEQ ID NO: 127); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3732 (e.g., SEQ ID NO: 137).

In an embodiment, the antibody molecule comprises: (i) a VH comprising: an HCDR1 comprising the amino acid sequence of the HCDR1 of monoclonal antibody 3732 (e.g., SEQ ID NO: 138); an HCDR2 comprising the amino acid sequence of the HCDR2 of monoclonal antibody 3732 (e.g., SEQ ID NO: 139); and an HCDR3 comprising the amino acid sequence of the HCDR3 of monoclonal antibody 3732 (e.g., SEQ ID NO: 135), and (ii) a VL comprising: an LCDR1 comprising the amino acid sequence of the LCDR1 of monoclonal antibody 3732 (e.g., SEQ ID NO: 136); an LCDR2 comprising the amino acid sequence of the LCDR2 of monoclonal antibody 3732 (e.g., SEQ ID NO: 127); and an LCDR3 comprising the amino acid sequence of the LCDR3 of monoclonal antibody 3732 (e.g., SEQ ID NO: 137).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3732 (e.g., SEQ ID NO: 140). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3732 (e.g., SEQ ID NO: 141).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3732 (e.g., SEQ ID NO: 140); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3732 (e.g., SEQ ID NO: 141). In an embodiment, the antibody molecule comprises: (i) a VH comprising the amino acid sequence of the VH of monoclonal antibody 3732 (e.g., SEQ ID NO: 140); and (ii) a VL comprising the amino acid sequence of the VL of monoclonal antibody 3732 (e.g., SEQ ID NO: 141).

In an embodiment the antibody molecule is monoclonal antibody 3732. In an embodiment, the antibody molecule is a humanized monoclonal antibody 3732.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4338 (e.g., SEQ ID NO: 11); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4338 (e.g., SEQ ID NO: 142); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4338 (e.g., SEQ ID NO: 143).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4338 (e.g., SEQ ID NO: 144 or 146); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4338 (e.g., SEQ ID NO: 107 or 147); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4338 (e.g., SEQ ID NO: 145 or 148).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4338 (e.g., SEQ ID NO: 11); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4338 (e.g., SEQ ID NO: 142); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4338 (e.g., SEQ ID NO: 143), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4338 (e.g., SEQ ID NO: 144 or 146); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4338 (e.g., SEQ ID NO: 107 or 147); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4338 (e.g., SEQ ID NO: 145 or 148).

In an embodiment, the antibody molecule comprises: (i) a VH comprising: an HCDR1 comprising the amino acid sequence of the HCDR1 of monoclonal antibody 4338 (e.g., SEQ ID NO: 11); an HCDR2 comprising the amino acid sequence of the HCDR2 of monoclonal antibody 4338 (e.g., SEQ ID NO: 142); and an HCDR3 comprising the amino acid sequence of the HCDR3 of monoclonal antibody 4338 (e.g., SEQ ID NO: 143), and (ii) a VL comprising: an LCDR1 comprising the amino acid sequence of the LCDR1 of monoclonal antibody 4338 (e.g., SEQ ID NO: 144 or 146); an LCDR2 comprising the amino acid sequence of the LCDR2 of monoclonal antibody 4338 (e.g., SEQ ID NO: 107 or 147); and an LCDR3 comprising the amino acid sequence of the LCDR3 of monoclonal antibody 4338 (e.g., SEQ ID NO: 145 or 148).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4338 (e.g., SEQ ID NO: 149); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4338 (e.g., SEQ ID NO: 150); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4338 (e.g., SEQ ID NO: 143).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4338 (e.g., SEQ ID NO: 144 or 146); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4338 (e.g., SEQ ID NO: 107 or 147); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4338 (e.g., SEQ ID NO: 145 or 148).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4338 (e.g., SEQ ID NO: 149); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4338 (e.g., SEQ ID NO: 150); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4338 (e.g., SEQ ID NO: 143), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4338 (e.g., SEQ ID NO: 144 or 146); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4338 (e.g., SEQ ID NO:107 or 147); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4338 (e.g., SEQ ID NO: 145 or 148).

In an embodiment, the antibody molecule comprises: (i) a VH comprising: an HCDR1 comprising the amino acid sequence of the HCDR1 of monoclonal antibody 4338 (e.g., SEQ ID NO: 149); an HCDR2 comprising the amino acid sequence of the HCDR2 of monoclonal antibody 4338 (e.g., SEQ ID NO: 150); and an HCDR3 comprising the amino acid sequence of the HCDR3 of monoclonal antibody 4338 (e.g., SEQ ID NO: 143), and (ii) a VL comprising: an LCDR1 comprising the amino acid sequence of the LCDR1 of monoclonal antibody 4338 (e.g., SEQ ID NO: 144 or 146); an LCDR2 comprising the amino acid sequence of the LCDR2 of monoclonal antibody 4338 (e.g., SEQ ID NO: 107 or 147); and an LCDR3 comprising the amino acid sequence of the LCDR3 of monoclonal antibody 4338 (e.g., SEQ ID NO: 145 or 148).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4338 (e.g., SEQ ID NO: 151). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4338 (e.g., SEQ ID NO: 152 or 153).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4338 (e.g., SEQ ID NO: 151); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4338 (e.g., SEQ ID NO: 152 or 153). In an embodiment, the antibody molecule comprises: (i) a VH comprising the amino acid sequence of the VH of monoclonal antibody 4338 (e.g., SEQ ID NO: 150); and (ii) a VL comprising the amino acid sequence of the VL of monoclonal antibody 4338 (e.g., SEQ ID NO: 152 or 153).

In an embodiment the antibody molecule is monoclonal antibody 4338. In an embodiment, the antibody molecule is a humanized monoclonal antibody 4338.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540, 4540-063, or 4540-033 (e.g., SEQ ID NO: 154); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540, 4540-063, or 4540-033 (e.g., SEQ ID NO: 155); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540, 4540-063, or 4540-033 (e.g., SEQ ID NO: 156).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540, 4540-063, or 4540-033 (e.g., SEQ ID NO: 158).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540, 4540-063, or 4540-033 (e.g., SEQ ID NO: 154); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540, 4540-063, or 4540-033 (e.g., SEQ ID NO: 155); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540, 4540-063, or 4540-033 (e.g., SEQ ID NO: 156), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540, 4540-063, or 4540-033 (e.g., SEQ ID NO: 158).

In an embodiment, the antibody molecule comprises: (i) a VH comprising three heavy chain complementarity determining regions (HCDR1, HCDR2, and HCDR3), wherein the heavy chain variable region comprises: an HCDR1 comprises the amino acid sequence of the HCDR1 of monoclonal antibody 4540, 4540-063, or 4540-033 (e.g., SEQ ID NO: 154); an HCDR2 comprising the amino acid sequence of the HCDR2 of monoclonal antibody 4540, 4540-063, or 4540-033 (e.g., SEQ ID NO: 155); and an HCDR3 comprising the amino acid sequence of the HCDR3 of monoclonal antibody 4540, 4540-063, or 4540-033 (e.g., SEQ ID NO: 156), and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); an LCDR2 comprising the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); and an LCDR3 comprising the amino acid sequence of the LCDR3 of monoclonal antibody 4540, 4540-063, or 4540-033 (e.g., SEQ ID NO: 158).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540 (e.g., SEQ ID NO: 159), 4540-063 (e.g., SEQ ID NO: 276), or 4540-033 (e.g., SEQ ID NO: 159); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540 (e.g., SEQ ID NO: 160), 4540-063 (e.g., SEQ ID NO: 277), or 4540-033 (e.g., SEQ ID NO: 278); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540, 4540-063, or 4540-033 (e.g., SEQ ID NO: 156).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540, 4540-063, or 4540-033 (e.g., SEQ ID NO: 158).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540 (e.g., SEQ ID NO: 159), 4540-063 (e.g., SEQ ID NO: 276), or 4540-033 (e.g., SEQ ID NO: 159); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540 (e.g., SEQ ID NO: 160), 4540-063 (e.g., SEQ ID NO: 277), or 4540-033 (e.g., SEQ ID NO: 278); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540, 4540-063, or 4540-033 (e.g., SEQ ID NO: 156), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540, 4540-063, or 4540-033 (e.g., SEQ ID NO: 158).

In an embodiment, the antibody molecule comprises: (i) a VH comprising one, two, or all of the following: an HCDR1 comprising the amino acid sequence of the HCDR1 of monoclonal antibody 4540 (e.g., SEQ ID NO: 159), 4540-063 (e.g., SEQ ID NO: 276), or 4540-033 (e.g., SEQ ID NO: 159); an HCDR2 comprising the amino acid sequence of the HCDR2 of monoclonal antibody 4540 (e.g., SEQ ID NO: 160), 4540-063 (e.g., SEQ ID NO: 277), or 4540-033 (e.g., SEQ ID NO: 278); or an HCDR3 comprising the amino acid sequence of the HCDR3 of monoclonal antibody 4540, 4540-063, or 4540-033 (e.g., SEQ ID NO: 156), and (ii) a VL comprising one, two, or all of the following: an LCDR1 comprising the amino acid sequence of the LCDR1 of monoclonal antibody 4540 (e.g., SEQ ID NO: 116), 4540-063 (e.g., SEQ ID NO: 274), or 4540-033 (e.g., SEQ ID NO: 274); an LCDR2 comprising the amino acid sequence of the LCDR2 of monoclonal antibody 4540 (e.g., SEQ ID NO: 157), 4540-063 (e.g., SEQ ID NO: 275), or 4540-033 (e.g., SEQ ID NO: 275); or an LCDR3 comprising the amino acid sequence of the LCDR3 of monoclonal antibody 4540, 4540-063, or 4540-033 (e.g., SEQ ID NO: 158).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4540 (e.g., SEQ ID NO: 161), 4540-063 (e.g., SEQ ID NO: 258), or 4540-033 (e.g., SEQ ID NO: 256). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4540 (e.g., SEQ ID NO: 162), 4540-063 (e.g., SEQ ID NO: 261), or 4540-033 (e.g., SEQ ID NO: 261).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4540 (e.g., SEQ ID NO: 161), 4540-063 (e.g., SEQ ID NO: 258), or 4540-033 (e.g., SEQ ID NO: 256); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4540 (e.g., SEQ ID NO: 162), 4540-063 (e.g., SEQ ID NO: 261), or 4540-033 (e.g., SEQ ID NO: 261). In an embodiment, the antibody molecule comprises: (i) a VH comprising the amino acid sequence of the VH of monoclonal antibody 4540 (e.g., SEQ ID NO: 161), 4540-063 (e.g., SEQ ID NO: 258), or 4540-033 (e.g., SEQ ID NO: 256); and (ii) a VL comprising the amino acid sequence of the VL of monoclonal antibody 4540 (e.g., SEQ ID NO: 162), 4540-063 (e.g., SEQ ID NO: 261), or 4540-033 (e.g., SEQ ID NO: 261).

In an embodiment the antibody molecule is monoclonal antibody 4540, 4540-063, or 4540-033. In an embodiment, monoclonal antibody 4540 is a humanized monoclonal antibody 4540 (e.g., antibodies 4540-063 or 4540-033). In an embodiment, the antibody molecule comprises a VH comprising the amino acid sequence of any of SEQ ID NOS: 254-258, a VL comprising the amino acid sequence of any of SEQ ID NOS: 259-261, or both.

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4237 (e.g., SEQ ID NO: 163); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4237 (e.g., SEQ ID NO: 164); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4237 (e.g., SEQ ID NO: 165).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4237 (e.g., SEQ ID NO: 166); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4237 (e.g., SEQ ID NO: 167); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4237 (e.g., SEQ ID NO: 168).

In an embodiment, the antibody molecule comprises:
(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4237 (e.g., SEQ ID NO: 163); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4237 (e.g., SEQ ID NO: 164); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4237 (e.g., SEQ ID NO: 165), and
(ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4237 (e.g., SEQ ID NO: 166); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4237 (e.g., SEQ ID NO: 167); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4237 (e.g., SEQ ID NO: 168).

In an embodiment, the antibody molecule comprises: (i) a VH comprising: an HCDR1 comprising the amino acid sequence of the HCDR1 of monoclonal antibody 4237 (e.g., SEQ ID NO: 163); an HCDR2 comprising the amino acid sequence of the HCDR2 of monoclonal antibody 4237 (e.g., SEQ ID NO: 164); and an HCDR3 comprising the amino acid sequence of the HCDR3 of monoclonal antibody 4237 (e.g., SEQ ID NO: 165), and (ii) a VL comprising: an LCDR1 comprising the amino acid sequence of the LCDR1 of monoclonal antibody 4237 (e.g., SEQ ID NO: 166); an LCDR2 comprising the amino acid sequence of the LCDR2 of monoclonal antibody 4237 (e.g., SEQ ID NO: 167); and an LCDR3 comprising the amino acid sequence of the LCDR3 of monoclonal antibody 4237 (e.g., SEQ ID NO: 168).

In an embodiment, the antibody molecule comprises a heavy chain variable region (VH), wherein the heavy chain variable region comprises three heavy chain complementarity determining regions (HCDR1, HCDR2, and HCDR3), wherein the heavy chain variable region comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4237 (e.g., SEQ ID NO: 169); (ii) an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4237 (e.g., SEQ ID NO: 170); or (iii) an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4237 (e.g., SEQ ID NO: 165).

In an embodiment, the antibody molecule comprises a light chain variable region (VL), wherein the light chain variable region comprises three light chain complementarity determining regions (LCDR1, LCDR2, and LCDR3), wherein the light chain variable region comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4237 (e.g., SEQ ID NO: 166); (ii) an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4237 (e.g., SEQ ID NO: 167); or (iii) an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4237 (e.g., SEQ ID NO: 168).

In an embodiment, the antibody molecule comprises:

(i) a VH comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4237 (e.g., SEQ ID NO: 169); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4237 (e.g., SEQ ID NO: 170); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4237 (e.g., SEQ ID NO: 165), and (ii) a VL comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4237 (e.g., SEQ ID NO: 166); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4237 (e.g., SEQ ID NO: 167); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4237 (e.g., SEQ ID NO: 168).

In an embodiment, the antibody molecule comprises: (i) a VH comprising: an HCDR1 comprising the amino acid sequence of the HCDR1 of monoclonal antibody 4237 (e.g., SEQ ID NO: 169); an HCDR2 comprising the amino acid sequence of the HCDR2 of monoclonal antibody 4237 (e.g., SEQ ID NO: 170); and an HCDR3 comprising the amino acid sequence of the HCDR3 of monoclonal antibody 4237 (e.g., SEQ ID NO: 165), and (ii) a VL comprising: an LCDR1 comprising the amino acid sequence of the LCDR1 of monoclonal antibody 4237 (e.g., SEQ ID NO: 166); an LCDR2 comprising the amino acid sequence of the LCDR2 of monoclonal antibody 4237 (e.g., SEQ ID NO: 167); and an LCDR3 comprising the amino acid sequence of the LCDR3 of monoclonal antibody 4237 (e.g., SEQ ID NO: 168).

In an embodiment, the antibody molecule comprises a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4237 (e.g., SEQ ID NO: 171). In an embodiment, the antibody molecule comprises a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4237 (e.g., SEQ ID NO: 172).

In an embodiment, the antibody molecule comprises: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4237 (e.g., SEQ ID NO: 171); and (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4237 (e.g., SEQ ID NO: 172). In an embodiment, the antibody molecule comprises: (i) a VH comprising the amino acid sequence of the VH of monoclonal antibody 4237 (e.g., SEQ ID NO: 171); and (ii) a VL comprising the amino acid sequence of the VL of monoclonal antibody 4237 (e.g., SEQ ID NO: 172).

In an embodiment the antibody molecule is monoclonal antibody 4237. In an embodiment, monoclonal antibody 4237 is a humanized monoclonal antibody 4237. In an embodiment, the antibody molecule comprises a VH comprising the amino acid sequence of any of SEQ ID NOS: 235-240, a VL comprising the amino acid sequence of any of SEQ ID NOS: 241-245, or both.

In another aspect, the disclosure features an anti-APRIL antibody molecule, which:

(i) binds, or substantially binds, to human APRIL;

(ii) inhibits, or substantially inhibits, binding of APRIL (e.g., human APRIL, mouse APRIL, or both) to TACI (e.g., human TACI, mouse TACI, or both);

(iii) inhibits, or substantially inhibits, binding of APRIL (e.g., human APRIL, mouse APRIL, or both) to BCMA (e.g., human BCMA, mouse BCMA, or both); and (iv) binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or more, residues within a region of human APRIL as defined in any of Tables 3-4 or 7-8.

In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule does not bind to mouse APRIL, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL, mouse APRIL, or both) to TACI (e.g., human TACI, mouse TACI, or both), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In an embodiment, the antibody molecule inhibits, or substantially inhibits, binding of APRIL (e.g., human APRIL, mouse APRIL, or both) to BCMA (e.g., human BCMA, mouse BCMA, or both), e.g., at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In an embodiment, the antibody molecule binds, or substantially binds, to an epitope that comprises APRIL residues from two monomers, e.g., one or more residues from monomer A and monomer B as shown in Table 3. In an embodiment, the antibody molecule binds, or substantially binds, to one or more APRIL residues from the C-D loop (e.g., the loop connecting β-sheets C and D), the G-H loop (e.g., the loop connecting β-sheets G and H), or both. In an embodiment, the antibody molecule binds, or substantially binds, to one or more (e.g., 2, 3, 4, 5, 6, 7, 8, 9, or all) residues of human APRIL from positions 105-114 and/or one or more (e.g., 2, 3, 4, 5, 6, 7, 8, 9, or all) residues of mouse APRIL from positions 96-105. In an embodiment, the antibody molecule does not bind, or binds with low affinity, to one, two or all of Asp129, Arg233, or His203 of human APRIL.

In an embodiment, the antibody molecule comprises one or both of:
(i) a heavy chain variable region (VH) comprising one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of a monoclonal antibody chosen from antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3125, 2621, 4035, 4035-062, 3934, 4338, 4439, or 4237; an HCDR2 comprising an amino acid sequence that differs by no more than 1, 2, or 3 amino acid residues from, or has at least 85, 90, 95, 99 or 100% homology with, the amino acid sequence of the HCDR2 of the (same) monoclonal antibody; or an HCDR3 comprising an amino acid sequence that differs by no more than 1, 2, or 3 amino acid residues from, or has at least 85, 90, 95, 99 or 100% homology with, the amino acid sequence of the HCDR3 of the (same) monoclonal antibody, or (ii) a light chain variable region (VL) comprising one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of the (same) monoclonal antibody; an LCDR2 comprising an amino acid sequence that differs by no more than 1, 2, or 3 amino acid residues from, or has at least 85, 90, 95, 99 or 100% homology with, the amino acid sequence of the LCDR2 of the (same) monoclonal antibody; or an LCDR3 comprising an amino acid sequence that differs by no more than 1, 2, or 3 amino acid residues from, or has at least 85, 90, 95, 99 or 100% homology with, the amino acid sequence of the LCDR3 of the (same) monoclonal antibody.

In an embodiment, the antibody molecule comprises one or both of:
(i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of a monoclonal antibody chosen from antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3125, 2621, 4035, 4035-062, 3934, 4338, 4439, or 4237; or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of the (same) monoclonal antibody.

In an embodiment, the antibody molecule is a synthetic antibody molecule. In an embodiment, the antibody molecule is an isolated antibody molecule. In an embodiment, the antibody molecule is a humanized antibody molecule, e.g., comprising one or more framework regions derived from human framework germline sequence.

In an embodiment, the antibody molecule is an IgG antibody molecule, e.g., comprising a heavy chain constant region of IgG, e.g., chosen from IgG1, IgG2 (e.g., IgG2a), IgG3, or IgG4, e.g., IgG2 or IgG4. In an embodiment, the antibody molecule is an IgG1 antibody molecule. In an embodiment, the antibody molecule is an IgG2 antibody molecule. In an embodiment, the antibody molecule comprises a light chain constant region of kappa or lambda light chain.

In an embodiment, the antibody molecule comprises an Fc region. In an embodiment, the Fc region comprises one or more mutations located at the interface between the CH2 and CH3 domains (e.g., to increase the binding affinity to neonatal receptor FcRn and/or the half-life of the antibody molecule). In an embodiment, the Fc region comprises one or more mutations, e.g., one or more (e.g., 2, 3, 4, 6 or all) mutations chosen from T250Q, M252Y, S254T, T256E, M428L, H433K, N434F, or any combination thereof, of IgG1. In an embodiment, the Fc region comprises one or more mutations at positions 233-236 or 322 of human IgG1 or IgG2, or one or more substitutions at positions 327, 330 or 331 of human IgG4 (e.g., to reduce complement-dependent cytotoxicity (CDC)). In an embodiment, the Fc region comprises one or more (e.g., 2, 3, 4, 6 7 or all) mutations chosen from E233P, L234V, L235A, G236, K322A, A327G, A330S, P331S, or any combination thereof.

In an embodiment, the antibody molecule comprises two heavy chain variable regions and two light chain variable regions. In an embodiment, the antibody molecule is a Fab, F(ab')2, Fv, Fd, or a single chain Fv fragment (scFv).

In an aspect, the disclosure features an anti-APRIL antibody, which:

a) competes for binding to APRIL with an antibody molecule comprising the heavy chain complementary determining regions (HCDR1, HCDR2 and HCDR3) and the light chain complementary determining regions (LCDR1, LCDR2 and LCDR3) of any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237, e.g., as described in Table 1 or 5; or b) binds, or substantially binds, to an epitope that completely or partially overlaps with the epitope of an antibody molecule comprising the heavy chain complementary determining regions (HCDR1, HCDR2 and HCDR3) and the light chain complementary determining regions (LCDR1, LCDR2 and LCDR3) of any of monoclonal antibodies 2218 (e.g., SEQ ID NOS: 1-6 according to Chothia numbering or SEQ ID NOS: 3-8 according to Kabat numbering), 2419 (e.g., SEQ ID NOS: 11-16 according to Chothia numbering or SEQ ID NOS: 13-18 according to Kabat numbering), 2419-0105 (e.g., SEQ ID NOS: 11-13, 16, 280 and 281 according to Chothia numbering or SEQ ID NOS: 13, 16, 17 and 280-282 according to Kabat numbering), 2419-0205 (e.g., SEQ ID NOS: 11-13, 16, 280 and 281 according to Chothia numbering or SEQ ID NOS: 13, 16, 17 and 280-282 according to Kabat numbering), 2419-0206 (e.g., SEQ ID NOS: 11-13, 16, 280 and 285 according to Chothia numbering or SEQ ID NOS: 13, 16, 17, 280, 282 and 285 according to Kabat numbering), 2419-0406 (e.g., SEQ ID NOS: 11-13, 16, 280 and 285 according to Chothia numbering or SEQ ID NOS: 13, 16, 17, 280, 285 and 290 according to Kabat numbering), 2419-0605 (e.g., SEQ ID NOS: 11-13, 16, 280 and 281 according to Chothia numbering or SEQ ID NOS: 13, 16, 17 and 280-282 according to Kabat numbering), 2419-0805 (e.g., SEQ ID NOS: 11-13, 16, 280 and 281 according to Chothia numbering or SEQ ID NOS: 13, 16, 17, 280, 281 and 287 according to Kabat numbering), 2419-0806 (e.g., SEQ ID NOS: 11-13, 16, 280 and 285 according to Chothia numbering or SEQ ID NOS: 13, 16, 17, 280, 285 and 287 according to Kabat numbering), 2419-1204 (e.g., SEQ ID NOS: 11-13, 16, 280 and 293 according to Chothia numbering or SEQ ID NOS: 13, 16, 17, 280, 282 and 293 according to Kabat numbering), 2419-1205 (e.g., SEQ ID NOS: 11-13, 16, 280 and 281 according to Chothia numbering or SEQ ID NOS: 13, 16, 17 and 280-282 according to Kabat numbering), 2419-1210 (e.g., SEQ ID NOS: 11-13, 16, 314 and 315 according to Chothia numbering or SEQ ID NOS: 13, 16, 17, 282, 314 and 315 according to Kabat numbering), 2419-1305 (e.g., SEQ ID NOS: 11-13, 16, 280 and 281 according to Chothia numbering or SEQ ID NOS: 13, 16, 17 and 280-282 according to Kabat numbering), 2419-1306 (e.g., SEQ ID NOS: 11-13, 16, 280 and 285 according to Chothia numbering or SEQ ID NOS: 13, 16, 17, 280, 282 and 285 according to Kabat numbering), 2419-1310 (e.g., SEQ ID NOS: 11-13, 16, 314 and 315 according to Chothia numbering or SEQ ID NOS: 13, 16, 17, 282, 314 and 315 according to Kabat numbering), 2419-1406 (e.g., SEQ ID NOS: 11-13, 16, 280 and 285 according to Chothia numbering or SEQ ID NOS: 13, 16, 17, 280, 282 and 285 according to Kabat numbering), 2922 (e.g., SEQ ID NOS: 21 and 32-36 according to Chothia numbering or SEQ ID NOS: 33-38 according to Kabat numbering), 3327 (e.g., SEQ ID NOS: 51-56 according to Chothia numbering or SEQ ID NOS: 53-58 according to Kabat numbering), 3530 (e.g., SEQ ID NOS: 61-63, 67, 45 and 46 according to Chothia numbering or SEQ ID NOS: 63-65, 67, 45 and 46 according to Kabat numbering), 3525 (e.g., SEQ ID NOS: 44-46 and 61-63 according to Chothia numbering or SEQ ID NOS: 44-46 and 63-65 according to Kabat numbering), 3125 (e.g., SEQ ID NOS: 11 and 42-46 according to Chothia numbering or SEQ ID NOS: 43-48 according to Kabat number), 2621 (e.g., SEQ ID NOS: 21-26 according to Chothia numbering or SEQ ID NOS: 23-28 according to Kabat numbering), 4035 (e.g., SEQ ID NOS: 93-98 according to Chothia numbering or SEQ ID NOS: 95-100 according to Kabat numbering), 4035-062 (e.g., SEQ ID NOS: 93-98 according to Chothia numbering or SEQ ID NOS: 95-99 and 273 according to Kabat numbering), 3934 (e.g., SEQ ID NOS: 103-108 according to Chothia numbering or SEQ ID NOS: 105-110 according to Kabat numbering), 3833 (e.g., SEQ ID NOS: 113-118 according to Chothia numbering or SEQ ID NOS: 115-120 according to Kabat numbering), 3631 (e.g., SEQ ID NOS: 123-128 according to Chothia numbering or SEQ ID NOS: 125-130 according to Kabat numbering), 3732 (e.g., SEQ ID NOS: 127 and 133-137 according to Chothia numbering or SEQ ID NOS: 127 and 135-139 according to Kabat numbering), 4338 (e.g., SEQ ID NOS: 11, 107 and 142-145, or SEQ ID NO: 11, 142, 143 and 146-148 according to Chothia numbering; or SEQ ID NOS: 107, 143-145 and 149-150, or SEQ ID NOS: 143 and 146-150 according to Kabat numbering), 4540 (e.g., SEQ ID NOS: 116 and 154-158 according to Chothia numbering or SEQ ID NOS: 116 and 156-160 according to Kabat numbering), 4540-063 (e.g., SEQ ID NOS: 154-156, 158, 274 and 275 according to Chothia numbering or SEQ ID NOS: 156, 158 and 274-277 according to Kabat numbering), 4540-033 (e.g., SEQ ID NOS: 154-156, 158, 274 and 275 according to Chothia numbering or SEQ ID NOS: 156, 158, 159, 274, 275 and 278 according to Kabat numbering), 4439 (e.g., SEQ ID NOS: 146-148 and 266-268 according to Chothia numbering or SEQ ID NOS: 146-148 and 269-270 according to Kabat numbering), or 4237 (e.g., SEQ ID NOS: 163-168 according to Chothia numbering or SEQ ID NOS: 165-170 according to Kabat numbering), e.g., as described in Table 1 or 5.

In an embodiment, the antibody molecule is a synthetic antibody molecule. In an embodiment, the antibody molecule is an isolated antibody molecule.

In an embodiment, the antibody molecule competes for binding with two, three, four, five, six, seven, eight, nine, ten, or more of the antibody molecules that comprise the HCDR1, HCDR2, HCDR3, LCDR1, LCDR2, and LCDR3 of any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237.

In an embodiment, the antibody molecule binds, or substantially binds, to an epitope that completely or partially overlaps with the epitopes of two, three, four, five, six, seven, eight, nine, ten, or more of the antibody molecules that comprise the HCDR1, HCDR2, HCDR3, LCDR1, LCDR2, and LCDR3 of any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237.

In an embodiment, the antibody molecule that comprises the HCDR1, HCDR2, HCDR3, LCDR1, LCDR2, and LCDR3 of any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 3934, 3833, 3631, 3732, 4338, 4540, 4439, or 4237 comprises a heavy chain variable region and a light chain variable region of any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 3934, 3833, 3631, 3732, 4338, 4540, 4439, or 4237.

In an embodiment, the antibody molecule that comprises the HCDR1, HCDR2, HCDR3, LCDR1, LCDR2, and LCDR3 of any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 3934, 3833, 3631, 3732, 4338, 4540, 4439, or 4237 is monoclonal antibody 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 3934, 3833, 3631, 3732, 4338, 4540, 4439, or 4237.

In an embodiment, the antibody molecule is a humanized monoclonal antibody 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, or 4237. In an embodiment, the antibody molecule comprises a heavy chain variable region (VH) having an amino acid sequence described in Table 1 or 5. In an embodiment, the antibody molecule comprises a light chain variable region (VL) having an amino acid sequence described in Table 1 or 5. In antibody molecule comprises a heavy chain variable region (VH) having an amino acid sequence described in Table 1 or 5 and a light chain variable region (VL) having an amino acid sequence described in Table 1 or 5.

In an embodiment, the antibody molecule competes for binding to human APRIL, mouse APRIL, or both. In an embodiment, the antibody molecule binds, or substantially binds, to human APRIL at an $EC_{50}$ of 20 nM or less, e.g., 10 nM or less, 9 nM or less or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 100 nM, e.g., between 0.001 nM and 50 nM, between 0.01 nM and 20 nM, between 0.1 nM and 20 nM, e.g., between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule binds, or substantially binds, to mouse APRIL at an $EC_{50}$ of 100 nM or less, e.g., 80 nM or less, 60 nM or less, 40 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 100 nM, e.g., between 0.001 nM and 50 nM, between 0.01 nM and 20 nM, between 0.1 nM and 20 nM, e.g., between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL, mouse APRIL, or both) to TACI (e.g., human TACI, mouse TACI, or both), inhibits, or substantially inhibits, binding of APRIL (e.g., human APRIL, mouse APRIL, or both) to BCMA (e.g., human BCMA, mouse BCMA, or both), or both.

In an embodiment, the antibody molecule inhibits, or substantially inhibits, binding of APRIL (e.g., human APRIL, mouse APRIL, or both) to TACI (e.g., human TACI, mouse TACI, or both), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In an embodiment, binding of the antibody molecule to APRIL (e.g., human APRIL) inhibits, or substantially inhibits, the binding of the CRD2 domain of TACI (e.g., human TACI) to APRIL (e.g., human APRIL).

In an embodiment, binding of the antibody molecule to human APRIL inhibits, or substantially inhibits, the binding of human TACI, to one or more, e.g., 2, 3, 4, 5, 6, 7, 8, 9, 10, 11, 12, 13, 14, 15, 16, 17, 18, 19, 20, 21, 22, 23, 24, 25, or all of the human APRIL residues from Table 3. In an embodiment, binding of the antibody molecule to human APRIL, inhibits, or substantially inhibits, the binding of human TACI to one or more, e.g., 2, 3, 4, 5, 6, 7, 8, 9, 10, or all of the human APRIL residues from Table 4. In an embodiment, binding of the antibody molecule to human APRIL, inhibits, or substantially inhibits, the binding of human TACI to one or more, e.g., 2, 3, 4, 5, 6, 7, 8, 9, 10, 11, 12, 13, 14, 15, 16, 17, or all of the human APRIL residues from Table 7. In an embodiment, binding of the antibody molecule to human APRIL, inhibits, or substantially inhibits, the binding of human TACI to one or more, e.g., 2, 3, 4, 5, 6, 7, 8, 9, 10, 11, 12, 13, 14, 15, 16, 17, 18, 19, 20, 21, 22, 23, 24, 25, or all of the human APRIL residues from Table 8.

In an embodiment, the antibody molecule inhibits, or substantially inhibits, binding of APRIL (e.g., human APRIL, mouse APRIL, or both) to BCMA (e.g., human BCMA, mouse BCMA, or both).

In an embodiment, the antibody molecule inhibits, or substantially inhibits, binding of APRIL (e.g., human APRIL, mouse APRIL, or both) to BCMA (e.g., human BCMA, mouse BCMA, or both), e.g., at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In an embodiment, the antibody molecule does not inhibit, or does not substantially inhibit, binding of APRIL (e.g., human APRIL, mouse APRIL, or both) to BCMA (e.g., human BCMA, mouse BCMA, or both).

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or more, residues within a region of human APRIL as defined in any of Tables 3-4 or 7-8. In an embodiment, the antibody molecule binds, or substantially binds, to a conformational epitope.

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or more, residues within a region of human APRIL as defined in Table 3. In an embodiment, the antibody molecule binds to an epitope that comprises or consists of one or more, e.g., 2, 3, 4, 5, 6, 7, 8, 9, 10, 11, 12, 13, 14, 15, 16, 17, 18, 19, 20, 21, 22, 23, 24, 25, or all of the human APRIL residues from Table 3. In an embodiment, the antibody molecule binds, or substantially binds, to an epitope that comprises APRIL residues from two monomers, e.g., one or more residues from monomer A and monomer B as shown in Table 3.

In an embodiment, the antibody molecule binds, or substantially binds, to one or more, e.g., 2, 3, 4, 5, 6, 7, 8, 9, 10, or more, residues within a region of human APRIL as defined in Table 4. In an embodiment, the antibody molecule binds, or substantially binds, to an epitope that comprises consists of one or more, e.g., 2, 3, 4, 5, 6, 7, 8, 9, 10, or all of the APRIL residues from Table 4. In an embodiment, the antibody molecule binds, or substantially binds, to an epitope that comprises one or more APRIL residues from the C-D loop (e.g., the loop connecting β-sheets C and D), the G-H loop (e.g., the loop connecting β-sheets G and H), or both.

In an embodiment, the antibody molecule binds, or substantially binds, to one or more, e.g., 2, 3, 4, 5, 6, 7, 8, 9, 10, 11, 12, 13, 14, 15, 16, 17, or all, residues within a region of human APRIL as defined in Table 7. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, or all, of the human APRIL residues from Table 7. In an embodiment, the antibody molecule binds, or substantially binds, to an epitope that overlaps an epitope that comprises or consists of all of the human APRIL residues from Table 7.

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or all, residues within a region of human APRIL as defined in Table 8. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 8. In an embodiment, the antibody molecule binds, or substantially binds, to an epitope that overlaps an epitope that comprises or consists of all of the human APRIL residues from Table 8.

In an embodiment, the antibody molecule binds, or substantially binds, to one or more (e.g., 2, 3, 4, 5, 6, 7, 8, 9, or all) residues of human APRIL from positions 105-114 and/or one or more (e.g., 2, 3, 4, 5, 6, 7, 8, 9, or all) residues of mouse APRIL from positions 96-105. In an embodiment, the antibody molecule does not bind, or does not substantially bind, to one, two or all of Asp129, Arg233, or His203 of human APRIL.

In an embodiment, the antibody molecule is an IgG antibody molecule, e.g., comprising a heavy chain constant region of IgG, e.g., chosen from IgG1, IgG2 (e.g., IgG2a), IgG3, or IgG4, e.g., IgG2 or IgG4. In an embodiment, the antibody molecule is an IgG1 antibody molecule. In another embodiment, the antibody molecule is an IgG2 antibody molecule. In an embodiment, the antibody molecule comprises a light chain constant region of kappa or lambda light chain.

In an embodiment, the antibody molecule comprises an Fc region. In an embodiment, the Fc region comprises one or more mutations located at the interface between the CH2 and CH3 domains (e.g., to increase the binding affinity to neonatal receptor FcRn and/or the half-life of the antibody molecule). In an embodiment, the Fc region comprises one or more mutations, e.g., one or more (e.g., 2, 3, 4, 6 or all) mutations chosen from T250Q, M252Y, S254T, T256E, M428L, H433K, N434F, or any combination thereof, of IgG1. In an embodiment, the Fc region comprises one or more mutations at positions 233-236 or 322 of human IgG1 or IgG2, or one or more substitutions at positions 327, 330 or 331 of human IgG4 (e.g., to reduce complement-dependent cytotoxicity (CDC)). In an embodiment, the Fc region comprises one or more (e.g., 2, 3, 4, 6 7 or all) mutations chosen from E233P, L234V, L235A, G236, K322A, A327G, A330S, P331S, or any combination thereof.

In an embodiment, the antibody molecule is a humanized antibody molecule, e.g., comprising one or more framework regions derived from human framework germline sequence. In an embodiment, the antibody molecule comprises two heavy chain variable regions and two light chain variable regions. In an embodiment, the antibody molecule is a Fab, F(ab')2, Fv, Fd, or a single chain Fv fragment (scFv).

In an aspect, the disclosure features an anti-APRIL antibody molecule described herein, e.g., a synthetic or isolated anti-APRIL antibody molecule described herein.

In an embodiment, the antibody molecule comprises:
(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2218 (e.g., SEQ ID NO: 1 or 7); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2218 (e.g., SEQ ID NO: 2 or 8); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2218 (e.g., SEQ ID NO: 3), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2218 (e.g., SEQ ID NO: 4); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2218 (e.g., SEQ ID NO: 5); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2218 (e.g., SEQ ID NO: 6).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2218 (e.g., SEQ ID NO: 9); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2218 (e.g., SEQ ID NO: 10).

In an embodiment, the antibody molecule comprises a VH encoded by the nucleotide sequence of SEQ ID NO: 71 (or a nucleotide sequence substantially identical thereto) or a VL encoded by the nucleotide sequence of SEQ ID NO: 72 (or a nucleotide sequence substantially identical thereto), or both.

In an embodiment, the antibody molecule is monoclonal antibody 2218. In an embodiment, monoclonal antibody 2218 is humanized monoclonal antibody 2218. In an embodiment, the antibody molecule comprises a VH comprising the amino acid sequence of any of SEQ ID NO: 190-201, a VL comprising the amino acid sequence of any of SEQ ID NO: 202-208, or both.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 1 nM or less, e.g., about 0.6 nM. In an embodiment, the antibody molecule does not bind to mouse APRIL, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both.

In an embodiment, the antibody molecule inhibits, or substantially inhibits, binding of human APRIL to human TACI at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 1 nM or less, e.g., about 0.74 nM.

In an embodiment, the antibody molecule inhibits, or substantially inhibits, binding of human APRIL to human BCMA at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 0.5 nM or less, e.g., about 0.22 nM.

In an embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence of G-Y-T-F-T-D-Y (SEQ ID NO: 11); an HCDR2 comprising an amino acid sequence of Y-P-L-R-G-S(SEQ ID NO: 12); or an HCCDR3 comprising an amino acid sequence of H-G-A-Y-Y-S-N-A-F-D-Y (SEQ ID NO: 13), or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence of X1-X2-S-X4-S-V-D-N-D-G-I-R-F-X14-H (SEQ ID NO: 327), wherein X1 is R or K; X2 is A or S; X4 is E or Q; and X14 is M or L; an LCDR2 comprising an amino acid sequence of R-A-S-X4-X5-X6-X7 (SEQ ID NO: 328), wherein X4 is N or T; X5 is L or R;

X6 is E or A; and X7 is S or T; or an LCDR3 comprising an amino acid sequence of Q-Q-S-N-K-D-P-Y-T (SEQ ID NO: 16).

In another embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence of D-Y-T-I-H (SEQ ID NO: 17); an HCDR2 comprising an amino acid sequence of W-I-Y-P-L-R-G-S-I-N-Y-X12-X13-X14-F-X16-X17 (SEQ ID NO: 329), wherein X12 is N, S, or A, X13 is E, P, or Q; X14 is K or S; X16 is K or Q; and X17 is D or G; or an HCCDR3 comprising an amino acid sequence of H-G-A-Y-Y-S-N-A-F-D-Y (SEQ ID NO: 13), or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence of X1-X2-S-X4-S-V-D-N-D-G-I-R-F-X14-H (SEQ ID NO: 327), wherein X1 is R or K; X2 is A or S; X4 is E or Q; and X14 is M or L; an LCDR2 comprising an amino acid sequence of R-A-S-X4-X5-X6-X7 (SEQ ID NO: 328), wherein X4 is N or T; X5 is L or R; X6 is E or A; and X7 is S or T; or an LCDR3 comprising an amino acid sequence of Q-Q-S-N-K-D-P-Y-T (SEQ ID NO: 16).

In an embodiment, the antibody molecule is any of antibodies 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, or 2419-1406.

In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 0.01 nM or less, e.g., about 0.001-0.005 nM or 0.002-0.004 nM, e.g., about 0.001, 0.002, 0.003, 0.004, or 0.005 nM. In an embodiment, the antibody molecule does not bind to mouse APRIL, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both.

In an embodiment, the antibody molecule inhibits, or substantially inhibits, binding of human APRIL to human TACI at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 0.5 nM or less, e.g., about 0.1-0.5 nM or 0.2-0.4 nM, e.g., about 0.1, 0.2, 0.3, 0.4, or 0.5 nM.

In an embodiment, the antibody molecule inhibits, or substantially inhibits, binding of human APRIL to human BCMA at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 0.5 nM or less, e.g., about 0.1-0.5 nM or 0.2-0.4 nM, e.g., about 0.1, 0.2, 0.3, 0.4, or 0.5 nM.

In another embodiment, the antibody molecule comprises (i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2419 (e.g., SEQ ID NO: 11 or 17); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2419 (e.g., SEQ ID NO: 12 or 18); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2419 (e.g., SEQ ID NO: 13), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2419 (e.g., SEQ ID NO: 14); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2419 (e.g., SEQ ID NO: 15); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2419 (e.g., SEQ ID NO: 16).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2419 (e.g., SEQ ID NO: 19); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2419 (e.g., SEQ ID NO: 20).

In an embodiment, the antibody molecule comprises a VH encoded by the nucleotide sequence of SEQ ID NO: 73 (or a nucleotide sequence substantially identical thereto) or a VL encoded by the nucleotide sequence of SEQ ID NO: 74 (or a nucleotide sequence substantially identical thereto), or both.

In an embodiment, the antibody molecule is monoclonal antibody 2419. In an embodiment, monoclonal antibody 2419 is humanized monoclonal antibody 2419. In an embodiment, the antibody molecule comprises a VH comprising the amino acid sequence of any of SEQ ID NOS: 209-214, a VL comprising the amino acid sequence of any of SEQ ID NOS: 215-219, or both.

In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 1 nM or less, e.g., about 0.8 nM, about 0.003 nM, or about 0.002 nM. In an embodiment, the antibody molecule does not bind, or bind to mouse APRIL with low affinity, e.g., at an $EC_{50}$ of 500 nM or more.

In an embodiment, the antibody molecule inhibits, or substantially inhibits, binding of APRIL (e.g., human APRIL) to TACI (e.g., human TACI), BCMA (e.g., human BCMA), or both.

In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 1 nM or less, e.g., about 0.74 nM, about 0.4 nM, 0.3 nM, or 0.2 nM.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 5 nM or less, e.g., about 4 nM, about 2 nM, or about 1 nM, or 0.5 nM or less, e.g., about 0.22 nM, about 1 nM, about 0.7 nM, about 0.3 nM, about 0.2 nM, or about 0.1 nM.

In another embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of a 2419-related antibody (e.g., SEQ ID NO: 11 or 17); an HCDR2 comprising an amino acid sequence that differs by no more than 1, 2, or 3 amino acid residues from, or has at least 85, 90, 95, 99 or 100% homology with, the amino acid sequence of the HCDR2 of the 2419-related antibody (e.g., SEQ ID NOS: 12, 282, 287, or 290); or an HCDR3 comprising an amino acid sequence that differs by no more than 1, 2, or 3 amino acid residues from, or has at least 85, 90, 95, 99 or 100% homology with, the amino acid sequence of the HCDR3 of the 2419-related antibody (e.g., SEQ ID NO: 13), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of the 2419-related antibody (e.g., SEQ ID NOS: 280 or 314); an LCDR2 comprising an amino acid sequence that differs by no more than 1, 2, or 3 amino acid residues from, or has at least 85, 90, 95, 99 or 100% homology with, the amino acid sequence of the LCDR2 of the 2419-related antibody (e.g., SEQ ID NOS: 281, 285, 293, or 315); or an LCDR3 comprising an amino acid sequence that differs by no more than 1, 2, or 3 amino acid residues from, or has at least 85, 90, 95, 99 or 100% homology with, the amino acid sequence of the LCDR3 of the 2419-related antibody (e.g., SEQ ID NO: 16).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of the 2419-related antibody (e.g., SEQ ID NOS: 283, 288, 289, 291, 292, 294, 296, or 317); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of the 2419-related antibody (e.g., SEQ ID NOS: 284, 286, 295, or 316).

In an embodiment, the antibody molecule comprises a VH encoded by the VH nucleotide sequence of the 2419-related antibody (e.g., SEQ ID NOS: 304, 307, 308, 309, 310, 311, 313, or 319) (or a nucleotide sequence substantially identical thereto) or a VL encoded by the VL nucleotide sequence of the 2419-related antibody (e.g., SEQ ID NOS: 305, 306, 312, or 318) (or a nucleotide sequence substantially identical thereto), or both.

In an embodiment, the 2419-related antibody molecule is chosen from antibodies 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, or 2419-1406. In an embodiment, the 2419-related antibody is humanized antibody molecule. In an embodiment, the antibody molecule comprises a VH comprising the amino acid sequence of any of SEQ ID NOS: 209-214, 283, 288, 289, 291, 292, 294, 296, or 317, a VL comprising the amino acid sequence of any of SEQ ID NOS: 215-219, 284, 286, 295, or 316, or both.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, e.g., between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 1 nM or less, e.g., about 0.8 nM, about 0.003 nM, or about 0.002 nM.

In an embodiment, the antibody molecule does not bind, or bind to mouse APRIL with low affinity, e.g., at an $EC_{50}$ of 500 nM or more.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 1 nM or less, e.g., about 0.74 nM, about 0.4 nM, 0.3 nM, or 0.2 nM.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 5 nM or less, e.g., about 4 nM, about 2 nM, or about 1 nM, or 0.5 nM or less, e.g., about 0.22 nM, about 1 nM, about 0.7 nM, about 0.3 nM, about 0.2 nM, or about 0.1 nM.

In another embodiment, the antibody molecule comprises (i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2922 (e.g., SEQ ID NO: 21 or 37); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2922 (e.g., SEQ ID NO: 32 or 38); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2922 (e.g., SEQ ID NO: 33), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2922 (e.g., SEQ ID NO: 34); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2922 (e.g., SEQ ID NO: 35); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2922 (e.g., SEQ ID NO: 36).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2922 (e.g., SEQ ID NO: 39); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2922 (e.g., SEQ ID NO: 40).

In an embodiment, the antibody molecule comprises a VH encoded by the nucleotide sequence of SEQ ID NO: 77 (or a nucleotide sequence substantially identical thereto) or a VL encoded by the nucleotide sequence of SEQ ID NO: 78 (or a nucleotide sequence substantially identical thereto), or both.

In an embodiment, the antibody molecule is monoclonal antibody 2922. In an embodiment, the antibody molecule is humanized monoclonal antibody 2922.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 5 nM or less, e.g., about 3.3 nM. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 50 nM or less, e.g., about 31.64 nM.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the $IC_{50}$ is 50 nM or less. In an embodiment, the antibody molecule inhibits binding of human TACI to human BCMA at an $IC_{50}$ of 25 nM or less, e.g., about 21.96 nM.

In another embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3327 (e.g., SEQ ID NO: 51 or 57); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3327 (e.g., SEQ ID NO: 52 or 58); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3327 (e.g., SEQ ID NO: 53), and (ii) a light chain variable region (VH), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3327 (e.g., SEQ ID NO: 54); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3327 (e.g., SEQ ID NO: 55); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3327 (e.g., SEQ ID NO: 56).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3327 (e.g., SEQ ID NO: 59); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3327 (e.g., SEQ ID NO: 60).

In an embodiment, the antibody molecule comprises a VH encoded by the nucleotide sequence of SEQ ID NO: 81 (or a nucleotide sequence substantially identical thereto) or a VL encoded by the nucleotide sequence of SEQ ID NO: 82 (or a nucleotide sequence substantially identical thereto), or both.

In an embodiment, the antibody molecule is monoclonal antibody 3327. In an embodiment, the antibody molecule is humanized antibody 3327.

In an embodiment, the antibody molecule binds, or substantially binds, to human APRIL. In an embodiment, the antibody molecule binds, or substantially binds, to human APRIL at an $EC_{50}$ of 100 nM or less, e.g., 80 nM or less, 60 nM or less, 40 nM or less, 20 nM or less, 10 nM or less, 9 nM or less 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 100 nM, e.g., between 0.001 nM and 50 nM, between 0.01 nM and 20 nM, between 0.1 nM and 10 nM, between 0.5 nM and 5 nM or between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 3.16 nM.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the $IC_{50}$ is 50 nM or less. In an embodiment, the antibody molecule inhibits binding of human APRIL to human BCMA at an $IC_{50}$ of 5 nM or less, e.g., about 2.35 nM.

In another embodiment, the antibody molecule comprises:
(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4035 (e.g., SEQ ID NO: 93 or 99); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4035 (e.g., SEQ ID NO: 94 or 100); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4035 (e.g., SEQ ID NO: 95), and (ii) a light chain variable region (VH), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4035 (e.g., SEQ ID NO: 96); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4035 (e.g., SEQ ID NO: 97); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4035 (e.g., SEQ ID NO: 98).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4035 (e.g., SEQ ID NO: 101); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4035 (e.g., SEQ ID NO: 102).

In an embodiment, the antibody molecule comprises a VH encoded by the nucleotide sequence of SEQ ID NO: 173 (or a nucleotide sequence substantially identical thereto) or a VL encoded by the nucleotide sequence of SEQ ID NO: 174 (or a nucleotide sequence substantially identical thereto), or both.

In an embodiment, the antibody molecule is monoclonal antibody 4035. In an embodiment, monoclonal antibody 4035 is humanized monoclonal antibody 4035. In an embodiment, the antibody molecule comprises a VH comprising the amino acid sequence of any of SEQ ID NO: 220-227 or 262-265, a VL comprising the amino acid sequence of any of SEQ ID NO: 228-234, or both.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 0.01 nM or less, e.g., about 0.001-0.002 nM. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 3.16 nM, or about 0.1-0.5 nM or 0.2-0.4 nM.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 5 nM or less, e.g., about 2.35 nM, or about 0.1-0.5 nM or 0.1-0.2 nM.

In another embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4035-062 (e.g., SEQ ID NO: 93 or 99); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4035-062 (e.g., SEQ ID NO: 94 or 273); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4035-062 (e.g., SEQ ID NO: 95), and (ii) a light chain variable region (VH), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4035-062 (e.g., SEQ ID NO: 96); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4035-062 (e.g., SEQ ID NO: 97); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4035-062 (e.g., SEQ ID NO: 98).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4035-062 (e.g., SEQ ID NO: 225); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4035-062 (e.g., SEQ ID NO: 229).

In an embodiment, the antibody molecule comprises a VH encoded by the nucleotide sequence of SEQ ID NO: 299 (or a nucleotide sequence substantially identical thereto) or a VL encoded by the nucleotide sequence of SEQ ID NO: 300 (or a nucleotide sequence substantially identical thereto), or both.

In an embodiment, the antibody molecule is monoclonal antibody 4035-062.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 0.01 nM or less, e.g., about 0.001-0.002 nM. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 1 nM or less, e.g., about 0.1-0.5 nM or 0.2-0.4 nM.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 1 nM or less, e.g., about 0.1-0.5 nM or 0.1-0.2 nM.

In another embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising the amino acid sequence of I-Y-D-V-H (SEQ ID NO: 99); an HCDR2 comprising the amino acid sequence of V-I-W-S-D-G-S-T-D-Y-N-X12-X13-X14-X15-S(SEQ ID NO: 342), X12 is A or P, X13 is A or S, X14 is F or L, and X15 is I or K; or an HCDR3 comprising the amino acid sequence of N-W-V-D-Q-A-W-F-A-Y (SEQ ID NO: 95), and (ii) a light chain variable region (VH), wherein the light chain variable region comprises three light chain complementarity determining regions (LCDR1, LCDR2, and LCDR3), wherein the light chain variable region comprises one, two, or all of the following: an LCDR1 comprising the amino acid sequence of R-A-S-K-N-I-Y-S-Y-L-A (SEQ ID NO: 96); an LCDR2 comprising the amino acid sequence of N-A-K-T-L-P-E (SEQ ID NO: 97); or an LCDR3 comprising the amino acid sequence of Q-H-H-Y-G-T-P-L-T (SEQ ID NO: 98).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO: 101 or 225; or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO: 102 or 229.

In an embodiment, the antibody molecule is monoclonal antibody 4035. In an embodiment, the antibody molecule is monoclonal antibody 4035-062.

In another embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3934 (e.g., SEQ ID NO: 103 or 109); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3934 (e.g., SEQ ID NO: 104 or 110); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3934 (e.g., SEQ ID NO: 105), and (ii) a light chain variable region (VH), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3934 (e.g., SEQ ID NO: 106); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3934 (e.g., SEQ ID NO: 107); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3934 (e.g., SEQ ID NO: 108).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3934 (e.g., SEQ ID NO: 111); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3934 (e.g., SEQ ID NO: 112).

In an embodiment, the antibody molecule comprises a VH encoded by the nucleotide sequence of SEQ ID NO: 175 (or a nucleotide sequence substantially identical thereto) or a VL encoded by the nucleotide sequence of SEQ ID NO: 176 (or a nucleotide sequence substantially identical thereto), or both.

In an embodiment, the antibody molecule is monoclonal antibody 3934. In an embodiment, the antibody molecule is humanized monoclonal antibody 3934.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 3.16 nM.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 5 nM or less, e.g., about 2.35 nM.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4338 (e.g., SEQ ID NO: 11 or 149); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4338 (e.g., SEQ ID NO: 142 or 150); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4338 (e.g., SEQ ID NO: 143), and (ii) a light chain variable region (VH), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4338 (e.g., SEQ ID NO: 144 or 146); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4338 (e.g., SEQ ID NO: 107 or 147); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4338 (e.g., SEQ ID NO: 145 or 148).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4338 (e.g., SEQ ID NO: 151); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4338 (e.g., SEQ ID NO: 152 or 153).

In an embodiment, the antibody molecule comprises a VH encoded by the nucleotide sequence of SEQ ID NO: 183 (or a nucleotide sequence substantially identical thereto) or a VL encoded by the nucleotide sequence of SEQ ID NO: 184 or 185 (or a nucleotide sequence substantially identical thereto), or both.

In an embodiment, the antibody molecule is monoclonal antibody 4338. In an embodiment, the antibody molecule is humanized monoclonal antibody 4338.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 3.16 nM.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 5 nM or less, e.g., about 2.35 nM.

In another embodiment, the antibody molecule comprises (i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4237 (e.g., SEQ ID NO: 163 or 169); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4237 (e.g., SEQ ID NO: 164 or 170); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4237 (e.g., SEQ ID NO: 165), and (ii) a light chain variable region (VH), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4237 (e.g., SEQ ID NO: 166); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4237 (e.g., SEQ ID NO: 167); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4237 (e.g., SEQ ID NO: 168).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4237 (e.g., SEQ ID NO: 171); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4237 (e.g., SEQ ID NO: 172).

In an embodiment, the antibody molecule comprises a VH encoded by the nucleotide sequence of SEQ ID NO: 188 (or a nucleotide sequence substantially identical thereto) or a VL encoded by the nucleotide sequence of SEQ ID NO: 189 (or a nucleotide sequence substantially identical thereto), or both.

In an embodiment, the antibody molecule is monoclonal antibody 4237. In an embodiment, monoclonal antibody 4237 is humanized monoclonal antibody 4237. In an embodiment, the antibody molecule comprises a VH comprising the amino acid sequence of any of SEQ ID NO: 235-240, a VL comprising the amino acid sequence of any of SEQ ID NO: 241-245, or both.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 3.16 nM.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 5 nM or less, e.g., about 2.35 nM.

In another embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence of G-Y-X3-X4-T-X6-X7-Y (SEQ ID NO: 330), wherein X3 is S or T; X4 is I or F; X6 is S or absent; and X7 is G, D or S; an HCDR2 comprising an amino acid sequence of X3-X4-X5-X6-X7-X8 (SEQ ID NO: 331), wherein X3 is absent, N or Y; X4 is S or P, X5 is Y, L or R; X6 is D, N or R; X7 is G or S; and X8 is Y, D or S; or an HCCDR3 comprising an amino acid sequence of X1-X2-X3-X4-Y-X6-X7-X8-X9-F-X11-X12 (SEQ ID NO: 332), wherein X1 is Y, E or H; X2 is absent or G; X3 is Y, D or A; X4 is D, G or Y; X6 is E, absent or D; X7 is D, Y, S or K; X8 is W, N or R; X9 is Y, A or G; X11 is G or D; and X12 is V or Y, or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence of X1-A-S-X4-S-V-X7-X8-X9-G-X11-X12-X13-X14-X15 (SEQ ID NO: 333), wherein X1 is R or K; X4 is E or Q; X7 is D or S; X8 is N, F, I or N; X9 is Y, A, I or D; X11 is I or T; X12 is S, N or R; X13 is F, L or S; X14 is M or I; and X15 is N or H; an LCDR2 comprising an amino acid sequence of X1-A-S-N-X5-X6-X7 (SEQ ID NO: 334), wherein X1 is A, R or H; X5 is Q or L; X6 is G or E; and X7 is S, P or T; or an LCDR3 comprising an amino acid sequence of X1-Q-S-X4-X5-X6-P-X8-T (SEQ ID NO: 335), wherein X1 is Q or L; X4 is K, R or N; X5 is E or K; X6 is V, Y, I or D; and X8 is R, W or Y.

In an embodiment, the antibody molecule is any of monoclonal antibodies 2218, 2419, 2922, or 3327.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, or 0.1 nM or less, e.g., between 0.1 and 50 nM, e.g., between 0.1 nM and 25 nM, between 0.1 nM and 10 nM, between 0.5 nM and 5 nM, or between 1 nM and 5 nM, e.g., as determined by a method described herein.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In another embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence of X6-X7-Y-X9-X10-X11 (SEQ ID NO: 336), wherein X6 is S or absent; X7 is G, D or S; X9 is Y, F, T or D; X10 is W, M, I or V; and X11 is N, H or F; an HCDR2 comprising an amino acid sequence of X1-I-X3-X4-X5-X6-X7-X8-X9-X10-Y-N-X13-X14-X15-K-X17 (SEQ ID NO: 337), wherein X1 is Y, R or W; X3 is absent, N or Y; X4 is S or P, X5 is Y, L or R; X6 is D, N or R; X7 is G or S; X8 is Y, D or S; X9 is N, T or I; X10 is N, F or K; X13 is P, Q or E; X14 is S or K; X15 is L or F; and X17 is N, G or D; or an HCCDR3 comprising an amino acid sequence of X1-X2-X3-X4-Y-X6-X7-X8-X9-F-X11-X12 (SEQ ID NO: 332), wherein X1 is Y, E or H; X2 is absent or G; X3 is Y, D or A; X4 is D, G or Y; X6 is E, absent or D; X7 is D, Y, S or K; X8 is W, N or R; X9 is Y, A or G; X11 is G or D; and X12 is V or Y, or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence of X1-A-S-X4-S-V-X7-X8-X9-G-X11-X12-X13-X14-X15 (SEQ ID NO: 333), wherein X1 is R or K; X4 is E or Q; X7 is D or S; X8 is N, F, I or N; X9 is Y, A, I or D; X11 is I or T; X12 is S, N or R; X13 is F, L or S; X14 is M or I; and X15 is N or H; an LCDR2 comprising an amino acid sequence of X1-A-S-N-X5-X6-X7 (SEQ ID NO: 334), wherein X1 is A, R or H; X5 is Q or L; X6 is G or E; and X7 is S, P or T; or an LCDR3 comprising an amino acid sequence of X1-Q-S-X4-X5-X6-P-X8-T (SEQ ID NO: 335), wherein X1 is Q or L; X4 is K, R or N; X5 is E or K; X6 is V, Y, I or D; and X8 is R, W or Y.

In an embodiment, the antibody molecule is any of monoclonal antibodies 2218, 2419, 2922, or 3327. In an embodiment, the antibody molecule is a humanized monoclonal antibody 2218, 2419, 2922, or 3327.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of human APRIL to human TACI, at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In an embodiment, the antibody molecule inhibits, or substantially inhibits, binding of human APRIL to human BCMA, at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein.

In another embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3530 (e.g., SEQ ID NO: 61 or 64); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3530 (e.g., SEQ ID NO: 62 or 65); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3530 (e.g., SEQ ID NO: 63), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3530 (e.g., SEQ ID NO: 67); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3530 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3530 (e.g., SEQ ID NO: 46).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3530 (e.g., SEQ ID NO: 66); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3530 (e.g., SEQ ID NO: 70).

In an embodiment, the antibody molecule comprises a VH encoded by the nucleotide sequence of SEQ ID NO: 83 (or a nucleotide sequence substantially identical thereto) or a VL encoded by the nucleotide sequence of SEQ ID NO: 84 (or a nucleotide sequence substantially identical thereto), or both.

In an embodiment, the antibody molecule is monoclonal antibody 3530. In an embodiment, the antibody molecule is a humanized monoclonal antibody 3530.

In an embodiment, the antibody molecule binds, or substantially binds, to human APRIL, mouse APRIL, or both.

In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 5 nM or less, e.g., about 2.7 nM.

In an embodiment, the antibody molecule binds, or substantially binds, to mouse APRIL at an $EC_{50}$ of 100 nM or less, e.g., 80 nM or less, 60 nM or less, 40 nM or less, 20 nM or less, 10 nM or less, 9 nM or less 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 100 nM, e.g., between 0.001 nM and 50 nM, between 0.01 nM and 20 nM, between 0.1 nM and 10 nM, between 0.5 nM and 5 nM or between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of APRIL (e.g., human APRIL, mouse APRIL, or both) to TACI (e.g., human TACI, mouse TACI, or both), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 4.95 nM.

In an embodiment, the antibody molecule inhibits, or substantially inhibits, binding of APRIL (e.g., human APRIL, mouse APRIL, or both) to BCMA (e.g., human BCMA, mouse BCMA, or both), at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 1 nM or less, e.g., about 0.68 nM.

In an embodiment, the antibody molecule comprises:
(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3525 (e.g., SEQ ID NO: 61 or 64); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3525 (e.g., SEQ ID NO: 62 or 65); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3525 (e.g., SEQ ID NO: 63), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3525 (e.g., SEQ ID NO: 44); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3525 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3525 (e.g., SEQ ID NO: 46).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3525 (e.g., SEQ ID NO: 66); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3525 (e.g., SEQ ID NO: 50).

In an embodiment, the antibody molecule comprises a VH encoded by the nucleotide sequence of SEQ ID NO: 83 (or a nucleotide sequence substantially identical thereto) or a VL encoded by the nucleotide sequence of SEQ ID NO: 80 (or a nucleotide sequence substantially identical thereto), or both.

In an embodiment, the antibody molecule is monoclonal antibody 3525. In an embodiment, the antibody molecule is a humanized monoclonal antibody 3525.

In an embodiment, the antibody molecule binds, or substantially binds, to human APRIL, mouse APRIL, or both.

In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 5 nM or less, e.g., about 2.5 nM.

In an embodiment, the antibody molecule binds, or substantially binds, to mouse APRIL at an $EC_{50}$ of 100 nM or less, e.g., 80 nM or less, 60 nM or less, 40 nM or less, 20 nM or less, 10 nM or less, 9 nM or less 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 100 nM, e.g., between 0.001 nM and 50 nM, between 0.01 nM and 20 nM, between 0.1 nM and 10 nM, between 0.5 nM and 5 nM or between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of APRIL (e.g., human APRIL, mouse APRIL, or both) to TACI (e.g., human TACI, mouse TACI, or both), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 4.05 nM.

In an embodiment, the antibody molecule inhibits, or substantially inhibits, binding of APRIL (e.g., human APRIL, mouse APRIL, or both) to BCMA (e.g., human BCMA, mouse BCMA, or both), at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 1 nM or less, e.g., about 0.85 nM.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3833 (e.g., SEQ ID NO: 113 or 119); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3833 (e.g., SEQ ID NO: 114 or 120); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3833 (e.g., SEQ ID NO: 115), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3833 (e.g., SEQ ID NO: 116); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3833 (e.g., SEQ ID NO: 117); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3833 (e.g., SEQ ID NO: 118).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3833 (e.g., SEQ ID NO: 121); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3833 (e.g., SEQ ID NO: 122).

In an embodiment, the antibody molecule comprises a VH encoded by the nucleotide sequence of SEQ ID NO: 177 (or a nucleotide sequence substantially identical thereto) or a VL encoded by the nucleotide sequence of SEQ ID NO: 178 (or a nucleotide sequence substantially identical thereto), or both.

In an embodiment, the antibody molecule is monoclonal antibody 3833. In an embodiment, monoclonal antibody 3833 is a humanized monoclonal antibody 3833. In an embodiment, the antibody molecule comprises a VH comprising the amino acid sequence of any of SEQ ID NO: 246-250, a VL comprising the amino acid sequence of any of SEQ ID NO: 251-253, or both.

In an embodiment, the antibody molecule binds, or substantially binds, to human APRIL, mouse APRIL, or both.

In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 5 nM or less, e.g., about 2.5 nM.

In an embodiment, the antibody molecule binds, or substantially binds, to mouse APRIL at an $EC_{50}$ of 100 nM or less, e.g., 80 nM or less, 60 nM or less, 40 nM or less, 20 nM or less, 10 nM or less, 9 nM or less 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 100 nM, e.g., between 0.001 nM and 50 nM, between 0.01 nM and 20 nM, between 0.1 nM and 10 nM, between 0.5 nM and 5 nM or between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of APRIL (e.g., human APRIL, mouse APRIL, or both) to TACI (e.g., human TACI, mouse TACI, or both), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 4.05 nM.

In an embodiment, the antibody molecule inhibits, or substantially inhibits, binding of APRIL (e.g., human APRIL, mouse APRIL, or both) to BCMA (e.g., human BCMA, mouse BCMA, or both), at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 1 nM or less, e.g., about 0.85 nM.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3631 (e.g., SEQ ID NO: 123 or 129); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3631 (e.g., SEQ ID NO: 124 or 130); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3631 (e.g., SEQ ID NO: 125), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3631 (e.g., SEQ ID NO: 126); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3631 (e.g., SEQ ID NO: 127); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3631 (e.g., SEQ ID NO: 128).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3631 (e.g., SEQ ID NO: 131); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3631 (e.g., SEQ ID NO: 132).

In an embodiment, the antibody molecule comprises a VH encoded by the nucleotide sequence of SEQ ID NO: 179 (or a nucleotide sequence substantially identical thereto) or a VL encoded by the nucleotide sequence of SEQ ID NO: 180 (or a nucleotide sequence substantially identical thereto), or both.

In an embodiment, the antibody molecule is monoclonal antibody 3631. In an embodiment, the antibody molecule is a humanized monoclonal antibody 3631.

In an embodiment, the antibody molecule binds, or substantially binds, to human APRIL, mouse APRIL, or both.

In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 5 nM or less, e.g., about 2.5 nM.

In an embodiment, the antibody molecule binds, or substantially binds, to mouse APRIL at an $EC_{50}$ of 100 nM or less, e.g., 80 nM or less, 60 nM or less, 40 nM or less, 20 nM or less, 10 nM or less, 9 nM or less 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 100 nM, e.g., between 0.001 nM and 50 nM, between 0.01 nM and 20 nM, between 0.1 nM and 10 nM, between 0.5 nM and 5 nM or between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both. In an embodiment, the antibody molecule inhibits, or substantially inhibits, binding of APRIL (e.g., human APRIL, mouse APRIL, or both) to TACI (e.g., human TACI, mouse TACI, or both), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 4.05 nM.

In an embodiment, the antibody molecule inhibits, or substantially inhibits, binding of APRIL (e.g., human APRIL, mouse APRIL, or both) to BCMA (e.g., human BCMA, mouse BCMA, or both), at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 1 nM or less, e.g., about 0.85 nM.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3732 (e.g., SEQ ID NO: 133 or 138); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3732 (e.g., SEQ ID NO: 134 or 139); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3732 (e.g., SEQ ID NO: 135), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3732 (e.g., SEQ ID NO: 136); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3732 (e.g., SEQ ID NO: 127); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3732 (e.g., SEQ ID NO: 137).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3732 (e.g., SEQ ID NO: 140); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3732 (e.g., SEQ ID NO: 141).

In an embodiment, the antibody molecule comprises a VH encoded by the nucleotide sequence of SEQ ID NO: 181 (or a nucleotide sequence substantially identical thereto) or a VL encoded by the nucleotide sequence of SEQ ID NO: 182 (or a nucleotide sequence substantially identical thereto), or both.

In an embodiment, the antibody molecule is monoclonal antibody 3732. In an embodiment, the antibody molecule is a humanized monoclonal antibody 3732.

In an embodiment, the antibody molecule binds, or substantially binds, to human APRIL, mouse APRIL, or both.

In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 5 nM or less, e.g., about 2.5 nM.

In an embodiment, the antibody molecule binds, or substantially binds, to mouse APRIL at an $EC_{50}$ of 100 nM or less, e.g., 80 nM or less, 60 nM or less, 40 nM or less, 20 nM or less, 10 nM or less, 9 nM or less 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 100 nM, e.g., between 0.001 nM and 50 nM, between 0.01 nM and 20 nM, between 0.1 nM and 10 nM, between 0.5 nM and 5 nM or between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both.

In an embodiment, the antibody molecule inhibits, or substantially inhibits, binding of APRIL (e.g., human APRIL, mouse APRIL, or both) to TACI (e.g., human TACI, mouse TACI, or both), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 4.05 nM.

In an embodiment, the antibody molecule inhibits, or substantially inhibits, binding of APRIL (e.g., human APRIL, mouse APRIL, or both) to BCMA (e.g., human BCMA, mouse BCMA, or both), at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 1 nM or less, e.g., about 0.85 nM.

In an embodiment, the antibody molecule comprises:
(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540 (e.g., SEQ ID NO: 154 or 159); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540 (e.g., SEQ ID NO: 155 or 160); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540 (e.g., SEQ ID NO: 156), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540 (e.g., SEQ ID NO: 116); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540 (e.g., SEQ ID NO: 157); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540 (e.g., SEQ ID NO: 158).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4540 (e.g., SEQ ID NO: 161); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4540 (e.g., SEQ ID NO: 162).

In an embodiment, the antibody molecule comprises a VH encoded by the nucleotide sequence of SEQ ID NO: 186 (or a nucleotide sequence substantially identical thereto) or a VL encoded by the nucleotide sequence of SEQ ID NO: 187 (or a nucleotide sequence substantially identical thereto), or both.

In an embodiment, the antibody molecule is monoclonal antibody 4540. In an embodiment, monoclonal antibody 4540 is a humanized monoclonal antibody 4540. In an embodiment, the antibody molecule comprises a VH comprising the amino acid sequence of any of SEQ ID NO: 254-258, a VL comprising the amino acid sequence of any of SEQ ID NO: 259-261, or both.

In an embodiment, the antibody molecule comprises:
(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540-063 (e.g., SEQ ID NO: 154 or 276); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540-063 (e.g., SEQ ID NO: 155 or 277); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540-063 (e.g., SEQ ID NO: 156), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540-063 (e.g., SEQ ID NO: 274); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540-063 (e.g., SEQ ID NO: 275); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540-063 (e.g., SEQ ID NO: 158).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4540-063 (e.g., SEQ ID NO: 258); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4540-063 (e.g., SEQ ID NO: 261).

In an embodiment, the antibody molecule comprises a VH encoded by the nucleotide sequence of SEQ ID NO: 301 (or a nucleotide sequence substantially identical thereto) or a VL encoded by the nucleotide sequence of SEQ ID NO: 302 (or a nucleotide sequence substantially identical thereto), or both.

In an embodiment, the antibody molecule is monoclonal antibody 4540-063.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4540-033 (e.g., SEQ ID NO: 154 or 159); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4540-033 (e.g., SEQ ID NO: 155 or 278); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4540-033 (e.g., SEQ ID NO: 156), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4540-033 (e.g., SEQ ID NO: 274); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4540-033 (e.g., SEQ ID NO: 275); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4540-033 (e.g., SEQ ID NO: 158).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4540-033 (e.g., SEQ ID NO: 256); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4540-033 (e.g., SEQ ID NO: 261).

In an embodiment, the antibody molecule comprises a VH encoded by the nucleotide sequence of SEQ ID NO: 303 (or a nucleotide sequence substantially identical thereto) or a VL encoded by the nucleotide sequence of SEQ ID NO: 302 (or a nucleotide sequence substantially identical thereto), or both.

In an embodiment, the antibody molecule is monoclonal antibody 4540-033.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the VH comprises one, two, or all of the following: an HCDR1 comprising the amino acid sequence of D-Y-Y-X4-N(SEQ ID NO: 343), where X4 is I or M; an HCDR2 comprising the amino acid sequence of W-I-F-P-G-S-G-S-T-Y-Y-X12-X13-K-X15-X16-G, where X12 is N or A, X13 is E or Q, X15 is F or L, and X16 is K or Q (SEQ ID NO: 344); or an HCDR3 comprising the amino acid sequence of G-D-S-G-R-A-M-D-Y (SEQ ID NO: 156), and (ii) a light chain variable region (VL), wherein the light chain variable region comprises three light chain complementarity determining regions (LCDR1, LCDR2, and LCDR3), wherein the VL comprises one, two, or all of the following: an LCDR1 comprising the amino acid sequence of X1-A-S-Q-D-I-N-K-Y-I-A, wherein X1 is K or Q (SEQ ID NO: 345); an LCDR2 comprising the amino acid sequence of Y-T-S-T-L-X6-X7, wherein X6 is Q or E, and X7 is S or T (SEQ ID NO: 346); or an LCDR3 comprising the amino acid sequence of L-Q-Y-D-N-L-L-T (SEQ ID NO: 158).

In another embodiment, the antibody molecule comprises:

(i) a heavy chain variable region (VH), wherein the heavy chain variable region comprises three heavy chain complementarity determining regions (HCDR1, HCDR2, and HCDR3), wherein the VH comprises one, two, or all of the following: an HCDR1 comprising the amino acid sequence of G-Y-T-F-A-D-Y (SEQ ID NO: 154); an HCDR2 comprising the amino acid sequence of F-P-G-S-G-S (SEQ ID NO: 155); or an HCDR3 comprising the amino acid sequence of G-D-S-G-R-A-M-D-Y (SEQ ID NO: 156), and (ii) a light chain variable region (VL), wherein the light chain variable region comprises three light chain complementarity determining regions (LCDR1, LCDR2, and LCDR3), wherein the VL comprises one, two, or all of the following: an LCDR1 comprising the amino acid sequence of X1-A-S-Q-D-I-N-K-Y-I-A, wherein X1 is K or Q (SEQ ID NO: 345); an LCDR2 comprising the amino acid sequence of Y-T-S-T-L-X6-X7 (SEQ ID NO: 346), wherein X6 is Q or E, and X7 is S or T; or an LCDR3 comprising the amino acid sequence of L-Q-Y-D-N-L-L-T (SEQ ID NO: 158).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NOS: 161, 256 or 258; or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of SEQ ID NO: 162 or 261.

In an embodiment, the antibody molecule is monoclonal antibody 4540. In another embodiment, the antibody molecule is monoclonal antibody 4540-063. In yet another embodiment, the antibody molecule is monoclonal antibody 4540-033.

In an embodiment, the antibody molecule binds, or substantially binds, to human APRIL, mouse APRIL, or both.

In an embodiment, the antibody molecule binds, or substantially binds, to human APRIL at an $EC_{50}$ of 20 nM or less, e.g., 10 nM or less, 9 nM or less or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, or 0.1 nM or less, e.g., between 0.1 nM and 20 nM, e.g., between 0.1 nM and 10 nM, between 0.5 nM and 5 nM, or between 1 nM and 5 nM, e.g., as determined by a method described herein. In an embodiment, the antibody molecule binds to human APRIL at an $EC_{50}$ of 5 nM or less, e.g., about 2.5 nM.

In an embodiment, the antibody molecule binds, or substantially binds, to mouse APRIL at an $EC_{50}$ of 100 nM or less, e.g., 80 nM or less, 60 nM or less, 40 nM or less, 20 nM or less, 10 nM or less, 9 nM or less or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, or 0.1 nM or less, e.g., between 0.1 nM and 20 nM, e.g., between 0.1 nM and 10 nM, between 0.5 nM and 5 nM, or between 1 nM and 5 nM, e.g., as determined by a method described herein.

In an embodiment, the antibody molecule inhibits, or substantially inhibits, binding of APRIL (e.g., human APRIL) to TACI (e.g., human TACI), BCMA (e.g., human BCMA), or both.

In an embodiment, the antibody molecule inhibits, or substantially inhibits, binding of APRIL (e.g., human APRIL, mouse APRIL, or both) to TACI (e.g., human TACI, mouse TACI, or both), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 5 nM or less, e.g., about 4.05 nM.

In an embodiment, the antibody molecule inhibits, or substantially inhibits, binding of APRIL (e.g., human APRIL, mouse APRIL, or both) to BCMA (e.g., human BCMA, mouse BCMA, or both), at an $IC_{50}$ of 200 nM or less, 150 nM or less, 100 nM or less, 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human BCMA at an $IC_{50}$ of 1 nM or less, e.g., about 0.85 nM.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 2621 (e.g., SEQ ID NO: 21 or 27); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 2621 (e.g., SEQ ID NO: 22 or 28); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 2621 (e.g., SEQ ID NO: 23), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 2621 (e.g., SEQ ID NO: 24); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 2621 (e.g., SEQ ID NO: 25); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 2621 (e.g., SEQ ID NO: 26).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 2621 (e.g., SEQ ID NO: 29); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 2621 (e.g., SEQ ID NO: 30).

In an embodiment, the antibody molecule comprises a VH encoded by the nucleotide sequence of SEQ ID NO: 75 (or a nucleotide sequence substantially identical thereto) or a VL encoded by the nucleotide sequence of SEQ ID NO: 76 (or a nucleotide sequence substantially identical thereto), or both.

In an embodiment, the antibody molecule is monoclonal antibody 2621. In an embodiment, the antibody molecule is a humanized monoclonal antibody 2621.

In an embodiment, the antibody molecule binds, or substantially binds, to human APRIL.

In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 1 nM or less, e.g., about 0.7 nM. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI). In an embodiment, the antibody molecule inhibits, or substantially inhibits, binding of APRIL (e.g., human APRIL) to TACI (e.g., human TACI), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of about 1 nM or less. In an embodiment, the antibody molecule does not inhibit, or does not substantially inhibit, binding of APRIL (e.g., human APRIL) to BCMA (e.g., human BCMA).

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 3125 (e.g., SEQ ID NO: 11 or 47); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 3125 (e.g., SEQ ID NO: 42 or 48); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 3125 (e.g., SEQ ID NO: 43), and (ii) a light chain variable region (VH), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 3125 (e.g., SEQ ID NO: 44); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 3125 (e.g., SEQ ID NO: 45); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 3125 (e.g., SEQ ID NO: 46).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 3125 (e.g., SEQ ID NO: 49); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 3125 (e.g., SEQ ID NO: 50).

In an embodiment, the antibody molecule comprises a VH encoded by the nucleotide sequence of SEQ ID NO: 79 (or a nucleotide sequence substantially identical thereto) or a VL encoded by the nucleotide sequence of SEQ ID NO: 80 (or a nucleotide sequence substantially identical thereto), or both.

In an embodiment, the antibody molecule is monoclonal antibody 3125. In an embodiment, the antibody molecule is a humanized monoclonal antibody 3125.

In an embodiment, the antibody molecule binds, or substantially binds, to human APRIL. In an embodiment, the antibody molecule binds, or substantially binds, to human APRIL at an $EC_{50}$ of 20 nM or less, e.g., 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, 0.01 nM or less, 0.005 nM or less, 0.002 nM or less, or 0.001 nM or less, e.g., between 0.001 nM and 20 nM, e.g., between 0.01 nM and 20 nM, between 0.1 nM and 20 nM, between 0.1 nM and 10 nM, between 0.5 nM and 5 nM, between 1 nM and 5 nM, between 0.001 nM and 0.1 nM, between 0.001 nM and 0.01 nM, between 0.001 nM and 0.005 nM, between 0.01 nM and 0.05 nM, or between 0.01 nM and 0.1 nM, e.g., as determined by a method described herein. In an embodiment, the antibody molecule binds to human APRIL at an $EC_{50}$ of 20 nM or less, e.g., about 13 nM. In an embodiment, the antibody molecule does not bind, or binds to mouse APRIL with low affinity, e.g., at an $EC_{50}$ of 1000 nM or more, e.g., 2000 nM or more, e.g., as determined by a method described herein.

In an embodiment, the antibody molecule inhibits, or substantially inhibits, binding of APRIL (e.g., human APRIL) to TACI (e.g., human TACI). In an embodiment, the antibody molecule inhibits, or substantially inhibits, binding of APRIL (e.g., human APRIL) to TACI (e.g., human TACI), at an $IC_{50}$ of 50 nM or less, e.g., 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, 0.8 nM or less, 0.6 nM or less, 0.4 nM or less, 0.2 nM or less, 0.1 nM or less, 0.05 nM or less, 0.02 nM or less, or 0.01 nM or less, e.g., between 0.01 nM and 50 nM, between 0.1 nM and 50 nM, between 0.1 nM and 25 nM, between 0.1 nM and 10 nM, between 0.1 nM and 5 nM, between 0.1 nM and 1 nM, between 0.1 nM and 0.5 nM, between 0.5 nM and 5 nM, or between 1 nM and 5 nM, e.g., as determined by a method described herein. In an embodiment, the antibody molecule inhibits binding of human APRIL to human TACI at an $IC_{50}$ of 150 nM or less, e.g., about 112.97 nM. In an embodiment, the antibody molecule does not inhibit, or does not substantially inhibit, binding of APRIL (e.g., human APRIL) to BCMA (e.g., human BCMA).

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of the HCDR1 of monoclonal antibody 4439 (e.g., SEQ ID NO: 266 or 269); an HCDR2 comprising an amino acid sequence that differs by no more than 1, 2, or 3 amino acid residues from, or has at least 85, 90, 95, 99 or 100% homology with, the amino acid sequence of the HCDR2 of monoclonal antibody 4439 (e.g., SEQ ID NO: 267 or 270); or an HCDR3 comprising an amino acid sequence that differs by no more than 1, 2, or 3 amino acid residues from, or has at least 85, 90, 95, 99 or 100% homology with, the amino acid sequence of the HCDR3 of monoclonal antibody 4439 (e.g., SEQ ID NO: 268), and (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of monoclonal antibody 4439 (e.g., SEQ ID NO: 146); an LCDR2 comprising an amino acid sequence that differs by no more than 1, 2, or 3 amino acid residues from, or has at least 85, 90, 95, 99 or 100% homology with, the amino acid sequence of the LCDR2 of monoclonal antibody 4439 (e.g., SEQ ID NO: 147); or an LCDR3 comprising an amino acid sequence that differs by no more than 1, 2, or 3 amino acid residues from, or has at least 85, 90, 95, 99 or 100% homology with, the amino acid sequence of the LCDR3 of monoclonal antibody 4439 (e.g., SEQ ID NO: 148).

In an embodiment, the antibody molecule comprises one or both of: (i) a VH comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VH of monoclonal antibody 4439 (e.g., SEQ ID NO: 271); or (ii) a VL comprising an amino acid sequence that differs by no more than 1, 2, 3, 4, 5, 6, 7, 8, 9, 10, 11, 12, 13, 14, or 15 amino acid residues from, or has at least 85, 90, 95, 96, 97, 98, 99, or 100% homology with, the amino acid sequence of the VL of monoclonal antibody 4439 (e.g., SEQ ID NO: 272).

In an embodiment, the antibody molecule comprises a VH encoded by the nucleotide sequence of SEQ ID NO: 297 (or a nucleotide sequence substantially identical thereto) or a VL encoded by the nucleotide sequence of SEQ ID NO: 298 (or a nucleotide sequence substantially identical thereto), or both.

In an embodiment, the antibody molecule is monoclonal antibody 4439. In an embodiment, monoclonal antibody 4439 is humanized monoclonal antibody 4439.

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or more, residues within a region of human APRIL as defined in any of Tables 3-4 or 7-8.

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or more, residues within a region of human APRIL as defined in Table 3. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 3. In an embodiment, the antibody molecule binds, or substantially binds, to an epitope that overlaps an epitope that comprises or consists of all of the human APRIL residues from Table 3. In an embodiment, the antibody molecule binds, or substantially binds, to an epitope that comprises APRIL residues from two monomers, e.g., one or more residues from monomer A and monomer B as shown in Table 3.

In an embodiment, the antibody molecule binds, or substantially binds, to one or more, e.g., 2, 3, 4, 5, 6, 7, 8, 9, 10, or more, residues within a region of human APRIL as defined in Table 4. In an embodiment, the antibody molecule binds, or substantially binds, to an epitope that comprises or consists of one or more, e.g., 2, 3, 4, 5, 6, 7, 8, 9, 10, or all, of the human APRIL residues from Table 4. In an embodiment, the antibody molecule binds, or substantially binds, to an epitope that overlaps an epitope that comprises or consists of all of the human APRIL residues from Table 4. In an embodiment, the antibody molecule binds, or substantially binds, to an epitope that comprises one or more APRIL residues from the C-D loop (e.g., the loop connecting β-sheets C and D), the G-H loop (e.g., the loop connecting β-sheets G and H), or both.

In an embodiment, the antibody molecule binds, or substantially binds, to one or more, e.g., 2, 3, 4, 5, 6, 7, 8, 9, 10, 11, 12, 13, 14, 15, 16, 17, or all, residues within a region of human APRIL as defined in Table 7. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, or all, of the human APRIL residues from Table 7. In an embodiment, the antibody molecule binds, or substantially binds, to an epitope that overlaps an epitope that comprises or consists of all of the human APRIL residues from Table 7.

In an embodiment, the antibody molecule binds, or substantially binds, to one or more, e.g., 2, 3, 4, 5, 6, 7, 8, 9, 10, 11, 12, 13, 14, 15, 16, 17, 18, 19, 20, 21, 22, 23, 24, 25, or more, residues within a region of human APRIL as defined in Table 8. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, 18, 19, 20, 21, 22, 23, 24, 25, or all, of the human APRIL residues from Table 8. In an embodiment, the antibody molecule binds, or substantially binds, to an epitope that overlaps an epitope that comprises or consists of all of the human APRIL residues from Table 8. In an embodiment, the antibody molecule binds, or substantially binds, to an epitope that comprises APRIL residues from two monomers, e.g., one or more residues from monomer A and monomer B as shown in Table 8.

In an embodiment, the antibody molecule is an IgG antibody molecule, e.g., comprising a heavy chain constant region of IgG, e.g., chosen from IgG1, IgG2 (e.g., IgG2a), IgG3, or IgG4, e.g., IgG2 or IgG4. In an embodiment, the antibody molecule is an IgG1 antibody molecule. In another embodiment, the antibody molecule is an IgG2 antibody molecule. In an embodiment, the antibody molecule comprises a light chain constant region of kappa or lambda light chain.

In an embodiment, the antibody molecule comprises an Fc region. In an embodiment, the Fc region comprises one or more mutations located at the interface between the CH2 and CH3 domains (e.g., to increase the binding affinity to neonatal receptor FcRn and/or the half-life of the antibody molecule). In an embodiment, the Fc region comprises one or more mutations, e.g., one or more (e.g., 2, 3, 4, 6 or all) mutations chosen from T250Q, M252Y, S254T, T256E, M428L, H433K, N434F, or any combination thereof, of IgG1. In an embodiment, the Fc region comprises one or more mutations at positions 233-236 or 322 of human IgG1 or IgG2, or one or more substitutions at positions 327, 330 or 331 of human IgG4 (e.g., to reduce complement-dependent cytotoxicity (CDC)). In an embodiment, the Fc region comprises one or more (e.g., 2, 3, 4, 6 7 or all) mutations chosen from E233P, L234V, L235A, G236, K322A, A327G, A330S, P331S, or any combination thereof.

In an embodiment, the antibody molecule is a humanized antibody molecule, e.g., as described in Table 5, e.g., comprising one or more framework regions derived from human framework germline sequence.

In an embodiment, the antibody molecule comprises two heavy chain variable regions and two light chain variable regions. In an embodiment, the antibody molecule is a Fab, F(ab')2, Fv, Fd, or a single chain Fv fragment (scFv).

In an aspect, the disclosure features a composition, e.g., pharmaceutical composition, comprising an antibody molecule described herein. In an embodiment, the composition further comprises a pharmaceutical acceptable carrier.

In an aspect, the disclosure features a nucleic acid molecule encoding a heavy chain variable region (VH), a light chain variable region (VL), or both, of an antibody molecule described herein.

In an aspect, the disclosure features a vector comprising a nucleic acid molecule described herein.

In an aspect, the disclosure features a cell, e.g., an isolated cell, comprising a nucleic acid molecule described herein or a vector described herein.

In an aspect, the disclosure features a kit comprising an antibody molecule described herein and instructions to use of the antibody molecule.

In an aspect, the disclosure features a container comprising an antibody molecule described herein.

In an aspect, the disclosure features a method of producing an anti-APRIL antibody molecule, the method comprising culturing a cell described herein under conditions that allow production of an antibody molecule, thereby producing the antibody molecule.

In an embodiment, the method further comprises isolating the antibody molecule.

In an aspect, the disclosure features a method of treating IgA nephropathy, the method comprising administering to a subject in need thereof an effective amount of an antibody molecule described herein or a composition described herein, thereby treating IgA nephropathy.

In an embodiment, the antibody molecule is administered to the subject intravenously.

In an embodiment, the antibody molecule is administered to the subject at a dose between 0.1 mg/kg and 50 mg/kg, e.g., between 0.2 mg/kg and 25 mg/kg, between 0.5 mg/kg and 10 mg/kg, between 0.5 mg/kg and 5 mg/kg, between 0.5 mg/kg and 3 mg/kg, between 0.5 mg/kg and 2.5 mg/kg, between 0.5 mg/kg and 2 mg/kg, between 0.5 mg/kg and 1.5 mg/kg, between 0.5 mg/kg and 1 mg/kg, between 1 mg/kg and 1.5 mg/kg, between 1 mg/kg and 2 mg/kg, between 1 mg/kg and 2.5 mg/kg, between 1 mg/kg and 3 mg/kg, between 1 mg/kg and 2.5 mg/kg, or between 1 mg/kg and 5 mg/kg.

In an embodiment, the antibody molecule is administered to the subject at a fixed dose between 10 mg and 1000 mg, e.g., between 10 mg and 500 mg, between 10 mg and 250 mg, between 10 mg and 150 mg, between 10 mg and 100 mg, between 10 mg and 50 mg, between 250 mg and 500 mg, between 150 mg and 500 mg, between 100 mg and 500 mg, between 50 mg and 500 mg, between 25 mg and 250 mg, between 50 mg and 150 mg, between 50 mg and 100 mg, between 100 mg and 150 mg. between 100 mg and 200 mg, or between 150 mg and 250 mg.

In an embodiment, the antibody molecule is administered once a week, twice a week, once every two weeks, once every three weeks, once every four weeks, once every eight weeks, once a month, once every two months, or once every three months.

In an embodiment, administration of the antibody molecule reduces the level of IgA in a peripheral tissue, e.g., in serum, mucosal tissue, bone marrow, or any combination thereof.

In an embodiment, administration of the antibody molecule reduces the level of IgA1. In an embodiment, administration of the antibody molecule reduces the level of IgA1 in polymeric form (pIgA1). In an embodiment, administration of the antibody molecule reduces the level of IgA1 with O-linked glycosylation variants (e.g., aberrant or reduced composition of galactose in CH1 hinge region).

In an embodiment, the method further comprises determining the level of IgA in a peripheral tissue sample from the subject, e.g., chosen from serum, mucosal tissue, or bone marrow.

In an embodiment, the method further comprises administering to the subject a second therapy for IgA nephropathy. In an embodiment, the second therapy is chosen from an angiotensin-converting enzyme (ACE) inhibitor, an angiotensin receptor blocker (ARB), omega-3 fatty acids, an immunosuppressant (e.g., a corticosteroid, e.g., prednisone), a statin, mycophenolate mofetil, or any combination thereof.

In an aspect, the disclosure features a method of treating diabetic nephropathy, the method comprising administering to a subject in need thereof an effective amount of an antibody molecule described herein or a composition described herein, thereby treating diabetic nephropathy.

In an aspect, the disclosure features a method of treating cancer, the method comprising administering to a subject in need thereof an effective amount of an antibody molecule described herein or a composition described herein, thereby treating cancer.

In an embodiment, the cancer is a hematological cancer. In an embodiment, the hematological cancer is chosen from B-cell non-Hodgkin's lymphoma, chronic lymphocytic leukemia (CLL), Hodgkin's lymphoma, multiple myeloma, Waldenström macroglobulinemia, or lymphoplasmacytic lymphoma. In an embodiment, the cancer is a multiple myeloma.

In an aspect, the disclosure features a method of treating an immunoproliferative disorder, the method comprising administering to a subject in need thereof an effective amount of an antibody molecule described herein or a composition described herein, thereby treating the immunoproliferative disorder.

In an embodiment, the immunoproliferative disorder is monoclonal IgA hypergammaglobulinemia.

In an aspect, the disclosure features a method of treating vasculitis, the method comprising administering to a subject in need thereof an effective amount of an antibody molecule described herein or a composition described herein, thereby treating vasculitis.

In an embodiment, the vasculitis is kidney vasculitis. In an embodiment, the vasculitis is an IgA associated vasculitis (e.g., Henoch-Schonlein purpura) or post-streptococcal glomerulonephritis. In an aspect, the disclosure features a method of treating an autoimmune disorder, the method comprising administering to a subject in need thereof an effective amount of an antibody molecule described herein or a composition described herein, thereby treating the autoimmune disorder.

In an embodiment, the autoimmune disorder is chosen from rheumatoid arthritis, systemic lupus erythematosus, a linear IgA bullous disease (e.g., linear immunoglobulin A (IgA) dermatosis), or IgA-mediated epidermolysis bullosa acquisita (EBA).

In an aspect, the disclosure features a method of treating IgA pemphigus, the method comprising administering to a subject in need thereof an effective amount of an antibody molecule described herein or a composition described herein, thereby treating IgA pemphigus.

In an aspect, the disclosure features a method of treating celiac disease, the method comprising administering to a subject in need thereof an effective amount of an antibody molecule described herein or a composition described herein, thereby treating celiac disease.

In an aspect, the disclosure features a method of treating alcoholic cirrhosis, the method comprising administering to a subject in need thereof an effective amount of an antibody molecule described herein or a composition described herein, thereby treating alcoholic cirrhosis.

In an aspect, the disclosure features a method of reducing the level of IgA in a cell or subject, the method comprising contacting the cell or subject, or administering to a subject in need thereof an effective amount of, an antibody molecule described herein or a composition described herein, thereby reducing the level of IgA.

In an embodiment, the antibody molecule is administered to the subject intravenously.

In an embodiment, the antibody molecule is administered to the subject at a dose between 0.1 mg/kg and 50 mg/kg, e.g., between 0.2 mg/kg and 25 mg/kg, between 0.5 mg/kg and 10 mg/kg, between 0.5 mg/kg and 5 mg/kg, between 0.5 mg/kg and 3 mg/kg, between 0.5 mg/kg and 2.5 mg/kg, between 0.5 mg/kg and 2 mg/kg, between 0.5 mg/kg and 1.5 mg/kg, between 0.5 mg/kg and 1 mg/kg, between 1 mg/kg and 1.5 mg/kg, between 1 mg/kg and 2 mg/kg, between 1 mg/kg and 2.5 mg/kg, between 1 mg/kg and 3 mg/kg, between 1 mg/kg and 2.5 mg/kg, or between 1 mg/kg and 5 mg/kg.

In an embodiment, the antibody molecule is administered to the subject at a fixed dose between 10 mg and 1000 mg, e.g., between 10 mg and 500 mg, between 10 mg and 250 mg, between 10 mg and 150 mg, between 10 mg and 100 mg, between 10 mg and 50 mg, between 250 mg and 500 mg, between 150 mg and 500 mg, between 100 mg and 500 mg, between 50 mg and 500 mg, between 25 mg and 250 mg, between 50 mg and 150 mg, between 50 mg and 100 mg, between 100 mg and 150 mg. between 100 mg and 200 mg, or between 150 mg and 250 mg.

In an embodiment, the antibody molecule is administered once a week, twice a week, once every two weeks, once every three weeks, once every four weeks, once every eight weeks, once a month, once every two months, once every three months.

In an embodiment, administration of the antibody molecule reduces the level of IgA in a peripheral tissue, e.g., in serum, mucosal tissue, bone marrow, or any combination thereof.

In an embodiment, administration of the antibody molecule reduces the level of IgA1. In an embodiment, administration of the antibody molecule reduces the level of IgA1 in polymeric form (pIgA1). In an embodiment, administration of the antibody molecule reduces the level of IgA1 with O-linked glycosylation variants (e.g., aberrant or reduced composition of galactose in CH1 hinge region).

In an aspect, the disclosure features use of an antibody molecule described herein or a composition described herein in the treatment, or in the manufacture of a medicament for the treatment, of a disorder described herein.

In another aspect, the disclosure features an antibody molecule described herein or a composition described herein for use in the treatment of a disorder described herein.

In an aspect, the disclosure features a method of detecting an APRIL molecule, the method comprising contacting a cell or a sample from a subject with an antibody molecule described herein, thereby detecting the APRIL molecule.

In an embodiment, the antibody molecule is coupled with a detectable label. In an embodiment, the APRIL molecule is detected in vitro or ex vivo. In another embodiment, the APRIL molecule is detected in vivo.

The disclosure contemplates all combinations of any one or more of the foregoing aspects and/or embodiments, as well as combinations with any one or more of the embodiments set forth in the detailed description and examples.

Other features, objects, and advantages of the compositions and methods herein will be apparent from the description and drawings, and from the claims.

BRIEF DESCRIPTION OF THE DRAWINGS

FIGS. 1A-1B depict the anti-APRIL antibody profiling from mouse-derived hybridomas. CD-1 mice were immunized with recombinant multimeric APRIL (human or mouse) as described. The splenocytes from anti-APRIL seropositive mice were immortalized through myeloma fusion to generate hybridomas. ELISA-based screening methods were used for evaluating anti-APRIL antibodies present in conditioned media of immunoglobulin producing hybridomas. Cell culture supernatants were initially screened both for binding to target (APRIL) by indirect ELISA and for functional activity with respect to ability to block interaction of APRIL with the recombinant, soluble human TNF receptor TACI-Fc (blocking ELISA). Screening against both human and mouse APRIL was carried out to identify potentially cross-reactive antibodies. Relative activities are based on single point measurements following normalization of immunoglobulin concentration to 10 µg/mL when possible. APRIL immunogen for final tail vein boost is noted in bold. Hybridoma-derived antibodies lacking blocking activity to either human or mouse APRIL (as initially defined by less than 10% receptor blocking in this first-pass screening assay) are not included in this summary table. Ig isotypes for select hybridomas are noted.

FIG. 2A (human APRIL); FIG. 2B (mouse APRIL). $IC_{50}$ values are reported in FIG. 3.

FIG. 3 depicts the activity profiles of select, purified mouse derived anti-APRIL antibodies. Binding and blocking activities are extrapolated from data summarized in FIGS. 2A-2B and are based on a non-linear regression of antibody titrations with 3 parameter curve fitting using Graphpad Prism. Dashes indicate no activity.

FIG. 6 depicts the relative binding affinities of select anti-APRIL antibodies. Data was derived from indirect ELISA (summarized in FIG. 5). Dashes indicate no binding activity.

FIG. 9 depicts antibody inhibition of APRIL binding to both human TACI-Fc and human BCMA-Fc. Relative inhibitory activities are summarized. Data derived from non-linear regression analyses of antibody inhibition curves depicted in FIGS. 7-8 using a 4-parameter fit. % inhibition was normalized to the no antibody control (100% inhibition) following subtraction of background (0% inhibition). Dashes represent lack of calculated $IC_{50}$ values due to poor or zero blocking activity measured.

FIG. 11A shows the inhibition of TACI-mediated NFB signaling; FIG. 11B shows the inhibition of BCMA mediated NF-κB signaling.

FIG. 12A shows the effect of treatment on total serum IgA levels; FIG. 12B shows the effect of treatment vs. control on total immunoglobulin levels in sera. Data represent summation of IgG+IgA+IgM levels measured separately.

FIG. 13 depicts sequence alignment of human and mouse APRIL (SEQ ID NOS: 85 and 91, respectively). Sequence alignments of soluble APRIL were determined using CLUSTALW Amino acid sequences correspond to SwissProt accession numbers O75888 (human) and Q9D777 (mouse).

FIG. 17 depicts the relative binding affinities of exemplary anti-APRIL antibodies. Data was derived from indirect ELISA (summarized in FIG. 16).

FIG. 20 depicts the antibody inhibition of APRIL binding to both human TACI-Fc and human BCMA-Fc (summary of relative inhibitory activities). Data derived from non-linear regression analyses of antibody inhibition curves depicted in FIG. 19 using a 4-parameter fit. % inhibition was normalized to the no antibody control (100% inhibition) following subtraction of background (0% inhibition). Dashes represent lack of calculated $IC_{50}$ values due to poor or partial blocking activity measured.

FIGS. 29A-29B depict the relative binding affinities of exemplary anti-APRIL antibodies. Data ($EC_{50}$ values) were derived from indirect ELISA (summarized in FIGS. 27A-27B and FIGS. 28A-28B). FIG. 29A shows relative binding affinities of exemplary, humanized anti-APRIL antibodies based on 2419 and 4035. FIG. 29B shows relative binding affinities of cross-reactive antibody 4540 and its humanized variant 4540-063. Binding data for both human and mouse APRIL are included.

FIG. 33 depicts $IC_{50}$ values of antibody inhibition of APRIL-receptor binding. $IC_{50}$ values are based on a non-linear regression analysis of data from FIGS. 30A-32B. Data are also normalized (relative activity) to parental, mouse derived antibody 2419.

FIG. 34A shows inhibition of TACI-mediated NFκB signaling. FIG. 34B shows inhibition of BCMA-mediated-NFκB signaling.

FIG. 35 depicts the approximate $IC_{50}$ values of antibody inhibition of APRIL-mediated receptor signaling. Data are extrapolated from FIGS. 34A-34B based on a non-linear regression analysis using a variable slope, three parameter fit of antibody concentration vs. response. Negative antibody control (no APRIL binding) demonstrated no activity in this assay (data not shown).

FIGS. 37B-37C depict the confirmatory/secondary screen of 12 proteins. Expression levels of secondary screening array of 12 human membrane proteins in 293 cells based on GFP are shown in left panels of FIGS. 37B-37C. Antibody binding to this same array is shown in right panels of FIGS. 37B-37C.

DETAILED DESCRIPTION

Figure 2A:
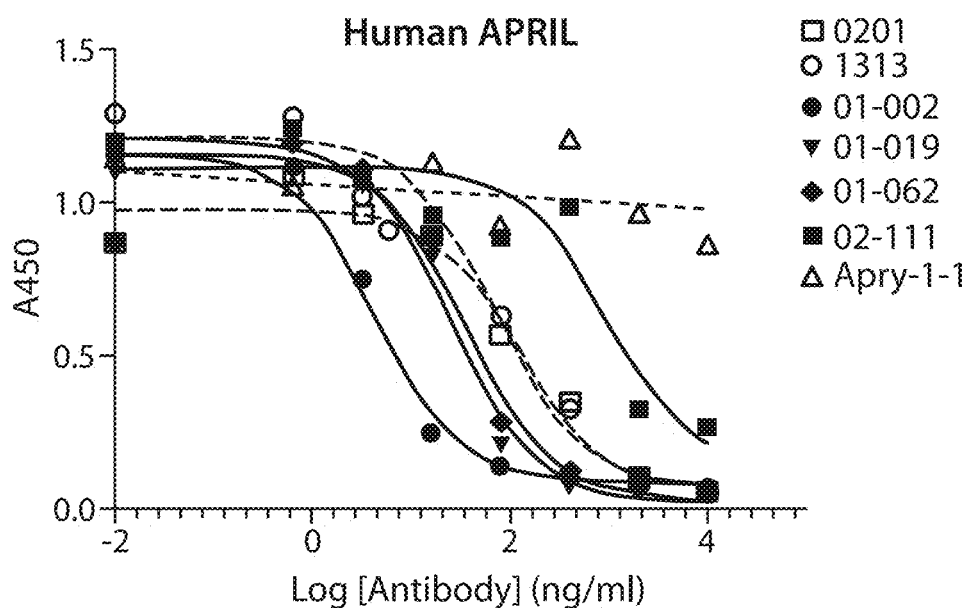
FIGS. 2A-2B depict the APRIL receptor blocking activity of exemplary anti-APRIL antibodies. Functional activities of select anti-APRIL antibodies purified from mouse-derived hybridoma clones were assessed by ELISA using recombinant TACI-Fc as soluble receptor. Assay involves two steps: 1) preincubation of APRIL with varying concentrations of purified mouse antibody; 2) subsequent measurement of APRIL binding to immobilized TACI-Fc as quantified by ELISA using the appropriate secondary antibody for detection of epitope tagged APRIL. Interference of APRIL-receptor binding was measured as a loss of $A_{450}$. Hybridoma antibodies are depicted by solid symbols. Control and comparator antibodies are depicted by open symbols. Apry-1-1 represents a mouse-specific blocking antibody used as a control. Human neutralizing antibodies 0201 and 1313 were likewise used as controls and for comparative purposes to antibodies described in the scientific literature. Data presented is representative of assay and method for assessing antibody inhibition (receptor blocking).

Disclosed herein are antibody molecules that bind to APRIL, e.g., human APRIL, mouse APRIL, or both, with high affinity and specificity. Advantageously, several of the antibody molecules describe herein have improved ability to reduce (e.g., inhibit, block, or neutralize) one or more biological activities of APRIL. Nucleic acid molecules encoding the antibody molecules, expression vectors, host cells, compositions (e.g., pharmaceutical compositions), kits, and methods for making the antibody molecules, are also provided. The antibody molecules and pharmaceutical compositions disclosed herein can be used (alone or in combination with other agents or therapeutic modalities) to treat, prevent and/or diagnose disorders and conditions, e.g., disorders and conditions associated with APRIL, e.g., IgA nephropathy.

Definitions

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods disclosed herein encompass polypeptides and nucleic acids having the sequences specified, or sequences substantially identical or similar thereto, e.g., sequences at least 85%, 90%, 95% identical or higher to the sequence specified.

In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a typical embodiment, the length of a reference sequence aligned for comparison purposes is at least 30%, e.g., at least 40%, 50%, 60%, e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch ((1970) *J. Mol. Biol.* 48:444-453) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package (available at gcg.com), using a NWSgapdna.CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid as described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (1997) *Nucleic Acids Res.* 25:3389-3402. When utilizing BLAST and gapped BLAST programs, the default parameters of the respective programs (e.g., XBLAST and NBLAST) can be used. See ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions 4) are suitable conditions and the ones that should be used unless otherwise specified.

It is understood that the molecules described herein may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide," "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "treat," e.g., IgA nephropathy, means that a subject (e.g., a human) who has a disorder, e.g., IgA nephropathy, and/or experiences a symptom of a disorder, e.g., IgA nephropathy, will, in an embodiment, suffer less a severe symptom and/or recover faster when an antibody molecule is administered than if the antibody molecule were never administered. In an embodiment, when IgA nephropathy is treated, a kidney biopsy will show less or no IgA deposits, e.g., in the form of immune complexes in the mesangium of the kidney, after effective treatment for IgA nephropathy. For example, a diagnostic assay using immunofluorescence or electron microscopy will detect less no IgA deposits in a biological sample of a subject after administration of an antibody molecule described herein for the effective treatment of IgA nephropathy. Other assays, urine tests, blood tests, iothalamate clearance tests, or kidney imaging (e.g., ultrasound, X-rays, or cystoscopy), can also be used to monitor treatment in a patient, or to detect the presence, e.g., decreased presence (or absence), of a symptom of IgA nephropathy, after treatment of IgA nephropathy in the subject. Treatment can, e.g., partially or completely, alleviate, ameliorate, relieve, inhibit, or reduce the severity of, and/or reduce incidence, and optionally, delay onset of, one or more manifestations of the effects or symptoms, features, and/or causes of a disorder, e.g., IgA nephropathy. In an embodiment, treatment is of a subject who does not exhibit certain signs of a disorder, e.g., IgA nephropathy, and/or of a subject who exhibits only early signs of a disorder, e.g., nephropathy. In an embodiment, treatment is of a subject who exhibits one or more established signs of a disorder, e.g., IgA nephropathy. In an embodiment, treatment is of a subject diagnosed as suffering from a disorder, e.g., IgA nephropathy.

As used herein, the term "prevent," a disorder, e.g., IgA nephropathy, means that a subject (e.g., a human) is less likely to have the disorder, e.g., IgA nephropathy, if the subject receives the antibody molecule.

Various aspects of the compositions and methods herein are described in further detail below. Additional definitions are set out throughout the specification.

APRIL

APRIL (A PRoliferation Inducing Ligand), also known as CD256, TNF- and APOL-related Leukocyte Expressed Ligand 2 (TALL-2), or TNF-related Death Ligand 1 (TRDL-1), is a TNF family cytokine encoded by the Tumor Necrosis Factor Ligand Superfamily Member 13 (TNFSF13) gene (also known as APRIL, TALL2, or ZTNF2). APRIL plays a role in a number of biological processes such as signal transduction, regulation of cell proliferation, and IgA class switching (Hahne et al. (1998) *J. Exp. Med.* 188:1185-1190 (1998); Castigli et al. *Proc. Natl. Acad. Sci. U.S.A.* 101: 3903-3908 (2004)).

APRIL is both functionally and structurally related to BAFF (B Cell Activating Factor F13B) also known as BLyS (B lymphocyte stimulator). Both cytokines are involved in regulating keys aspects of innate and adaptive immune functions. Both APRIL and BAFF bind the lymphocyte receptors TACI (transmembrane activator and CAML interactor) and BCMA (B cell maturation antigen). APRIL and BAFF appear to heterologously interact with each other through protein-protein interactions. While both APRIL and BAFF share biochemical (receptor binding), immunological and even some structural overlap (e.g., as it relates to the three-dimensional topology of their respective receptor binding domains), the two cytokines, nevertheless, are both structurally and functionally distinct. APRIL binds to biologically relevant heparan sulfate (present in the extracellular matrices of cells as heparan sulfate proteoglycans); BAFF does not. This interaction plays a critical biological function with respect to promoting the oligomerization state of APRIL in concert with its localized interaction with TACI, which likewise requires HSPGS for full activity. Unlike BAFF which acts as a potent activator of B cells inclusive of both proliferation and differentiation, APRIL would appear to function more particularly with respect to the modulation of B cell phenotype, e.g., as it relates to IgA production and the differentiation/survival of IgA positive plasma cells. As such, a targeted disruption in APRIL-receptor signaling is expected to have less perturbative effects on B cell homeostasis and overall immune function in comparison to other immune related therapeutics that target BAFF (e.g., belimumab) or anti CD20 therapies (e.g., rituximab) that largely target pre and early B cells. APRIL has also been shown to be expressed at high levels on other myeloid related cells and lymphoid tissues, as well as hematological cancers (e.g., myeloma, chronic lymphocytic leukemia (CLL)) and solid tumors (e.g., colon, thyroid, and breast).

Exemplary amino acid and nucleotide sequences of human APRIL are described, e.g., in Hahne et al. *J. Exp. Med.* 188:1185-1190 (1998); Shu et al. *J. Leukoc. Biol.* 65:680-683 (1999); Kelly et al. *Cancer Res.* 60:1021-1027 (2000); and Pradet-Balade et al. *EMBO J.* 21:5711-5720 (2002).

The amino acid sequence of human APRIL (isoform alpha, also referred to as the "canonical" sequence (SEQ ID NO: 85)) is provided as follows.
>huAPRIL
MPASSPFLLAPKGPPGNMGGPVREPALSVALWLSWGAALGAVACAMALLT

QQTELQSLRREVSRLQGTGGPSQNGEGYPWQSLPEQSSDALEAWENGERS

RKRRAVLTQKQKKQHSVLHLVPINATSKDDSDVTEVMWQPALRRGRGLQA

QGYGVRIQDAGVYLLYSQVLFQDVTFTMGQVVSREGQGRQETLFRCIRSM

PSHPDRAYNSCYSAGVFHLHQGDILSVIIPRARAKLNLSPHGTFLGFVKL

There are several isoforms of human APRIL produced by alternative splicing.
Isoform beta has the following amino acid sequence (SEQ ID NO: 86):
>sp|O75888-2|TNF13_HUMAN Isoform Beta of Tumor necrosis factor ligand superfamily member 13
OS = Homo sapiens GN = TNFSF13
MPASSPFLLAPKGPPGNMGGPVREPALSVALWLSWGAALGAVACAMALLT

QQTELQSLRREVSRLQGTGGPSQNGEGYPWQSLPEQSSDALEAWENGERS

RKRRAVLTQKQKNDSDVTEVMWQPALRRGRGLQAQGYGVRIQDAGVYLLY

SQVLFQDVTFTMGQVVSREGQGRQETLFRCIRSMPSHPDRAYNSCYSAGV

FHLHQGDILSVIIPRARAKLNLSPHGTFLGFVKL

The sequence of isoform beta differs from the canonical sequence as follows amino acids 113-129 of SEQ ID NO: 85: KQHSVLHLVPINATSKD → N
Isoform gamma has the following amino acid sequence (SEQ ID NO: 87):
>sp|O75888-3|TNF13_HUMAN Isoform Gamma of Tumor necrosis factor ligand superfamily member 13
OS = Homo sapiens GN = TNFSF13
MPASSPFLLAPKGPPGNMGGPVREPALSVALWLSWGAALGAVACAMALL

TQQTELQSLRREVSRLQGTGGPSQNGEGYPWQSLPEQSSDALEAWENGE

RSRKRRAVLTQKQKKQHSVLHLVPINATSKDDSDVTEVMWQPALRRGRG

LQAQGYGVRIQDAGVYLLYSQVLFQDVTFTMGQVVSREGQGRQETLFRC

IRSMPSHPDRAYNSCYSAGVFHLHQGDILSVIIPRARAKLNLSPHGTFL

GL

The sequence of isoform gamma differs from the canonical sequence as follows amino acids 247-249: Missing.
Isoform 4 has the following amino acid sequence (SEQ ID NO: 88):
>sp|O75888-4|TNF13_HUMAN Isoform 4 of Tumor necrosis factor ligand superfamily member 13
OS = Homo sapiens GN = TNFSF13
MPASSPFLLAPKGPPGNMGGPVREPALSVALWLSWGAALGAVACAMALL

TQQTELQSLRREVSRLQGTGGPSQNGEGYPWQSLPEQHSVLHLVPINAT

SKDDSDVTEVMWQPALRRGRGLQAQGYGVRIQDAGVYLLYSQVLFQDVT

FTMGQVVSREGQGRQETLFRCIRSMPSHPDRAYNSCYSAGVFHLHQGDI

LSVIIPRARAKLNLSPHGTFLGFVKL

The sequence of isoform 4 differs from the canonical sequence as follows amino acids 86-113: Missing.
Isoform TWE-PRIL has the following amino acid sequence (SEQ ID NO: 89):
>sp|O43508-2|TNF12_HUMAN Isoform TWE-PRIL of Tumor necrosis factor ligand superfamily member 12 OS = Homo sapiens GN = TNFSF12
MAARRSQRRRGRRGEPGTALLVPLALGLGLALACLGLLLAVVSLGSRA

SLSAQEPAQEELVAEEDQDPSELNPQTEESQDPAPFLNRLVRPRRSAP

-continued
KGRKTRARRAIAAHYEVHPRPGQDGAQAGVDGTVSGWEEARINSSSPL

RYNRQIGEFIVTRAGLYYLYCQSSDALEAWENGERSRKRRAVLTQKQK

KQHSVLHLVPINATSKDDSDVTEVMWQPALRRGRGLQAQGYGVRIQDA

GVYLLYSQVLFQDVTFTMGQVVSREGQGRQETLFRCIRSMPSHPDRAY

NSCYSAGVFHLHQGDILSVIIPRARAKLNLSPHGTFLGFVKL

```
Isoform 5 has the following amino acid sequence
(SEQ ID NO: 90):
>sp|O75888-5|TNF13_HUMAN Isoform 5 of Tumor
necrosis factor ligand superfamily member 13
OS = Homo sapiens GN = TNFSF13
```
MGGPVREPALSVALWLSWGAALGAVACAMALLTQQTELQSLRREVSRLQ

GTGGPSQNGEGYPWQSLPEQHSVLHLVPINATSKDDSDVTEVMWQPALR

RGRGLQAQGYGVRIQDAGVYLLYSQVLFQDVTFTMGQVVSREGQGRQET

LFRCIRSMPSHPDRAYNSCYSAGVFHLHQGDILSVIIPRARAKLNLSPH

GTFLGFVKL

The sequence of isoform 5 differs from the canonical sequence as follows: amino acids 1-17: Missing; amino acids 87-114: Missing.

Other variant and alternative sequences of human APRIL are described, e.g., in The MGC Project Team, *Genome Res.* 14:2121-2127 (2004); Ota et al. *Nat. Genet.* 36:40-45 (2004); and Kelly et al. *Cancer Res.* 60:1021-1027 (2000).

As used herein, when an anti-APRIL antibody molecule binds, or substantially binds, to human APRIL, it binds, or substantially binds, to one or more isoforms of human APRIL, e.g., one or more isoforms of human APRIL described herein. In an embodiment, the antibody molecule binds or substantially binds to human APRIL having the amino acid sequence of SEQ ID NO: 85.

Exemplary amino acid and nucleotide sequences of mouse APRIL are described, e.g., in Yu et al. Nat. Immunol. 1:252-256 (2000); Carninci et al. Science 309:1559-1563 (2005); The MGC Project Team, Genome Res. 14:2121-2127 (2004); and Bossen et al. J. Biol Chem. 281: 13964-13971 (2006).

```
The amino acid sequence of mouse APRIL isoform 1
(SEQ ID NO: 91) is provided as follows.
>muAPRIL
```
MPASSPGHMGGSVREPALSVALWLSWGAVLGAVTCAVALLIQQTELQSLR

REVSRLQRSGGPSQKQGERPWQSLWEQSPDVLEAWKDGAKSRRRRAVLTQ

KHKKKHSVLHLVPVNITSKADSDVTEVMWQPVLRRGRGLEAQGDIVRVWD

TGIYLLYSQVLFHDVTFTMGQVVSREGQGRRETLFRCIRSMPSDPDRAYN

SCYSAGVFHLHQGDIITVKIPRANAKLSLSPHGTFLGFVKL

```
The amino acid sequence of mouse APRIL isoform 2
(SEQ ID NO: 92) is provided as follows.
```
MPASSPGHMGGSVREPALSVALWLSWGAVLGAVTCAVALLIQQTELQSLR

REVSRLQRSGGPSQKQGERPWQSLWEQSPDVLEAWKDGAKSRRRRAVLTQ

KHKKKHSVLHLVPVNITSKDSDVTEVMWQPVLRRGRGLEAQGDIVRVWDT

GIYLLYSQVLFHDVTFTMGQVVSREGQGRRETLFRCIRSMPSDPDRAYNS

CYSAGVFHLHQGDIITVKIPRANAKLSLSPHGTFLGFVKL

As used herein, when an anti-APRIL antibody molecule binds, or substantially binds, to mouse APRIL, it binds, or substantially binds, to one or more isoforms of mouse APRIL, e.g., one or more isoforms of mouse APRIL described herein. In an embodiment, the antibody molecule binds or substantially binds to mouse APRIL having the amino acid sequence of SEQ ID NO: 91, SEQ ID NO: 92, or both.

As used herein, when an anti-APRIL antibody molecule does not bind, or does not substantially bind, to mouse APRIL, it does not bind, or does not substantially bind, to one or more isoforms of mouse APRIL, e.g., one or more isoforms of mouse APRIL described herein. In an embodiment, the antibody molecule does not bind, or does not substantially bind, to mouse APRIL having the amino acid sequence of SEQ ID NO: 91 or 92. In a typical embodiment, the antibody molecule does not bind, or does not substantially bind, to mouse APRIL having the amino acid sequence of SEQ ID NO: 91 and mouse APRIL having the amino acid sequence of SEQ ID NO: 92.

Sequence alignment of exemplary human and mouse APRIL proteins (SEQ ID NOS: 85 and 91, respectively) is shown in FIG. 13.

Epitope

The antibody molecule described herein can bind to an epitope on APRIL (e.g., human APRIL, mouse APRIL, or both). For example, an epitope bound by an antibody molecule described herein can include one or more epitope contact points described herein.

In an embodiment, the antibody molecule contacts (e.g., binds, or substantially binds, to) one or more residues, or one or more regions, as described in any of Tables 3-4 or 6-8, or any of FIG. 14, 22, 23A-23B, 24A-24B, 25A-25B, or 38A-38B.

In an embodiment, the antibody molecule contacts (e.g., binds or substantially binds to) one or more (e.g., 2, 3, 4, 5, 6, 7, 8, 9, 10, 11, 12, 13, 14, 15, 16, 17, 18, 19, 20, 21, 22, 23, 24, 25, or all) of the amino acid residues shown in Table 3. In an embodiment, the antibody molecule contacts (e.g., binds or substantially binds to) all of the amino acid residues shown in Table 3. For example, the antibody molecules described herein can contact the amino acid residues shown in Table 3 in a manner that includes binding across two APRIL monomers (e.g., as depicted positionally in Table 3 as A vs. B). While not wishing to be bound by theory, it is believed that in an embodiment, at least some of the amino acid residues shown in Table 3 contribute to high affinity interactions between APRIL and the CDR2 domain of TACI. In an embodiment, contacting one or more of the amino acid residues in Table 3 with an antibody molecule described herein inhibits, or substantially inhibits, binding of APRIL to TACI.

Figure 14:
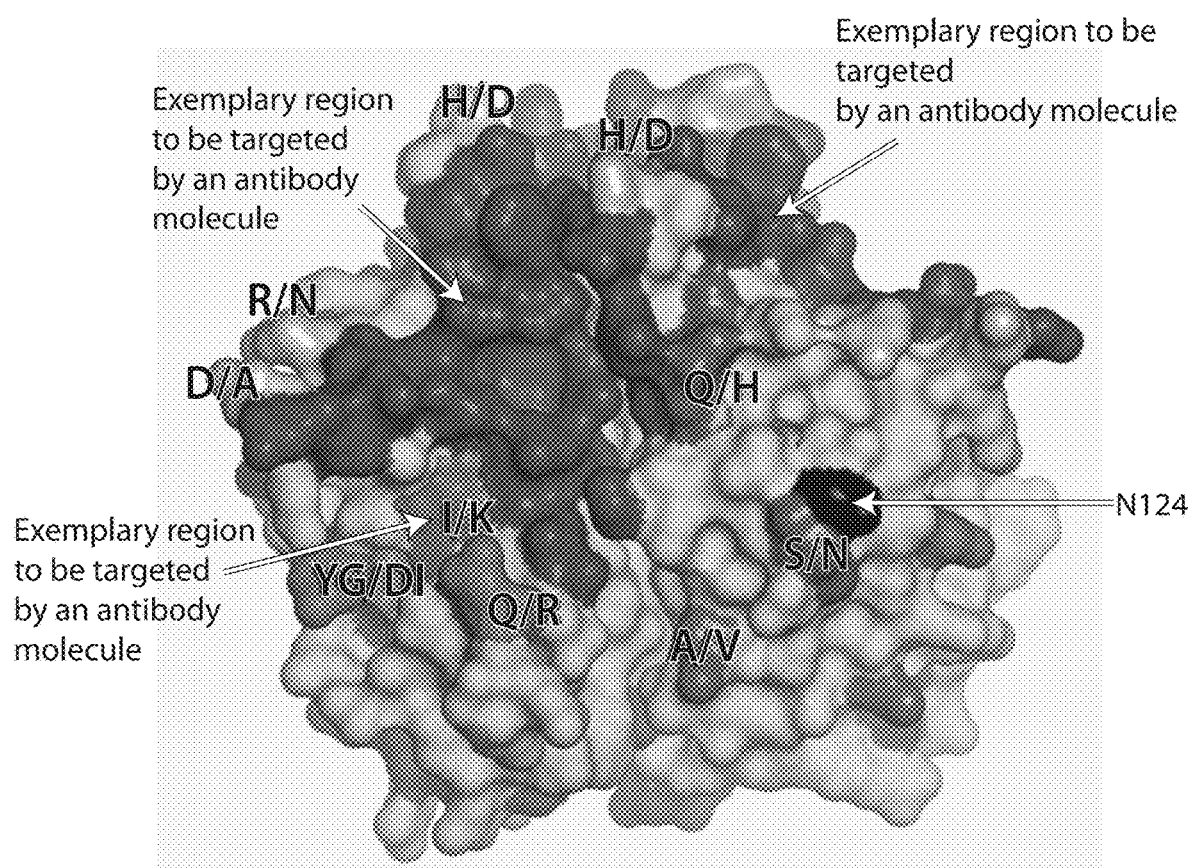
FIG. 14 depicts the structural definition of exemplary APRIL epitope for antibody targeting. A space filling model of trimeric APRIL is depicted. Exemplary (spatially defined) region to be targeted by an antibody molecule is depicted in darker gray and indicated by arrow. This epitope includes positions in APRIL that bridge monomers. Differences between mouse and human APRIL sequences are highlighted with corresponding amino acid differences at these positions noted. The putative N-glycosylation site (N124) is noted in black and indicated by arrow.

Exemplary human APRIL amino acid residues that can bind to the anti-APRIL antibody molecules described herein are shown in Table 3. A structural representation of this epitope (e.g., defined both spatially and conformationally) is depicted in FIG. 14.

TABLE 3

Exemplary Human APRIL Amino
Acid Residues that Bind to Anti-APRIL Antibodies
(amino acid numbering based on SEQ ID NO: 85)

| Monomer | Amino Acid Position | Amino Acid |
|---------|---------------------|------------|
| A | 130 | Asp |
| A | 131 | Ser |
| A | 132 | Asp |
| A | 174 | Val |
| A | 175 | Thr |
| A | 176 | Phe |

TABLE 3-continued

Exemplary Human APRIL Amino
Acid Residues that Bind to Anti-APRIL Antibodies
(amino acid numbering based on SEQ ID NO: 85)

| Monomer | Amino Acid Position | Amino Acid |
|---|---|---|
| A | 177 | Thr |
| A | 178 | Met |
| A | 179 | Gly |
| A | 180 | Gln |
| A | 181 | Val |
| A | 192 | Thr |
| A | 195 | Arg |
| A | 196 | Cys |
| A | 197 | Ile |
| A | 200 | Met |
| A | 201 | Pro |
| A | 202 | Ser |
| A | 208 | Tyr |
| A | 230 | Pro |
| A | 231 | Arg |
| A | 232 | Ala |
| A | 241 | His |
| B | 170 | Leu |
| B | 205 | Asp |
| B | 206 | Arg |

In another embodiment, the antibody molecule contacts (e.g., binds or substantially binds to) one or more (e.g., 2, 3, 4, 5, 6, 7, 8, 9, 10, or all) of the amino acid residues shown in Table 4. In another embodiment, the antibody molecule contacts (e.g., binds or substantially binds to) all of the amino acid residues shown in Table 4. In an embodiment, the antibody molecule binds, or substantially binds to, the C-D loop (e.g., the loop connecting β-sheets C and D), the G-H loop (e.g., the loop connecting β-sheets G and H), or both, on APRIL.

Figure 15:
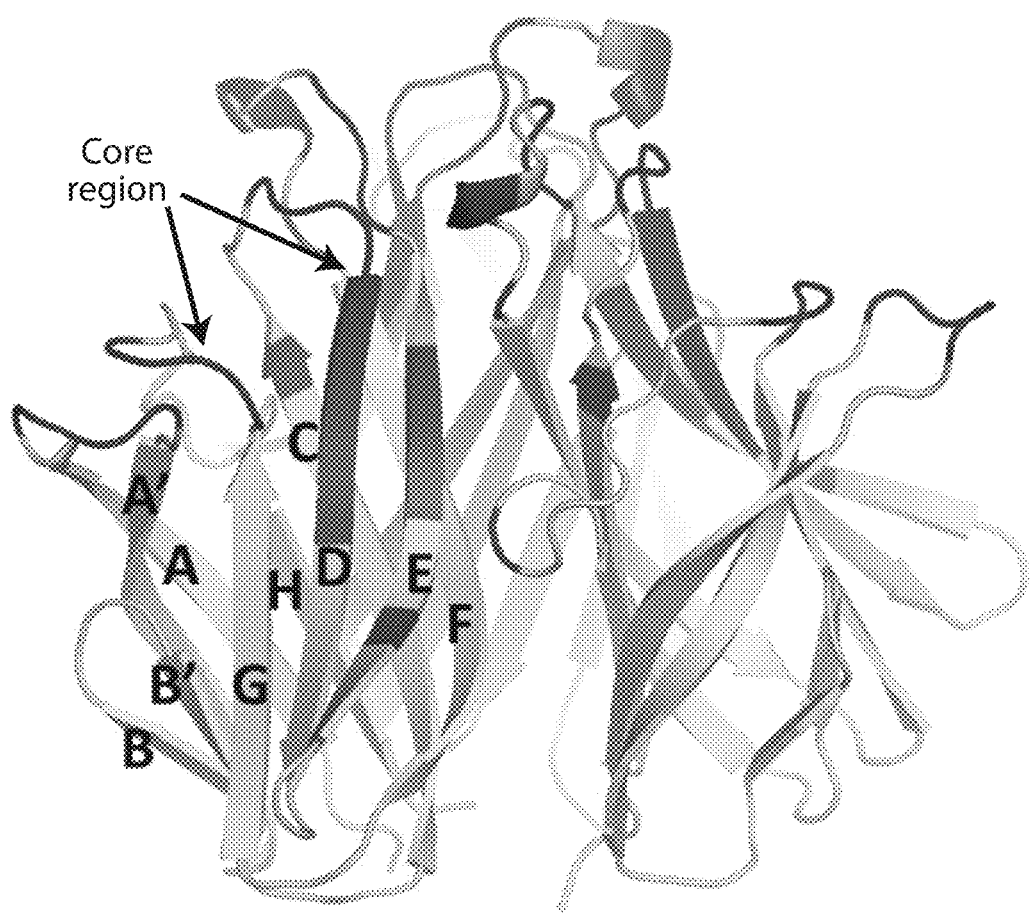
FIG. 15 depicts the structural definition of exemplary APRIL epitope for antibody targeting. Ribbon model of trimeric APRIL is depicted and core epitope for anti-APRIL targeting is highlighted in dark gray.

A structural (spatial) representation of this epitope (sometimes referred herein as "core region") is depicted in FIG. 15. As shown in FIG. 15, each APRIL protein molecule contains two packed antiparallel eight-stranded β-sheets (A to G), one inner and one outer, in a β jelly roll topology. These B sheets are connected by loops that also define (based on secondary structure definitions) a desired epitope. While not wishing to be bound by theory, it is believed that as these positions/structures define a subset of key interactions with APRIL and the CRD2 domain of TACI, optimal inhibition of APRIL binding to TACI by such an antibody would be achieved.

TABLE 4

Exemplary Human APRIL Amino Acid
Residues that Bind to Anti-APRIL Antibodies
(amino acid numbering based on SEQ ID NO: 85)

| Amino Acid Position | Amino Acid |
|---|---|
| 174 | Val |
| 175 | Thr |
| 176 | Phe |
| 177 | Thr |
| 178 | Met |
| 179 | Gly |
| 180 | Gln |
| 181 | Val |
| 230 | Pro |
| 231 | Arg |
| 232 | Ala |

In another embodiment, the antibody molecule does not bind to one, two, or all of Asp129, Arg233, or HIS203, on human APRIL (e.g., SEQ ID NO: 85). For example, one or more mutations at these positions, e.g., Asp129Ala, Arg233Asn, His203Asp, or any combination thereof, would not reduce, or substantially reduce, the binding affinity of the antibody molecule to human APRIL, or the inhibitory effect of the antibody molecule on a human APRIL activity (e.g., neutralization of APRIL binding to TACI).

In yet another embodiment, the antibody molecule binds, or substantially binds, to one or more (e.g., 2, 3, 4, 5, 6, 7, 8, 9, or all) residues of human APRIL (e.g., SEQ ID NO: 85) from positions 105-114 and/or one or more (e.g., 2, 3, 4, 5, 6, 7, 8, 9, or all) residues of mouse APRIL (e.g., SEQ ID NO: 91) from positions 96-105.

In another embodiment, the antibody molecule contacts (e.g., binds or substantially binds to) one or more (e.g., 2, 3, 4, 5, 6, 7, 8, 9, 10, 11, 12, 13, 14, 15, 16, 17, or all) of the amino acid residues shown in Table 7. In another embodiment, the antibody molecule contacts (e.g., binds or substantially binds to) all of the amino acid residues shown in Table 7.

TABLE 7

Exemplary Human APRIL Amino Acid
Residues that Bind to Anti-APRIL Antibodies
(amino acid numbering based on SEQ ID NO: 85)

| Amino Acid Position | Amino Acid |
|---|---|
| 132 | Asp |
| 170 | Leu |
| 175 | Thr |
| 176 | Phe |
| 177 | Thr |
| 178 | Met |
| 181 | Val |
| 192 | Thr |
| 195 | Arg |
| 197 | Ile |
| 205 | Asp |
| 206 | Arg |
| 208 | Tyr |
| 228 | Iso |
| 230 | Pro |
| 231 | Arg |
| 232 | Ala |
| 241 | His |

In an embodiment, the antibody molecule, e.g., an anti-APRIL antibody molecule having one, two, three, four, five or six CDRs of any of monoclonal antibodies 2419, 2419-0105, 2419-0205, 2419-0206, 2419-0406, 2419-0605, 2419-0805, 2419-0806, 2419-1204, 2419-1210, 2419-1305, 2419-1306, 2419-1310, or 2419-1406, binds to one or more amino acids described in Table 7. In another embodiment, the antibody molecule, e.g., a human-specific, anti-APRIL antibody molecule, e.g., having one, two, three, four, five or six CDRs of any of monoclonal antibodies 2419, 2419-0105, 2419-0205, 2419-0206, 2419-0406, 2419-0605, 2419-0805, 2419-0806, 2419-1204, 2419-1210, 2419-1305, 2419-1306, 2419-1310, 2419-1406, binds to mouse APRIL when one or more (e.g., 2, 3, 4 or all) following positions within mouse APRIL (mouse APRIL numbering applies) are mutated, e.g., to the following: A120D, N224R, H163Q, K219I, or R181Q. In yet another embodiment, the antibody molecule, e.g., a human-specific, anti-APRIL antibody molecule, e.g., having one, two, three, four, five or six CDRs of any of monoclonal antibodies 2419, 2419-0105, 2419-0205, 2419-0206, 2419-0406, 2419-0605, 2419-0805, 2419-0806, 2419-1204, 2419-1210, 2419-1305, 2419-1306, 2419-1310, 2419-1406, binds to mouse APRIL when the lysine at position 219 (mouse APRIL numbering applies) is mutated, e.g., to an isoleucine (i.e., K219I).

In an embodiment, the antibody molecule contacts (e.g., binds or substantially binds to) one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or all) of the amino acid residues of human APRIL shown in Table 6. In an embodiment, the antibody molecule is an antibody molecule described herein, e.g., monoclonal antibody 2218, 2419, 2621, 2622, 3125, 3327, 3525, 3530, 4035, 3934, 3833, 3631, 3732, 4338, 4540, or 4237.

In an embodiment, the antibody molecule contacts (e.g., binds or substantially binds to) one or more (e.g., 2, 3, 4, 5, 6, 7, 8, 9, or all) of the amino acid residues of human APRIL chosen from D132, V174, F176, V181, Q190, R195, R206, Y208, I228, or N237. In an embodiment, the antibody molecule contacts (e.g., binds or substantially binds to) one or more (e.g., 2, 3, 4, 5, or all) of the amino acid residues of human APRIL chosen from V174, F176, Q190, R195, R206, or Y208. In an embodiment, the antibody molecule contacts (e.g., binds or substantially binds to) one or more (e.g., 2, 3, or all) of the amino acid residues of human APRIL chosen from F176, V181, Q190, or I228. In an embodiment, the antibody molecule contacts (e.g., binds or substantially binds to) one or more (e.g., 2, or all) of the amino acid residues of human APRIL chosen from V174, R206, or Y208.

In an embodiment, the antibody molecule does not contact (e.g., does not bind or does not substantially bind to) at least one (e.g., 1, 2, 3, 4, 5, 6, 7, 8, 9, 10, 11, 12, 13, 14, 15, 16, 17, 18, 19, or 20) of the amino acid residues of human APRIL shown in Table 6. In an embodiment, the antibody molecule is an antibody molecule described herein, e.g., monoclonal antibody 2218, 2419, 2621, 2622, 3125, 3327, 3525, 3530, 4035, 3934, 3833, 3631, 3732, 4338, 4540, or 4237.

In an embodiment, the antibody molecule does not contact (e.g., does not bind or does not substantially bind to) one or more (e.g., 2, 3, 4, 5, 6, or all) of the amino acid residues of human APRIL chosen from F176, V181, Q190, S226, I228, Y208, or N237. In an embodiment, the antibody molecule does not contact (e.g., does not bind or does not substantially bind to) one or more (e.g., 2, 3, or all) of the amino acid residues of human APRIL chosen from V181, S226, I228, or N237. In an embodiment, the antibody molecule does not contact (e.g., does not bind or does not substantially bind to) one or both of the amino acid residues of human APRIL chosen from Y208 or N237. In an embodiment, the antibody molecule does not contact (e.g., does not bind or does not substantially bind to) one or more (e.g., 2, 3, or all) of the amino acid residues of human APRIL chosen from F176, V181, Q190, or N237.

In an embodiment, the antibody molecule contacts (e.g., binds or substantially binds to) one or more (e.g., 2, 3, 4, 5, or all) of the amino acid residues of human APRIL chosen from V174, F176, Q190, R195, R206, or Y208; and does not contact (e.g., does not bind or does not substantially bind to) one or more (e.g., 2, 3, or all) of the amino acid residues of human APRIL chosen from V181, S226, I228, or N237. In an embodiment, the antibody molecule contacts (e.g., binds or substantially binds to) one or both of the amino acid residues of human APRIL chosen from V174 or R206; and does not contact (e.g., does not bind or does not substantially bind to) one or both of the amino acid residues of human APRIL chosen from V181 or N237 (and optionally S226). In an embodiment, the antibody molecule comprises one or more (e.g., two or three) heavy chain CDRs, one or more (e.g., two or three) light chain CDRs, or both of monoclonal antibody 4035. In an embodiment, the antibody molecule comprises a heavy chain region, a light chain variable region, or both, of monoclonal antibody 4035. In an embodiment, monoclonal antibody 4035 is a humanized antibody molecule.

In an embodiment, the antibody molecule contacts (e.g., binds or substantially binds to) one or more (e.g., 2, 3, or all) of the amino acid residues of human APRIL chosen from F176, V181, Q190, or I228; and does not contact (e.g., does not bind or does not substantially bind to) one or both of the amino acid residues of human APRIL chosen from Y208 or N237. In an embodiment, the antibody molecule contacts (e.g., binds or substantially binds to) amino acid residue I228 of human APRIL; and does not contact (e.g., does not bind or does not substantially bind to) one or both of the amino acid residues of human APRIL chosen from Y208 or N237. In an embodiment, the antibody molecule comprises one or more (e.g., two or three) heavy chain CDRs, one or more (e.g., two or three) light chain CDRs, or both of monoclonal antibody 2419. In an embodiment, the antibody molecule comprises a heavy chain region, a light chain variable region, or both, of monoclonal antibody 2419. In an embodiment, monoclonal antibody 2419 is a humanized antibody molecule.

In an embodiment, the antibody molecule contacts (e.g., binds or substantially binds to) one or more (e.g., 2, or all) of the amino acid residues of human APRIL chosen from V174, R206, or Y208; and does not contact (e.g., does not bind or does not substantially bind to) one or more (e.g., 2, 3, or all) of the amino acid residues of human APRIL chosen from F176, V181, Q190, or N237. In an embodiment, the antibody molecule contacts (e.g., binds or substantially binds to) one or both of the amino acid residues of human APRIL chosen from V174 or R206; and does not contact (e.g., does not bind or does not substantially bind to) one or more (e.g., 2, 3, or all) of the amino acid residues of human APRIL chosen from F176, V181, Q190, or N237. In an embodiment, the antibody molecule comprises one or more (e.g., two or three) heavy chain CDRs, one or more (e.g., two or three) light chain CDRs, or both of monoclonal antibody 3833. In an embodiment, the antibody molecule comprises a heavy chain region, a light chain variable region, or both, of monoclonal antibody 3833. In an embodiment, monoclonal antibody 3833 is a humanized antibody molecule.

In an embodiment, the epitope overlaps with a CRD2 receptor binding site. In an embodiment, the epitope is non-linear epitope, e.g., that spans across a monomer interface. In an embodiment, the epitope is in a region associated with both TACI and BCMA receptor blocking.

In an embodiment, the antibody molecule contacts (e.g., binds or substantially binds to) one or more (e.g., 2, 3, 4, 5, 6, 7, 8, 9, 10, 11, 12, 13, 14, 15, or all) of the amino acid residues of human APRIL chosen from V133, V181, E185, Q187, G188, R189, Q190, E191, T192, R195, H218, L219, H220, S226, I228, P230 (located in monomer A). In an embodiment, the antibody molecule contacts (e.g., binds or substantially binds to) one or more (e.g., 2, 3, 4, 5, 6, 7, 8, 9, or all) of the amino acid residues of human APRIL chosen from V121, I123, Q139, P140, A141, L142, N237, S239, P240, or H241 (located in monomer B). In an embodiment, the antibody molecule contacts (e.g., binds or substantially binds to) one or more (e.g., 2, 3, 4, 5, 6, 7, 8, 9, 10, 11, 12, 13, 14, 15, 16, 17, 18, 19, 20, 21, 22, 23, 24, 25, or all) of the amino acid residues of human APRIL chosen from V133, V181, E185, Q187, G188, R189, Q190, E191, T192, R195, H218, L219, H220, S226, I228, P230 (located in monomer A); V121, I123, Q139, P140, A141, L142, N237, S239, P240, or H241 (located in monomer B).

In an embodiment, the antibody molecule contacts (e.g., binds or substantially binds to) one or more (e.g., 2, 3, or all) of the amino acid residues of human APRIL chosen from V181, Q190, T192, and I228 (located in monomer A). In an embodiment, the antibody molecule contacts (e.g., binds or substantially binds to) one or both of the amino acid residues of human APRIL chosen from A141 or H241 (located in monomer B). In an embodiment, the antibody molecule contacts (e.g., binds or substantially binds to) one or more (e.g., 2, 3, 4, 5, or all) of the amino acid residues of human APRIL chosen from V181, Q190, T192, and I228 (located in monomer A); A141 or H241 (located in monomer B).

In an embodiment, the antibody molecule comprises one or more (e.g., two or three) heavy chain CDRs, one or more (e.g., two or three) light chain CDRs, or both of monoclonal antibody 2419. In an embodiment, the antibody molecule comprises a heavy chain region, a light chain variable region, or both, of monoclonal antibody 2419. In an embodiment, monoclonal antibody 2419 is a humanized antibody molecule.

In an embodiment, the epitope comprise one or more (e.g., 2, 3, 4, 5, 6, 7, 8, 9, 10, 11, 12, 13, 14, 15, 16, 17, 18, 19, 20, 21, 22, 23, 24, 25, or all) of the amino acid residues of human APRIL chosen from V133, V181, E185, Q187, G188, R189, Q190, E191, T192, R195, H218, L219, H220, S226, I228, P230 (located in monomer A); V121, I123, Q139, P140, A141, L142, N237, S239, P240, or H241 (located in monomer B). In an embodiment, the epitope comprises one or more (e.g., 2, 3, 4, 5, or all) of the amino acid residues of human APRIL chosen from V181, Q190, T192, and I228 (located in monomer A); A141 or H241 (located in monomer B).

Figure 38A:
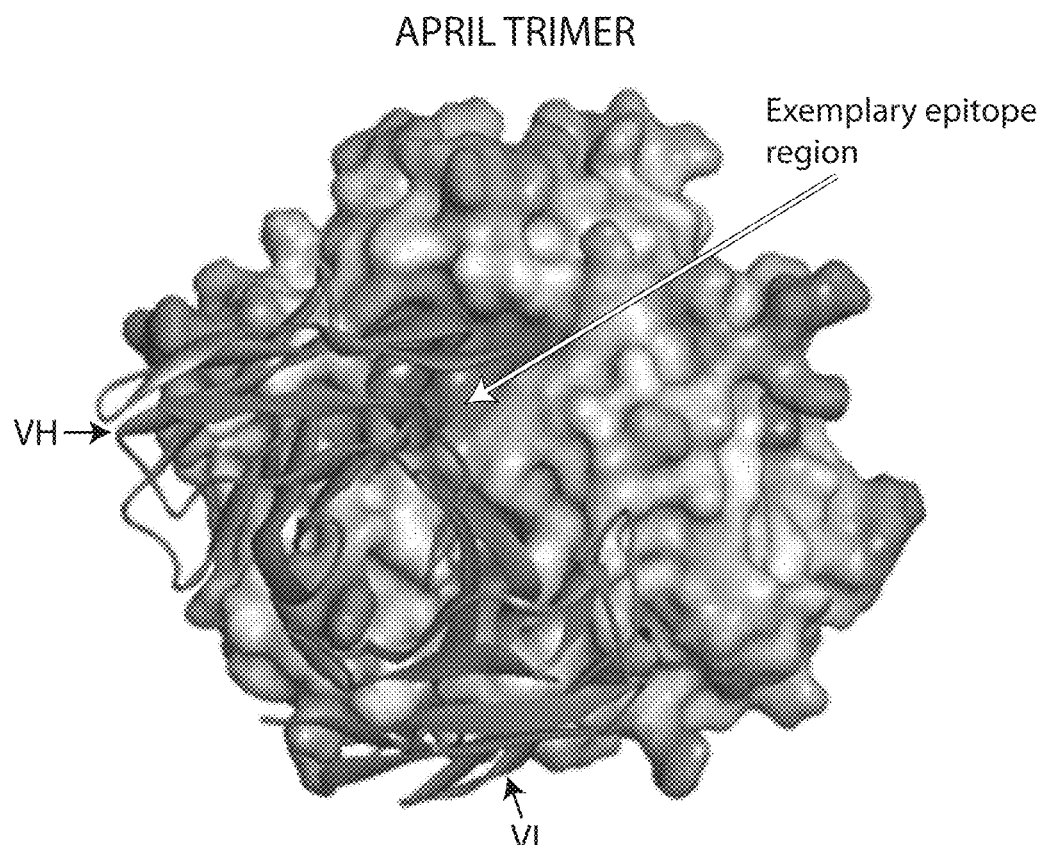
FIG. 38A depicts the molecular engagement of the anti-APRIL mAb 2419 binding to APRIL based on low resolution X-ray co-crystallographic data of human APRIL (amino acids 115-250) and Fab region of mouse 2419. Structure was solved by molecular replacement using mouse APRIL described in the protein structure database. 2419 epitope within APRIL is indicated by arrow. Variable heavy and light chains of mAb 2419 are also indicated. Structure of APRIL is depicted as a trimer.
Figure 38B:
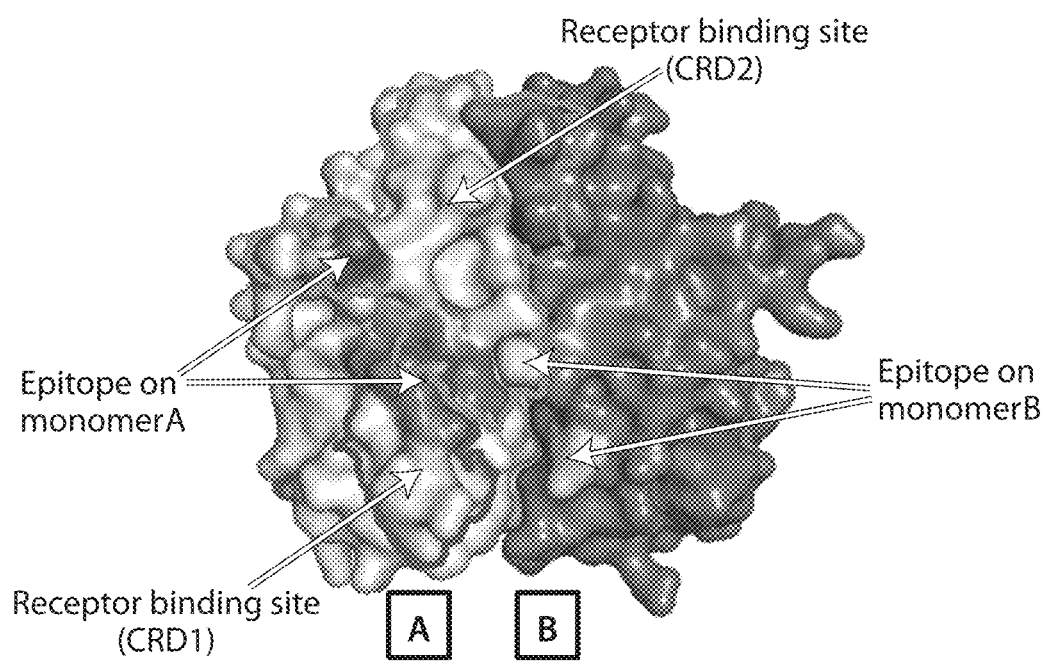
FIG. 38B depicts residues within APRIL that comprise a subset of the 2419 epitope. This structural depiction of the 2419 epitope also highlights the fact that 2419 binds to a non-linear, quaternary epitope spanning two different monomers of APRIL within a larger trimeric complex depicted here as monomer A and monomer B. Epitope on monomer A and epitope on monomer B are indicated. 2419 epitope substantially overlaps with the high affinity receptor binding site (CRD2) and lower affinity receptor binding site (CRD1) critical for APRIL-mediated receptor signaling. CRD2 receptor binding site and CRD1 receptor binding site are outlined and indicated.

In an embodiment, a structural representation of this epitope is depicted in FIG. 38B. In an embodiment, the epitope comprises one or more (e.g., 2, 3, 4, 5, 6, 7, 8, 9, 10, 11, 12, 13, 14, 15, 16, 17, 18, 19, 20, 21, 22, 23, 24, 25, or all) of the amino acid residues shown in Table 8.

In an embodiment, the antibody molecule contacts (e.g., binds, or substantially binds, to) all of the amino acid residues shown in any of Tables 3-4 or 7-8. In an embodiment, the epitope comprises, or consists of, all of the amino acid residues shown in any of Tables 3-4 or 7-8.

In an embodiment, the antibody molecule has one or more of the following properties described herein, e.g., one or more (e.g., two, three or all) of: (i) binds, or substantially binds, to human APRIL; (ii) binds, or substantially binds, to mouse APRIL; (iii) inhibits, or substantially inhibits, binding of APRIL (e.g., human APRIL, mouse APRIL, or both) to TACI (e.g., human TACI, mouse TACI, or both); or (iv) inhibits, or substantially inhibits, binding of APRIL (e.g., human APRIL, mouse APRIL, or both) to BCMA (e.g., human BCMA, mouse BCMA, or both). In an embodiment, the antibody molecule binds, or substantially binds, to mouse APRIL. In another embodiment, the antibody molecule does not bind, or binds with low affinity, to mouse APRIL.

Antibody Molecules

Disclosed herein are antibody molecules that bind to APRIL, e.g., an APRIL molecule described herein.

As used herein, the term "antibody molecule" refers to a protein, e.g., an immunoglobulin chain or a fragment thereof, comprising at least one immunoglobulin variable domain sequence. The term "antibody molecule" includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibody molecules can be monoclonal or polyclonal. The antibody molecule can also be a human, humanized, CDR-grafted, or in vitro generated antibody. The antibody molecule can have a heavy chain constant region chosen from, e.g., IgG1, IgG2, IgG3, or IgG4. The antibody molecule can also have a light chain chosen from, e.g., kappa or lambda. The term "immunoglobulin" (Ig) is used interchangeably with the term "antibody" herein.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments may be obtained using any suitable method, including several conventional techniques known to those with skill in the art, and the fragments can be screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

The antibody molecule can be a single chain antibody. A single-chain antibody (scFv) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

The antibody molecules disclosed herein can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to some aspects, a single domain antibody is a naturally occurring single domain antibody known as heavy chain antibody devoid of light chains. Such single domain antibodies are disclosed in WO 94/04678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in *Camelidae* species, for example in camel, llama, dromedary, alpaca and guanaco. Other species besides *Camelidae* may produce heavy chain antibodies naturally devoid of light chain; such VHHs are also contemplated.

The VH and VL regions can be subdivided into regions of hypervariability, termed "complementarity determining regions" (CDR), interspersed with regions that are more conserved, termed "framework regions" (FR or FW). The terms "complementarity determining region," and "CDR," as used herein refer to the sequences of amino acids within antibody variable regions which confer antigen specificity and binding affinity. As used herein, the terms "framework," "FW" and "FR" are used interchangeably.

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). In an embodiment, the following definitions are used: AbM definition of CDR1 of the heavy chain variable domain and Kabat definitions for the other CDRs. In an embodiment, Kabat definitions are used for all CDRs. In addition, embodiments described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, and FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding region" refers to the part of an antibody molecule that comprises determinants that form an interface that binds to an antigen, e.g., APRIL, or an epitope thereof. With respect to proteins (or protein mimetics), the antigen-binding region typically includes one or more loops (of at least, e.g., four amino acids or amino acid mimics) that form an interface that binds to the antigen, e.g., APRIL. Typically, the antigen-binding region of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of an anti-APRIL antibody molecule, e.g., an anti-APRIL antibody molecule provided herein, to a target, e.g., APRIL. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In an embodiment, a competition binding assay is a quantitative competition assay. In an embodiment, a first anti-APRIL antibody molecule is said to compete for binding to the target with a second anti-APRIL antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

The antibody molecule can be a polyclonal or a monoclonal antibody. In some embodiments, the antibody can be recombinantly produced, e.g., produced by any suitable phage display or combinatorial methods.

Various phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In an embodiment, the antibody molecule is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. In an embodiment, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by any suitable recombinant DNA technique. Several are known in the art (see Robinson et al., International Patent Application Publication No. WO1987/002671; Akira, et al., European Patent Application Publication No. 184,187; Taniguchi, M., European Patent Application Publication No. 171,496; Morrison et al., European Patent Application Publication No. 173,494; Neuberger et al., International Patent Application Publication No. WO 86/01533; Cabilly et al. U.S. Pat. No. 4,816,567; Cabilly et al., European Patent Application Publication No. 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to lipopolysaccharide. In an embodiment, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In some embodiments, the donor immunoglobulin is a non-human (e.g., rodent). The acceptor framework is typically a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by any suitable method, and several such methods known in the art (see e.g., Morrison, S. L., 1985, Science 229:1202-1207, by Oi et al., 1986, BioTechniques 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare humanized antibodies (UK Patent Application GB 2188638A, filed on Mar. 26, 1987; Winter U.S. Pat. No. 5,225,539), the contents of which is expressly incorporated by reference.

Also provided are humanized antibodies in which specific amino acids have been substituted, deleted or added. Criteria for selecting amino acids from the donor are described in, e.g., U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In an embodiment, the antibody molecule has a heavy chain constant region chosen from, e.g., the heavy chain constant regions of IgG1, IgG2 (e.g., IgG2a), IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody molecule (e.g., to increase or decrease one or more of: Fc receptor binding, antibody glycosylation, the number of cysteine residues, effector cell function, and/or complement function). In an embodiment, the antibody molecule has effector function and can fix complement. In another embodiment, the antibody molecule does not recruit effector cells or fix complement. In certain embodiments, the antibody molecule has reduced or no ability to bind an Fc receptor. For example, it may be an isotype or subtype, fragment or other mutant, which does not support binding to an Fc receptor, e.g., it has a mutagenized or deleted Fc receptor binding region.

In an embodiment, a constant region of the antibody molecule is altered. Methods for altering an antibody constant region are known in the art. Antibody molecules s with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference) Amino acid mutations which stabilize antibody structure, such as S228P (EU nomenclature, S241P in Kabat nomenclature) in human IgG4 are also contemplated. Similar type of alterations could be described which if applied to the murine, or other species immunoglobulin would reduce or eliminate these functions.

In an embodiment, the only amino acids in the antibody molecule are canonical amino acids. In an embodiment, the antibody molecule comprises naturally-occurring amino acids; analogs, derivatives and congeners thereof; amino acid analogs having variant side chains; and/or all stereoisomers of any of any of the foregoing. The antibody molecule may comprise the D- or L-optical isomers of amino acids and peptidomimetics.

A polypeptide of an antibody molecule described herein may be linear or branched, it may comprise modified amino acids, and it may be interrupted by non-amino acids. The antibody molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The antibody molecule described herein can be used alone in unconjugated form, or can be bound to a substance, e.g., a toxin or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the anti-APRIL antibody can be coupled to a radioactive isotope such as an α-, β-, or γ-emitter, or a β- and γ-emitter.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a toxin, a pharmaceutical agent, and/or a protein or peptide that can mediate association of the antibody or antibody portion with another molecule (such as a streptavidin core region or a polyhistidine tag).

Some types of derivatized antibody molecule are produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an anti-dengue antibody molecule may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecule may be conjugated to another molecular entity, typically a label or a therapeutic (e.g., antimicrobial (e.g., antibacterial or bactericidal), immunomodulatory, immunostimulatory, cytotoxic, or cytostatic) agent or moiety. Radioactive isotopes can be used in diagnostic or therapeutic applications. Radioactive isotopes that can be coupled to the antibody molecules include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The present disclosure provides radiolabeled antibody molecules and methods of labeling the same. In an embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

In some aspects, this disclosure provides a method of making an antibody molecule disclosed herein. The method includes: providing an antigen, e.g., APRIL or a fragment thereof; obtaining an antibody molecule that specifically binds to the antigen; evaluating efficacy of the antibody molecule in modulating activity of the antigen and/or organism expressing the antigen, e.g., APRIL. The method can further include administering the antibody molecule, including a derivative thereof (e.g., a humanized antibody molecule) to a subject, e.g., a human.

This disclosure provides an isolated nucleic acid molecule encoding the above antibody molecule, vectors and host cells thereof. The nucleic acid molecule includes, but is not limited to, RNA, genomic DNA and cDNA.

Amino acid and nucleotide sequences of exemplary antibody molecules are described in Tables 1 and 2, respectively. Amino acid sequences of additional exemplary humanized antibody molecules are described in Table 5.

TABLE 1

The amino acid sequences of the heavy chain variable region (VH) and light chain variable region (VL) of the exemplary anti-APRIL antibodies are provided as follows. CDRs, defined according to the Kabat system, are underlined and bold, while CDRs defined according to the Chothia system are italicized.

| Antibody | Chain | Amino Acid Sequence | SEQ ID NO | Chothia CDR | SEQ ID NO | Kabat CDR | SEQ ID NO |
|---|---|---|---|---|---|---|---|
| 2218 | VH | DVQLQESGPGLVKPSQSLSLTCSVT*GYSIT*SGYYW NWIRQFPGNKLEWMG*YISYDGYNNYNPSLKN*RISI TRDTSKNQFFLKLNSVTTEDTATYYCANYYDYEDW YFGVWGTGTTVTSS | 9 | HCDR1 GYSITSGY HCDR2 SYDGY HCDR3 YYDYEDWYF GV | 1 2 3 | HCDR1 SGYYWN HCDR2 YISYDGYNNYN PSLKN HCDR3 YYDYEDWYFGV | 7 8 3 |
| | VL | DIVLTQSPASLAMSLGKRATISCRASESVSIIGTN *SIH*WYQQKPGQPPKLLIYHASNLETGVPARFSGSG SRTDFTLTIDPVEEDDVAIYYCLQSRKIPYTFGGG TKLEIK | 10 | LCDR1 RASESVSII LCDR2 GTNSIH LCDR3 HASNLET LQSRKIPYT | 4 5 6 | LCDR1 RASESVSIIGT NSIH LCDR2 HASNLET LCDR3 LQSRKIPYT | 4 5 6 |
| 2419 | VH | QVQLQQSGAELVKPGASVRLSCEASGYTFTDYTIH WVKQRSGQGLEWIG*WIYPLRGSINYNEKFKD*KATL TADKSSSTVYLELGRLTSKDSAVYFCARHGAYYSN AFDYWGQGTTLTVSS | 19 | HCDR1 GYTFTDY HCDR2 YPLRGS HCDR3 HGAYYSNAF DY | 11 12 13 | HCDR1 DYTIH HCDR2 WIYPLRGSINY NEKFKD HCDR3 HGAYYSNAFDY | 17 18 13 |
| | VL | NIVMTQSPASLAVSLGQRATISCRASESVDNDGIR *FMH*WYQQKPGQPPKLLIYRASNLESGIPARFSGSG SRTDFTLTINPVETDDVATYYCQQSNKDPYTFGGG TKLELK | 20 | LCDR1 RASESVDND LCDR2 GIRFMH LCDR3 RASNLES QQSNKDPYT | 14 15 16 | LCDR1 RASESVDNDGI LCDR2 RFMH LCDR3 RASNLES QQSNKDPYT | 14 15 16 |
| 2419-1305 | VH | QVQLVQSGAEVKKPGASVKVSCKASGYTFTDYTIH WVRQATGQGLEWMG*WIYPLRGSINYAQKFQG*RVTM TANKSISTVYMELSSLRSEDTAVYFCARHGAYYSN AFDYWGQGTLVTVSS | 283 | HCDR1 GYTFTDY HCDR2 YPLRGS HCDR3 HGAYYSNAFDY | 11 12 13 | HCDR1 DYTIH HCDR2 WIYPLRGSINY AQKFQG HCDR3 HGAYYSNAFDY | 17 282 13 |
| | VL | EIVMTQSPATLSVSPGERATLSCRASESVDNDGIR *FLH*WYQQKPGQAPRLLIYRASNRETGIPARFSGSG SGTEFTLTISSLQSEDFAVYYCQQSNKDPYTFGGG TKVEIK | 284 | LCDR1 RASESVDNDGI LCDR2 RFLH LCDR3 RASNRET QQSNKDPYT | 280 281 16 | LCDR1 RASESVDNDGI LCDR2 RFLH LCDR3 RASNRET QQSNKDPYT | 280 281 16 |
| 2419-1306 | VH | QVQLVQSGAEVKKPGASVKVSCKASGYTFTDYTIH WVRQATGQGLEWMG*WIYPLRGSINYAQKFQG*RVTM TANKSISTVYMELSSLRSEDTAVYFCARHGAYYSN AFDYWGQGTLVTVSS | 283 | HCDR1 GYTFTDY HCDR2 YPLRGS HCDR3 HGAYYSNAFDY | 11 12 13 | HCDR1 DYTIH HCDR2 WIYPLRGSINY AQKFQG HCDR3 HGAYYSNAFDY | 17 282 13 |
| | VL | EIVMTQSPATLSVSPGERATLSCRASESVDNDGIR *FLH*WYQQKPGQAPRLLIYRASTRATGIPARFSGSG SRTEFTLTISSLQSEDFAVYYCQQSNKDPYTFGGG TKVEIK | 286 | LCDR1 RASESVDNDGI LCDR2 RFLH LCDR3 RASTRAT QQSNKDPYT | 280 285 16 | LCDR1 RASESVDNDGI LCDR2 RFLH LCDR3 RASTRAT QQSNKDPYT | 280 285 16 |
| 2419-1310 | VH | QVQLVQSGAEVKKPGASVKVSCKASGYTFTDYTIH WVRQATGQGLEWMG*WIYPLRGSINYAQKFQG*RVTM TANKSISTVYMELSSLRSEDTAVYFCARHGAYYSN AFDYWGQGTLVTVSS | 283 | HCDR1 GYTFTDY HCDR2 YPLRGS HCDR3 HGAYYSNAFDY | 11 12 13 | HCDR1 DYTIH HCDR2 WIYPLRGSINY AQKFQG HCDR3 HGAYYSNAFDY | 17 282 13 |
| | VL | DIVMTQSPDSLAVSLGERATINCKSSQSVDNDGIR *FLH*WYQQKPGQPPKLLIYRASTRESGVPDRFSGSG SGTDFTLTISSLQAEDVAVYYCQQSNKDPYTFGGG TKVEIK | 316 | LCDR1 KSSQSVDNDGI LCDR2 RFLH LCDR3 RASTRES QQSNKDPYT | 314 315 16 | LCDR1 KSSQSVDNDGI LCDR2 RFLH LCDR3 RASTRES QQSNKDPYT | 314 315 16 |
| 2419-0806 | VH | EVQLVQSGAEVKKPGESLKISCKASGYTFTDYTIH WVRQMPGKGLEWMG*WIYPLRGSINYSPSFQG*QVTI SADKSISTVYLQWSSLKASDTAMYFCARHGAYYSN AFDYWGQGTLVTVSS | 288 | HCDR1 GYTFTDY HCDR2 YPLRGS HCDR3 HGAYYSNAFDY | 11 12 13 | HCDR1 DYTIH HCDR2 WIYPLRGSINY SPSFQG HCDR3 HGAYYSNAFDY | 17 287 13 |
| | VL | EIVMTQSPATLSVSPGERATLSCRASESVDNDGIR *FLH*WYQQKPGQAPRLLIYRASTRATGIPARFSGSG SRTEFTLTISSLQSEDFAVYYCQQSNKDPYTFGGG TKVEIK | 286 | LCDR1 RASESVDNDGI LCDR2 RFLH LCDR3 RASTRAT QQSNKDPYT | 280 285 16 | LCDR1 RASESVDNDGI LCDR2 RFLH LCDR3 RASTRAT QQSNKDPYT | 280 285 16 |

TABLE 1-continued

The amino acid sequences of the heavy chain variable region (VH) and light chain variable region (VL) of the exemplary anti-APRIL antibodies are provided as follows. CDRs, defined according to the Kabat system, are underlined and bold, while CDRs defined according to the Chothia system are italicized.

| Antibody | Chain | Amino Acid Sequence | SEQ ID NO | Chothia CDR | SEQ ID NO | Kabat CDR | SEQ ID NO |
|---|---|---|---|---|---|---|---|
| 2419-0205 | VH | QVQLVQSGAEVKKPGSSVKVSCKASGYTFTDYTIHWVRQAPGQGLEWMGWIYPLRGSINYSPSFQGRVTITADKSTSTAYMELSSLRSEDTAVYFCARHGAYYSNAFDYWGQGTLVTVSS | 289 | HCDR1 GYTFTDY HCDR2 YPLRGS HCDR3 HGAYYSNAFDY | 11 12 13 | HCDR1 DYTIH HCDR2 WIYPLRGSINY HCDR3 AQKFQG HGAYYSNAFDY | 17 282 13 |
| | VL | EIVMTQSPATLSVSPGERATLSCRASESVDNDGIRFLHWYQQKPGQAPRLLIYRASNRETGIPARFSGSGSGTEFTLTISSLQSEDFAVYYCQQSNKDPYTFGGGTKVEIK | 284 | LCDR1 RASESVDNDGI LCDR2 RFLH LCDR3 RASNRET QQSNKDPYT | 280 281 16 | LCDR1 RASESVDNDGI LCDR2 RFLH LCDR3 RASNRET QQSNKDPYT | 280 281 16 |
| 2419-0406 | VH | QVQLVQSGAEVKKPGSSVKVSCKASGYTFTDYTIHWVRQAPGQGLEWMGWIYPLRGSINYAEKFKGRVTLTADKSTSTVYMELSSLRSEDTAVYFCARHGAYYSNAFDYWGQGTLVTVSS | 291 | HCDR1 GYTFTDY HCDR2 YPLRGS HCDR3 HGAYYSNAFDY | 11 12 13 | HCDR1 DYTIH HCDR2 WIYPLRGSINY HCDR3 AEKFKG HGAYYSNAFDY | 17 290 13 |
| | VL | EIVMTQSPATLSVSPGERATLSCRASESVDNDGIRFLHWYQQKPGQAPRLLIYRASTRATGIPARFSGSGSRTEFTLTISSLQSEDFAVYYCQQSNKDPYTFGGGTKVEIK | 286 | LCDR1 RASESVDNDGI LCDR2 RFLH LCDR3 RASTRAT QQSNKDPYT | 280 285 16 | LCDR1 RASESVDNDGI LCDR2 RFLH LCDR3 RASTRAT QQSNKDPYT | 280 285 16 |
| 2419-0605 | VH | QVQLVQSGAEVKKPGASVKVSCKASGYTFTDYTIHWVRQAPGQGLEWMGWIYPLRGSINYAEKFKGRVTLTADKSTSTVYMELSSLRSEDTAVYFCARHGAYYSNAFDYWGQGTLVTVSS | 317 | HCDR1 GYTFTDY HCDR2 YPLRGS HCDR3 HGAYYSNAFDY | 11 12 13 | HCDR1 DYTIH HCDR2 WIYPLRGSINY HCDR3 AQKFQG HGAYYSNAFDY | 17 282 13 |
| | VL | EIVMTQSPATLSVSPGERATLSCRASESVDNDGIRFLHWYQQKPGQAPRLLIYRASNRETGIPARFSGSGSGTEFTLTISSLQSEDFAVYYCQQSNKDPYTFGGGTKVEIK | 284 | LCDR1 RASESVDNDGI LCDR2 RFLH LCDR3 RASNRET QQSNKDPYT | 280 281 16 | LCDR1 RASESVDNDGI LCDR2 RFLH LCDR3 RASNRET QQSNKDPYT | 280 281 16 |
| 2419-0805 | VH | EVQLVQSGAEVKKPGESLKISCKASGYTFTDYTIHWVRQMPGKGLEWMGWIYPLRGSINYSPSFQGQVTISADKSISTVYLQWSSLKASDTAMYFCARHGAYYSNAFDYWGQGTLVTVSS | 288 | HCDR1 GYTFTDY HCDR2 YPLRGS HCDR3 HGAYYSNAFDY | 11 12 13 | HCDR1 DYTIH HCDR2 WIYPLRGSINY HCDR3 SPSFQG HGAYYSNAFDY | 17 287 13 |
| | VL | EIVMTQSPATLSVSPGERATLSCRASESVDNDGIRFLHWYQQKPGQAPRLLIYRASNRETGIPARFSGSGSGTEFTLTISSLQSEDFAVYYCQQSNKDPYTFGGGTKVEIK | 284 | LCDR1 RASESVDNDGI LCDR2 RFLH LCDR3 RASNRET QQSNKDPYT | 280 281 16 | LCDR1 RASESVDNDGI LCDR2 RFLH LCDR3 RASNRET QQSNKDPYT | 280 281 16 |
| 2419-0105 | VH | QVQLVQSGAEVKKPGASVKVSCKASGYTFTDYTIHWVRQAPGQGLEWMGWIYPLRGSINYAQKFQGRVTMTADKSISTVYMELSRLRSDDTAVYYCARHGAYYSNAFDYWGQGTLVTVSS | 292 | HCDR1 GYTFTDY HCDR2 YPLRGS HCDR3 HGAYYSNAFDY | 11 12 13 | HCDR1 DYTIH HCDR2 WIYPLRGSINY HCDR3 AQKFQG HGAYYSNAFDY | 17 282 13 |
| | VL | EIVMTQSPATLSVSPGERATLSCRASESVDNDGIRFLHWYQQKPGQAPRLLIYRASNRETGIPARFSGSGSGTEFTLTISSLQSEDFAVYYCQQSNKDPYTFGGGTKVEIK | 284 | LCDR1 RASESVDNDGI LCDR2 RFLH LCDR3 RASNRET QQSNKDPYT | 280 281 16 | LCDR1 RASESVDNDGI LCDR2 RFLH LCDR3 RASNRET QQSNKDPYT | 280 281 16 |
| 2419-1204 | VH | QVQLVQSGAEVKKPGASVKVSCKASGYTFTDYTIHWVRQATGQGLEWMGWIYPLRGSINYAQKFQGRVTMTANKSSSTVYMELSSLRSEDTAVYFCARHGAYYSNAFDYWGQGTLVTVSS | 294 | HCDR1 GYTFTDY HCDR2 YPLRGS HCDR3 HGAYYSNAFDY | 11 12 13 | HCDR1 DYTIH HCDR2 WIYPLRGSINY HCDR3 AQKFQG HGAYYSNAFDY | 17 282 13 |
| | VL | EIVMTQSPATLSVSPGERATLSCRASESVDNDGIRFLHWYQQKPGQAPRLLIYRASTLETGIPARFSGSGSGTEFTLTISSLQSEDFAVYYCQQSNKDPYTFGGGTKVEIK | 295 | LCDR1 RASESVDNDGI LCDR2 RFLH LCDR3 RASTLET QQSNKDPYT | 280 293 16 | LCDR1 RASESVDNDGI LCDR2 RFLH LCDR3 RASTLET QQSNKDPYT | 280 293 16 |
| 2419-1205 | VH | QVQLVQSGAEVKKPGASVKVSCKASGYTFTDYTIHWVRQATGQGLEWMGWIYPLRGSINYAQKFQGRVTMTANKSSSTVYMELSSLRSEDTAVYFCARHGAYYSNAFDYWGQGTLVTVSS | 294 | HCDR1 GYTFTDY HCDR2 YPLRGS HCDR3 HGAYYSNAFDY | 11 12 13 | HCDR1 DYTIH HCDR2 WIYPLRGSINY HCDR3 AQKFQG HGAYYSNAFDY | 17 282 13 |
| | VL | EIVMTQSPATLSVSPGERATLSCRASESVDNDGIRFLHWYQQKPGQAPRLLIYRASNRETGIPARFSGSGSGTEFTLTISSLQSEDFAVYYCQQSNKDPYTFGGGTKVEIK | 284 | LCDR1 RASESVDNDGI LCDR2 RFLH LCDR3 RASNRET QQSNKDPYT | 280 281 16 | LCDR1 RASESVDNDGI LCDR2 RFLH LCDR3 RASNRET QQSNKDPYT | 280 281 16 |

TABLE 1-continued

The amino acid sequences of the heavy chain variable region (VH) and light chain variable region (VL) of the exemplary anti-APRIL antibodies are provided as follows. CDRs, defined according to the Kabat system, are underlined and bold, while CDRs defined according to the Chothia system are italicized.

| Antibody | Chain | Amino Acid Sequence | SEQ ID NO | Chothia CDR | SEQ ID NO | Kabat CDR | SEQ ID NO |
|---|---|---|---|---|---|---|---|
| 2419-1210 | VH | QVQLVQSGAEVKKPGASVKVSCKASGYTFTDYTIHWVRQATGQGLEWMGWIYPLRGSINYAQKFQGRVTMTANKSSTVYMELSSLRSEDTAVYFCARHGAYYSNAFDYWGQGTLVTVSS | 294 | HCDR1 GYTFTDY<br>HCDR2 YPLRGS<br>HCDR3 HGAYYSNAFDY | 11<br>12<br>13 | HCDR1 DYTIH<br>HCDR2 WIYPLRGSINYAQKFQG<br>HCDR3 HGAYYSNAFDY | 17<br>282<br>13 |
| | VL | DIVMTQSPDSLAVSLGERATINCKSSQSVDNDGIRFLHWYQQKPGQPPKLLIYRASTRESGVPDRFSGSGSGTDFTLTISSLQAEDVAVYYCQQSNKDPYTFGGGTKVEIK | 316 | LCDR1 KSSQSVDNDGIFLH<br>LCDR2 RFLH<br>LCDR3 RASTRES<br>QQSNKDPYT | 314<br>315<br>16 | LCDR1 KSSQSVDNDGIFLH<br>LCDR2 RFLH<br>LCDR3 RASTRES<br>QQSNKDPYT | 314<br>315<br>16 |
| 2419-1406 | VH | QVQLVQSGAEVKKPGASVKVSCKASGYTFTDYTIHWVRQATGQGLEWMGWIYPLRGSINYAQKFQGRVTMTADKSISTVYMELSSLRSEDTAVYFCARHGAYYSNAFDYWGQGTLVTVSS | 296 | HCDR1 GYTFTDY<br>HCDR2 YPLRGS<br>HCDR3 HGAYYSNAFDY | 11<br>12<br>13 | HCDR1 DYTIH<br>HCDR2 WIYPLRGSINYAQKFQG<br>HCDR3 HGAYYSNAFDY | 17<br>282<br>13 |
| | VL | EIVMTQSPATLSVSPGERATLSCRASESVDNDGIRFLHWYQQKPGQAPRLLIYRASTRATGIPARFSGSGSRTEFTLTISSLQSEDFAVYYCQQSNKDPYTFGGGTKVEIK | 286 | LCDR1 RASESVDNDGIFLH<br>LCDR2 RFLH<br>LCDR3 RASTRAT<br>QQSNKDPYT | 280<br>285<br>16 | LCDR1 RASESVDNDGIFLH<br>LCDR2 RFLH<br>LCDR3 RASTRAT<br>QQSNKDPYT | 280<br>285<br>16 |
| 2419-0206 | VH | QVQLVQSGAEVKKPGSSVKVSCKASGYTFTDYTIHWVRQAPGQGLEWMGWIYPLRGSINYAQKFQGRVTITADKSTSTAYMELSSLRSEDTAVYFCARHGAYYSNAFDYWGQGTLVTVSS | 289 | HCDR1 GYTFTDY<br>HCDR2 YPLRGS<br>HCDR3 HGAYYSNAFDY | 11<br>12<br>13 | HCDR1 DYTIH<br>HCDR2 WIYPLRGSINYAQKFQG<br>HCDR3 HGAYYSNAFDY | 17<br>282<br>13 |
| | VL | EIVMTQSPATLSVSPGERATLSCRASESVDNDGIRFLHWYQQKPGQAPRLLIYRASTRATGIPARFSGSGSRTEFTLTISSLQSEDFAVYYCQQSNKDPYTFGGGTKVEIK | 286 | LCDR1 RASESVDNDGIFLH<br>LCDR2 RFLH<br>LCDR3 RASTRAT<br>QQSNKDPYT | 280<br>285<br>16 | LCDR1 RASESVDNDGIFLH<br>LCDR2 RFLH<br>LCDR3 RASTRAT<br>QQSNKDPYT | 280<br>285<br>16 |
| 2621 | VH | EVQLQQSGAELVRPGSSVKMSCKTSGYTFTSYGINWVKQRPGQGLEWIGYIYIGNGYAEYNERFKGKATLTSDTSSSTAYMQLSSLTSEDSAIYFCALYYPWFTYWGQGTLVTVSA | 29 | HCDR1 GYTFTSY<br>HCDR2 YIGNGY<br>HCDR3 YYPWFTY | 21<br>22<br>23 | HCDR1 SYGIN<br>HCDR2 YIYIGNGYAEYNERFKG<br>HCDR3 YYPWFTY | 27<br>28<br>23 |
| | VL | DIQMTQSPASLSASVGDSVTITCRAENIYSYLAWYQQKQGKSPQLLVYNAKTLAEGVPSRFSGSGSGTQFSLKINSLQPEDFGNYYCQHHYDTPFTFGGGTKLEIK | 30 | LCDR1 RASENIYSYLA<br>LCDR2 NAKTLAE<br>LCDR3 QHHYDTPFT | 24<br>25<br>26 | LCDR1 RASENIYSYLA<br>LCDR2 NAKTLAE<br>LCDR3 QHHYDTPFT | 24<br>25<br>26 |
| 2922 | VH | QVQLHQSGPELVKPGASVKLSCKTSGYTFTSYDVFWVKQRPGQGLEWIGWIYPRDSSTKYNEKFKGKATLTVDTSSSTAYMELHSLTSEDSAVYFCAKEGYDYDKRGFDYWGQGTTLTVSS | 39 | HCDR1 GYTFTSY<br>HCDR2 YPRDSS<br>HCDR3 EGYDYDKRGFDY | 21<br>32<br>33 | HCDR1 SYDVF<br>HCDR2 WIYPROSSTKYNEKFKG<br>HCDR3 EGYDYDKRGFDY | 37<br>38<br>33 |
| | VL | DIVLTQSPASLAVSLGQRAIISCKASQSVSFAGTNLMHWYQQRPGQPPKLLIYRASNLEPGVPTRFSGSGSRTDFTLNIHPVEEDDAATYYCQQSREYPWTFGGGTKLEIK | 40 | LCDR1 KASQSVSFAGTNLMH<br>LCDR2 NLMH<br>LCDR3 RASNLEP<br>QQSREYPWT | 34<br>35<br>36 | LCDR1 KASQSVSFAGTNLMH<br>LCDR2 LMH<br>LCDR3 RASNLEP<br>QQSREYPWT | 34<br>35<br>36 |
| 3125 | VH | QVQLQQSGAELVRPGASVTLSCKASGYTFTDYEMHWVKQTPVHGLEWIAIDPETGGTAYNQRFKGKAILTTDKSSITAYMELRSLTSEDSAVYYCTRWNDGDYWGQGTTLTVSS | 49 | HCDR1 GYTFTDY<br>HCDR2 DPETGG<br>HCDR3 WNDGDY | 11<br>42<br>43 | HCDR1 DYEMH<br>HCDR2 AIDPETGGTAYNQRFKG<br>HCDR3 WNDGDY | 47<br>48<br>43 |
| | VL | DVVMTQTPLSLSVTIGQPASISCKSSQSLLYSNGKTYLNWFQQRPGQSPKRLMYQVSKLDPGIPDRFSGSGSETDFTLKISRVEAEDLGLYYCLQGTYYPYTFGGGTKLEIK | 50 | LCDR1 KSSQSLLYSNGTYLN<br>LCDR2 KTYLN<br>LCDR3 QVSKLDP<br>LQGTYYPYT | 44<br>45<br>46 | LCDR1 KSSQSLLYSNGK<br>LCDR2 TYLN<br>LCDR3 QVSKLDP<br>LQGTYYPYT | 44<br>45<br>46 |
| 3327 | VH | EVQLQQSGPELVKPGASVKMSCKASGYSFTGYFMNWVKQSHGKSLEWIGRINPYNGDTFYNQKFKGKATLTVDKSSTAHMELRSLTSEDSALYYCASEGDGYYWYFDVWGAGTTVTVSS | 59 | HCDR1 GYSFTGY<br>HCDR2 NPYNGD<br>HCDR3 EGDGYYWYFDV | 51<br>52<br>53 | HCDR1 GYFMN<br>HCDR2 RINPYNGDTFYNQKFKG<br>HCDR3 EGDGYYWYFDV | 57<br>58<br>53 |

TABLE 1-continued

The amino acid sequences of the heavy chain variable region (VH) and light chain variable region (VL) of the exemplary anti-APRIL antibodies are provided as follows. CDRs, defined according to the Kabat system, are underlined and bold, while CDRs defined according to the Chothia system are italicized.

| Antibody | Chain | Amino Acid Sequence | SEQ ID NO | Chothia CDR | SEQ ID NO | Kabat CDR | SEQ ID NO |
|---|---|---|---|---|---|---|---|
| | VL | DIVLTQSPASLAVSLGQRATISCRASESVDNYGIS FMNWFQQKPGQPPKLLIYAASNQGSGVPARFSGSG SGTDFSLNIHPMEEDDTAMYFCQQSKEVPRTFGGG TKLEIK | 60 | LCDR1 RASESVDNYGI LCDR2 SFMN LCDR3 AASNQGS QQSKEVPRT | 54 55 56 | LCDR1 RASESVDNYGI LCDR2 SFMN LCDR3 AASNQGS QQSKEVPRT | 54 55 56 |
| 3525 | VH | QVQLQQSGAELVRPGASVKLSCKASGYTF*TDHEMHWVRQTPVHGLEWIG*VIDPDTGDTTYNQKFKGKATL TADKSSSTAYMDLRSLTSEDSAVFYCTR***WTGGDY*W GHGTTLTVSS | 66 | HCDR1 GYTFTDH HCDR2 DPDTGD HCDR3 WTGGDY | 61 62 63 | HCDR1 DHEMH HCDR2 VIDPDTGDTTY NQKFKG WTGGDY | 64 65 63 |
| | VL | DVVMTQTPLSLSVTIGQPASISC*KSSQSLLYSNGK TYLN*WFQQRPGQSPKRLMY*QVSKLDP*GIPDRFSGS GSETDFTLKISRVEAEDLGLYYC*LQGTYYPYT*FGG GTKLEIK | 50 | LCDR1 KSSQSLLYSNG LCDR2 KTYLN LCDR3 QVSKLDP LQGTYYPYT | 44 45 46 | LCDR1 KSSQSLLYSNG LCDR2 KTYLN LCDR3 QVSKLDP LQGTYYPYT | 44 45 46 |
| 3530 | VH | QVQLQQSGAELVRPGASVKLSCKASGYTF*TDHEMHWVRQTPVHGLEWIG*VIDPDTGDTTYNQKFKGKATL TADKSSSTAYMDLRSLTSEDSAVFYCTR***WTGGDY*W GHGTTLTVSS | 66 | HCDR1 GYTFTDH HCDR2 DPDTGD HCDR3 WTGGDY | 61 62 63 | HCDR1 DHEMH HCDR2 VIDPDTGDTTY NQKFKG WTGGDY | 64 65 63 |
| | VL | DAVMTQTPLSLSVTIGQPASISC*KSSQSLLYSDGK TYLN*WFQQRPGQSPKRLMY*QVSKLDP*GIPDRFSGS GSETDFTLKISRVEAEDLGVYYC*QVSKLDP*FGS GTKLEIK | 70 | LCDR1 KSSQSLLYSDG LCDR2 KTYLN LCDR3 QVSKLDP LQGTYYPYT | 67 45 46 | LCDR1 KSSQSLLYSDG LCDR2 KTYLN LCDR3 QVSKLDP LQGTYYPYT | 67 45 46 |
| 4035 | VH | QVQLKESGPGLVAPSQSLSITCTVS*GFSLT*IYDVHWVRQSPGKGLEWLG*VIWSDGSTDYNAAFISRLSIS KDNSKSQVFFKMNSLQADDTAIYYCAR*NWVDQAWF AY***WGQGTLVTVSA | 101 | HCDR1 GFSLTIY HCDR2 WSDGS HCDR3 NWVDQAWFAY | 93 94 95 | HCDR1 IYDVH HCDR2 VIWSDGSTDYN AAFIS NWVDQAWFAY | 99 100 95 |
| | VL | DIQMTQSPASLSASVGETITITC*RASKNIYSYLA*W YQQKQGKSPQLLV*NAKTLPE*GVPSRFSGSGSGTQ FSLKINSLQPEDFGSYYC*QHHYGTPLT*FGAGTKLE LK | 102 | LCDR1 RASKNIYSYLA LCDR2 NAKTLPE LCDR3 QHHYGTPLT | 96 97 98 | LCDR1 RASKNIYSYLA LCDR2 NAKTLPE LCDR3 QHHYGTPLT | 96 97 98 |
| 4035-062 | VH | QVQLQESGPGLVKPSETLSLTCTVS*GFSLT***IYDVHWVRQPPGKGLEWIG*VIWSDGSTDYNPSLKSRVTIS KDTSKNQVSLKLSSVTAADTAVYYCAR*NWVDQAWF AY***WGQGTLVTVSS | 225 | HCDR1 GFSLTIY HCDR2 WSDGS HCDR3 NWVDQAWFAY | 93 94 95 | HCDR1 IYDVH HCDR2 VIWSDGSTDYN PSLKS NWVDQAWFAY | 99 273 95 |
| | VL | DIQMTQSPSSLSASVGDRVTITC*RASKNIYSYLA*W YQQKPGKAPKLLV*NAKTLPE*GVPSRFSGSGSGTD FTLTISSLQPEDFATYYC*QHHYGTPLT*FGQGTKLE IK | 229 | LCDR1 RASKNIYSYLA LCDR2 NAKTLPE LCDR3 QHHYGTPLT | 96 97 98 | LCDR1 RASKNIYSYLA LCDR2 NAKTLPE LCDR3 QHHYGTPLT | 96 97 98 |
| 3934 | VH | QVQLQQSGPELVKPGASVKLSCKAAGYIFT*DYTIN*WVKQSPGQGLEWIG*WIYPGSGNRKYNDKFKG*KATM TADKSSSTAYMQLSSLTSEDSAVYFCAR*ESNYVGY YAMDY*WGQGTSVTVSS | 111 | HCDR1 GYIFTDY HCDR2 YPGSGN HCDR3 ESNYVGYYAMD Y | 103 104 105 | HCDR1 DYTIN HCDR2 WIYPGSGNRKYN DKFKG ESNYVGYYAMDY | 109 110 105 |
| | VL | DVLMTQTPLSLPVSLGDQASISC*RSSQSVVNSNGN TYLE*WYLQKPGQSPNLLIY*KVSNRFS*GVPDRFSGS GSGTDFTLKISRVEAEDLGVYYC*FQGHSVPWT*FGG GTKLEIK | 112 | LCDR1 RSSQSVVNSNG NTYLE LCDR2 KVSNRFS LCDR3 FQGSHVPWT | 106 107 108 | LCDR1 RSSQSVVNSNGN TYLE LCDR2 KVSNRFS LCDR3 FQGSHVPWT | 106 107 108 |
| 3833 | VH | QVQLQQSGAELVRPGTSVKMSCKAAGYTF*NYWIG*WVKQRPGHGLEWIG*DIYPGGIGGGYTKYNEKFKG*K ATLTADTSSSTAYMQLGSLTSEDSAIYFCSR*SETG RAMDY*WGQGTSVTVSS | 121 | HCDR1 GYTFTNY HCDR2 YPGGIGGGY HCDR3 SETGRAMDY | 113 114 115 | HCDR1 NYWIG HCDR2 DIYPGGIGG- GYT KYNEKFKG SETGRAMDY | 119 120 115 |
| | VL | DIQMTQSPSSLSASLGGKVTITC*KASQDINKYIA*W YQHKPGKGPRLLIH*YTSTLKP*GIPSRFSGSGSRD YSFSISDLEPEDIATYYC*LQYDNLNT*FGGGTKLEI K | 122 | LCDR1 KASQDINKYIA LCDR2 YTSTLKP LCDR3 LQYDNLNT | 116 117 118 | LCDR1 KASQDINKYIA LCDR2 YTSTLKP LCDR3 LQYDNLNT | 116 117 118 |
| 3631 | VH | EIQLQQSGPELVKPGASVKVSCKAS*GYSFT*DYNIY*WVKQSHGKSLEWIG*YIDPSNGGPGYNQKFRG*KATL TVDKSSSTAFLHLNSLTSEDSAVYYCAR*RDNYGSG TMDY***WGQGTSVTVSS | 131 | HCDR1 GYSFTDY HCDR2 DPSNGG HCDR3 RDNYGSGTMDY | 123 124 125 | HCDR1 DYNIY HCDR2 YIDPSNGGPGY NQKFRG RDNYGSGTMDY | 129 130 125 |

TABLE 1-continued

The amino acid sequences of the heavy chain variable region (VH) and light chain variable region (VL) of the exemplary anti-APRIL antibodies are provided as follows. CDRs, defined according to the Kabat system, are underlined and bold, while CDRs defined according to the Chothia system are italicized.

| Antibody | Chain | Amino Acid Sequence | SEQ ID NO | Chothia CDR | SEQ ID NO | Kabat CDR | SEQ ID NO |
|---|---|---|---|---|---|---|---|
| | VL | DIVMTQSQKFMSTSVGDRVSITC_KASQNVGTDVS_W YQQKPGKSPKPLIY_WASNRFT_GVPDRFIGSGSGTD FTLTISNVQSEDLADYFC_EQYSIYPLT_FGAGTKLE LK | 132 | LCDR1 KASQNVGTDVS LCDR2 WASNRFT LCDR3 EQYSIYPLT | 126 127 128 | LCDR1 KASQNVGTDVS LCDR2 WASNRFT LCDR3 EQYSIYPLT | 126 127 128 |
| 3732 | VH | EIQLQQSGPELVKPGASVKVSCKASGYSFT_DDNMY_ WVKQSHGKSLEWIG_YIDPLNGGTGYNQKFKG_KATL TVDKSSTAFLHLMSLTSEDSAVYYCAR_RDNYATG TMDY_WGQGTSVTVSS | 140 | HCDR1 GYSFTDD HCDR2 DPLNGG HCDR3 RDNYATGTMDY | 133 134 135 | HCDR1 DDNMY HCDR2 YIDPLNGGTGY HCDR3 NQKFKG RDNYATGTMDY | 138 139 135 |
| | VL | DIVMTQSQKFMSTSVGDRVSITC_KASKNVGTDVS_W YQQKPGKSPKPLIY_WASNRFT_GVPDRFTGSGSGTD FTLTINNVQSEDLADYFC_EQYSSYPLT_FGAGTKLE LK | 141 | LCDR1 KASKNVGTDVS LCDR2 WASNRFT LCDR3 EQYSSYPLT | 136 127 137 | LCDR1 KASKNVGTDVS LCDR2 WASNRFT LCDR3 EQYSSYPLT | 136 127 137 |
| 4338 | VH | EVQLQQSGPELVKPGASVKISCKASGYTFT_DYNMD_ WVKQSHGKSLEWIG_NIYPINGYTGYNQRFKN_KATL TVDKSSTAYMELHSLTSEDSAVYYCAR_DSNYVGW YFDV_WGAGTTVTVSS | 151 | HCDR1 GYTFTDY HCDR2 YPINGY HCDR3 DSNYVGWYFDV | 11 142 143 | HCDR1 DYNMD HCDR2 NIYPINGYTGY HCDR3 NQRFKN DSNYVGWYFDV | 149 150 143 |
| | VL | DVVMTQTPLSLPVSLGDQASISC_RSSQSLVHSNGN TYLH_WYLQKPGQSPKLLIY_KVSNRFS_GVPDRFSGS GSGTDFTFKISRVEAEDLGVYFC_SQSTHVPRT_FGG GTKLEIK | 152 | LCDR1 RSSQSLVHSNG LCDR2 NTYLH LCDR3 KVSNRFS SQSTHVPRT | 144 107 145 | LCDR1 RSSQSLVHSNG LCDR2 NTYLH LCDR3 KVSNRFS SQSTHVPRT | 144 107 145 |
| | VL | DIVLTQSPASLTVSLGQRATFSC_RASKSVSTSGYS YMH_WYQQKPGQPPKLLIY_FTSDLEP_GVPARFTSGS SGTDFTLNIHPVEEEDAATYYC_QHSRELPYP_FGGG TKLEIK | 153 | LCDR1 RASKSVSTSGY LCDR2 SYMH LCDR3 FTSDLEP QHSRELPYP | 146 147 148 | LCDR1 RASKSVSTSGY LCDR2 SYMH LCDR3 FTSDLEP QHSRELPYP | 146 147 148 |
| 4540 | VH | QVQLQQSGPELVKPGASVKISCKASGYTFA_DYYIN_ WVKQRPGQGLEWIG_WIFPGSGSTYYNEKFKG_KATL TVDKSSTAYMLLSSLTSEDSAVYFCAR_GDSGRAM DY_WGQGTSVTVSS | 161 | HCDR1 GYTFADY HCDR2 FPGSGS HCDR3 GDSGRAMDY | 154 155 156 | HCDR1 DYYIN HCDR2 WIFPGSGSTYY HCDR3 NEKFKG GDSGRAMDY | 159 160 156 |
| | VL | DIQMTQSPSSLSASLGGKVTITC_KASQDINKYIA_W YQHKPGKGPRLLIH_TYSTLQS_GIPSRFSGSGSGRD YSFSISNLEPEDNATYYC_LQYDNLLT_FGAGTKLEL K | 162 | LCDR1 KASQDINKYIA LCDR2 YTSTLQS LCDR3 LQYDNLLT | 116 157 158 | LCDR1 KASQDINKYIA LCDR2 YTSTLQS LCDR3 LQYDNLLT | 116 157 158 |
| 4540-063 | VH | QVQLVQSGAELKKPGASVKVSCKASGYTFA_DYYMN_ WVRQAPGQGLEWMG_WIFPGSGSTYYNQKFQG_RVTM TVDKSSTAYMELSRLRSDDTAVYYCAR_GDSGRAM DY_WGQGTLVTVSS | 258 | HCDR1 GYTFADY HCDR2 FPGSGS HCDR3 GDSGRAMDY | 154 155 156 | HCDR1 DYYMN HCDR2 WIFPGSGSTYY HCDR3 NQKFQG GDSGRAMDY | 276 277 156 |
| | VL | DIQMTQSPSSLSASVGDRVTITC_QASQDINKYLA_W YQHKPGKAPKLLIH_YTSTLET_GVPSRFSGSGSGTD FTFTISSLQPEDIATYYC_LQYDNLLT_FGGGTKVEI K | 261 | LCDR1 QASQDINKYLA LCDR2 YTSTLET LCDR3 LQYDNLLT | 274 275 158 | LCDR1 QASQDINKYLA LCDR2 YTSTLET LCDR3 LQYDNLLT | 274 275 158 |
| 4540-033 | VH | QVQLVQSGAEVKKPGASVKVSCKASGYTFA_DYYIN_ WVRQAPGQGLEWMG_WIFPGSGSTYYAQKLQG_RVTM TTDTSTSTAYMELRSLRSDDTAVYYCAR_GDSGRAM DY_WGQGTLVTVSS | 256 | HCDR1 GYTFADY HCDR2 FPGSGS HCDR3 GDSGRAMDY | 154 155 156 | HCDR1 DYYIN HCDR2 WIFPGSGSTYY HCDR3 AQKLQG GDSGRAMDY | 159 278 156 |
| | VL | DIQMTQSPSSLSASVGDRVTITC_QASQDINKYLA_W YQHKPGKAPKLLIH_YTSTLET_GVPSRFSGSGSGTD FTFTISSLQPEDIATYYC_LQYDNLLT_FGGGTKVEI K | 261 | LCDR1 QASQDINKYLA LCDR2 YTSTLET LCDR3 LQYDNLLT | 274 275 158 | LCDR1 QASQDINKYLA LCDR2 YTSTLET LCDR3 LQYDNLLT | 274 275 158 |
| 4237 | VH | QAHLKESGPGLVAPSQSLSITCTVSGFSLT_DYDVH_ WVRQSPGKGLEWLG_VIWNDGSTDYNTAFIS_RLTIS KDNSKSQVFFKMNSLQADDTAIYYCAR_NWYGGYWF AY_WGQGTLVTVSA | 171 | HCDR1 GFSLTDY HCDR2 WNDGS HCDR3 NWYGGYWFAY | 163 164 165 | HCDR1 DYDVH HCDR2 VIWNDGSTDYN TAFIS NWYGGYWFAY | 169 170 165 |
| | VL | DIQMTQSPASLSASAGETVTITC_RSSENIYSYLA_W YQQKQGKSPQLLVY_NANALAE_GVPSRFSGSGSVTQ FSLKINSLQPEDFGSYYC_QHHYGTPFT_FGSGTKLE IK | 172 | LCDR1 RSSENIYSYLA LCDR2 NANALAE LCDR3 HHYGTPFT | 166 167 168 | LCDR1 RSSENIYSYLA LCDR2 NANALAE LCDR3 QHHYGTPFT | 166 167 168 |

TABLE 1-continued

The amino acid sequences of the heavy chain variable region (VH) and light chain variable region (VL) of the exemplary anti-APRIL antibodies are provided as follows. CDRs, defined according to the Kabat system, are underlined and bold, while CDRs defined according to the Chothia system are italicized.

| Antibody | Chain | Amino Acid Sequence | Chothia CDR | SEQ ID NO | Kabat CDR | SEQ ID NO | | SEQ ID NO |
|---|---|---|---|---|---|---|---|---|
| 4439 | VH | EIQLQQSGAELVKPGASVKISCKAS*DYSFT*GYNMN WVMQSHGKSLEWIG***NIHPYYGGTS*FNQKFMGKATL TADKSSSTAYMQLNSLTSEDSAVYYCARERSNFHA LDY**WGQGTSVTVSS | HCDR1 DYSFTGY HCDR2 HPYYGG HCDR3 ERSNFHALDY | 271 | HCDR1 HCDR2 HCDR3 | GYNMN NIHPYYGGTSF NQKFMG ERSNFHALDY | 266 267 268 | 269 270 268 |
| | VL | DIVLTQSPASLTVSLGQRATFSCRASKSVSTSGYS YMHWYQQKPGQPPKLLIY*FTSDLEP*GVPARFTGSG SGTDFTLNIHPVEEEDAATYYCQHSRELPYPFGGG TKLEIK | LCDR1 RASKSVSTSGY LCDR2 SYMH LCDR3 FTSDLEP QHSRELPYP | 272 | LCDR1 LCDR2 LCDR3 | RASKSVSTSGY SYMH FTSDLEP QHSRELPYP | 146 147 148 | 146 147 148 |

TABLE 2

Nucleotide sequences of heavy chain variable regions (VHs) and light chain variable regions (VLs) of exemplary antibody molecules

| Antibody | Chain | Nucleotide Sequence | SEQ ID NO |
|---|---|---|---|
| 2218 | VH | GATGTACAGCTTCAGGAGTCAGGACCTGGCCTCGTGAAACCTTCTCAGTCTCTGTCTCTCACCTGCTCTGTCACTGGC TACTCCATCACCAGTGGTTATTACTGGAACTGGATCCGGCAGTTTCCAGGAAACAAACTGGAATGGATGGGCTACATA AGCTACGATGGTTACAATAACTACAACCCATCTCTCAAAAATCGAATCTCCATCACTCGTGACACATCTAAGAACCAG TTTTTCCTGAAGTTGAATTCTGTGACTACTGAGGACACAGCCACATATTACTGTGCAAACTACTATGATTACGAAGAC TGGTACTTCGGTGTCTGGGGCACAGGGACCACGGTCACCGTCTCCTCA | 71 |
| | VL | GACATTGTGCTGACCCAATCTCCAGCTTCTTTGGCTATGTCTCTAGGGAAGAGGGCCACCATCTCCTGCAGAGCCAGC GAAAGTGTCAGTATTATTGGTACTAATTCAATACACTGGTACCAACAGAAACCAGGACAGCCACCCAAACTCCTCATC TATCATGCATCCAACCTAGAAACTGGAGTCCCTGCCAGGTTCAGTGGCAGTGGGTCTAGAACAGACTTCACCCTCACC ATTGATCCTGTGGAGGAAGATGATGTTGCAATCTATTACTGTCTGCAAAGTAGGAAGATTCCGTACACGTTCGGAGGG GGGACCAAGCTGGAAATAAAA | 72 |
| 2419 | VH | CAGGTCCAGCTGCAGCAGTCTGGAGCTGAGCTGGTGAAACCCGGGGCATCAGTGAGGCTGTCCTGCGAGGCTTCTGGC TACACCTTCACGGACTATACTATACACTGGGTAAAGCAGAGGTCTGGACAGGGTCTTGAGTGGATTGGATGGATTTAC CCTCTAAGAGGTAGTATAAACTACAATGAGAAATTCAAGGACAAGGCCACATTGACTGCGGACAAATCCTCCAGCACA GTCTATTTGGAGCTTGGTAGATTGACATCTAAGGACTCTGCGGTCTATTTCTGTGCAAGACACGGAGCCTACTATAGT AACGCCTTTGACTACTGGGGCCAAGGCACCACTCTCACAGTCTCCTCA | 73 |
| | VL | AACATTGTAATGACCCAATCTCCAGCTTCATTGGCTGTGTCTCTAGGTCAGAGGGCCACCATCTCCTGCAGAGCCAGC GAGAGTGTTGATAATGATGGCATTAGATTTATGCACTGGTACCAGCAGAAACCAGGACAGCCACCCAAACTCCTCATC TATCGTGCATCCAACCTAGAATCTGGGATCCCTGCCAGGTTCAGTGGCAGTGGGTCTAGGACAGACTTCACCCTCACT ATTAATCCTGTGGAGACTGATGATGTTGCAACCTATTACTGTCAGCAAAGTAATAAGGATCCGTACACGTTCGGAGGG GGGACCAAGCTGGAGCTGAAA | 74 |
| 2419-1305 | VH | CAAGTTCAGTTGGTGCAAAGCGGGGCAGAAGTGAAGAAACCTGGTGCTTCTGTGAAAGTTTCCTGCAAGGCCAGCGGC TACACCTTTACTGATTACACAATACACTGGGTACGGCAGGCAACTGGGCAAGGATTGGAATGGATGGGGTGGATATAC CCATTGCGAGGGTCTATAAACTACGCACAGAAATTTCAAGGTCGAGTAACAATGACAGCCAACAAATCAATAAGCACC GTTTATATGGAACTCTCATCTCTCAGGAGTGAGGATACCGCCGTGTATTTCTGCGCACGACACGGTGCATATTACTCA AACGCCTTTGACTATTGGGGCCAGGGCACCCTTGTGACTGTTAGTAGC | 304 |
| | VL | GAGATAGTAATGACTCAGTCTCCCGCTACACTTAGTGTAAGCCCAGGGGAGCGAGCAACCCTCAGTTGCAGAGCATCT GAGAGTGTTGATAATGATGGAATACGTTTTCTCCATTGGTATCAACAAAAACCAGGGCAGGCCCCCAGATTGCTGATC TACCGTGCTTCCAATCGCGAGACTGGCATTCCTGCACGTTTCAGCGGCAGCGGCTCCGGAACCGAGTTTACACTTACT ATTAGCCACTCCAGTCTGAAGACTTCGCTGTGTATTACTGTCAGCAATCCAACAAGGACCCATACACTTTCGGAGGC GGCACTAAGGTTGAGATCAAA | 305 |
| 2419-1306 | VH | CAAGTTCAGTTGGTGCAAAGCGGGGCAGAAGTGAAGAAACCTGGTGCTTCTGTGAAAGTTTCCTGCAAGGCCAGCGGC TACACCTTTACTGATTACACAATACACTGGGTACGGCAGGCAACTGGGCAAGGATTGGAATGGATGGGGTGGATATAC CCATTGCGAGGGTCTATAAACTACGCACAGAAATTTCAAGGTCGAGTAACAATGACAGCCAACAAATCAATAAGCACC GTTTATATGGAACTCTCATCTCTCAGGAGTGAGGATACCGCCGTGTATTTCTGCGCACGACACGGTGCATATTACTCA AACGCCTTTGACTATTGGGGCCAGGGCACCCTTGTGACTGTTAGTAGC | 304 |
| | VL | GAGATAGTTATGACTCAGTCTCCCGCCACACTTTCAGTAAGTCCCGGTGAACGCGCCACCCTGTCCTGCCGTGCTTCC GAATCAGTGGATAATGACGGCATTAGGTTTTTGCACTGGTACCAACAAAAGCCCGGACAGGCCCCCCGCCTGCTGATA TATCGTGCATCAACACGAGCAACAGGGATCCCCGCTCGATTTAGTGGATCCGGAAGCAGGACCGAATTTACACTTACC ATTTCCTCACTTCAGTCAGAAGATTTCGCCGTTTACTACTGTCAGCAGTCAAATAAGGATCCTTACACATTTGGGGGC GGTACAAAAGTCGAGATCAAA | 306 |

TABLE 2-continued

Nucleotide sequences of heavy chain variable regions (VHs) and
light chain variable regions (VLs) of exemplary antibody molecules

| Antibody | Chain | Nucleotide Sequence | SEQ ID NO |
|---|---|---|---|
| 2419-1310 | VH | CAAGTTCAGTTGGTGCAAAGCGGGGCAGAAGTGAAGAAACCTGGTGCTTCTGTGAAAGTTTCCTGCAAGGCCAGCGGC<br>TACACCTTTACTGATTACACAATACACTGGGTACGGCAGGCAACTGGGCAAGGATTGGAATGGATGGGGTGGATATAC<br>CCATTGCGAGGGTCTATAAACTACGCACAGAAATTTCAAGGTCGAGTAACAATGACAGCCAACAAATCAATAAGCACC<br>GTTTATATGGAACTCTCATCTCTCAGGAGTGAGGATACCGCCGTGTATTTCTGCGCACGACACGGTGCATATTACTCA<br>AACGCTTTCGACTATTGGGGCCAGGGCACCCTTGTGACTGTTAGTAGC | 304 |
| | VL | GACATTGTAATGACCCAGTCTCCCGATAGCCTCGCTGTCTCACTCGGAGAACGCGCAACCATCAACTGCAAGTCCTCC<br>CAAAGCGTTGACAATGACGGCATTAGGTTTTTGCACTGGTACCAGCAGAAACCCGGTCAACCTCCTAAGTTGCTCATT<br>TACCGAGCATCTACCCGCGAGTCAGGAGTACCTGATCGCTTTTCCGGTAGCGGTAGTGGAACAGATTTTACTCTGACC<br>ATTAGTTCACTCCAGGCAGAAGATGTGGCTGTCTACTACTGCCAACAGTCAAATAAAGACCCTTATACCTTCGGTGGG<br>GGTACCAAAGTAGAGATCAAA | 318 |
| 2419-0806 | VH | GAGGTCCAGTTGGTCCAGTCAGGAGCCGAAGTCAAGAAGCCTGGGGAAAGCCTGAAAATAAGTTGCAAAGCTAGTGGA<br>TATACATTTACAGATTATACCATTCATTGGGTCCGGCAAATGCCAGGAAAAGGCTTGGAGTGGATGGGGTGGATTTAT<br>CCCCTCCGAGGCTCAATAAATTATAGTCCTAGTTTTCAGGGGCAGGTAACTATTAGCGCTGATAAAGTATTTCTACA<br>GTTTATTTGCAGTGGAGTTCATTGAAGGCTAGTGACACCGCTATGTATTTCTGCGCTAGACATGGTGCATATTATTCA<br>AATGCCTTCGACTATTGGGGCCAGGGCACCCTCGTCACTGTGAGTTCC | 307 |
| | VL | GAGATAGTTATGACTCAGTCTCCCGCCACACTTTCAGTAAGTCCCGGTGAACGCGCCACCCTGTCCTGCCGTGCTTCC<br>GAATCAGTGGATAATGACGGCATTAGGTTTTTGCACTGGTACCAACAAAAGCCCGGACAGGCCCCCCGCCTGCTGATA<br>TATCGTGCATCAACACGAGCAACAGGGATCCCCGCTCGATTTAGTGGATCCGGAAGCAGGACCGAATTTACACTTACC<br>ATTTCCTCACTTCAGTCAGAAGATTTCGCCGTTTACTACTGTCAGCAGTCAAATAAGGATCCTTACACATTTGGGGGC<br>GGTACAAAAGTCGAGATCAAA | 306 |
| 2419-0205 | VH | CAGGTGCAACTTGTTCAGTCAGGGGCTGAAGTAAAGAAGCCAGGCTCATCAGTCAAGGTATCATGCAAAGCATCTGGC<br>TATACATTTACAGATTACACCATTCACTGGGTGAGGCAAGCTCCCGGTCAAGGTCTCGAGTGGATGGGGTGGATATAC<br>CCTCTCAGAGGCTCTATAAATTACGCTCAGAAATTTCAAGGGAGAGTTACAATTACTGCTGATAAAGTACCAGCACT<br>GCTTATATGGAGCTTTCCTCACTTCGTTCAGAGGACACCGCCGTTTACTTTTGTGCCCGGCATGGTGCCTATTATTCA<br>AATGCCTTCGATTATTGGGGCAGGGAACTTGGTCACAGTTTCATCT | 308 |
| | VL | GAGATAGTAATGACTCAGTCTCCCGCTACACTTAGTGTAAGCCCAGGGGAGCGAGCAACCCTCAGTTGCAGAGCATCT<br>GAGAGTGTTGATAATGATGGAATACGTTTTCTCCATTGGTATCAACAAAAACCAGGGCAGGCCCCCAGATTGCTGATC<br>TACCGTGCTTCCAATCGCGAGACTGGCATTCCTGCACGTTTCAGCGGCAGCGGCTCCGGAACCGAGTTTACACTTACT<br>ATTAGCTCACTCCAGTCTGAAGACTTCGCTGTGTATTACTGTCAGCAATCCAACAAGGACCCATACACTTTCGGAGGC<br>GGCACTAAGGTTGAGATCAAA | 305 |
| 2419-0406 | VH | CAAGTTCAACTTGTCCAAAGTGGGGCTGAAGTTAAAAAACCTGGATCATCAGTCAAGGTTTCATGCAAAGCCAGCGGT<br>TACACATTTACAGACTATACAATACATTGGGTTCGACAGGCTCCCGGCAAGGGCTCGAGTGGATGGGGATGGTTTAT<br>CCCCTCAGGGGCTCAATTAACTATGCTGAGAAATTTAAGGGTCGTGTAACACTCACCGCCGATAAATCCACCTCAACC<br>GTATATATGGAGCTTTCTTCTTCGCTCTGAAGATACCGCCGTCTATTTCTGCGCACGACACGGGGCATACTATTCT<br>AATGCCTTTGACTACTGGGGACAAGGGACACTTGTGACCGTTAGTAGC | 309 |
| | VL | GAGATAGTTATGACTCAGTCTCCCGCCACACTTTCAGTAAGTCCCGGTGAACGCGCCACCCTGTCCTGCCGTGCTTCC<br>GAATCAGTGGATAATGACGGCATTAGGTTTTTGCACTGGTACCAACAAAAGCCCGGACAGGCCCCCCGCCTGCTGATA<br>TATCGTGCATCAACACGAGCAACAGGGATCCCCGCTCGATTTAGTGGATCCGGAAGCAGGACCGAATTTACACTTACC<br>ATTTCCTCACTTCAGTCAGAAGATTTCGCCGTTTACTACTGTCAGCAGTCAAATAAGGATCCTTACACATTTGGGGGC<br>GGTACAAAAGTCGAGATCAAA | 306 |
| 2419-0605 | VH | CAGGTGCAGTTGGTCCAGAGCGGGGCAGAGGTTAAGAAGCCTGGGGCCTCAGTAAAGGTATCCTGCAAGGCTTCTGGG<br>TACACCTTCACAGATTACACTATTCATTGGGTGCGCCAAGCACCTGGTCAAGGCCTTGAATGGATGGGGATGGATTAC<br>CCCTTGCGAGGGAGTATTAATTATGCACAGAAGTTCCAGGGAAGGGTTACTCTTACCGCCGACAAGTCCACATCAACC<br>GTTTACATGGAGCTTTCCTCTCTCAGGTCCGAAGACACTGCTGTATATTTCTGCGCTCGGCATGGGGCTTATTACAGC<br>AACGCCTTCGATTACTGGGGTCAGGGTACATTGGTCACAGTGTCCAGT | 319 |
| | VL | GAGATAGTAATGACTCAGTCTCCCGCTACACTTAGTGTAAGCCCAGGGGAGCGAGCAACCCTCAGTTGCAGAGCATCT<br>GAGAGTGTTGATAATGATGGAATACGTTTTCTCCATTGGTATCAACAAAAACCAGGGCAGGCCCCCAGATTGCTGATC<br>TACCGTGCTTCCAATCGCGAGACTGGCATTCCTGCACGTTTCAGCGGCAGCGGCTCCGGAACCGAGTTTACACTTACT<br>ATTAGCTCACTCCAGTCTGAAGACTTCGCTGTGTATTACTGTCAGCAATCCAACAAGGACCCATACACTTTCGGAGGC<br>GGCACTAAGGTTGAGATCAAA | 305 |
| 2419-0805 | VH | GAGGTCCAGTTGGTCCAGTCAGGAGCCGAAGTCAAGAAGCCTGGGGAAAGCCTGAAAATAAGTTGCAAAGCTAGTGGA<br>TATACATTTACAGATTATACCATTCATTGGGTCCGGCAAATGCCAGGAAAAGGCTTGGAGTGGATGGGGTGGATTTAT<br>CCCCTCCGAGGCTCAATAAATTATAGTCCTAGTTTTCAGGGGCAGGTAACTATTAGCGCTGATAAAGTATTTCTACA<br>GTTTATTTGCAGTGGAGTTCATTGAAGGCTAGTGACACCGCTATGTATTTCTGCGCTAGACATGGTGCATATTATTCA<br>AATGCCTTCGACTATTGGGGCCAGGGCACCCTCGTCACTGTGAGTTCC | 307 |
| | VL | GAGATAGTAATGACTCAGTCTCCCGCTACACTTAGTGTAAGCCCAGGGGAGCGAGCAACCCTCAGTTGCAGAGCATCT<br>GAGAGTGTTGATAATGATGGAATACGTTTTCTCCATTGGTATCAACAAAAACCAGGGCAGGCCCCCAGATTGCTGATC<br>TACCGTGCTTCCAATCGCGAGACTGGCATTCCTGCACGTTTCAGCGGCAGCGGCTCCGGAACCGAGTTTACACTTACT<br>ATTAGCTCACTCCAGTCTGAAGACTTCGCTGTGTATTACTGTCAGCAATCCAACAAGGACCCATACACTTTCGGAGGC<br>GGCACTAAGGTTGAGATCAAA | 305 |

TABLE 2-continued

Nucleotide sequences of heavy chain variable regions (VHs) and
light chain variable regions (VLs) of exemplary antibody molecules

| Antibody | Chain | Nucleotide Sequence | SEQ ID NO |
|---|---|---|---|
| 2419-0105 | VH | CAAGTGCAGTTGGTCCAGAGTGGAGCAGAGGTGAAGAAGCCTGGTGCTTCCGTCAAGGTGAGTTGCAAGGCATCTGGT TATACTTTCACTGACTACACAATTCATTGGGTCAGGCAGGCCCCTGGACAGGGACTGGAATGGATGGGATGGATCTAT CCACTTAGAGGATCAATCAACTATGCTCAAAAGTTCCAGGGTCGTGTAACAATGACCGCAGACAAAAGTATCTCAACT GTATACATGGAATTGTCCCGATTGAGGAGCGACGACACAGCCGTATATTATTGTGCCAGGCACGGAGCCTACTACAGT AATGCCTTCGACTACTGGGGCAGGGCACCCTTGTTACCGTGTCCAGC | 310 |
|  | VL | GAGATAGTAATGACTCAGTCTCCCGCTACACTTAGTGTAAGCCCAGGGGAGCGAGCAACCCTCAGTTGCAGAGCATCT GAGAGTGTTGATAATGATGGAATACGTTTTCTCCATTGGTATCAACAAAAACCAGGGCAGGCCCCCAGATTGCTGATC TACCGTGCTTCCAATCGCGAGACTGGCATTCCTGCACGTTTCAGCGGCAGCGGCTCCGGAACCGAGTTTACACTTACT ATTAGCTCACTCCAGTCTGAAGCTTCGCTGTGTATTACTGTCAGCAATCCAACAAGGACCCATACACTTTCGGAGGC GGCACTAAGGTTGAGATCAAA | 305 |
| 2419-1204 | VH | CAAGTGCAGCTCGTTCAGTCTGGCGCAGAAGTGAAGAAGCCAGGAGCTTCCGTTAAAGTGTCCTGTAAAGCCTCTGGA TATACATTCACAGATTATACAATTCACTGGGTGAGACAAGCAACCGGTCAAGGTCTCGAATGGATGGGCTGGATATAC CCCCTCCGAGGTTCCATCAACTACGCTCAAAAATTCCAAGGACGAGTCACTATGACAGCAAACAAGAGTTCCTCCACT GTATATATGGAACTCTCTAGTTTGCGCTCTGAAGACACCGCCGTGTACTTCTGTGCCAGGCACGGCGCATACTATTCT AATGCATTTGACTATTGGGGCAGGGCACATTGGTAACAGTTAGTTCC | 311 |
|  | VL | GAAATTGTAATGACCCAGAGCCCCGCCACCCTTAGTGTGTCCCAGGCGAGAGGGCCACTCTTTCTTGCCGCGCAAGC GAATCCGTAGACAACGATGGTATAAGATTTTTGCATTGGTATCAGCAAAAGCCAGGCCAGGCACCCCGGCTTCTCATC TACAGAGCTAGCACCCTCGAAACTGGAATCCCCGCTCGTTTTTCAGGATCTGGTAGCGGAACAGAATTTACTTTGACA ATTAGTAGTTTGCAGTCAGAGGACTTTGCTGTCTATTATTGCCAGCAGTCTAATAAAGATCCATACACCTTCGGCGGA GGGACCAAAGTAGAGATTAAA | 312 |
| 2419-1210 | VH | CAAGTGCAGCTCGTTCAGTCTGGCGCAGAAGTGAAGAAGCCAGGAGCTTCCGTTAAAGTGTCCTGTAAAGCCTCTGGA TATACATTCACAGATTATACAATTCACTGGGTGAGACAAGCAACCGGTCAAGGTCTCGAATGGATGGGCTGGATATAC CCCCTCCGAGGTTCCATCAACTACGCTCAAAAATTCCAAGGACGAGTCACTATGACAGCAAACAAGAGTTCCTCCACT GTATATATGGAACTCTCTAGTTTGCGCTCTGAAGACACCGCCGTGTACTTCTGTGCCAGGCACGGCGCATACTATTCT AATGCATTTGACTATTGGGGCAGGGCACATTGGTAACAGTTAGTTCC | 311 |
|  | VL | GACATTGTAATGACCCAGTCTCCCGATAGCCTCGCTGTCTCACTCGGAGAACGCGCAACCATCAACTGCAAGTCCTCC CAAAGCGTTGACAATGACGGCATTAGGTTTTTGCACTGGTACCAGCAGAAACCCGGTCAACCTCCTAAGTTGCTCATT TACCGAGCATCTACCCGCGAGTCAGGAGTACCTGATCGCTTTTCCGGTAGCGGTAGTGGAACAGATTTACTCTGACC ATTAGTTCACTCCAGGCAGAAGATGTGGCTGTCTACTACTGCCAACAGTCAAATAAAGACCCTTATACCTTCGGTGGG GGTACCAAAGTAGAGATCAAA | 318 |
| 2419-1406 | VH | CAAGTTCAGTTGGTGCAAAGCGGGGCAGAAGTGAAGAAACCTGGTGCTTCTGTGAAAGTTTCCTGCAAGGCCAGCGGC TACACCTTTACTGATTACACAATACACTGGGTACGGCAGGCAACTGGGCAAGGATTGGAATGGATGGGGTGGATATAC CCATTGCGAGGGTCTATAAACTACGCACAGAAATTTCAAGGTCGAGTAACAATGACAGCCGACAAATCAATAAGCACC GTTTATATGGAACTCTCCATCTCTCAGGAGTGAGGATACCGCCGTGTATTTCTGCGCACGACACGGTGCATATTACTCA AACGCTTTCGACTATTGGGGCCAGGGCACCCTTGTGACTGTTAGTAGC | 313 |
|  | VL | GAGATAGTTATGACTCAGTCTCCCGCCACACTTTCAGTAAGTCCCGGTGAACGCGCCACCCTGTCCTGCCGTGCTTCC GAATCAGTGGATAATGACGGCATTAGGTTTTTGCACTGGTACCAACAAAAGCCGGACAGGCCCCCGCCTGCTGATA TATCGTGCATCAACACGAGCAACAGGGATCCCCGCTCGATTTAGTGGATCCGGAAGCAGGACCGAATTTACACTTACC ATTTCCTCACTTCAGTCAGAAGATTTCGCCGTTTACTACTGTCAGCAGTCAAATAAGGATCCTTACACATTTGGGGGC GGTACAAAAGTCGAGATCAAA | 306 |
| 2419-1205 | VH | CAAGTGCAGCTCGTTCAGTCTGGCGCAGAAGTGAAGAAGCCAGGAGCTTCCGTTAAAGTGTCCTGTAAAGCCTCTGGA TATACATTCACAGATTATACAATTCACTGGGTGAGACAAGCAACCGGTCAAGGTCTCGAATGGATGGGCTGGATATAC CCCCTCCGAGGTTCCATCAACTACGCTCAAAAATTCCAAGGACGAGTCACTATGACAGCAAACAAGAGTTCCTCCACT GTATATATGGAACTCTCTAGTTTGCGCTCTGAAGACACCGCCGTGTACTTCTGTGCCAGGCACGGCGCATACTATTCT AATGCATTTGACTATTGGGGCAGGGCACATTGGTAACAGTTAGTTCC | 311 |
|  | VL | GAGATAGTAATGACTCAGTCTCCCGCTACACTTAGTGTAAGCCCAGGGGAGCGAGCAACCCTCAGTTGCAGAGCATCT GAGAGTGTTGATAATGATGGAATACGTTTTCTCCATTGGTATCAACAAAAACCAGGGCAGGCCCCCAGATTGCTGATC TACCGTGCTTCCAATCGCGAGACTGGCATTCCTGCACGTTTCAGCGGCAGCGGCTCCGGAACCGAGTTTACACTTACT ATTAGCTCACTCCAGTCTGAAGCTTCGCTGTGTATTACTGTCAGCAATCCAACAAGGACCCATACACTTTCGGAGGC GGCACTAAGGTTGAGATCAAA | 305 |
| 2419-0206 | VH | CAGGTGCAACTTGTTCAGTCAGGGGCTGAAGTAAAGAAGCCAGGCTCATCAGTCAAGGTATCATGCAAAGCATCTGGC TATACATTTACAGATTACACCATTCACTGGGTGAGGCAAGCTCCCGGTCAAGGTCTCGAGTGGATGGGGTGGATATAC CCTCTCAGAGGCTCTATAAATTACGCTCAGAATTTCAAGGGAGAGTTACAATTACTGCTGATAAAAGTACCAGCACT GCTTATATGGAGCTTTCCTCACTTCGTTCAGAGGACACCGCCGTTTACTTTTGTGCCCGGCATGGTGCCTATTATTCA AATGCCTTCGATTATTGGGGCAGGGAACTTGGTCACAGTTTCATCT | 308 |
|  | VL | GAGATAGTTATGACTCAGTCTCCCGCCACACTTTCAGTAAGTCCCGGTGAACGCGCCACCCTGTCCTGCCGTGCTTCC GAATCAGTGGATAATGACGGCATTAGGTTTTTGCACTGGTACCAACAAAAGCCCGGACAGGCCCCCGCCTGCTGATA TATCGTGCATCAACACGAGCAACAGGGATCCCCGCTCGATTTAGTGGATCCGGAAGCAGGACCGAATTTACACTTACC ATTTCCTCACTTCAGTCAGAAGATTTCGCCGTTTACTACTGTCAGCAGTCAAATAAGGATCCTTACACATTTGGGGGC GGTACAAAAGTCGAGATCAAA | 306 |

TABLE 2-continued

Nucleotide sequences of heavy chain variable regions (VHs) and
light chain variable regions (VLs) of exemplary antibody molecules

| Antibody | Chain | Nucleotide Sequence | SEQ ID NO |
|---|---|---|---|
| 2621 | VH | GAGGTCCAGCTTCAGCAGTCTGGAGCTGAGCTGGTGAGGCCTGGGTCCTCAGTGAAGATGTCCTGCAAGACTTCTGGA<br>TATACTTTCACAAGCTACGGTATAAACTGGGTGAAGCAGAGGCCTGGACAGGGCCTGGAATGGATTGGATATATTTAT<br>ATTGGAAATGGTTATGCTGAGTACAATGAGAGGTTCAAGGGCAAGGCCACACTGACTTCAGACACATCCTCCAGCACA<br>GCCTACATGCAGCTCAGCAGCCTGACATCTGAGGACTCTGCAATCTATTTCTGTGCACTATACTATCCCTGGTTTACT<br>TACTGGGGCCAGGGGACTCTGGTCACTGTCTCTGCA | 75 |
| | VL | GACATCCAGATGACTCAGTCTCCAGCCTCCCTTTCTGCATCTGTGGGAGATTCTGTCACCATCACATGTCGAGCAAGT<br>GAGAATATTTACAGTTATTTAGCATGGTATCAGCAGAAACAGGGAAAATCTCCTCAGCTCCTGGTCTATAATGCAAAA<br>ACCTTAGCTGAAGGTGTGCCATCAAGGTTCAGTGGCAGTGGATCAGGCACACAGTTTTCTCTGAAGATCAACAGCCTG<br>CAGCCTGAAGATTTTGGGAATTATTACTGTCAACATCATTATGATACTCCGTTCACGTTCGGAGGGGGGACCAAGCTG<br>GAAATAAAA | 76 |
| 2922 | VH | CAGGTTCAGCTGCACCAGTCTGGACCTGAGCTGGTGAAGCCTGGGGCTTCAGTGAAGTTGTCCTGCAAGACTTCTGGC<br>TACACCTTCACAAGCTACGATGTCTTCTGGGTGAAGCAGAGGCCTGGACAGGGACTTGAGTGGATTGGATGGATTTAT<br>CCTAGAGATAGTAGTACTAAATACAATGAGAAGTTCAAGGGCAAGGCCACATTGACTGTAGACACATCCTCCAGCACA<br>GCATACATGGAGCTCCACAGCCTGACATCTGAGGACTCTGCGGTCTATTTCTGTGCAAAAGAGGGGTATGATTATGAC<br>AAGAGGGGCTTTGACTACTGGGGCCAAGGCACCACTCTCACAGTCTCCTCA | 77 |
| | VL | GACATTGTGCTGACCCAATCTCCAGCTTCTTTGGCTGTGTCTCTAGGGCAGAGGGCCATCATCTCCTGCAAGGCCAGC<br>CAAAGTGTCAGTTTTGCTGGTACTAATTTAATGCACTGGTACCAACAGAGACCAGGGCAGCAACCCAAACTCCTCATC<br>TATCGTGCATCCAACCTAGAACCTGGGGTTCCTACCAGGTTTAGTGGCAGTGGGTCTAGGACAGACTTCACCCTCAAT<br>ATCCATCCTGTGGAGGAAGATGATGCTGCAACCTATTACTGTCAGCAAAGTAGGGAATATCCGTGGACGTTCGGTGGA<br>GGCACCAAGCTGGAAATCAAA | 78 |
| 3125 | VH | CAGGTTCAACTGCAGCAGTCTGGGGCTGAGCTGGTGAGGCCTGGGGCTTCAGTGACGCTGTCCTGCAAGGCTTCGGGC<br>TACACTTTTACTGACTATGAAATGCACTGGGTGAAGCAGACACCTGTGCATGGCCTGGAATGGATTGGAGCTATTGAT<br>CCTGAAACTGGTGGTACTGCCTACAATCAGAGGTTCAAGGGCAAGGCCATACTGACTACAGACAAATCCTCCATCACA<br>GCCTACATGGAGCTCCGCAGCCTGACATCTGAGGACTCTGCCGTCTATTACTGTACAAGATGGAATGATGGCGACTAC<br>TGGGGCCAAGGCACCACTCTCACAGTCTCCTCA | 79 |
| | VL | GATGTTGTGATGACCCAGACTCCACTGTCTTTGTCGGTTACCATTGGACAACCAGCCTCCATTTCTTGCAAGTCAAGT<br>CAGAGCCTCTTATACAGTAATGGAAAGACATATTTGAATTGGTTTCAACAGAGGCCTGGCCAGTCTCCAAAGCGCCTA<br>ATGTATCAGGTGTCCAAACTGGACCCTGGCATCCCTGACAGGTTCAGTGGCAGTGGATCAGAAACAGATTTTACACTT<br>AAAATCAGCAGAGTGGAGGCTGAAGATTTGGGACTTTATTACTGCTTGCAAGGTACATATTATCCGTACACGTTCGGA<br>GGGGGGACCAAGCTGGAAATAAAA | 80 |
| 3327 | VH | GAGGTCCAGCTGCAGCAGTCTGGACCTGAGCTGGTGAAGCCTGGGGCTTCAGTGAAGATGTCCTGCAAGGCTTCTGGT<br>TACTCCTTTACTGGCTACTTTATGAACTGGGTGAAGCAGAGCCATGGAAAGAGCCTTGAGTGGATTGGACGTATTAAT<br>CCTTACAATGGTGATACTTTCTACAACCAGAAGTTCAAGGGCAAGGCCACATTGACTGTAGACAAATCCTCTAGCACA<br>GCCCACATGGAGCTCCGGAGCCTGACATCTGAGGACTCTGCACTCTATTATTGTGCAAGCGAAGGTGATGGTTACTAC<br>TGGTACTTCGATGTCTGGGGCGCAGGGACCACGGTCACCGTCTCCTCA | 81 |
| | VL | GACATTGTGCTGACCCAATCTCCAGCTTCTTTGGCTGTGTCTCTAGGGCAGAGGGCCACCATCTCCTGCAGAGCCAGC<br>GAAAGTGTTGATAATTATGGCATTAGTTTTATGAACTGGTTCCAACAGAAACCAGGACAGCCACCCAAACTCCTCATC<br>TATGCTGCATCCAACCAAGGATCCGGGGTCCCTGCCAGGTTTAGTGGCAGTGGGTCTGGGACAGACTTCAGCCTCAAC<br>ATCCATCCTATGGAGGAGGATGATACTGCAATGTATTTCTGTCAGCAAAGTAAGGAGGTTCCTCGGACGTTCGGTGGA<br>GGCACCAAGCTGGAAATCAAA | 82 |
| 3525 | VH | CAGGTTCAACTGCAGCAGTCTGGGGCTGAGCTGGTGAGGCCTGGGGCTTCAGTGAAGCTGTCCTGCAAGGCTTCGGGC<br>TACACATTTACTGACCATGAAATGCACTGGGTGAAGACAGACACCTGTGCATGGCCTGGAATGGATTGGAGTTATTGAT<br>CCTGACACTGGTGATACTACCTACAATCAGAAATTCAAGGGCAAGGCCACACTGACTGCAGACAAATCCTCCAGCACA<br>GCCTACATGGACCTCCGCAGCCTGACATCTGAGGACTCTGCCGTCTTTTACTGTACACGGTGGACTGGGGGGACTAC<br>TGGGGCCATGGCACCACTCTCACAGTCTCCTCA | 83 |
| | VL | GATGTTGTGATGACCCAGACTCCACTGTCTTTGTCGGTTACCATTGGACAACCAGCCTCCATTTCTTGCAAGTCAAGT<br>CAGAGCCTCTTATACAGTAATGGAAAGACATATTTGAATTGGTTTCAACAGAGGCCTGGCCAGTCTCCAAAGCGCCTA<br>ATGTATCAGGTGTCCAAACTGGACCCTGGCATCCCTGACAGGTTCAGTGGCAGTGGATCAGAAACAGATTTTACACTT<br>AAAATCAGCAGAGTGGAGGCTGAAGATTTGGGACTTTATTACTGCTTGCAAGGTACATATTATCCGTACACGTTCGGA<br>GGGGGGACCAAGCTGGAAATAAAA | 80 |
| 3530 | VH | CAGGTTCAACTGCAGCAGTCTGGGGCTGAGCTGGTGAGGCCTGGGGCTTCAGTGAAGCTGTCCTGCAAGGCTTCGGGC<br>TACACATTTACTGACCATGAAATGCACTGGGTGAGACAGACACCTGTGCATGGCCTGGAATGGATTGGAGTTATTGAT<br>CCTGACACTGGTGATACTACCTACAATCAGAAATTCAAGGGCAAGGCCACACTGACTGCAGACAAATCCTCCAGCACA<br>GCCTACATGGACCTCCGCAGCCTGACATCTGAGGACTCTGCCGTCTTTTACTGTACACGGTGGACTGGGGGGACTAC<br>TGGGGCCATGGCACCACTCTCACAGTCTCCTCA | 83 |
| | VL | GATGCTGTGATGACCCAGACTCCACTGTCTTTGTCGGTTACCATTGGACAACCAGCCTCTATCTCTTGCAAGTCGAGT<br>CAGAGCCTCTTATATAGTGATGGAAAGACATATTTGAATTGGTTCCAACAGAGGCCAGGCCAGTCTCCAAAGCGCCTA<br>ATGTATCAGGTGTCCAAACTGGACCCTGGCATCCCTGACAGGTTCAGTGGCAGTGGATCAGAGACAGATTTTACACTT<br>AAAATCAGCAGAGTGGAGGCTGAGGATTTGGGAGTTTATTACTGCTTGCAAGGTACATATTATCCGTATACGTTCGGA<br>TCGGGGACCAAGCTGGAAATAAAA | 84 |

TABLE 2-continued

Nucleotide sequences of heavy chain variable regions (VHs) and
light chain variable regions (VLs) of exemplary antibody molecules

| Antibody | Chain | Nucleotide Sequence | SEQ ID NO |
|---|---|---|---|
| 4035 | VH | CAGGTGCAGCTGAAGGAGTCAGGACCTGGCCTGGTGGCGCCCTCACAGAGCCTGTCCATCACCTGCACAGTCTCTGGT TTCTCATTAACCATCTATGATGTACACTGGGTTCGCCAGTCTCCAGGAAAGGGTCTGGAGTGGCTGGGAGTGATATGG AGTGATGGAAGCACAGACTATAATGCAGCTTTCATATCTAGACTGAGCATCAGCAAGGACAACTCCAAGAGCCAAGTT TTCTTTAAAATGAACAGTCTGCAAGCTGATGACACAGCCATATACTACTGTGCCAGAAATTGGGTCGACCAGGCCTGG TTTGCTTACTGGGGCCAAGGGACTCTGGTCACTGTCTCTGCA | 173 |
| | VL | GACATCCAGATGACTCAGTCTCCAGCCTCCCTATCTGCATCTGTGGGAGAAACTATCACCATCACATGTCGAGCAAGT AAGAATATTTACAGTTATTTAGCATGGTATCAGCAGAAACAGGGAAAATCTCCTCAGCTCCTGGTCTATAATGCAAAA ACCTTACCAGAAGGTGTGCCATCAAGGTTCAGTGGCAGTGGATCAGGCACACAGTTTTCTCTGAAGATCAACAGCCTG CAGCCTGAAGATTTTGGGAGTTATTACTGTCAACATCATTATGGTACTCCGCTCACGTTCGGTGCTGGGACCAAGCTG GAGCTGAAA | 174 |
| 4035-062 | VH | CAGGTACAACTCCAGGAATCCGGGCCTGGGCTCGTCAAACCAAGCGAAACACTCTCTCTCACCTGCACCGTTTCTGGG TTTTTCTCTTACTATCTATGACGTACATTGGGTAAGGCAACCACCCGGGAAGGGGCTGGAGTGGATCGGTGTAATCTGG TCAGATGGATCTACAGACTACAACCCATCCCTTAAAAGCAGGGTGACCATTTCTAAGGACACTTCCAAGAACCAAGTA TCCCTTAAATTGTCCTCTGTAACCGCAGCAGACACCGCAGTTTACTACTGCGCACGAAATTGGGTTGACCAAGCATGG TTTGCATATTGGGGACAGGGAACTCTTGTCACTGTGTCTTCA | 299 |
| | VL | GATATTCAAATGACCCAATCCCCCTCATCACTTTCAGCATCTGTCGGTGATCGGGTCACCATTACTTGCAGAGCCAGT AAGAATATCTACAGCTACCTGGCTTGGTATCAGCAAAAACCTGGTAAGGCCCCTAAACTTCTCGTTTACAATGCTAAG ACCCTTCCCGAGGGAGTTCCTTCCAGGTTTTCCGGTAGCGGGAGTGGAACAGATTTCACCTTGACTATTTCTAGCTTG CAGCCCGAGGATTTCGCTACATACTACTGCCAGCATCACTATGGAACCCCCTGACCTTCGGTCAGGGAACCAAGCTC GAGATCAAA | 300 |
| 3934 | VH | CAGGTCCAACTGCAGCAGTCTGGACCTGAGCTGGTGAAGCCTGGAGCTTCAGTGAAGCTGTCCTGCAAGGCTGCTGGC TACATCTTCACTGACTATACTATAAACTGGGTGAAGCAGAGTCCTGGACAGGGACTTGAGTGGATTGGATGGATTTAT CCTGGAAGTGGTAATCGTAAATACAATGACAAGTTCAAGGGCAAGGCCACAATGACTGCAGACAAATCCTCCAGCACA GCCTACATGCAGCTCAGCAGCCTGACCTCTGAGGATTCTGCGGTCTATTTCTGTGCAAGAGAGAGTAACTACGTGGGG TACTATGCTATGGACTATTGGGGTCAAGGAACCTCAGTCACCGTCTCCTCA | 175 |
| | VL | GATGTTTTGATGACCCAAACTCCACTCTCCCTGCCTGTCAGTCTTGGAGATCAAGCCTCCATCTCTTGCAGATCTAGT CAGAGCCTTGTAAATAGTAATGGAAACACCTATTTAGAATGGTACCTGCAGAAACCAGGCCAGTCTCCAAATCTCCTG ATCTACAAAGTTTCCAATCGATTTTCTGGGGTCCCAGACAGGTTCAGTGGCAGTGGATCGGGGACAGATTTCACACTC AAGATCAGCAGAGTGGAGGCTGAGGATCTGGGAGTTTATTACTGTTTTCAAGGTTCACATGTTCCGTGGACGTTCGGT GGAGGCACCAAGCTGGAAATCAAA | 176 |
| 3833 | VH | CAGGTCCAGCTGCAGCAGTCTGGAGCTGAGCTGGTAAGGCCTGGGACTTCAGTGAAGATGTCCTGCAAGGCTGCTGGA TACACCTTCACAAACTACTGGATAGGTTGGGTAAAGCAGAGGCCTGGACATGGCCTTGAGTGGATTGGAGATATTTAC CCTGGAGGTATAGGAGGTGGTTATACTAAGTACAATGAGAAGTTCAAGGGCAAGGCCACACTGACTGCAGACACATCC TCCAGCACAGCCTACATGCAGCTCCGGCCTGACATCTGAGGACTCTGCCATCTATTTCTGTTCAAGATCGGAAACT GGACGGGCTATGGACTACTGGGGTCAAGGAACCTCAGTCACCGTCTCCTCA | 177 |
| | VL | GACATCCAGATGACACAGTCTCCATCCTCACTGTCTGCATCTCTGGGAGGCAAAGTCACCATCACTTGCAAGGCAAGC CAAGACATTAATAAGTATATAGCTTGGTACCAACAAAAGCCTGGAAAAGGTCCTAGGCTGCTCATACATTACACATCT ACATTAAAGCCAGGCATCCCATCAAGGTTCAGTGGAAGTGGGTCTGGGAGAGATTATTCCTTCAGCATCAGTGACCTG GAGCCTGAAGATATTGCAACTTATTATTGTCTACAGTATGATAATCTGAACACGTTCGGAGGGGGGACCAAGCTGGAA ATAAAA | 178 |
| 3631 | VH | GAGATCCAGCTGCAGCAGTCTGGACCTGAGCTGGTGAAGCCTGGGGCTTCAGTGAAGGTGTCCTGCAAGGCTTCTGGT TATTCATTCACTGACTACAACATCTACTGGGTGAAGCAGAGCCATGGAAAGAGCCTTGAGTGGATTGGATATATTGAT CCTTCCAATGGTGGTCCTGGCTACAACCAGAAGTTCAGGGGCAAGGCCACATTGACTGTTGACAAGTCCTCCAGCACA GCCTTCCTGCATCTCAACAGCCTGACATCTGAGGACTCTGCAGTCTATTACTGTGCAAGAAGGGACAACTACGGCTCG GGGACTATGGACTACTGGGGTCAAGGAACCTCAGTCACCGTCTCCTCA | 179 |
| | VL | GACATTGTGATGACCCAGTCTCAAAAATTCATGTCCACATCAGTAGGAGACAGGGTCAGCATCACCTGTAAGGCCAGT CAGAATGTGGGTACTGATGTATCCTGGTATCAACAGAAACCAGGGAAATCTCCTAAACCACTGATTTACTGGGCATCA AACCGGTTCACTGGAGTCCCTGATCGCTTCATAGGTAGTGGATCTGGGACAGATTTCACTCTCACCATCAGCAATGTG CAGTCTGAAGACTTGGCAGATTATTTCTGTGAGCAATATAGCATCTATCCGCTCACGTTCGGTGCTGGGACCAAGCTG GAGCTGAAA | 180 |
| 3732 | VH | GAGATCCAGCTGCAGCAGTCTGGACCTGAGCTGGTGAAGCCTGGGGCGTCAGTGAAGGTATCCTGCAAGGCTTCTGGT TACTCATTCACTGACGACAACATGTACTGGGTGAAGCAGAGCCATGGAAAGAGCCTTGAGTGGATTGGATATATTGAT CCTCTCAATGGTGGTACTGGCTACAACCAGAAATTCAAGGGCAAGGCCACACTGACTGTTGACAAGTCCTCCAGCACA GCCTTCCTGCATCTCAACAGCCTGACATCTGAGGACTCTGCAGTCTATTACTGTGCAAGAAGGGACAACTACGCCACG GGGACTATGGACTACTGGGGTCAAGGAACCTCAGTCACCGTCTCCTCA | 181 |
| | VL | GACATTGTGATGACCCAGTCTCAAAAATTCATGTCCACATCAGTAGGAGACAGGGTCAGCATCACCTGCAAGGCCAGT AAGAATGTGGGTACTGATGTATCCTGGTATCAACAGAAACCAGGGAAATCTCCTAAACCACTGATTTACTGGGCATCA AACCGGTTCACTGGAGTCCCTGATCGCTTCACAGGCAGTGGATCTGGGACAGATTTCACTCTCACCATCAACAATGTG CAGTCTGAAGACTTGGCAGATTATTTCTGTGAGCAATATAGCAGCTATCCGCTCACGTTCGGTGCTGGGACCAAGCTG GAGCTGAAA | 182 |

TABLE 2-continued

Nucleotide sequences of heavy chain variable regions (VHs) and
light chain variable regions (VLs) of exemplary antibody molecules

| Antibody | Chain | Nucleotide Sequence | SEQ ID NO |
|---|---|---|---|
| 4338 | VH | GAGGTCCAGCTGCAGCAGTCTGGCCCTGAGCTGGTGAAGCCTGGGGCTTCAGTGAAGATATCCTGCAAGGCTTCTGGA TACACATTCACTGACTACAACATGGACTGGGTGAAGCAGAGCCATGGAAAGAGCCTTGAGTGGATTGGAAATATTTAT CCTATCAATGGTTATACTGGCTACAACCAGAGGTTCAAGAACAAGGCCACATTGACTGTAGACAAGTCCTCCAGCACA GCCTACATGGAACTCCACAGCCTGACATCTGAGGACTCTGCGGTCTATTACTGCGCAAGAGATAGTAACTACGTTGGC TGGTACTTCGATGTCTGGGGCGCAGGGACCACGGTCACCGTCTCCTCA | 183 |
|  | VL | GATGTTGTGATGACCCAAACTCCACTCTCCCTGCCTGTCAGTCTTGGAGATCAAGCCTCCATCTCTTGCAGATCTAGT CAGAGCCTTGTACACAGTAATGGAAACACCTATTTACATTGGTACCTGCAGAAGCCAGGCCAGTCTCCAAAGCTCCTG ATCTACAAAGTTTCCAACCGATTTTCTGGGGTCCCAGACAGGTTCAGTGGCAGTGGATCAGGGACAGATTTCACATTC AAGATCAGCGAGTGGAGGCTGAGGATCTGGGAGTTTATTTCTGCTCTCAAAGTACACATGTTCCTCGGACGTTCGGT GGAGGCACCAAGCTGGAAATCAAA | 184 |
|  | VL | GACATTGTGCTGACACAGTCTCCTGCTTCCTTAACTGTATCTCTGGGGCAGAGGGCCACCTTCTCATGCAGGGCCAGC AAAAGTGTCAGTACATCTGGCTATAGTTATATGCACTGGTACCAACAGAAACCAGGACAGCCACCCAAACTCCTCATC TATTTTACATCCGACCTAGAACCTGGGGTCCCTGCCAGGTTCACTGGCAGTGGGTCTGGGACAGATTCACCCTCAAC ATCCATCCTGTGGAGGAGGAGGATGCTGCAACCTATTACTGTCAGCACAGTAGGGAGCTTCCGTACCCCTTCGGAGGG GGGACCAAGTTGGAAATAAAA | 185 |
| 4540 | VH | caggtccagctacagcagtctggacctgagctggtgaagcctgggcttcagtgaagatatcctgcaaggcttctggc tacaccttcgctgactactatataaactgggtgaagcagaggcctggacagggacttgagtggattggatggatttttt cctggaagtggtagtacttactacaatgagaagttcaagggcaaggccacacttactgtagacaaatcctccagcaca gcctacatgttgctcagcagcctgacctctgaggactctgcggtctatttctgtgcaagaggggactccggtagggct atggactactgggtcaaggaacctcagtcaccgtctcctca | 186 |
|  | VL | gacatccagatgacacagtctccatcctcactgtctgcatctctgggaggcaaagtcaccatcacttgcaaggcaagc caagacattaacaaatatatagcttggtaccaacaagcctgaaaaggtcctaggctgctcatacattacacatct acattacagtcaggcatcccatcaaggttcagtggaagtgggtctgggagagattattccttcagcatcagcaacctg gagcctgaagataatgcaacttattattgtctacagtatgataatcttctcacgttcggtgctgggaccaagctggag ctgaaa | 187 |
| 4540-063 | VH | CAAGTCCAGCTCGTACAGAGCGGGGCAGAGCTGAAGAAGCCTGGGGCCTCCGTCAAGGTCTCCTGTAAGGCTTCTGGT TACACATTTGCCGACTACTACATGAACTGGGTACGGCAAGCCCCAGGTCAAGGGCTGGAATGGATGGGATGGATTTTT CCAGGGAGCGGCAGCACTTACTACAACCAGAAATTTCAAGGTCGTGTGACAATGACCGTGGATAAAAGCAGCTCTACA GCTTACATGGAGCTTTCCCGCTTGAGGTCCGATGATACTGCCGTATATTATTGTGCCCGTGGTGACTCAGGTAGGGCC ATGGACTATTGGGGACAGGGCACCCTCGTGACCGTGTCCAGC | 301 |
|  | VL | GATATCCAGATGACACAATCCCCTTCATCCTTGAGCGCATCAGTTGGCGACAGGGTCACCATAACTTGTCAGGCTAGT CAGGATATTAACAAGTACCTGGCTTGGTATCAACAAGCCTGGAAAGGCCCCCAAATTGCTGATTCACTACACCTCT ACATTGGAAACTGGCGTACCCAGTCGCTTTTCTGGGAGTGGAAGCGGAACTGATTTCACTTTCACTATATCCAGTCTT CAGCCAGAAGATATCGCAACTTACTATTGTCTTCAGTATGATAACTTGCTTACTTTCGGAGGAGGGACCAAAGTTGAA ATCAAG | 302 |
| 4540-033 | VH | CAGGTGCAGTTGGTCCAATCCGGGGCTGAGGTGAAGAAGCCTGGGGCCTCTGTTAAAGTTAGTTGCAAGGCATCAGGC TACACCTTCGCTGACTACTACATCAACTGGGTTAGACAGGCCCCCGGGCAGGGGTTGGAGTGGATGGGTTGGATTTTT CCAGGATCAGGTTCAACATATTACGCACAAAAACTGCAAGGTAGAGTAACCATGACAACTGATACTAGCACCTCCACA GCCTATATGGAACTCCGCTCTCAGGAGTGACGATACAGCCGTTTATTACTGCGCCCGTGGGGATTCAGGCCGTGCA ATGGATTACTGGGGTCAAGGGACCCTCGTGACCGTAAGTTCA | 303 |
|  | VL | GATATCCAGATGACACAATCCCCTTCATCCTTGAGCGCATCAGTTGGCGACAGGGTCACCATAACTTGTCAGGCTAGT CAGGATATTAACAAGTACCTGGCTTGGTATCAACAACAAGCCTGGAAAGGCCCCCAAATTGCTGTTCACTACACCTCT ACATTGGAAACTGGCGTACCCAGTCGCTTTTCTGGGAGTGGAAGCGGAACTGATTTCACTTTCACTATATCCAGTCTT CAGCCAGAAGATATCGCAACTTACTATTGTCTTCAGTATGATAACTTGCTTACTTTCGGAGGAGGGACCAAAGTTGAA ATCAAG | 302 |
| 4237 | VH | CAGGCGCACCTGAAGGAGTCAGGACCTGGCCTGGTGGCGCCCTCACAGAGCCTGTCCATCACCTGCACAGTCTCTGGT TTCTCATTAACCGACTATGATGTACACTGGGTTCGCCAGTCTCCAGGAAAGGGTCTGGAGTGGCTGGGAGTGATATGG AATGATGGAAGCACAGACTATAATACAGCTTTCATATCTAGACTGACCATCAGCAAGGACAACTCCAAGAGCCAAGTT TTCTTTAAAATGAACAGTCTGCAAGCTGATGACACAGCCATATACTACTGTGCCAGAAATTGGTATGGTGGCTACTGG TTTGCTTACTGGGGCCAAGGGACTCTGGTCACTGTCTCTGCA | 188 |
|  | VL | GACATCCAGATGACTCAGTCTCCAGCCTCCCTATCTGCATCTGCGGAGAAACTGTCACCATCACATGTCGATCAAGT GAGAATATTTACAGTTATTTAGCATGGTATCAGCAGAAACAGGGAAAATCTCCTCAGCTCCTAGTCTATAATGCAAAT GCCTTAGCAGAAGGTGTGCCATCGAGGTTCAGTGGCAGTGGATCAGTCACACAGTTTTCTCTGAAGATCAACAGCCTG CAGCCTGAAGATTTTGGGAGTTATTACTGTCAACATCATTATGGTACTCCATTCACGTTCGGCTCGGGGACAAAGTTG GAAATAAAA | 189 |
| 4439 | VH | GAGATCCAGCTGCAGCAGTCTGGAGCTGAACTGGTGAAGCCTGGGGCTTCAGTGAAGATATCCTGCAAGGCTTCTGAT TACTCATTCACTGGCTACAACATGAACTGGGTGATGCAGAGCCATGGAAAGAGCCTTGAGTGGATTGGAAATATTCAT CCTTACTATGGTGGTACTAGCTTCAATCAGAAGTTCATGGGCAAGGCCACATTGACTGCAGACAAATCTTCCAGCACA GCCTACATGCAGCTCAACAGCCTGACATCTGAGACTCTGCAGTCTATTACTGTGCAAGAGAGAAGTAACTTCCAT GCTCTGGACTACTGGGGTCAGGGAACCCTCAGTCACCGTCTCCTCA | 297 |

TABLE 2-continued

Nucleotide sequences of heavy chain variable regions (VHs) and
light chain variable regions (VLs) of exemplary antibody molecules

| Antibody | Chain | Nucleotide Sequence | SEQ ID NO |
|---|---|---|---|
| | VL | GACATTGTGCTGACACAGTCCTGCTTCCTTAACTGTATCTCTGGGGCAGAGGGCCACCTTCTCATGCAGGGCCAGC AAAAGTGTCAGTACATCTGGCTATAGTTATATGCACTGGTACCAACAGAAACCAGGACAGCCACCCAAACTCCTCATC TATTTTACATCCGACCTAGAACCTGGGGTCCCTGCCAGGTTCACTGGCAGTGGGTCTGGGACAGACTTCACCCTCAAC ATCCATCCTGTGGAGGAGGAGGATGCTGCAACCTATTACTGTCAGCACAGTAGGGAGCTTCCGTACCCCTTCGGAGGG GGGACCAAGTTGGAAATAAAA | 298 |

TABLE 5

The Amino Acid Sequence, of the Heavy Chain Variable Region (VH) and
Light Chain Variable Region (VL) of the Exemplary Humanized Anti-
APRIL Antibodies Are Provided As Follows.

| Antibody Chain | Amino Acid Sequence | SEQ ID NO |
|---|---|---|
| >Hu_2218_VH01 | QVQLQESGPGLVKPSQTLSLTCTVSGYSITSGYYWNWIRQHPGKGLEWIGYISYDGYNNYNPSLKNRVTISVDTSKNQF SLKLSSVTAADTAVYYCARYYDYEDWYFGVWGQGTMVTVSS | 190 |
| >Hu_2218_VH02 | QVQLQESGPGLVKPSQTLSLTCTVSGYSITSGYYWSWIRQHPGKGLEWIGYISYDGYTYYNPSLKSRVTISVDTSKNQF SLKLSSVTAADTAVYYCARYYDYEDWYFGVWGQGTMVTVSS | 191 |
| >Hu_2218_VH03 | QVQLQESGPGLVKPSQTLSLTCTVSGYSITSGYYWNWIRQHPGKGLEWIGYISYDGYNNYNPSLKSRVTISRDTSKNQF SLKLSSVTAADTAVYYCARYYDYEDWYFGVWGQGTMVTVSS | 192 |
| >Hu_2218_VH04 | QVQLQQWGAGLLKPSETLSLTCAVYGYSITSGYYWNWIRQPPGKGLEWIGYISYDGYNNYNPSLKNRVTISVDTSKNQF SLKLSSVTAADTAVYYCANYYDYEDWYFGVWGQGTTVTVSS | 193 |
| >Hu_2218_VH05 | QVQLQQWGAGLVKPSETLSLTCAVYGYSITSGYYWNWIRQPPGKGLEWIGYISYDGYNNYNPSLKNRVTISRDTSKNQF SLKLSSVTAADTAVYYCANYYDYEDWYFGVWGQGTTVTVSS | 194 |
| >Hu_2218_VH06 | QVQLQESGPGLVKPSETLSLTCTVSGYSITSGYYWNWIRQPPGKGLEWIGYISYDGYNNYNPSLKNRVTISVDTSKNQF SLKLSSVTAADTAVYYCANYYDYEDWYFGVWGQGTTVTVSS | 195 |
| >Hu_2218_VH07 | QVQLQESGPGLVKPSETLSLTCTVSGYSITSGYYWNWIRQPPGKGLEWIGYISYDGYNNYNPSLKNRVTISRDTSKNQF SLKLSSVTAADTAVYYCANYYDYEDWYFGVWGQGTTVTVSS | 196 |
| >Hu_2218_VH08 | QVQLQESGPGLMKPSETLSLTCSVSGYSITSGYYWSWIRKPPGKGLEYIGYVSYDGSTYYNPSLKSRVTISVDTSKNRF SLKLNSVTAADTAVYYCANYYDYEDWYFGVWGQGILVTVSS | 197 |
| >Hu_2218_VH09 | QVQLQESGPGLMKPSETLSLTCSVSGYSITSGYYWNWIRKPPGKGLEWIGYISYDGYNNYNPSLKSRVTISRDTSKNRF SLKLNSVTAADTAVYYCANYYDYEDWYFGVWGQGILVTVSS | 198 |
| >Hu_2218_VH10 | EVQLVESGGGLVQPGGSLRLSCAVSGYSITSGYYWNWIRQAPGKGLEWVASISYDGYNNYNPSVKGRITISRDDSKNTF YLQMNSLRAEDTAVYYCANYYDYEDWYFGVWGQGTLVTVSS | 199 |
| >Hu_2218_VH11 | EVQLVESGGGLVQPGGSLRLSCAVSGYSITSGYYWNWIRQAPGKGLEWVAYISYDGYNNYNPSVKGRITISRDTSKNTF YLQMNSLRAEDTAVYYCANYYDYEDWYFGVWGQGTLVTVSS | 200 |
| >Hu_2218_VH12 | QVQLVESGGGVVQPGRSLRLSCAASGYSITSGYYWNWVRQAPGKGLEWVAYISYDGYNNYNPSVKGRFTISRDNSKNTL YLQMNSLRAEDTAVYYCANYYDYEDWYFGVWGQGTMVTVSS | 201 |
| >Hu_2218_VL01 | EIVLTQSPATLSLSPGERATLSCRASESVSIIGTNSIHWYQQKPGQAPRLLIYHASNLETGIPARFSGSGPGTDFTLTI SSLEPEDFAVYYCLQSRKIPYTFGQGTKLEIK | 202 |
| >Hu_2218_VL02 | DIVLTQSPASLAVSPGQRATITCRASESVSIIGTNSIHWYQQKPGQPPKLLIYHASNLETGVPARFSGSGSGTDFTLTI NPVEANDTANYYCLQSRKIPYTFGGGTKLEIK | 203 |
| >Hu_2218_VL03 | EIVMTQSPATLSVSPGERATLSCRASESVSIIGTNSLHWYQQKPGQAPRLLIYHASQSISGIPARFSGSGSGTEFTLTI SSLQSEDFAVYYCQQSRKIPYTFGGGTKVEIK | 204 |
| >Hu_2218_VL04 | EIVMTQSPATLSVSPGERATLSCRASESVSIIGTNSIHWYQQKPGQAPRLLIYHASNLETGIPARFSGSGSRTEFTLTI SSLQSEDFAVYYCLQSRKIPYTFGGGTKVEIK | 205 |
| >Hu_2218_VL05 | DIQLTQSPSSLSASVGDRVTITCRASESVSIIGTNSMNWYQQKPGKAPKLLIYHASYLESGVPSRFSGSGSGTDFTLTI SSLQPEDFATYYCLQSRKIPYTFGQGTKVEIK | 206 |
| >Hu_2218_VL06 | DIQLTQSPSSLSASVGDRVTITCRASESVSIIGTNSMHWYQQKPGKAPKLLIYHASNLESGVPSRFSGSGSRTDFTLTI SSLQPEDFATYYCLQSRKIPYTFGQGTKVEIK | 207 |

TABLE 5-continued

The Amino Acid Sequence, of the Heavy Chain Variable Region (VH) and
Light Chain Variable Region (VL) of the Exemplary Humanized Anti-
APRIL Antibodies Are Provided As Follows.

| Antibody Chain | Amino Acid Sequence | SEQ ID NO |
|---|---|---|
| >Hu_2218_VL07 | DIQMTQSPSSLSASVGDRVTITCRASESVSIIGTNSMHWYQQKPGKAPKLLIYHASNLESGVPSRFSGSGSGTDFTFTISSLQPEDIATYYCLQSRKIPYTFGQGTKVEIK | 208 |
| >Hu_2419_VH01 | QVQLVQSGAEVKKPGASVKVSCKASGYTFTDYTIHWVRQAPGQGLEWMGWIYPLRGSINYNEKFKDRVTSTRDTSISTAYMELSRLRSDDTVVYYCARHGAYYSNAFDYWGQGTLVTVSS | 209 |
| >Hu_2419_VH02 | QVQLVQSGAEVKKPGASVKVSCKASGYTFTDYYMHWVRQAPGQGLEWMGRIYPLRGSTNYAQKFQGRVTSTRDTSISTAYMELSRLRSDDTVVYYCARHGAYYSNAFDYWGQGTLVTVSS | 210 |
| >Hu_2419_VH03 | QVQLVQSGAEVKKPGASVKVSCKASGYTFTDYTIHWVRQAPGQGLEWMGWIYPLRGSINYNEKFKDRVTMTADTSSSTAYMELSRLRSDDTVVYYCARHGAYYSNAFDYWGQGTLVTVSS | 211 |
| >Hu_2419_VH04 | QVQLVQSGAEVKKPGASVKVSCEASGYTFTDYTIHWVRQAPGKGLEWMGWIYPLRGSINYNEKFKDRVTMTADTSTDTAYMELSSLRSKDTAVYYCARHGAYYSNAFDYWGQGTLVTVSS | 212 |
| >Hu_2419_VH05 | QVQLVQSGAEVVKPGASVKLSCKASGYTFTDYTMYWVKQAPGQGLEWIGEIYPLRGSINFNEKFKSKATLTVDKSASTAYMELSSLRSEDTAVYYCARHGAYYSNAFDYWGQGTLVTVSS | 213 |
| >Hu_2419_VH06 | QVQLVQSGAEVVKPGASVKLSCKASGYTFTDYTMHWVKQAPGQGLEWIGEIYPLRGSINFNEKFKSKATLTVDKSASTAYMELSSLRSEDTAVYYCARHGAYYSNAFDYWGQGTLVTVSS | 214 |
| >Hu_2419_VL01 | EIVLTQSPATLSLSPGERATLSCRASESVDNDGIRFMHWYQQKPGQAPRLLIYRASNLESGIPARFSGSGPGTDFTLTISSLEPEDFAVYYCQQSNKDPYTFGQGTKLEIK | 215 |
| >Hu_2419_VL02 | EIVLTQSPATLSLSPGERATLSCRASESVDNDGIRFMHWYQQKPGQAPRLLIYRASNLESGIPARFSGSGPGTDFTLTISSLEPEDVAVYYCQQSNKDPYTFGQGTKLEIK | 216 |
| >Hu_2419_VL03 | DIVMTQSPASLAVSLGERATINCRASESVDNDGIRFMHWYQQKPGQPPKLLIYRASNLESGVPDRFSGSGSRTDFTLTISSLQAEDVAVYYCQQSNKDPYTFGGGTKVEIK | 217 |
| >Hu_2419_VL04 | DIVMTQSPASLAVSLGERATINCRASESVDNDGIRFMHWYQQKPGQPPKLLIYRASNLESGVPDRFSGSGSRTDFTLTINSLQAEDVAVYYCQQSNKDPYTFGGGTKVELK | 218 |
| >Hu_2419_VL05 | DIVLTQSPATLSVSPGERATISCRASESVDNDGIRFMHWYQQKPGQPPKLLIYRASNLESGVPARFSGSGSRTDFTLTISSVEPEDFATYYCQHSWEIPPTFGGGTKLEIK | 219 |
| >hu_4035_VH01 | QVQLVESGGGVVQPGRSLRLSCAASGFSLTIYDVHWVRQAPGKGLEWVAVIWSDGSTDYNAAFISRFTISRDNSKNTLYLQMNSLRAEDTAVYYCARNWVDQAWFAYWGQGTLVTVSS | 220 |
| >hu_4035_VH02 | QVQLVESGGGVVQPGRSLRLSCAASGFSLTIYDVHWVRQAPGKGLEWVGVIWSDGSTDYNAAFISRFTISKDNSKNTLYLQMNSLRAEDTAVYYCARNWVDQAWFAYWGQGTLVTVSS | 221 |
| >hu_4035_VH03 | QVQLVESGGGVVQPGRSLRLSCAASGFSLTIYDVHWVRQAPGKGLEWVAVIWSDGSTDYADSVKGRFTISKDNSKNTLYLQMNSLRAEDTAVYYCARNWVDQAWFAYWGQGTLVTVSS | 222 |
| >hu_4035_VH04 | QVQLVESGGGVVQPGRSLRLSCAVSGFSLTIYDVHWVRQAPGKGLEWVGVIWSDGSTDYADSVKGRFTISKDNSKNTVYLQMNSLRAEDTAVYYCARNWVDQAWFAYWGQGTLVTVSS | 223 |
| >hu_4035_VH05 | QVQLQESGPGLVKPSETLSLTCTVSGFSLTIYDVHWIRQPPGKGLEWIGVIWSDGSTDYNAAFISRVTISVDTSKNQFSLKLSSVTAADTAVYYCARNWVDQAWFAYWGQGTLVTVSS | 224 |
| >hu_4035_VH06 | QVQLQESGPGLVKPSETLSLTCTVSGFSLTIYDVHWVRQPPGKGLEWIGVIWSDGSTDYNPSLKSRVTISKDTSKNQVSLKLSSVTAADTAVYYCARNWVDQAWFAYWGQGTLVTVSS | 225 |
| >hu_4035_VH07 | QVQLQESGPGLMKPSETLSLTCSVSGDSITIYDWHWIRQPPGKGLEWIGVVWSDGSTDYNPSLKSRVTISVDTSKNRFSLKLSSVTAADTAVYYCARNWVDQAWFAYWGQGTLVTVSS | 226 |
| >hu_4035_VH07 | QVQLQESGPGLVKPSETLSLTCTVSGFSLTIYDVHWIRQPPGKGLEWIGVIWSDGSTDYNPSLKSRVTISKDNSKNQFSLKLSSVTAADTAVYYCARNWVDQAWFAYWGQGTLVTVSS | 227 |
| >hu_4035_VH09 | QVQLQESGPGLVKPSETLSLTCTVSGFSLTIYDVHWIRQPPGKGLEWIGVIWSDGSTDYNPSLKSRVTISKDTSKNQVSLKLSSVTAADTAVYYCARNWVDQAWFAYWGQGTLVTVSS | 262 |
| >hu_4035_VH10 | QVQLQESGPGLVKPSETLSLTCTVSGGSITIYDWHWVRQPPGKGLEWIGVIWSDGSTDYNPSLKSRVTISKDTSKNQFSLKLSSVTAADTAVYYCARNWVDQAWFAYWGQGTLVTVSS | 263 |
| >hu_4035_VH11 | QVQLQESGPGLVKPSETLSLTCTVSGGSITIYDWHWVRQPPGKGLEWIGVIWSDGSTDYNPSLKSRVTISVDTSKNQFSLKLSSVTAADTAVYYCARNWVDQAWFAYWGQGTLVTVSS | 264 |
| >hu_4035_VH12 | QVQLQESGPGLVKPSETLSLTCTVSGGSITIYDWHWIRQPPGKGLEWIGVIWSDGSTDYNPSLKSRVTISVDTSKNQFSLKLSSVTAADTAVYYCARNWVDQAWFAYWGQGTLVTVSS | 265 |

TABLE 5-continued

The Amino Acid Sequence, of the Heavy Chain Variable Region (VH) and
Light Chain Variable Region (VL) of the Exemplary Humanized Anti-
APRIL Antibodies Arc Provided As Follows.

| Antibody Chain | Amino Acid Sequence | SEQ ID NO |
|---|---|---|
| >hu_4035_VL01 | DIQMTQSPSSLSASVGDRVTITCRASKNIYSYLAWYQQKPGKAPKLLIYNAKTLPEGVPSRFSGSGSGTDFTLTISSLQ PEDFATYYCQHHYGTPLTFGQGTKLEIK | 228 |
| >hu_4035_VL02 | DIQMTQSPSSLSASVGDRVTITCRASKNIYSYLAWYQQKPGKAPKLLVYNAKTLPEGVPSRFSGSGSGTDFTLTISSLQ PEDFATYYCQHHYGTPLTFGQGTKLEIK | 229 |
| >hu_4035_VL03 | EIVLTQSPATLSLSPGERATLSCRASKNIYSYLAWYQQKPGQAPRLLIYNAKTRATGIPARFSGSGSGTDFTLTISSLE PEDFAVYYCQHHYGTPLTFGQGTKLEIK | 230 |
| >hu_4035_VL04 | EIVLTQSPATLSLSPGERATLSCRASKNIYSYLAWYQQKPGQAPRLLVYNAKTLPEGIPARFSGSGSGTDFTLTISSLE PEDFAVYYCQHHYGTPLTFGQGTKLEIK | 231 |
| >hu_4035_VL05 | EIVMTQSPATLSVSPGERATLSCRASKNIYSYLAWYQQKPGQAPRLLIYNAKTRATGIPARFSGSGSGTEFTLTISSLQ SEDFAVYYCQHHYGTPLTFGGGTKVEIK | 232 |
| >hu_4035_VL06 | DIQLTQSPSFLSASVGDRVTITCRASKNIYSYLAWYQQKPGKAPKLLIYNAKSLQSGVPSRFSGSGSGTEFTLTISSLQ PEDFATYYCQHHYGTPLTFGGGTKLEIK | 233 |
| >hu_4035_VL07 | DIQLTQSPSFLSASVGDRVTITCRASKNIYSYLAWYQQKPGKAPKLLIYNAKSLQSGVPSRFSGSGSGTEFTLTISSLQ PEDFATYYCQHHYGTPLTFGGGTKLEIK | 234 |
| >hu_4237_VH01 | QLQLQESGSGLVKPSQTLSLTCAVSGFSLTDYDVHWVRQPPGKGLEWIGVIWNDGSTDYNPSLISRVTISKDNSKNQVS LKLSSVTAADTAVYYCARNWYGGYWFAYWGQGTLVTVSS | 235 |
| >hu_4237_VH02 | QLQLQESGSGLVKPSQTLSLTCAVSGGSITDYDWHWVRQPPGKGLEWIGVIWNDGSTDYNPSLISRVTISVDNSKNQFS LKLSSVTAADTAVYYCARNWYGGYWFAYWGQGTLVTVSS | 236 |
| >hu_4237_VH03 | QVQLVESGGGVVQPGRSLRLSCAASGESETDYDMHWVRQAPGKGLEWVAVIWNDGSTDYATSVIGRFTISRDNSKNTLY LQMNSLRAEDTAVYYCARNWYGGYWFAYWGQGTLVTVSS | 237 |
| >hu_4237_VH04 | QVQLVESGGGVVQPGRSLRLSCAASGESETDYDMHWVRQAPGKGLEWVGVIWNDGSTDYATSVIGRFTISRDNSKNTLY LQMNSLRAEDTAVYYCARNWYGGYWFAYWGQGTLVTVSS | 238 |
| >hu_4237_VH05 | QVQLQESGPGLMKPSETLSLTCSVSGGSITDYDWHWIRQPPGKGLEWIGVVWNDGSTDYNPSLKSRVTISVDTSKNRFS LKLNSVTAADTAVYYCARNWYGGYWFAYWGQGILVTVSS | 239 |
| >hu_4237_VH06 | QVTLKESGPALVKPTQTLTLTCTFSGESLTDYDVHWIRQPPGKALEWLAVIWNDGSTDYSPSLKSRLTITKDTSKNQVV LTMTNMDPVDTATYYCARNWYGGYWFAYWGQGTLVTVSS | 240 |
| >hu_4237_VL01 | DIQMTQSPSSLSASVGDRVTITCRSSENTYSYLAWYQQKPGKAPKLLVYNANALAEGVPSRFSGSGSVTDFTLTISSLQ PEDFATYYCQHHYGTPFTFGQGTKLEIK | 241 |
| >hu_4237_VL02 | DIQMTQSPSTLSASVGDRVTITCRSSENTYSYLAWYQQKPGKAPKLLVYNANALAEGVPSRFSGSGSVTEFTLTISSLQ PDDFATYYCQHHYGTPFTFGQGTKLEIK | 242 |
| >hu_4237_VL03 | EIVMTQSPATLSVSPGERATLSCRASENIYSYLAWYQQKPGQAPRLLIYNANASAEGIPARFSGSGSGTEFTLTISSLQ SEDFAVYYCQQHYGTPFTEGGGTKVEIK | 243 |
| >hu_4237_VL04 | DIQMTQSPSSLSASVGDRVTITCRASENIYSYLAWYQQKPGKAPKLLLYNANRLESGVPSRFSGSGSGTDFTLTISSLQ PEDFASYYCQHHYGTPFTFGSGTKLEIK | 244 |
| >hu_4237_VL05 | DIQMTQSPSSLSASVGDRVTITCRASENIYSYLAWYQQKPGKAPKLLLYNANRLESGVPSRFSGSGSGTDYTLTISSLQ PEDFASYYCQHHYGTPFTFGSGTKLEIK | 245 |
| >hu_3833_VH01 | QVQLVQSGAEVKKPGASVKVSCKASGYTFTNYWIGWVRQAPGQGLEWMGDIYPGGIGGGYTKYNEKFKGRVTMTADTST STAYMELRSLRSDDTAVYYCSRSETGRAMDYWGQGTLVTVSS | 246 |
| >hu_3833_VH02 | QVQLVQSGAEVKKPGASVKVSCKASGYTFTNYWIGWVRQAPGQGLEWMGDIYPGGIGGGYTKYAQKLQGRVTMTADTST STAYMELRSLRSDDTAVYYCSRSETGRAMDYWGQGTLVTVSS | 247 |
| >hu_3833_VH03 | QVQLVQSGAEVKKPGASVKVSCKASGYTFTNYWIGWVRQAPGQGLEWMGDIYPGGIGGGYTKYAQKFQGRVTMTADTST STAYMELSSLRSEDTAVYYCSRSETGRAMDYWGQGTLVTVSS | 248 |
| >hu_3833_VH04 | QVQLVQSGAEVKKPGASVKVSCKASGYTFTNYWIGWVRQAPGQGLEWMGDIYPGGIGGGYTKYNEKFKGRVTMTADTST STAYMELSSLRSEDTAVYFCSRSETGRAMDYWGQGTLVTVSS | 249 |
| >hu_3833_VH05 | QVQLVQSGAELKRPGASVKVSCKASGYTFTNYWMGWVKQAPGQGLEWMGDIYPGGIGGGYTNYAQKFKGKATMTADTSS STAYMQLSRLRSEDTAVYYCSRSETGRAMDYWGQGTLVTVSS | 250 |
| >hu_3833_VL01 | DIQMTQSPSSLSASVGDRVTITCQASQDINKYLAWYQQKPGKAPKLLIHYTSTLKPGVPSRFSGSGSGTDFTFTISSLQ PEDIATYYCLQYDNLNTFGGGTKLEIK | 251 |

TABLE 5-continued

The Amino Acid Sequence, of the Heavy Chain Variable Region (VH) and
Light Chain Variable Region (VL) of the Exemplary Humanized Anti-
APRIL Antibodies Are Provided As Follows.

| Antibody Chain | Amino Acid Sequence | SEQ ID NO |
|---|---|---|
| >hu_3833_VL02 | DIQMTQSPSSLSASVGDRVTITCKASQDINKYIAWYQQKPGKAPKLLIHYTSTLKPGVPSRFSGSGSGRDYTFTISSLQPEDIATYYCLQYDNLNTFGGGTKLEIK | 252 |
| >hu_3833_VL03 | DIQMTQSPSSLSASVGDRVTITCQASQDINKYLAWYQQKPGKAPKLLIYYTSTLETGVPSRFSGSGSGTDFTESISSLQPEDIATYYCLQYDNLNTFGGGTKLEIK | 253 |
| >hu_4540_VH01 | QVQLVQSGAEVKKPGASVKVSCKASGYTFADYYINWVRQAPGKGLEWMGWIFPGSGSTYYNEKFKGRVTMTVDKSTSTAYMELSSLRSEDTAVYFCARGDSGRAMDYWGQGTLVTVSS | 254 |
| >hu_4540_VH02 | QVQLVQSGAEVKKPGASVKVSCKASGYTFADYYMNWVRQAPGQGLEWMGWIFPGSGSTYYAEKFKGRVTSTRDTSISTAYMELSRLRSDDTVVYYCARGDSGRAMDYWGQGTLVTVSS | 255 |
| >hu_4540_VH03 | QVQLVQSGAEVKKPGASVKVSCKASGYTFADYYINWVRQAPGQGLEWMGWIFPGSGSTYYAQKLQGRVTMTTDTSTSTAYMELRSLRSDDTAVYYCARGDSGRAMDYWGQGTLVTVSS | 256 |
| >hu_4540_VH04 | QVQLVQSGAEVKKPGASVKVSCKASGYTFADYYINWVRQAPGQGLEWMGWIFPGSGSTYYAQKLQGRVTMTVDKSSSTAYMELRSLRSDDTAVYYCARGDSGRAMDYWGQGTLVTVSS | 257 |
| >hu_4540_VH05 | QVQLVQSGAELKKPGASVKVSCKASGYTFADYYMNWVRQAPGQGLEWMGWIFPGSGSTYYNQKFQGRVTMTVDKSSSTAYMELSRLRSDDTAVYYCARGDSGRAMDYWGQGTLVTVSS | 258 |
| >hu_4540_VL01 | DIQMTQSPSSLSASVGDRVTITCKASQDINKYIAWYQQKPGKAPKLLIHYTSTLQSGVPSRFSGSGSGTDFTFTISSLQPEDIATYYCLQYDNLLTFGQGTKLEIK | 259 |
| >hu_4540_VL02 | DIQMTQSPSSLSASVGDRVTITCKASQDINKYIAWYQHKPGKAPKLLIHYTSTLQSGVPSRFSGSGSGRDYTFTISSLQPEDIATYYCLQYDNLLTFGQGTKLEIK | 260 |
| >hu_4540_VL03 | DIQMTQSPSSLSASVGDRVTITCQASQDINKYLAWYQHKPGKAPKLLIHYTSTLETGVPSRFSGSGSGTDFTFTISSLQPEDIATYYCLQYDNLLTFGGGTKVEIK | 261 |

In an embodiment, the antibody molecule comprises one, two, or three CDRs of the VH region of an antibody molecule described herein, e.g., in Table 1 or 5 (e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, 4439, or 4237), using the Kabat or Chothia definitions of CDRs. In an embodiment, the antibody molecule comprises one, two, or three CDRs of the VL region of an antibody molecule described herein, e.g., in Table 1 or 5 (e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, 4439, or 4237), using the Kabat or Chothia definitions of CDRs. In an embodiment, the antibody molecule comprises one or more (e.g., two or three) CDRs of the VH region and/or one or more (e.g., two or three) CDRs of the VL region of an antibody molecule described herein, e.g., in Table 1 or 5 (e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, 4439, or 4237), using the Kabat or Chothia definitions of CDRs.

In an embodiment, the antibody molecule comprises one, two, or three VH CDRs described in Table 1 or 5. In an embodiment, the antibody molecule comprises one, two, or three VL CDRs described in Table 1 or 5. In an embodiment, the antibody molecule comprises one or more (e.g., two or three) VH CDRs and/or one or more (e.g., two or three) VL CDRs described in Table 1 or 5.

In an embodiment, the antibody molecule comprises one, two, three, or four frameworks of the VH region of an antibody molecule described in Table 1 or 5 (e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, 4439, or 4237). In an embodiment, the antibody molecule comprises one, two, three, or four frameworks of the VL region of an antibody molecule described in Table 1 or 5 (e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, 4439, or 4237). In an embodiment, the antibody molecule comprises one or more (e.g., two, three, or four) frameworks of the VH region and/or one or more (e.g., two, three, or four) frameworks of the VL region of an antibody molecule described in Table 1 or 5 (e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, 4439, or 4237).

In an embodiment, the antibody molecule comprises a heavy chain variable region of an antibody molecule described herein, e.g., in Table 1 or 5 (e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, 4439, or 4237). In an embodiment, the antibody molecule comprises a light chain variable region of an antibody molecule described herein, e.g., in Table 1 or 5 (e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, 4439, or 4237). In an embodiment, the antibody molecule comprises a heavy chain variable region and a light chain variable region of an antibody molecule described herein, e.g., in Table 1 or 5 (e.g., any of monoclonal antibodies 2218, 2419, 2419-0105, 2419-0205, 2419-0206, 2419-0406, 2419-0605, 2419-0805, 2419-0806, 2419-1204, 2419-1205, 2419-1210, 2419-1305, 2419-1306, 2419-1310, 2419-1406, 2922, 3327, 3530, 3525, 3125, 2621, 4035, 4035-062, 3934, 3833, 3631, 3732, 4338, 4540, 4540-063, 4540-033, 4439, 4439, or 4237).

In an embodiment, the antibody molecule comprises a heavy chain variable region having an amino acid sequence described in Table 1 or 5, or an amino acid sequence substantially identical thereof. In an embodiment, the antibody molecule comprises a light chain variable region having an amino acid sequence described in Table 1 or 5, or an amino acid sequence substantially identical thereof. In an embodiment, the antibody molecule comprises a heavy chain variable region having an amino acid sequence described in Table 1 or 5 (or an amino acid sequence substantially identical thereof) and a light chain variable region having an amino acid sequences described in Table 1 or 5 (or an amino acid sequence substantially identical thereof).

In an embodiment, the antibody molecule comprises a heavy chain variable region encoded by a nucleotide sequence described in Table 2, or a nucleotide sequence substantially identical thereof. In an embodiment, the antibody molecule comprises a light chain variable region encoded by a nucleotide sequence described in Table 2, or a nucleotide sequence substantially identical thereof. In an embodiment, the antibody molecule comprises a heavy chain variable region encoded by a nucleotide sequence described in Table 2 (or a nucleotide sequence substantially identical thereof) and a light chain variable region encoded by a nucleotide sequence described in Table 2 (or a nucleotide sequence substantially identical thereof).

In an embodiment, the antibody molecule further comprises a heavy chain constant region. In an embodiment, the heavy chain constant region is an IgG1 constant region, e.g., any of SEQ ID NOS: 320-322, or a functional portion thereof. In another embodiment, the heavy chain constant region is an IgG2 constant region, e.g., any of SEQ ID NOS: 323-326, or a functional portion thereof. In an embodiment, the antibody molecule further comprises a light chain constant region. In an embodiment, the antibody molecule further comprises a heavy chain constant region and a light chain constant region. In an embodiment, the antibody molecule comprises a heavy chain constant region, a light chain constant region, and heavy and light chain variable regions of an antibody molecule described in Table 1 or 5. In certain embodiments, the antibody molecule comprises a heavy chain constant region, a light chain constant region, and variable regions that comprise one, two, three, four, five, or six CDRs of an antibody molecule described in Table 1 or 5.

Exemplary heavy chain constant regions are described below.

```
Exemplary IgG1 constant regions
>IGHG1*01
                                    (SEQ ID NO: 320)
STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPK

SCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVFSCSVMHEALHNHYTQKSLSLSP

>IGHG1*03
                                    (SEQ ID NO: 321)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSP

>IGHG1*04
                                    (SEQ ID NO: 322)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNIFSCSVMHEALHNHYTQKSLSLSP

Exemplary IgG2 constant regions
>IGHG2*01
                                    (SEQ ID NO: 323)
STKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERK

CCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCK

VSNKGLPAPIEKTISKTKGQPREPQVYTLPPSREEMTKNQVSLTCLVKGF

YPSDIAVEWESNGQPENNYKTTPPMLDSDGSFFLYSKLTVDKSRWQQGNV

FSCSVMHEALHNHYTQKSLSLSP
```

```
>IGHG2*02
                                             (SEQ ID NO: 324)
STKGPSVFPLAPCSRSTSESTAALGCLVKDYFPEPVTVSWNSGALTSGVH

TFPAVLQSSGLYSLSSVVTVTSSNFGTQTYTCNVDHKPSNTKVDKTVERK

CCVECPPCPAPPVAGPSVFLFPPKPKDTLMISRTPEVTCVVVDVSHEDPE

VQFNWYVDGMEVHNAKTKPREEQFNSTFRVVSVLTVVHQDWLNGKEYKCK

VSNKGLPAPIEKTISKTKGQPREPQVYTLPPSREEMTKNQVSLTCLVKGF

YPSDIAVEWESNGQPENNYKTTPPMLDSDGSFFLYSKLTVDKSRWQQGNV

FSCSVMHEALHNHYTQKSLSLSP

>IGHG2*04
                                             (SEQ ID NO: 325)
STKGPSVFPLAPCSRSTSESTAALGCLVKDYFPEPVTVSWNSGALTSGVH

TFPAVLQSSGLYSLSSVVTVPSSSLGTQTYTCNVDHKPSNTKVDKTVERK

CCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCK

VSNKGLPAPIEKTISKTKGQPREPQVYTLPPSREEMTKNQVSLTCLVKGF

YPSDIAVEWESNGQPENNYKTTPPMLDSDGSFFLYSKLTVDKSRWQQGNV

FSCSVMHEALHNHYTQKSLSLSP

>IGHG2*06
                                             (SEQ ID NO: 326)
STKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERK

CCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCK

VSNKGLPAPIEKTISKTKGQPREPQVYTLPPSREEMTKNQVSLTCLVKGF

YPSDISVEWESNGQPENNYKTTPPMLDSDGSFFLYSKLTVDKSRWQQGNV

FSCSVMHEALHNHYTQKSLSLSP
```

In an embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of SEQ ID NO: 11; an HCDR2 comprising an amino acid sequence that differs by no more than 1, 2, or 3 amino acid residues from, or has at least 85, 90, 95, 99 or 100% homology with, the amino acid sequence of SEQ ID NO: 12; or an HCDR3 comprising an amino acid sequence that differs by no more than 1, 2, or 3 amino acid residues from, or has at least 85, 90, 95, 99 or 100% homology with, the amino acid sequence of SEQ ID NO: 13, or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of SEQ ID NO: 280; an LCDR2 comprising an amino acid sequence that differs by no more than 1, 2, or 3 amino acid residues from, or has at least 85, 90, 95, 99 or 100% homology with, the amino acid sequence of the SEQ ID NO: 285; or an LCDR3 comprising an amino acid sequence that differs by no more than 1, 2, or 3 amino acid residues from, or has at least 85, 90, 95, 99 or 100% homology with, the amino acid sequence of SEQ ID NO: 16.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises: an HCDR1 comprising the amino acid sequence of SEQ ID NO: 11; an HCDR2 comprising the amino acid sequence of SEQ ID NO: 12; and an HCDR3 comprising the amino acid sequence of SEQ ID NO: 13, and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of the LCDR1 of SEQ ID NO: 280; an LCDR2 comprising the amino acid sequence of SEQ ID NO: 285; or an LCDR3 comprising the amino acid sequence of SEQ ID NO: 16.

In an embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of SEQ ID NO: 17; an HCDR2 comprising an amino acid sequence that differs by no more than 1, 2, or 3 amino acid residues from, or has at least 85, 90, 95, 99 or 100% homology with, the amino acid sequence of SEQ ID NO: 282; or an HCDR3 comprising an amino acid sequence that differs by no more than 1, 2, or 3 amino acid residues from, or has at least 85, 90, 95, 99 or 100% homology with, the amino acid sequence of SEQ ID NO: 13, or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of SEQ ID NO: 280; an LCDR2 comprising an amino acid sequence that differs by no more than 1, 2, or 3 amino acid residues from, or has at least 85, 90, 95, 99 or 100% homology with, the amino acid sequence of the SEQ ID NO: 285; or an LCDR3 comprising an amino acid sequence that differs by no more than 1, 2, or 3 amino acid residues from, or has at least 85, 90, 95, 99 or 100% homology with, the amino acid sequence of SEQ ID NO: 16.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises: an HCDR1 comprising the amino acid sequence of SEQ ID NO: 17; an HCDR2 comprising the amino acid sequence of SEQ ID NO: 282; and an HCDR3 comprising the amino acid sequence of SEQ ID NO: 13, and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of SEQ ID NO: 280; an LCDR2 comprising the amino acid sequence of SEQ ID NO: 285; or an LCDR3 comprising the amino acid sequence of SEQ ID NO: 16.

In an embodiment, the antibody molecule comprises a VH comprising the amino acid sequence of SEQ ID NO: 296. In an embodiment, the antibody molecule comprises a VL comprising the amino acid sequence of SEQ ID NO: 286. In an embodiment, the antibody molecule comprises a VH comprising the amino acid sequence of SEQ ID NO: 296 and a VL comprising the amino acid sequence of SEQ ID NO: 286.

In an embodiment, the antibody molecule comprises a VH encoded by a nucleic acid comprising the nucleotide sequence of SEQ ID NO: 313. In an embodiment, the antibody molecule comprises a VL encoded by a nucleic acid comprising the nucleotide sequence of SEQ ID NO: 306. In an embodiment, the antibody molecule comprises a VH encoded by a nucleic acid comprising the nucleotide sequence of SEQ ID NO: 313 and a VL encoded by a nucleic acid comprising the nucleotide sequence of SEQ ID NO: 306.

In an embodiment, the antibody molecule further comprises a heavy constant region of IgG2, e.g., any of SEQ ID NOS: 323-326.

In an embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of SEQ ID NO: 11; an HCDR2 comprising an amino acid sequence that differs by no more than 1, 2, or 3 amino acid residues from, or has at least 85, 90, 95, 99 or 100% homology with, the amino acid sequence of SEQ ID NO: 12; or an HCDR3 comprising an amino acid sequence that differs by no more than 1, 2, or 3 amino acid residues from, or has at least 85, 90, 95, 99 or 100% homology with, the amino acid sequence of SEQ ID NO: 13, or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of SEQ ID NO: 280; an LCDR2 comprising an amino acid sequence that differs by no more than 1, 2, or 3 amino acid residues from, or has at least 85, 90, 95, 99 or 100% homology with, the amino acid sequence of the SEQ ID NO: 285; or an LCDR3 comprising an amino acid sequence that differs by no more than 1, 2, or 3 amino acid residues from, or has at least 85, 90, 95, 99 or 100% homology with, the amino acid sequence of SEQ ID NO: 16.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises: an HCDR1 comprising the amino acid sequence of SEQ ID NO: 11; an HCDR2 comprising the amino acid sequence of SEQ ID NO: 12; and an HCDR3 comprising the amino acid sequence of SEQ ID NO: 13, and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of the LCDR1 of SEQ ID NO: 280; an LCDR2 comprising the amino acid sequence of SEQ ID NO: 285; or an LCDR3 comprising the amino acid sequence of SEQ ID NO: 16.

In an embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of SEQ ID NO: 17; an HCDR2 comprising an amino acid sequence that differs by no more than 1, 2, or 3 amino acid residues from, or has at least 85, 90, 95, 99 or 100% homology with, the amino acid sequence of SEQ ID NO: 282; or an HCDR3 comprising an amino acid sequence that differs by no more than 1, 2, or 3 amino acid residues from, or has at least 85, 90, 95, 99 or 100% homology with, the amino acid sequence of SEQ ID NO: 13, or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of SEQ ID NO: 280; an LCDR2 comprising an amino acid sequence that differs by no more than 1, 2, or 3 amino acid residues from, or has at least 85, 90, 95, 99 or 100% homology with, the amino acid sequence of the SEQ ID NO: 285; or an LCDR3 comprising an amino acid sequence that differs by no more than 1, 2, or 3 amino acid residues from, or has at least 85, 90, 95, 99 or 100% homology with, the amino acid sequence of SEQ ID NO: 16.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises: an HCDR1 comprising the amino acid sequence of SEQ ID NO: 17; an HCDR2 comprising the amino acid sequence of SEQ ID NO: 282; and an HCDR3 comprising the amino acid sequence of SEQ ID NO: 13, and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of SEQ ID NO: 280; an LCDR2 comprising the amino acid sequence of SEQ ID NO: 285; or an LCDR3 comprising the amino acid sequence of SEQ ID NO: 16.

In an embodiment, the antibody molecule comprises a VH comprising the amino acid sequence of SEQ ID NO: 289. In an embodiment, the antibody molecule comprises a VL comprising the amino acid sequence of SEQ ID NO: 286. In an embodiment, the antibody molecule comprises a VH comprising the amino acid sequence of SEQ ID NO: 289 and a VL comprising the amino acid sequence of SEQ ID NO: 286.

In an embodiment, the antibody molecule comprises a VH encoded by a nucleic acid comprising the nucleotide sequence of SEQ ID NO: 308. In an embodiment, the antibody molecule comprises a VL encoded by a nucleic acid comprising the nucleotide sequence of SEQ ID NO: 305. In an embodiment, the antibody molecule comprises a VH encoded by a nucleic acid comprising the nucleotide sequence of SEQ ID NO: 308 and a VL encoded by a nucleic acid comprising the nucleotide sequence of SEQ ID NO: 306.

In an embodiment, the antibody molecule further comprises a heavy constant region of IgG2, e.g., any of SEQ ID NOS: 323-326.

In an embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of SEQ ID NO: 11; an HCDR2 comprising an amino acid sequence that differs by no more than 1, 2, or 3 amino acid residues from, or has at least 85, 90, 95, 99 or 100% homology with, the amino acid sequence of SEQ ID NO: 12; or an HCDR3 comprising an amino acid sequence that differs by no more than 1, 2, or 3 amino acid residues from, or has at least 85, 90, 95, 99 or 100% homology with, the amino acid sequence of SEQ ID NO: 13, or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of SEQ ID NO: 280; an LCDR2 comprising an amino acid sequence that differs by no more than 1, 2, or 3 amino acid residues from, or has at least 85, 90, 95, 99 or 100% homology with, the amino acid sequence of the SEQ ID NO: 281; or an LCDR3 comprising an amino acid sequence that differs by no more than 1, 2, or 3 amino acid residues from, or has at least 85, 90, 95, 99 or 100% homology with, the amino acid sequence of SEQ ID NO: 16.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises: an HCDR1 comprising the amino acid sequence of SEQ ID NO: 11; an HCDR2 comprising the amino acid sequence of SEQ ID NO: 12; and an HCDR3 comprising the amino acid sequence of SEQ ID NO: 13, and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of the LCDR1 of SEQ ID NO: 280; an LCDR2 comprising the amino acid sequence of SEQ ID NO: 281; or an LCDR3 comprising the amino acid sequence of SEQ ID NO: 16.

In an embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of SEQ ID NO: 17; an HCDR2 comprising an amino acid sequence that differs by no more than 1, 2, or 3 amino acid residues from, or has at least 85, 90, 95, 99 or 100% homology with, the amino acid sequence of SEQ ID NO: 282; or an HCDR3 comprising an amino acid sequence that differs by no more than 1, 2, or 3 amino acid residues from, or has at least 85, 90, 95, 99 or 100% homology with, the amino acid sequence of SEQ ID NO: 13, or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of SEQ ID NO: 280; an LCDR2 comprising an amino acid sequence that differs by no more than 1, 2, or 3 amino acid residues from, or has at least 85, 90, 95, 99 or 100% homology with, the amino acid sequence of the SEQ ID NO: 281; or an LCDR3 comprising an amino acid sequence that differs by no more than 1, 2, or 3 amino acid residues from, or has at least 85, 90, 95, 99 or 100% homology with, the amino acid sequence of SEQ ID NO: 16.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises: an HCDR1 comprising the amino acid sequence of SEQ ID NO: 17; an HCDR2 comprising the amino acid sequence of SEQ ID NO: 282; and an HCDR3 comprising the amino acid sequence of SEQ ID NO: 13, and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of SEQ ID NO: 280; an LCDR2 comprising the amino acid sequence of SEQ ID NO: 281; or an LCDR3 comprising the amino acid sequence of SEQ ID NO: 16.

In an embodiment, the antibody molecule comprises a VH comprising the amino acid sequence of SEQ ID NO: 289. In an embodiment, the antibody molecule comprises a VL comprising the amino acid sequence of SEQ ID NO: 284. In an embodiment, the antibody molecule comprises a VH comprising the amino acid sequence of SEQ ID NO: 289 and a VL comprising the amino acid sequence of SEQ ID NO: 284.

In an embodiment, the antibody molecule comprises a VH encoded by a nucleic acid comprising the nucleotide sequence of SEQ ID NO: 308. In an embodiment, the antibody molecule comprises a VL encoded by a nucleic acid comprising the nucleotide sequence of SEQ ID NO: 305. In an embodiment, the antibody molecule comprises a VH encoded by a nucleic acid comprising the nucleotide sequence of SEQ ID NO: 308 and a VL encoded by a nucleic acid comprising the nucleotide sequence of SEQ ID NO: 305.

In an embodiment, the antibody molecule further comprises a heavy constant region of IgG2, e.g., any of SEQ ID NOS: 323-326.

In an embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of SEQ ID NO: 93; an HCDR2 comprising an amino acid sequence that differs by no more than 1, 2, or 3 amino acid residues from, or has at least 85, 90, 95, 99 or 100% homology with, the amino acid sequence of SEQ ID NO: 94; or an HCDR3 comprising an amino acid sequence that differs by no more than 1, 2, or 3 amino acid residues from, or has at least 85, 90, 95, 99 or 100% homology with, the amino acid sequence of SEQ ID NO: 95, or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of the LCDR1 of SEQ ID NO: 96; an LCDR2 comprising an amino acid sequence that differs by no more than 1, 2, or 3 amino acid residues from, or has at least 85, 90, 95, 99 or 100% homology with, the amino acid sequence of the SEQ ID NO: 97; or an LCDR3 comprising an amino acid sequence that differs by no more than 1, 2, or 3 amino acid residues from, or has at least 85, 90, 95, 99 or 100% homology with, the amino acid sequence of SEQ ID NO: 98.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises: an HCDR1 comprising the amino acid sequence of SEQ ID NO: 93; an HCDR2 comprising the amino acid sequence of SEQ ID NO: 94; and an HCDR3 comprising the amino acid sequence of SEQ ID NO: 95, and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of the LCDR1 of SEQ ID NO: 96; an LCDR2 comprising the amino acid sequence of SEQ ID NO: 97; or an LCDR3 comprising the amino acid sequence of SEQ ID NO: 98.

In an embodiment, the antibody molecule comprises one or both of:

(i) a heavy chain variable region (VH), wherein the heavy chain variable region comprises three heavy chain complementarity determining regions (HCDR1, HCDR2, and HCDR3), wherein the heavy chain variable region comprises one, two, or all of the following: an HCDR1 comprising an amino acid sequence that differs by no more than 1, 2, or 3 amino acid residues from, or has at least 85, 90, 95, 99 or 100% homology with, the amino acid sequence of SEQ ID NO: 99; an HCDR2 comprising an amino acid sequence that differs by no more than 1, 2, or 3 amino acid residues from, or has at least 85, 90, 95, 99 or 100% homology with, the amino acid sequence of SEQ ID NO: 273; or an HCDR3 comprising an amino acid sequence that differs by no more than 1, 2, or 3 amino acid residues from, or has at least 85, 90, 95, 99 or 100% homology with, the amino acid sequence of SEQ ID NO: 95, or (ii) a light chain variable region (VL), wherein the light chain variable region comprises three light chain complementarity determining regions (LCDR1, LCDR2, and LCDR3), wherein the light chain variable region comprises one, two, or all of the following: an LCDR1 comprising an amino acid sequence that differs by no more than 1, 2, or 3 amino acid residues from, or has at least 85, 90, 95, 99 or 100% homology with, the amino acid sequence of SEQ ID NO: 96; an LCDR2 comprising an amino acid sequence that differs by no more than 1, 2, or 3 amino acid residues from, or has at least 85, 90, 95, 99 or 100% homology with, the amino acid sequence of the SEQ ID NO: 97; or an LCDR3 comprising an amino acid sequence that differs by no more than 1, 2, or 3 amino acid residues from, or has at least 85, 90, 95, 99 or 100% homology with, the amino acid sequence of SEQ ID NO: 98.

In an embodiment, the antibody molecule comprises:

(i) a heavy chain variable region (VH), wherein the heavy chain variable region comprises three heavy chain complementarity determining regions (HCDR1, HCDR2, and HCDR3), wherein the heavy chain variable region comprises: an HCDR1 comprising the amino acid sequence of SEQ ID NO: 99; an HCDR2 comprising the amino acid sequence of SEQ ID NO: 273; and an HCDR3 comprising the amino acid sequence of SEQ ID NO: 95, and (ii) a light chain variable region (VL), wherein the light chain variable region comprises three light chain complementarity determining regions (LCDR1, LCDR2, and LCDR3), wherein the light chain variable region comprises: an LCDR1 comprising the amino acid sequence of SEQ ID NO: 96; an LCDR2 comprising the amino acid sequence of SEQ ID NO: 97; or an LCDR3 comprising the amino acid sequence of SEQ ID NO: 98.

In an embodiment, the antibody molecule comprises a VH comprising the amino acid sequence of SEQ ID NO: 225. In an embodiment, the antibody molecule comprises a VL comprising the amino acid sequence of SEQ ID NO: 229. In an embodiment, the antibody molecule comprises a VH comprising the amino acid sequence of SEQ ID NO: 225 and a VL comprising the amino acid sequence of SEQ ID NO: 229.

In an embodiment, the antibody molecule comprises a VH encoded by a nucleic acid comprising the nucleotide sequence of SEQ ID NO: 299. In an embodiment, the antibody molecule comprises a VL encoded by a nucleic acid comprising the nucleotide sequence of SEQ ID NO: 300. In an embodiment, the antibody molecule comprises a VH encoded by a nucleic acid comprising the nucleotide sequence of SEQ ID NO: 299 and a VL encoded by a nucleic acid comprising the nucleotide sequence of SEQ ID NO: 300.

In an embodiment, the antibody molecule further comprises a heavy chain constant region of IgG1, e.g., any of SEQ ID NOS: 320-322.

In an embodiment, the antibody molecule described herein has one or more (e.g., 2, 3, 4, 5, or all) of the following properties: (a) is a humanized antibody molecule; (b) binds to human APRIL at an $EC_{50}$ of 60 pM or less, as determined by ELISA; (c) inhibits binding of human APRIL to TACI, e.g., in vitro, at an $IC_{50}$ of 0.5 nM or less; (d) inhibits binding of human APRIL to BCMI, e.g., in vitro, at an $IC_{50}$ of 0.6 nM or less; (e) is an IgG2κ; or (f) has an Fc region engineered to reduce complement activation. In an embodiment, the antibody molecule comprises one or more (e.g., 2, 3, 4, 5, or all) CDRs, one or both of heavy chain variable region or light chain variable regions, or one or both of heavy chain or light chain, of any of antibody molecules 2419-1406, 2419-0205, or 2419-0206. In an embodiment, the antibody molecule is suitable for use in treating a disorder in kidney, e.g., IgA nephropathy. In another embodiment, the antibody molecule is suitable for use in treating a caner, e.g., a multiple myeloma.

In an embodiment, the antibody molecule described herein has one or more (e.g., 2, 3, 4, 5, or all) of the following properties: (a) is a humanized antibody molecule; (b) binds to human APRIL at an $EC_{50}$ of 50 pM or less, as determined by ELISA; (c) inhibits binding of human APRIL to TACI, e.g., in vitro, at an $IC_{50}$ of 0.3 nM or less; (d) inhibits binding of human APRIL to BCMA, e.g., in vitro, at an $IC_{50}$ of 0.2 nM or less; (e) is an IgG1κ; or (f) has higher BCMA neutralization activity, e.g., has an $IC_{50}$ of 0.1 nM or less. In an embodiment, the antibody molecule comprises one or more (e.g., 2, 3, 4, 5, or all) CDRs, one or both of heavy chain variable region or light chain variable regions, or one or both of heavy chain or light chain, of antibody molecule 4035-062. In an embodiment, the antibody molecule is suitable for use in treating a cancer or an autoimmune disorder.

The antibody molecules described herein can have several advantageous properties. For example, the antibody molecules can be used to effectively treat, prevent or diagnose a disorder associated with APRIL, e.g., a disorder described herein, e.g., IgA nephropathy.

In an embodiment, the antibody molecule is capable of binding, or substantially binding, to human APRIL and mouse APRIL. In an embodiment, the antibody molecule is capable of binding, or substantially binding, to human APRIL, but is not capable of binding, or substantially binding to mouse APRIL. In an embodiment, the antibody molecule binds to APRIL with high affinity, e.g., with a dissociation constant ($K_D$) of less than about 100 nM, typically about 10 nM, and more typically, about 10-0.001 nM, about 10-0.01 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM. In an embodiment, the antibody molecule binds to APRIL with a $K_{off}$ slower than $1 \times 10^{-4}$, $5 \times 10^{-5}$, or $1 \times 10^{-5}$ $s^{-1}$. In an embodiment, the antibody molecule binds to APRIL with a $K_{on}$ faster than $1 \times 10^{4}$, $5 \times 10^{4}$, $1 \times 10^{5}$, or $5 \times 10^{5}$ $M^{-1}s^{-1}$.

In an embodiment, the antibody molecule is capable of inhibiting, or substantially inhibiting, binding of human APRIL to TACI. In an embodiment, the antibody molecule is capable of inhibiting, or substantially inhibiting, binding of human APRIL to TACI. In an embodiment, the antibody molecule is capable of inhibiting, or substantially inhibiting, binding of human APRIL to BCMA. In an embodiment, the antibody molecule is capable of inhibiting, or substantially inhibiting, binding of human APRIL to TACI and BCMA. In an embodiment, the antibody molecule is capable of inhibiting, or substantially inhibiting, binding of human APRIL to TACI, but is not capable of inhibiting, or substantially inhibiting, binding of human APRIL to BCMA. In an embodiment, the antibody molecule is capable of inhibiting, or substantially inhibiting, binding of human APRIL to BCMA, but is not capable of inhibiting, or substantially inhibiting, binding of human APRIL to TACI.

In an embodiment, the antibody molecule inhibits binding of human APRIL to human TACI by 50% or more, e.g., 60% or more, 70% or more, 80% or more, 85% or more, 90% or more, 95% or more, 96% or more, 97% or more, 98% or more, 99% or more, or 100%, as determined by a method described herein (e.g., normalized to the no antibody control).

In an embodiment, the antibody molecule inhibits binding of human APRIL to human BCMA by 30% or more, e.g., 40% or more, 50% or more, 60% or more, 70% or more, 80% or more, 85% or more, 90% or more, 95% or more, 96% or more, 97% or more, 98% or more, 99% or more, or 100%, as determined by a method described herein (e.g., normalized to the no antibody control).

In an embodiment, the antibody molecule does not substantially inhibit binding of human APRIL to human BCMA, e.g., inhibits binding of human APRIL to human BCMA by less than 10%, as determined by a method described herein (e.g., normalized to the no antibody control).

In an embodiment, the antibody molecule binds to a linear or conformational epitope on APRIL. In an embodiment, the antibody molecule binds to an epitope conserved between human APRIL and mouse APRIL. In an embodiment, the antibody molecule binds to an epitope described herein. In an embodiment, the antibody molecule binds, or substantially binds, to the same, similar, or overlapping epitope on APRIL, as a second antibody molecule (e.g., a monoclonal antibody described in Table 1 or 5). In an embodiment, the antibody molecule competes with a second antibody molecule (e.g., a monoclonal antibody described in Table 1 or 5) for binding to APRIL.

In an embodiment, the antibody molecule binds, or substantially binds, one or more, e.g., 2, 3, 4, 5, 6, 7, 8, 9, 10, 11, 12, 13, 14, 15, 16, 17, 18, 19, 20, 21, 22, 23, 24, 25, or more, residues within a region of APRIL as defined in Table 3. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, 18, 19, 20, 21, 22, 23, 24, 25, or all of the human APRIL residues from Table 3. In an embodiment, the antibody molecule binds, or substantially binds, to an epitope that overlaps an epitope that comprises or consists of all of the human APRIL residues from Table 3. In an embodiment, the antibody molecule binds, or substantially binds, to an epitope that comprises APRIL residues from two monomers, e.g., one or more residues from monomer A and monomer B as shown in Table 3.

In an embodiment, the antibody molecule binds, or substantially binds, one or more, e.g., 2, 3, 4, 5, 6, 7, 8, 9, 10, or more, residues within a region of APRIL as defined in Table 4. In an embodiment, the antibody molecule binds, or substantially binds, to an epitope that comprises or consists of one or more, e.g., 2, 3, 4, 5, 6, 7, 8, 9, 10, or all of the human APRIL residues from Table 4. In an embodiment, the antibody molecule binds, or substantially binds, to an epitope that overlaps an epitope that comprises or consists of all of the human APRIL residues from Table 4. In an embodiment, the antibody molecule binds, or substantially binds, to an epitope that comprises one or more APRIL residues from the C-D loop (e.g., the loop connecting β-sheets C and D), the G-H loop (e.g., the loop connecting β-sheets G and H), or both.

In an embodiment, the antibody molecule binds, or substantially binds, to one or more (e.g., 2, 3, 4, 5, 6, 7, 8, 9, or all) residues of human APRIL from positions 105-114 and/or one or more (e.g., 2, 3, 4, 5, 6, 7, 8, 9, or all) residues of mouse APRIL from positions 96-105.

In an embodiment, the antibody molecule binds, or substantially binds, one or more, e.g., 2, 3, 4, 5, 6, 7, 8, 9, 10, 11, 12, 13, 14, 15, 16, 17, or more, residues within a region of APRIL as defined in Table 7. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, or all of the human APRIL residues from Table 7. In an embodiment, the antibody molecule binds, or substantially binds, to an epitope that overlaps an epitope that comprises or consists of all of the human APRIL residues from Table 7.

In an embodiment, the antibody molecule binds, or substantially binds, one or more, e.g., 2, 3, 4, 5, 6, 7, 8, 9, 10, 11, 12, 13, 14, 15, 16, 17, 18, 19, 20, 21, 22, 23, 24, 25, or more, residues within a region of APRIL as defined in Table 8. In an embodiment, the antibody molecule binds, or substantially binds, to an epitope that comprises or consists of one or more, e.g., 2, 3, 4, 5, 6, 7, 8, 9, 10, 11, 12, 13, 14, 15, 16, 17, 18, 19, 20, 21, 22, 23, 24, 25, or all of the human APRIL residues from Table 8. In an embodiment, the antibody molecule binds, or substantially binds, to an epitope that overlaps an epitope that comprises or consists of all of the human APRIL residues from Table 8.

In an embodiment, the epitope is a conformational epitope.

In an embodiment, the antibody molecule does not bind, or does not substantially bind, to one, two or all of Asp129, Arg233, or His203 of human APRIL.

In an embodiment, binding of the antibody molecule to APRIL (e.g., human APRIL) inhibits, or substantially inhibits, the binding of the CRD2 domain of TACI (e.g., human TACI) to APRIL (e.g., human APRIL). In another embodiment, binding of the antibody molecule to human APRIL, inhibits, or substantially inhibits, the binding of human TACI, to one or more, e.g., 2, 3, 4, 5, 6, 7, 8, 9, 10, 11, 12, 13, 14, 15, 16, 17, 18, 19, 20, 21, 22, 23, 24, 25, or all of the APRIL residues from Table 3. In yet another embodiment, binding of the antibody molecule to human APRIL, inhibits, or substantially inhibits, the binding of human TACI, to one or more, e.g., 2, 3, 4, 5, 6, 7, 8, 9, 10, or all of the human APRIL residues from Table 4. In still another embodiment, binding of the antibody molecule to human APRIL, inhibits, or substantially inhibits, the binding of human TACI, to one or more, e.g., 2, 3, 4, 5, 6, 7, 8, 9, 10, 11, 12, 13, 14, 15, 16, 17, or all of the human APRIL residues from Table 7. In still another embodiment, binding of the antibody molecule to human APRIL, inhibits, or substantially inhibits, the binding of human TACI, to one or more, e.g., 2, 3, 4, 5, 6, 7, 8, 9, 10, 11, 12, 13, 14, 15, 16, 17, 18, 19, 20, 21, 22, 23, 24, 25, or all of the human APRIL residues from Table 8.

Animal Models

The antibody molecules described herein can be evaluated in vivo, e.g., using various animal models. For example, an animal model can be used to test the efficacy of an antibody molecule described herein in inhibiting APRIL and/or in treating or preventing a disorder described herein, e.g., IgA nephropathy. Animal models can also be used, e.g., to investigate for side effects, measure concentrations of antibody molecules in situ, demonstrate correlations between an APRIL function and a disorder described herein (e.g., IgA nephropathy).

Exemplary animal models for IgA nephropathy that can be used for evaluating an antibody molecule described herein include, but are not limited to, a ddY mouse model for spontaneous IgA nephritis (Imai et al. *Kidney Int.* 1985; 27(5):756-761); a mouse model utilizing inert proteins or a common viral pathogen as the inciting antigen (Emancipator et al. *Curr. Protoc. Immunol.* 2001 May; Chapter 15: Unit 15.11), a rat model by noninfectious protein antigens (Emancipator et al. *Curr. Protoc. Immunol.* 2001 May; Chapter 15: Unit 15.11); a chronic mouse model of IgA immune-complex-associated nephropathy (Montinaro et al. *Nephrol. Dial. Transplant.* 1995; 10(11): 2035-2042); the Gene M712T mouse as a model for human glomerulopathy (Kakani et al. *Am. J. Pathol.* 2012; 180(4):1431-1440); a mouse IgA nephropathy model with the MBP-20-peptide fusion protein (Zhang et al. *Anat. Rec. (Hoboken).* 2010; 293(10): 1729-1737); and a mouse model for IgA immune complex nephritis (Rifai et al. *J Exp Med.* 1979; 150(5):1161-1173). Other animal models for IgA nephropathy are described, e.g., in Tomino et al. *J. Nephrol.* 2008; 21(4):463-467; Endo *Ren. Fail.* 1997; 19(3):347-371; and Rifai *Kidney Int.* 1987; 31(1):1-7.

Exemplary animal models for other disorders described herein are also known in the art. Exemplary types of animals that can be used to evaluate the antibody molecules described herein include, but are not limited to, mice, rats, rabbits, guinea pigs, and monkeys.

Pharmaceutical Compositions and Kits

In some aspects, this disclosure provides compositions, e.g., pharmaceutically acceptable compositions, which include an antibody molecule described herein (e.g., a humanized antibody molecule described herein), formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion). In certain embodiments, less than about 5%, e.g., less than about 4%, 3%, 2%, or 1% of the antibody molecules in the pharmaceutical composition are present as aggregates. In other embodiments, at least about 95%, e.g., at least about 96%, 97%, 98%, 98.5%, 99%, 99.5%, 99.8%, or more of the antibody molecules in the pharmaceutical composition are present as monomers. In some embodiments, the level of aggregates or monomers is determined by chromatography, e.g., high performance size exclusion chromatography (HP-SEC).

The compositions set out herein may be in a variety of forms. These include, for example, liquid, semi-solid and solid dosage forms, such as liquid solutions (e.g., injectable and infusible solutions), dispersions or suspensions, liposomes, and suppositories. A suitable form depends on the intended mode of administration and therapeutic application. Typical suitable compositions are in the form of injectable or infusible solutions. One suitable mode of administration is parenteral (e.g., intravenous, subcutaneous, intraperitoneal, intramuscular). In some embodiments, the antibody molecule is administered by intravenous infusion or injection. In certain embodiments, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules described herein can be administered by a variety of methods. Several are known in the art, and for many therapeutic, prophylactic, or diagnostic applications, an appropriate route/mode of administration is intravenous injection or infusion. For example, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The antibody molecule (and other ingredients, if desired) may also be enclosed in a hard or soft shell gelatin capsule, compressed into tablets, or incorporated directly into the subject's diet. For oral therapeutic administration, the antibody molecule may be incorporated with excipients and used in the form of ingestible tablets, buccal tablets, troches, capsules, elixirs, suspensions, syrups, wafers, and the like. To administer an antibody molecule by other than parenteral administration, it may be necessary to coat the compound with, or co-administer the compound with, a material to prevent its inactivation. Therapeutic, prophylactic, or diagnostic compositions can also be administered with medical devices, and several are known in the art.

Dosage regimens are adjusted to provide the desired response (e.g., a therapeutic, prophylactic, or diagnostic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the antibody molecule and the particular therapeutic, prophylactic, or diagnostic effect to be achieved, and (b) the limitations inherent in the art of compounding such an antibody molecule for the treatment of sensitivity in individuals.

An exemplary, non-limiting range for a therapeutically, prophylactically, or diagnostically effective amount of an antibody molecule is about 0.1-50 mg/kg body weight of a subject, e.g., about 0.1-30 mg/kg, e.g., about 1-30, 1-15, 1-10, 1-5, 5-10, or 1-3 mg/kg, e.g., about 1, 2, 3, 4, 5, 6, 7, 8, 9, 10, 15, 20, 30, 40, or 50 mg/kg. The antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, e.g., about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed compositions.

The pharmaceutical compositions herein may include a "therapeutically effective amount," "prophylactically effective amount," or "diagnostically effectively amount" of an antibody molecule described herein.

A "therapeutically effective amount" refers to an amount effective, at dosages and for periods of time necessary, to achieve the desired therapeutic result. A therapeutically effective amount of the antibody molecule may vary according to factors such as the disease state, age, sex, and weight of the individual, and the ability of the antibody or antibody portion to elicit a desired response in the individual. A therapeutically effective amount is also one in which any toxic or detrimental effect of the antibody molecule is outweighed by the therapeutically beneficial effects. A "therapeutically effective dosage" typically inhibits a measurable parameter by at least about 20%, e.g., by at least about 40%, by at least about 60%, or by at least about 80% relative to untreated subjects. The measurable parameter may be, e.g., hematuria, colored urine, foamy urine, pain, swelling (edema) in the hands and feet, or high blood pressure. The ability of an antibody molecule to inhibit a measurable parameter can be evaluated in an animal model system predictive of efficacy in treating or preventing IgA nephropathy. Alternatively, this property of a composition can be evaluated by examining the ability of the antibody molecule to inhibit APRIL, e.g., by an in vitro assay.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A "diagnostically effective amount" refers to an amount effective, at dosages and for periods of time necessary, to achieve the desired diagnostic result. Typically, a diagnostically effective amount is one in which a disorder, e.g., a disorder described herein, e.g., IgA nephropathy, can be diagnosed in vitro, ex vivo, or in vivo.

Also within this disclosure is a kit that comprises an antibody molecule, described herein. The kit can include one or more other elements including: instructions for use; other reagents, e.g., a label, a therapeutic agent, or an agent useful for chelating, or otherwise coupling, an antibody molecule to a label or therapeutic agent, or a radioprotective composition; devices or other materials for preparing the antibody molecule for administration; pharmaceutically acceptable carriers; and devices or other materials for administration to a subject.

Nucleic Acids

The present disclosure also features nucleic acids comprising nucleotide sequences that encode the antibody molecules (e.g., heavy and light chain variable regions and CDRs of the antibody molecules), as described herein.

For example, the present disclosure features a first and second nucleic acid encoding heavy and light chain variable regions, respectively, of an antibody molecule chosen from one or more of the antibody molecules disclosed herein, e.g., an antibody molecule of Table 1 or 5, or a portion of an antibody molecule, e.g., the variable regions of Table 2. The nucleic acid can comprise a nucleotide sequence encoding any one of the amino acid sequences in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein).

In certain embodiments, the nucleic acid can comprise a nucleotide sequence encoding at least one, two, or three CDRs from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding at least one, two, or three CDRs from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding at least one, two, three, four, five, or six CDRs from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs from a heavy chain variable region having the nucleotide sequence as set forth in Table 2, a sequence substantially homologous thereto (e.g., a sequence at least about 85%, 90%, 95%, 99% or more identical thereto, and/or capable of hybridizing under the stringency conditions described herein). In some embodiments, the nucleic acid can comprise a nucleotide sequence encoding at least one, two, or three CDRs from a light chain variable region having the nucleotide sequence as set forth in Table 2, or a sequence substantially homologous thereto (e.g., a sequence at least about 85%, 90%, 95%, 99% or more identical thereto, and/or capable of hybridizing under the stringency conditions described herein). In certain embodiments, the nucleic acid can comprise a nucleotide sequence encoding at least one, two, three, four, five, or six CDRs from heavy and light chain variable regions having the nucleotide sequence as set forth in Table 2, or a sequence substantially homologous thereto (e.g., a sequence at least about 85%, 90%, 95%, 99% or more identical thereto, and/or capable of hybridizing under the stringency conditions described herein).

In certain embodiments, the nucleic acid comprises a nucleotide sequence as set forth in Table 2 or a sequence substantially homologous thereto (e.g., a sequence at least about 85%, 90%, 95%, 99% or more identical thereto, and/or capable of hybridizing under the stringency conditions described herein). In some embodiments, the nucleic acid comprises a portion of a nucleotide sequence as set forth in Table 2 or a sequence substantially homologous thereto (e.g., a sequence at least about 85%, 90%, 95%, 99% or more identical thereto, and/or capable of hybridizing under the stringency conditions described herein). The portion may encode, for example, a variable region (e.g., VH or VL); one, two, or three or more CDRs; or one, two, three, or four or more framework regions.

The nucleic acids disclosed herein include deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

In some aspects, the application features host cells and vectors containing the nucleic acids described herein. The nucleic acids may be present in a single vector or separate vectors present in the same host cell or separate host cell, as described in more detail below.

Vectors

Further provided herein are vectors that comprise nucleotide sequences encoding an antibody molecule described herein.

In an embodiment, the vector comprises a nucleotide encoding an antibody molecule described herein, e.g., as described in Table 1 or 5. In another embodiment, the vector comprises a nucleotide sequence described herein, e.g., in Table 2. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The present disclosure also provides cells (e.g., host cells) comprising a nucleic acid encoding an antibody molecule as described herein. For example, the host cells may comprise a nucleic acid molecule having a nucleotide sequence described in Table 2, a sequence substantially homologous thereto (e.g., a sequence at least about 85%, 90%, 95%, 99% or more identical thereto, and/or capable of hybridizing under the stringency conditions described herein), or a portion of one of said nucleic acids. Additionally, the host cells may comprise a nucleic acid molecule encoding an amino acid sequence of Table 1 or 5, a sequence substantially homologous thereto (e.g., a sequence at least about 80%, 85%, 90%, 95%, 99% or more identical thereto), or a portion of one of said sequences.

In some embodiments, the host cells are genetically engineered to comprise nucleic acids encoding the antibody molecule described herein.

In certain embodiments, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells. In an embodiment, the cell (e.g., host cell) is an isolated cell.

Uses of Antibody Molecules

The antibody molecules disclosed herein, as well as the pharmaceutical compositions disclosed herein, have in vitro, ex vivo, and in vivo therapeutic, prophylactic, and/or diagnostic utilities.

In an embodiment, the antibody molecule reduces (e.g., inhibits, blocks, or neutralizes) one or more biological activities of APRIL. For example, these antibodies molecules can be administered to cells in culture, in vitro or ex vivo, or to a subject, e.g., a human subject, e.g., in vivo, to reduce (e.g., inhibits, blocks, or neutralizes) one or more biological activities of APRIL. In an embodiment, the antibody molecule inhibits, or substantially inhibit, binding of APRIL, e.g., human APRIL, to TACI, BCMA, or both. Accordingly, in an aspect, the disclosure provides a method of treating, preventing, or diagnosing a disorder, e.g., a disorder described herein (e.g., IgA nephropathy), in a subject, comprising administering to the subject an antibody molecule described herein, such that the disorder is treated, prevented, or diagnosed. For example, the disclosure provides a method comprising contacting the antibody molecule described herein with cells in culture, e.g. in vitro or ex vivo, or administering the antibody molecule described herein to a subject, e.g., in vivo, to treat, prevent, or diagnose a disorder, e.g., a disorder associated with APRIL (e.g., IgA nephropathy).

As used herein, the term "subject" is intended to include human and non-human animals. In some embodiments, the subject is a human subject, e.g., a human patient having a disorder described herein (e.g., IgA nephropathy), or at risk of having a disorder described herein (e.g., IgA nephropathy). The term "non-human animals" includes mammals and non-mammals, such as non-human primates. In some embodiments, the subject is a human. The methods and compositions described herein are suitable for treating human patients a disorder described herein (e.g., IgA nephropathy). Patients having a disorder described herein (e.g., IgA nephropathy) include those who have developed a disorder described herein (e.g., IgA nephropathy) but are (at least temporarily) asymptomatic, patients who have exhibited a symptom of a disorder described herein (e.g., IgA nephropathy), or patients having a disorder related to or associated with a disorder described herein (e.g., IgA nephropathy).

Methods of Treating or Preventing Disorders

The antibody molecules described herein can be used to treat or prevent disorders associated with APRIL or symptoms thereof.

Exemplary disorders or conditions that can be associated with APRIL include, but are not limited to IgA nephropathy, diabetic nephropathy, cancer (e.g., hematological cancer (e.g., B-cell non-Hodgkin's lymphoma, chronic lymphocytic leukemia, Hodgkin's lymphoma, multiple myeloma, Waldenström macroglobulinemia, and lymphoplasmacytic lymphoma) or solid tumors (e.g., colorectal cancer, breast cancer (e.g., breast carcinoma), esophageal cancer (e.g., esophageal adenocarcinoma), brain cancer (e.g., glioblastoma), and kidney cancer (e.g., renal cell carcinoma)), immunoproliferative disorders (e.g., monoclonal IgA hypergammaglobulinemia), vasculitis (e.g., kidney vasculitis, Henoch-Schonlein purpura (IgA associated vasculitis), and post-streptococcal glomerulonephritis), autoimmune disorders (e.g., rheumatoid arthritis, systemic lupus erythematosus, linear IgA bullous disease/linear immunoglobulin A (IgA) dermatosis, and IgA-mediated epidermolysis bullosa acquisita), IgA pemphigus, celiac disease, and alcoholic cirrhosis. In an embodiment, the disorder is associated with aberrant expression of IgA. In an embodiment, the antibody molecule is used to treat a subject having a disorder described herein, or is at risk of developing a disorder described herein.

The antibody molecules described herein are typically administered at a frequency that keeps a therapeutically effective level of antibody molecules in the patient's system until the patient recovers. For example, the antibody molecules may be administered at a frequency that achieves a serum concentration sufficient for at least about 1, 2, 5, 10, 20, 30, or 40 antibody molecules to bind each APRIL molecule. In an embodiment, the antibody molecules are administered every 1, 2, 3, 4, 5, 6, or 7 days, every 1, 2, 3, 4, 5, or 6 weeks, or every 1, 2, 3, 4, 5, or 6 months.

Methods of administering various antibody molecules are known in the art and are described below. Suitable dosages of the antibody molecules used will depend on the age and weight of the subject and the particular drug used.

In an embodiment, the antibody molecule is administered to the subject (e.g., a human subject) intravenously. In an embodiment, the antibody molecule is administered to the subject at a dose between 0.1 mg/kg and 50 mg/kg, e.g., between 0.2 mg/kg and 25 mg/kg, between 0.5 mg/kg and 10 mg/kg, between 0.5 mg/kg and 5 mg/kg, between 0.5 mg/kg and 3 mg/kg, between 0.5 mg/kg and 2.5 mg/kg, between 0.5 mg/kg and 2 mg/kg, between 0.5 mg/kg and 1.5 mg/kg, between 0.5 mg/kg and 1 mg/kg, between 1 mg/kg and 1.5 mg/kg, between 1 mg/kg and 2 mg/kg, between 1 mg/kg and 2.5 mg/kg, between 1 mg/kg and 3 mg/kg, between 1 mg/kg and 2.5 mg/kg, or between 1 mg/kg and 5 mg/kg. In an embodiment, the antibody molecule is administered to the subject at a fixed dose between 10 mg and 1000 mg, e.g., between 10 mg and 500 mg, between 10 mg and 250 mg, between 10 mg and 150 mg, between 10 mg and 100 mg, between 10 mg and 50 mg, between 250 mg and 500 mg, between 150 mg and 500 mg, between 100 mg and 500 mg, between 50 mg and 500 mg, between 25 mg and 250 mg, between 50 mg and 150 mg, between 50 mg and 100 mg, between 100 mg and 150 mg. between 100 mg and 200 mg, or between 150 mg and 250 mg. In an embodiment, the antibody molecule is administered once a week, twice a week, once every two weeks, once every three weeks, once every four weeks, once every eight weeks, once a month, once every two months, or once every three months. In an embodiment, the antibody molecule is administered between 0.5 mg/kg and 3 mg/kg or between 50 mg and 150 mg, once a week, twice a week, once every two weeks, or once every four weeks.

The antibody molecules can be used by themselves or conjugated to a second agent, e.g., a bacterial agent, toxin, or protein, e.g., a second anti-APRIL antibody molecule. This method includes: administering the antibody molecule, alone or conjugated to a second agent, to a subject requiring such treatment. The antibody molecules can be used to deliver a variety of therapeutic agents, e.g., a toxin, or mixtures thereof.

IgA Nephropathy

IgA nephropathy (also known as Berger's disease, Berger disease, Berger's syndrome, Berger syndrome, IgA nephritis, IgAN, or synpharyngitic glomerulonephritis) is the most prevalent, chronic glomerular disease worldwide. Conservative epidemiological estimates cite a global incidence of approximately 5-50 cases/million (children) and 10-40 cases/million (adults). This incidence of disease presents a regional bias with a higher prevalence in Asia and the Americas, with a particularly higher disease burden in Japan and regions of China. Biopsy confirmed cases of IgA nephropathy in Japan are projected at approximately 350,000. In the US, this projection is approximately 100,000—as such, it is the most frequently diagnosed 1° glomerular disease in adults. While a relatively indolent disease, IgA nephropathy leads to end stage renal disease (ESRD), i.e., renal failure in 20-50% of patients within a 20-30 year span. These numbers are likely grossly underreported given the need to confirm the disease by kidney biopsy, a protocol that is variably practiced in various clinical settings. The disease has a complex pathogenesis with genetic, epidemiological, and potentially environmental components to disease etiology, pathology, and progression. It likewise has a variable clinical presentation ranging from asymptomatic to end-stage renal failure (ESRD). There are currently no disease-specific treatments to address primary disease or progression.

The etiology of this disease, as its name implies, has been established. In brief, the disease is caused by the deposition of IgA, typically in the form of immune complexes in the mesangium of the kidney. A molecular characterization of these particular immunoglobulins has been carried out. These IgAs are of the A1 subclass (IgA1 vs. IgA2), predominantly polymeric (with J chain-mediated linkages), and apparently differentially o-glycosylated in the hinge region that is intervening between CH1 and CH2 domains. In particular, these o-glycans are heterogeneously lacking $\beta 1,3$ galactose linkages and, as such, are commonly referred to as galactose-deficient IgA1 (or gdIgA1). As the pathogenesis of this disease can involve a polygenic, multi-hit mechanism for inducing renal pathology and aberrant physiology, IgA1 may be viewed as the so-called auto-antigen representing this first critical "hit" in a multi-hit model for IgA nephropathy. A set of autoantibodies for this disease has likewise been defined and it relates to immunoglobulins (predominantly IgG) that specifically recognize this differentially glycosylated epitope and promote the formation of immune complexes (representing so-called "hit 2"). It should also be noted that IgA itself is subject to aggregation due to misfolding, conformational changes, and potential changes in the N-glycosylation state of the CH2/CH3 glycans.

Without wishing to be bound by theory, it is believed that in an embodiment, aberrantly glycosylated IgA1 levels correlate with disease and clinical outcomes in IgA nephropathy. Aberrantly glycosylated IgA1 has been characterized directly from kidney biopsies and increased production of aberrantly glycosylated IgA1 was observed in B cells (tonsillar, PBMC) in IgA nephropathy patients. The level of galactose-deficient IgA1 in the sera of patients with IgA nephropathy is associated with disease progression (Zhao et al. *Kidney Int.* 2012; 82(7):790-6). Differential lectin staining demonstrated elevated levels of aberrantly glycosylated IgA1 in serum and glomeruli of IgA nephropathy patients relative to healthy controls (Allen et al. *Kidney Int.* 2001; 60(3):969-73).

Based on this evolving disease model, IgA nephropathy may be appropriately viewed as an autoimmune disease with strong and critical extra-renal involvement. The identification and validation of select immune-based targets proposed to play a critical role in disease pathogenesis, namely the production of IgA and subsequent production of autoreactive antibodies to this target, represent a logical therapeutic strategy for treatment. APRIL (TNFSF13) represents particular area of focus for this reason. Additional rationale for targeting APRIL include emerging genetic data based on multiple, comprehensive genome wide association (GWAS) studies along with IgA related genetic disorders e.g., IgA hypogammaglobulinemia related common variable immunoglobulin deficiency (CVID) whose locus maps to defects in TNFRSF13B (TACI) with direct implications of the role of APRIL-TACI interactions in regulating IgA synthesis.

IgA nephropathy often does not cause symptoms in the early stages. The disease can go unnoticed for years and is sometimes first diagnosed when routine tests reveal protein and red blood cells in urine that cannot be seen without a microscope (microscopic hematuria). Signs and symptoms of IgA nephropathy when kidney function is impaired include, e.g., cola- or tea-colored urine (caused by red blood cells in the urine); repeated episodes of cola- or tea-colored urine, sometimes even visible blood in the urine, usually during or after an upper respiratory or other type of infection; pain in the side(s) of the back below the ribs (flank); foam in the toilet water from protein in the urine; swelling (edema) in the hands and feet; and high blood pressure. In an embodiment, the sign or symptom includes, e.g., one or more of hematuria, proteinuria, albuminuria, hypertension, or an early stage kidney disease (e.g., requiring dialysis or transplantation). In an embodiment, the sign or symptom is associated with, e.g., one or more of aberrantly glycosylated IgA1, auto-antibody formation, deposition of nephrogenic immune complexes in the kidney, or inflammation and loss of kidney function.

The classic presentation (in about 40-50% of the cases, more common in younger adults) of IgA nephropathy is episodic hematuria which usually starts within a day or two of a non-specific upper respiratory tract infection (hence synpharyngitic). Less commonly gastrointestinal or urinary infection can be the inciting agent. All of these infections have in common the activation of mucosal defenses and hence IgA antibody production. These episodes can occur on an irregular basis every few months and in most patients eventually subsides. Renal function usually remains normal, though rarely, acute kidney failure may occur.

A smaller proportion (in about 20-30% of the cases, usually the older population) of IgA nephropathy patients have microscopic hematuria and proteinuria (less than 2 gram/day). These patients may not have any symptoms and are only clinically found if a doctor decides to take a urine sample. Hence, the disease is more commonly diagnosed in situations where screening of urine is compulsory, e.g., school children in Japan.

Some (about 5% each) IgA nephropathy patients have the following disease presentation: nephrotic syndrome (e.g., 3-3.5 grams of protein loss in the urine, associated with a poorer prognosis); acute kidney failure (e.g., either as a complication of the frank hematuria, when it usually recovers, or due to rapidly progressive glomerulonephritis which often leads to chronic kidney failure); chronic kidney failure (e.g., no previous symptoms, presents with anemia, hypertension and other symptoms of kidney failure, in people who probably had longstanding undetected microscopic hematuria and/or proteinuria).

A variety of systemic diseases can be associated with IgA nephropathy such as liver failure, celiac disease, rheumatoid arthritis, reactive arthritis, ankylosing spondylitis and HIV. Diagnosis of IgA nephropathy and a search for any associated disease occasionally reveals such an underlying serious systemic disease. Occasionally, there are simultaneous symptoms of Henoch-Schönlein purpura. Some HLA alleles have been suspected along with complement phenotypes as being genetic factors.

IgA nephropathy can be diagnosed by various tests, e.g., urine test, blood tests (e.g., to show increased blood levels of the waste product creatinine), iothalamate clearance test, kidney imaging (e.g., ultrasound, X-rays, or cystoscopy), kidney biopsy, or a combination thereof.

For an adult patient with isolated hematuria, tests such as ultrasound of the kidney and cystoscopy are usually done first to pinpoint the source of the bleeding. These tests would rule out kidney stones and bladder cancer, two other common urological causes of hematuria. In children and younger adults, the history and association with respiratory infection can raise the suspicion of IgA nephropathy. A kidney biopsy is often necessary to confirm the diagnosis. The biopsy specimen shows proliferation of the mesangium, with IgA deposits on immunofluorescence and electron microscopy. However, patients with isolated microscopic hematuria (i.e., without associated proteinuria and with normal kidney function) are not usually biopsied since this is associated with an excellent prognosis. A urinalysis will show red blood cells, usually as red cell urinary casts. Proteinuria, usually less than 2 grams per day, also may be present. Other renal causes of isolated hematuria include, e.g., thin basement membrane disease and Alport syndrome, the latter being a hereditary disease associated with hearing impairment and eye problems. Other blood tests done to aid in the diagnosis include CRP or ESR, complement levels, ANA, and LDH. Protein electrophoresis and immunoglobulin levels can show increased IgA in 50% of all patients.

Treatment with a number of medications can slow the progress of the disease and help manage symptoms such as high blood pressure, protein in the urine (proteinuria), and swelling (edema) in the hands and feet. Exemplary therapies for IgA nephropathy include, e.g., high blood pressure medications (e.g., angiotensin-converting enzyme (ACE) inhibitors or angiotensin receptor blockers (ARBs)), omega-3 fatty acids, immunosuppressants (e.g., corticosteroid medications, such as prednisone), statin therapy, mycophenolate mofetil, ciclosporin, mizoribine, cyclophosphamide (e.g., in combination with anti-platelet/anticoagulants, or in combination with steroids and azathioprine), kidney dialysis, or kidney transplantation. Exemplary therapies for IgA nephropathy are also described in Floege and Eitner *J. Am. Soc. Nephrol.* 22: 1785-1794, 2011. Other exemplary therapies for IgA nephropathy are described in the section of "Combination Therapies" herein.

Without wishing to be bound by theory, it is believed that in an embodiment, targeting APRIL selectively reduces IgA. APRIL-/- mice have normal T and B lymphocyte development, normal T and B cell proliferation in vitro, but decreased serum IgA levels (Castigli et al. *Proc Natl Acad Sci USA*. 2004; 101(11):3903-8). Discovery of new risk loci for IgA nephropathy implicates genes involved in immunity against intestinal pathogens (Kiryluk et al. *Nat Genet.* 2014; 46(11):1187-96). Serum levels and B cell production of APRIL are elevated in patients with IgA nephropathy and correlate with aberrantly glycosylated IgA levels (Zhai et al. *Medicine* (Baltimore). 2016; 95(11):e3099). Plasma levels of APRIL (TNFSF13) correlate with progression of chronic kidney disease in IgA nephropathy (Han et al. *J Am Soc Nephrol.* 2016; 27(2):439-53). Treatment with anti-APRIL antibody results in reduction of serum IgA, clearing of kidney mesangium, and reduction of inflammatory cell infiltration and glomerular injury, in mice (Kim et al. *PLoS One*. 2015; 10(9):e0137044). Anti-APRIL antibody preserves immune cell homeostasis in bone marrow and spleen (Kim et al. *PLoS One.* 2015; 10(9):e0137044).

APRIL (TNFSF13) represents a logical biological and therapeutic target for the treatment of IgA nephropathy. Without wishing to be bound by theory, it is believed that in an embodiment, the efficacy of the antibody molecules described herein with respect to the targeted modulation of APRIL-mediated immunobiological mechanisms is directly relevant to treatment of IgA nephropathy. The anti-APRIL antibody molecules described herein (e.g., humanized anti-APRIL antibody molecules), e.g., with high biological potency and/or low complement activation, can be used to treat IgA nephropathy. In an embodiment, the antibody molecule has picomolar APRIL binding affinity and sub-nanomolar receptor blocking activity to both TACI and BCMA, e.g., in vitro. In another embodiment, the antibody molecule functionally interfere with APRIL mediated downstream cellular signaling, e.g., through the canonical NFκB activation pathway. In an embodiment, the antibody molecule is engineered, e.g., as an IgG2 subtype, for purposes of clinically mitigating against antibody-dependent exacerbation of complement recruitment, e.g., in the kidneys of IgA nephropathy patients. In an embodiment, an antibody molecule described herein can have an improved safety profile in comparison to more depletive B cell-based therapeutic approaches, e.g., due to a lesser perturbation of B and T cell homeostasis as shown in a murine model (Kim et al. *PLoS One*. 2015; 10(9):e0137044).

The antibody molecules described herein can be used to treat or prevent different stages of IgA nephropathy. In an embodiment, the antibody molecule is used to treat a symptom associated with IgA nephropathy, e.g., hematuria, proteinuria, albuminuria, hypertension, an early stage kidney disease (e.g., requiring dialysis or transplantation), or a combination thereof. In an embodiment, the antibody molecule reduces aberrantly glycosylated IgA1, auto-antibody formation, deposition of nephritogenic immune complexes in the kidney, inflammation and loss of kidney function, or a combination thereof. In an embodiment, the subject is at low risk, e.g., having minor urinary abnormalities (e.g., micro-hematuria), normal glomerular filtration rate (GFR), and/or no hypertension. In another embodiment, the subject is at moderate to high risk, e.g., having proteinuria greater than 0.5-1 g/d and/or GFR reduced (e.g., below 30-50 ml/min) and/or hypertension. In yet another embodiment, the subject has acute or rapid GFR loss, e.g., having nephrotic syndrome or rapidly progressive glomerulonephritis (RPGN), or acute kidney injury (AKI) due to macro-hematuria or other common cause. In an embodiment, the subject has proteinuria greater than 0.5 g/day, e.g., between 0.5-1 g/day or greater than 1 g/day. In an embodiment, the subject treated for IgA nephropathy has glomerular filtration rate (GFR) less than 50 ml/min, e.g., less than 30 ml/min. In an embodiment, the antibody molecule does not significantly change (e.g., capable of preserving) immune cell homeostasis. In another embodiment, the antibody molecule results in a reduction of IgA not total ablation of IgA.

Diabetic Nephropathy

The antibody molecule described herein can be used to treat or prevent diabetic nephropathy. Diabetic nephropathy (or known as diabetic kidney disease) is a progressive kidney disease caused, e.g., by damage to the capillaries in the kidneys' glomeruli. It is typically characterized by nephrotic syndrome and diffuse scarring of the glomeruli. It is often due to longstanding diabetes mellitus, and is a prime reason for dialysis. It is classified as a small blood vessel complication of diabetes.

Exemplary symptoms of diabetic nephropathy include, but are not limited to, severe tiredness, headaches, a general feeling of illness, nausea, vomiting, frequent voiding, lack of appetite, itchy skin, or leg swelling. The cause of diabetic nephropathy can include, e.g., high blood sugar, advanced glycation end product formation. Cytokines may be involved in the development of diabetic nephropathy.

Diabetes can cause a number of changes to the body's metabolism and blood circulation, which likely combine to produce excess reactive oxygen species. These changes damage the kidney's glomeruli, which leads to the hallmark feature of albuminuria (Cao and Cooper *J Diabetes Investig*. 2011; 2(4): 243-247). As diabetic nephropathy progresses, the glomerular filtration barrier (GFB), which is composed of the fenestrated endothelium, glomerular basement membrane, and epithelial podocytes, is increasingly damaged (Mora-Fernández et al. *J. Physiol. (Lond.)* 2014; 592 (Pt 18): 3997-4012). Damage to the glomerular basement membrane allows proteins in the blood to leak through, leading to accumulation in Bowman's space as distinct periodic-acid schiff positive nodules (Kimmelstiel-Wilson nodules).

Diagnosis of diabetic nephropathy can be based on the measurement of high levels of albumin in the urine or evidence of reduced kidney function (Lewis and Maxwell Practitioner. 2014; 258(1768):13-7, 2). Albumin measurements can be defined as follows: normal albuminuria: urinary albumin excretion <30 mg/24 h; microalbuminuria: urinary albumin excretion in the range of 30-299 mg/24 h; clinical (overt) albuminuria: urinary albumin excretion ≥300 mg/24 h. To test kidney function, the person's estimated glomerular filtration rate (eGFR) is measured from a blood sample. Normal eGFR ranges from 90 to 120 ml/min/1.73 m$^2$.

Other treatments that can be used in combination with the antibody molecule described herein to treat diabetic nephropathy include, e.g., an angiotensin-converting enzyme (ACE) inhibitor (e.g., captopril, enalapril, lisinopril, or ramipril), an angiotensin II receptor blocker (ARB) (e.g., candesartan cilexetil, irbesartan, losartan, or telmisartan), a calcium channel blocker (e.g., amlodipine, diltiazem, or verapamil), a diuretic (e.g., chlorthalidone, hydrochlorothiazide, or spironolactone), a beta-blocker (e.g., atenolol, carvedilol, or metoprolol), and diabetes management (e.g., control of high blood pressure or blood sugar levels, or reduction of dietary salt intake).

Cancer

The antibody molecule described herein can be used to treat or prevent a cancer. Exemplary cancers that can be treated or prevented by the antibody molecules described herein include, but are not limited to, acute lymphoblastic leukemia (ALL), acute myeloid leukemia (AML), adrenocortical carcinoma, Kaposi sarcoma, an AIDS-related lymphoma, primary central nervous system (CNS) lymphoma, anal cancer, appendix cancer, astrocytoma, atypical teratoid/rhabdoid tumor, basal cell carcinoma, bile duct cancer, bladder cancer, bone cancer (e.g., Ewing sarcoma or osteosarcoma and malignant fibrous histiocytoma), brain tumor (e.g., astrocytomas, brain stem glioma, central nervous system atypical teratoid/rhabdoid tumor, central nervous system embryonal tumor, central nervous system germ cell tumor, craniopharyngioma, or ependymoma), breast cancer, bronchial tumor, Burkitt lymphoma, carcinoid tumor (e.g., gastrointestinal carcinoid tumor), cardiac (heart) tumor, embryonal tumor, germ cell tumor, lymphoma, cervical cancer, cholangiocarcinoma, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma in situ (DCIS), endometrial cancer, ependymoma, esophageal cancer, esthesioneuroblastoma, Ewing sarcoma, extracranial germ cell tumor, extragonadal germ cell tumor, eye cancer (e.g., intraocular melanoma or retinoblastoma), fallopian tube cancer, fibrous histiocytoma of bone, osteosarcoma, gallbladder cancer, gastric (stomach) cancer, gastrointestinal carcinoid tumor, gastrointestinal stromal tumors (GIST), germ cell tumor (e.g., central nervous system tumor, extracranial tumor, extragonadal tumor, ovarian cancer, or testicular cancer), gestational trophoblastic disease, glioma, hairy cell leukemia, head and neck cancer, hepatocellular (liver) cancer, Hodgkin lymphoma, hypopharyngeal cancer, intraocular melanoma, islet cell tumor, pancreatic neuroendocrine tumor, Kaposi sarcoma, kidney cancer (e.g., renal cell cancer or Wilms tumor), Langerhans cell histiocytosis (LCH), laryngeal cancer, leukemia (e.g., acute lymphoblastic leukemia (ALL), acute myeloid leukemia (AML), chronic lymphocytic leukemia (CLL), chronic myelogenous leukemia (CML), or hairy cell leukemia), lip and oral cavity cancer, liver cancer, lung cancer (e.g., non-small cell lung cancer (NSCLC) or small cell lung cancer), lymphoma (e.g., aids-related, Burkitt lymphoma, cutaneous T-cell lymphoma, Hodgkin lymphoma, non-Hodgkin lymphoma, or primary central nervous system (CNS) lymphoma), Waldenström macroglobulinemia, male breast cancer, malignant fibrous histiocytoma of bone and osteosarcoma, melanoma (e.g., intraocular (eye) melanoma), Merkel cell carcinoma, mesothelioma, metastatic squamous neck cancer, midline tract carcinoma, mouth cancer, multiple endocrine neoplasia syndrome, multiple myeloma/plasma cell neoplasm, mycosis fungoides, myelodysplastic syndrome, myelodysplastic/myeloproliferative neoplasm, chronic myeloproliferative neoplasm, nasal cavity and paranasal sinus cancer, nasopharyngeal cancer, neuroblastoma, oral cancer, lip and oral cavity cancer, oropharyngeal cancer, osteosarcoma and malignant fibrous histiocytoma of bone, ovarian cancer (e.g., epithelial ovarian cancer or germ cell ovarian tumor), pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, pleuropulmonary blastoma, peritoneal cancer, prostate cancer, rectal cancer, retinoblastoma, rhabdomyosarcoma, salivary gland cancer, sarcoma (e.g., Ewing sarcoma, Kaposi sarcoma, osteosarcoma, rhabdomyosarcoma, soft tissue sarcoma, or uterine sarcoma), Sézary syndrome, skin cancer (e.g., melanoma, Merkel cell carcinoma, or nonmelanoma skin cancer), small intestine cancer, squamous cell carcinoma, testicular cancer, throat cancer, thymoma and thymic carcinoma, thyroid cancer, transitional cell cancer of the renal pelvis and ureter, urethral cancer, endometrial uterine cancer, vaginal cancer, vulvar cancer, or a metastatic lesion thereof.

In an embodiment, the cancer is a hematological cancer, e.g., a lymphoma or leukemia, e.g., chosen from B-cell non-Hodgkin's lymphoma, chronic lymphocytic leukemia (CLL), Hodgkin's lymphoma, multiple myeloma, Waldenström macroglobulinemia, or lymphoplasmacytic lymphoma. In an embodiment, the cancer is a multiple myeloma. In another embodiment, the cancer is a solid tumor, e.g., chosen from colorectal cancer, breast cancer (e.g., breast carcinoma), esophageal cancer (e.g., esophageal adenocarcinoma), brain cancer (e.g., glioblastoma), or kidney cancer (e.g., renal cell carcinoma).

In an embodiment, the antibody molecule is used to treat a lymphoma. Other treatments that can be used in combination with the antibody molecule described herein to treat lymphoma include, e.g., chemotherapy, immunotherapy, targeted drug therapy, radiation therapy, and stem cell transplant. Exemplary targeted drug therapy includes a CD20 inhibitor (e.g., rituximab (RITUXAN® or ibritumornab tiuxetan (ZEVALIN®)).

In an embodiment, the antibody molecule is used to treat a leukemia. Other treatments that can be used in combination with the antibody molecule described herein to treat leukemia include, e.g., chemotherapy, immunotherapy, targeted drug therapy, radiation therapy, and stem cell transplant. Exemplary targeted drug therapy includes a tyrosine kinase inhibitor (e.g., imatinib (GLEEVEC®).

In an embodiment, the antibody molecule is used to treat a multiple myeloma. Other treatments that can be used in combination with the antibody molecule described herein to treat multiple myeloma include, e.g., chemotherapy, corticosteroids, immunotherapy, targeted drug therapy, radiation therapy, and stem cell transplant. Exemplary targeted drug therapy includes, e.g., a thalidomide analog (e.g., thalidomide (THALOMID®), lenalidomide (REVLIMID®), or pomalidomide (POMALYST®)).

In an embodiment, the antibody molecule is used to treat Waldenström macroglobulinemia. Other treatments that can be used in combination with the antibody molecule described herein to treat Waldenström macroglobulinemia include, e.g., plasma exchange, chemotherapy, immunotherapy, targeted drug therapy, and stem cell transplant.

In an embodiment, the antibody molecule is used to treat a colorectal cancer. Other treatments that can be used in combination with the antibody molecule described herein to treat colorectal cancer include, e.g., surgery, chemotherapy, radiation therapy, immunotherapy, and targeted drug therapy. Exemplary targeted drug therapy includes, e.g., a VEGF inhibitor (e.g., bevacizumab (AVASTIN®)), an EGFR inhibitor (e.g., cetuximab (ERBITUX®), panitumumab (VECTIBIX®)), and dual VEGFR2-TIE2 tyrosine kinase inhibitor (e.g., regorafenib (STIVARGA®)).

In an embodiment, the antibody molecule is used to treat a breast cancer, e.g., a breast carcinoma. Other treatments that can be used in combination with the antibody molecule described herein to treat breast cancer include, e.g., surgery, chemotherapy, radiation therapy, hormone therapy, immunotherapy, and targeted drug therapy. Exemplary target drug therapy includes, e.g., an HER2 inhibitor (e.g., trastuzumab (HERCEPTIN®), pertuzumab (PERJETA®), ado-trastuzumab (KADCYLA®), or lapatinib (TYKERB®)) or a VEGF inhibitor (e.g., bevacizumab (AVASTIN®)).

In an embodiment, the antibody molecule is used to treat an esophageal cancer, e.g., an esophageal adenocarcinoma. Other treatments that can be used in combination with the antibody molecule described herein to treat esophageal cancer include, e.g., surgery, chemotherapy, radiation therapy, and immunotherapy.

In an embodiment, the antibody molecule is used to treat a brain cancer, e.g., a glioblastoma. Other treatments that can be used in combination with the antibody molecule described herein to treat brain cancer include, e.g., surgery, chemotherapy, radiation therapy, radiosurgery, immunotherapy, and targeted drug therapy. Exemplary targeted drug therapy includes, e.g., a VEGF inhibitor (e.g., bevacizumab (AVASTIN®)).

In an embodiment, the antibody molecule is used to treat a kidney cancer, e.g., a renal cell carcinoma. Other treatments that can be used in combination with the antibody molecule described herein to treat kidney cancer include, e.g., surgery, cryoablation, radiofrequency ablation, radiation therapy, immunotherapy, and targeted drug therapy. Exemplary targeted drug therapy includes, e.g., a VEGF inhibitor (e.g., bevacizumab (AVASTIN®)), a tyrosine kinase inhibitor (e.g., axitinib (INLYTA®), pazopanib (VOTRIENT®), sorafenib (NEXAVAR®), or sunitinib (SUTENT®), or an mTOR inhibitor (e.g., temsirolimus (TORISEL®) or everolimus (AFINITOR®).

Immunoproliferative Disorders

The antibody molecule described herein can be used to treat or prevent an immunoproliferative disorder Immunoproliferative disorders (also known as immunoproliferative diseases or immunoproliferative neoplasms) are disorders of the immune system that are characterized by the abnormal proliferation of the primary cells of the immune system (e.g., B cells, T cells and Natural killer (NK) cells) or by the excessive production of immunoglobulins (e.g., antibodies).

Exemplary immunoproliferative disorders include, but are not limited to, lymphoproliferative disorders (LPDs), hypergammaglobulinemia, and paraproteinemia. Lymphoproliferative disorders include several conditions in which lymphocytes are produced in excessive quantities. They typically occur in patients who have compromised immune systems. Hypergammaglobulinemia is often characterized by increased levels of immunoglobulins in the blood serum. Paraproteinemia or monoclonal gammopathy is the presence of excessive amounts of a single monoclonal gammaglobulin (e.g., a paraprotein) in the blood. In an embodiment, the antibody molecule is used to treat monoclonal IgA hypergammaglobulinemia.

Vasculitis

The antibody molecule described herein can be used to treat or prevent vasculitis. Vasculitis is a group of disorders that destroy blood vessels by inflammation. Vasculitis is primarily caused by leukocyte migration and resultant damage. Exemplary types of vasculitis include, but are not limited to, microscopic polyarteritis (poly-angiitis), Wegener's granulomatosis, Henoch Schonlein purpura and polyarteritis nodosa.

In an embodiment, the antibody molecule is used to treat Henoch-Schonlein purpura (IgA associated vasculitis).

Henoch-Schönlein purpura (HSP, also known as anaphylactoid purpura, purpura rheumatica, or Schönlein-Henoch purpura) is a disease of the skin and other organs that most commonly affects children. HSP is a systemic vasculitis (inflammation of blood vessels) and is characterized by deposition of immune complexes of IgA and complement component 3 (C3) on arterioles, capillaries, and venules. In the skin, the disease causes palpable purpura (small hemorrhages); often with joint and abdominal pain. With kidney involvement, there may be a loss of small amounts of blood and protein in the urine; in a small proportion of cases, the kidney involvement proceeds to chronic kidney disease even irreversible kidney damage. HSP is often preceded by an infection, such as a throat infection.

Symptoms of Henoch-Schönlein purpura include, e.g., rash (purpura), swollen or sore joints (arthritis), gastrointestinal symptoms (e.g., abdominal pain, nausea, vomiting or bloody stools), and kidney involvement (e.g., protein or blood in the urine). Serum levels of IgA are high in HSP patients.

Standards for defining Henoch-Schönlein purpura include, e.g., the 1990 American College of Rheumatology (ACR) classification (Mills et al. (1990). Arthritis and Rheumatism 33 (8): 1114-21), the 1994 Chapel Hill Consensus Conference (CHCC) (Jennette et al. (1994) Arthritis and Rheumatism 37 (2): 187-92), and the 2006 European League Against Rheumatism (EULAR) and Pediatric Rheumatology Society (PReS) classification, which includes palpable purpura as a mandatory criterion, together with at least one of the following findings: diffuse abdominal pain, predominant IgA deposition (confirmed on skin biopsy), acute arthritis in any joint, and renal involvement (as evidenced by the presence of blood and/or protein in the urine) (Ozen et al. (2006) Annals of Rheumatic Diseases 65 (7): 936-41).

Other treatments that can be used in combination with the antibody molecule described herein to treat Henoch-Schönlein purpura include, e.g., analgesics for the abdominal and joint pains, steroids (e.g., oral steroids or a combination of intravenous methylprednisolone (steroid), cyclophosphamide and dipyridamole followed by prednisone). Other regimens also include, e.g., steroids/azathioprine, and steroids/cyclophosphamide (with or without heparin and warfarin), or intravenous immunoglobulin (IVIG).

In another embodiment, the antibody molecule is used to treat acute proliferative glomerulonephritis, e.g., post-streptococcal glomerulonephritis.

Acute proliferative glomerulonephritis is a disorder of the glomeruli (glomerulonephritis), or small blood vessels in the kidneys. It is a common complication of bacterial infections, typically skin infection by Streptococcus bacteria types 12, 4 and 1 (impetigo) but also after streptococcal pharyngitis, for which it is also known as postinfectious or poststreptococcal glomerulonephritis. The infection causes blood vessels in the kidneys to develop inflammation, which hampers the renal organs ability to filter urine.

The pathophysiology of this disorder is consistent with an immune complex mediated mechanism. This disorder produces proteins that have different antigenic determinants, which in turn have an affinity for sites in the glomerulus. As soon as binding occurs to the glomerulus, via interaction with properdin, complement is activated. Complement fixation causes the generation of additional inflammatory mediators.

Symptoms of acute proliferative glomerulonephritis include, e.g., hematuria, oliguria, edema, hypertension, fever, headache, malaise, anorexia, and nausea.

Other treatments that can be used in combination with the antibody molecule described herein to treat cute proliferative glomerulonephritis includes, e.g., blood pressure (BP) control and control of the amount of potassium in individuals with oliguric acute kidney injury.

Autoimmune Disorders

The antibody molecule described herein can be used to treat or prevent an autoimmune disorder. Exemplary autoimmune disorders that can be treated or prevented by the antibody molecule described herein include, but are not limited to, acute Disseminated Encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticaria, axonal & neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, Erythema nodosum, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis (GPA) (formerly called Wegener's Granulomatosis), Graves' disease, Guillain-Barre syndrome, Hashimoto's encephalitis, Hashimoto's thyroiditis, hemolytic anemia, Henoch-Schonlein purpura, Herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile diabetes (type 1 diabetes), juvenile myositis, Kawasaki syndrome, Lambert-Eaton syndrome, Leukocytoclastic vasculitis, Lichen planus, Lichen sclerosus, Ligneous conjunctivitis, linear IgA disease (LAD), pupus (SLE), Lyme disease, chronic, Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with Streptococcus), paraneoplastic cerebellar degeneration, paroxysmal nocturnal hemoglobinuria (PNH), Parry Romberg syndrome, Parsonnage-Turner syndrome, Pars planitis (peripheral uveitis), pemphigus, peripheral neuropathy, perivenous encephalomyelitis, pernicious anemia, POEMS syndrome, polyarteritis nodosa, Type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, raynauds phenomenon, reactive arthritis, reflex sympathetic dystrophy, reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/Giant cell arteritis, thrombocytopenic purpura (TTP), Tolosa-Hunt syndrome, transverse myelitis, Type 1 diabetes, ulcerative colitis, undifferentiated connective tissue disease (UCTD), uveitis, vasculitis, vesiculobullous dermatosis, vitiligo, Wegener's granulomatosis (also known as Granulomatosis with Polyangiitis (GPA).

In an embodiment, the autoimmune disorder is rheumatoid arthritis, systemic lupus erythematosus, a linear IgA bullous disease (e.g., linear immunoglobulin A (IgA) dermatosis), or IgA-mediated epidermolysis bullosa acquisita.

In an embodiment, the antibody molecule is used to treat rheumatoid arthritis. Other treatments that can be used in combination with the antibody molecule described herein to treat rheumatoid arthritis includes, e.g., an NSAID, a steroid (e.g., corticosteroid), a disease-modifying antirheumatic drug (DMARD) (e.g., methotrexate (TREXALL®), leflunomide (ARAVA®), hydroxychloroquine (PLAQUENIL®), or sulfasalazine (AZULFIDINE®), a biologic response modifier (e.g., abatacept (ORENCIA®), adalimumab (HU- MIRA®), anakinra (KINERET®), certolizumab (CIMZIA®), etanercept (ENBREL®), golimumab (SIMPONI®), infliximab (REMICADE®), rituximab (RITUXAN®) and tocilizumab (ACTEMRA®), or Tofacitinib (XELJANZ®)), or surgery.

In an embodiment, the antibody molecule is used to treat systemic lupus erythematosus. Other treatments that can be used in combination with the antibody molecule described herein to treat rheumatoid arthritis includes, e.g., an NSAID, an antimalarial drug (e.g., hydroxychloroquine (PLAQUENIL®), corticosteroid (e.g., prednisone), an immunosuppressant (e.g., azathioprine (IMURAN®, AZASAN®), mycophenolate (CELLCEPT®), leflunomide (ARAVA®), or methotrexate (TREXALL®)), or a BAFF inhibitor (e.g., belimumab (BENLYSTA®).

In an embodiment, the antibody molecule is used to treat a linear IgA bullous disease (e.g., linear immunoglobulin A (IgA) dermatosis). Other treatments that can be used in combination with the antibody molecule described herein to treat a linear IgA bullous disease (e.g., linear immunoglobulin A (IgA) dermatosis) include, e.g., corticosteroids (e.g., prednisone or prednisolone), an antibiotic (e.g., tetracycline, erythromycin, sulfapyridine), colchicine, or mycophenolate mofetil.

In an embodiment, the antibody molecule is used to treat IgA-mediated epidermolysis bullosa acquisita. Other treatments that can be used in combination with the antibody molecule described herein to treat IgA-mediated epidermolysis bullosa acquisita includes, e.g., an antibiotic, an anti-inflammatory drug (e.g., corticosteroid), or surgery.

Other Disorders

The antibody molecule described herein can be used to treat or prevent other disorders, e.g., IgA pemphigus, celiac disease, or alcoholic cirrhosis.

In an embodiment, the antibody molecule is used to treat or prevent IgA pemphigus. Other treatments that can be used in combination with the antibody molecule described herein to treat IgA pemphigus include, e.g., corticosteroid, an immunosuppressant (e.g., azathioprine (IMURAN®), methotrexate (TREXALL®), or mycophenolate mofetil (CELLCEPT®)), an CD-20 inhibitor (e.g., rituximab (RITUXAN®), an antibiotic, an antiviral agent, or an antifungal agent.

In an embodiment, the antibody molecule is used to treat or prevent celiac disease. Other treatments that can be used in combination with the antibody molecule described herein to treat celiac disease include, e.g., a gluten-free diet, a vitamin or mineral supplement, or a steroid.

In an embodiment, the antibody molecule is used to treat or prevent alcoholic cirrhosis. Other treatments that can be used in combination with the antibody molecule described herein to treat alcoholic cirrhosis include, e.g., an immunosuppressant (e.g., azathioprine, prednisone, azathioprine, cyclosporine, or methotrexate) or liver transplant.

Combination Therapies

The antibody molecules can be used in combination with other therapies. For example, the combination therapy can include an antibody molecule co-formulated with, and/or co-administered with, one or more additional therapeutic agents, e.g., one or more additional therapeutic agents described herein. In other embodiments, the antibody molecules are administered in combination with other therapeutic treatment modalities, e.g., other therapeutic treatment modalities described herein. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject before, or during the course of the subject's affliction with a disorder. In an embodiment, two or more treatments are delivered prophylactically, e.g., before the subject has the disorder or is diagnosed with the disorder. In another embodiment, the two or more treatments are delivered after the subject has developed or diagnosed with the disorder. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In certain embodiments, the additional agent is a second antibody molecule, e.g., an antibody molecule different from a first antibody molecule. Exemplary antibody molecules that can be used in combination include, but are not limited to, any combination of the antibody molecules listed in Table 1 or 5.

In an embodiment, the antibody molecule is administered in combination with a second therapy to treat or prevent IgA nephropathy.

In an embodiment, the antibody molecule is administered in combination with an angiotensin-converting-enzyme (ACE) inhibitor or an angiotensin receptor blocker (ARB).

In an embodiment, the antibody molecule is administered in combination with an Fc decoy receptor, e.g., a soluble Fc receptor. In an embodiment, the soluble Fc receptor is a soluble Fc-gamma receptor IIB. In an embodiment, the soluble Fc receptor is SM101/BAX 1810 (Baxalta). In an embodiment, the soluble Fc receptor is administered at a dose between 1 mg/kg and 50 mg/kg, e.g., between 5 mg/kg and 15 mg/kg, between 12 mg/kg and 24 mg/kg, or between 20 mg/kg and 30 mg/kg.

In an embodiment, the antibody molecule is administered in combination with repository corticotropin (ACTHAR®). Repository corticotropin is an adrenocorticotropic hormone (ACTH) analogue. In an embodiment, repository corticotropin is administered at a dose between 50 U and 150 U, e.g., between 80 U and 120 U, by subcutaneous injection, twice or three times a week. In an embodiment, repository corticotropin is administered at a dose of 120 U, by subcutaneous injection, e.g., once, twice, or three times a week.

In an embodiment, the antibody molecule is administered in combination with mycophenolate mofetil (MMF). Mycophenolate mofetil is the 2-morpholinoethyl ester of mycophenolic acid (MPA), an immunosuppressive agent and inosine monophosphate dehydrogenase (IMPDH) inhibitor. In an embodiment, mycophenolate mofetil is administered at a dose of between 0.5 g and 2 g, e.g., between 1 g and 1.5 g or between 1.5 g and 2 g, orally or intravenously, e.g., once, twice, or three times a day.

In an embodiment, the antibody molecule is administered in combination with bortezomib (VELCADE®). Bortezomib, also known as [(1R)-3-methyl-1-({(2S)-3-phenyl-2-[(pyrazin-2-ylcarbonyl)amino]propanoyl}amino)butyl] boronic acid, is a proteasome inhibitor. In an embodiment, bortezomib is administered at a dose at between 0.5 mg/m$^2$ and 2.5 mg/m$^2$, e.g., between 1 mg/m$^2$ and 1.5 mg/m$^2$, e.g. every three days or every week.

In an embodiment, the antibody molecule is administered in combination with allopurinol (ZYLOPRIM®). Allopurinol, also known as 1H-pyrazolo[3,4-d]pyrimidin-4(2H)-one, is a purine analog. In an embodiment, allopurinol is administered at a dose between about 50 mg and 1000 mg, e.g., between 100 mg and 600 mg or between 200 and 300 mg, orally, e.g., once a day or once two days.

In an embodiment, the antibody molecule is administered in combination with prednisone and/or cyclophosphamide. In an embodiment, prednisone is administered at a dose between 0.2 mg/kg and 2 mg/kg, e.g., between 0.5 mg/kg and 1 mg/kg, e.g., once a day. In an embodiment, cyclophosphamide is administered at a dose between 0.2 g and 2 g, e.g., between 0.5 g and 1 g, e.g., once a day.

In an embodiment, the antibody molecule is administered in combination with rituximab (RITUXAN®). Rituximab is a chimeric anti-CD20 monoclonal antibody. In an embodiment, rituximab is administered at a dose between 100 mg/m$^2$ and 500 mg/m$^2$, e.g., between 200 mg/m$^2$ and 450 mg/m$^2$ or between 300 mg/m$^2$ and 400 mg/m$^2$, intravenously, e.g., once weekly, once every two weeks, once every four weeks, or once every eight weeks.

In an embodiment, the antibody molecule is administered in combination with blisibimod. Blisibimod, also known as A-623 or AMG 623, is a selective antagonist of B-cell activating factor (BAFF, also known as B-lymphocyte stimulator or BLyS).

In an embodiment, the antibody molecule is administered with budesonide. In an embodiment, the budesonide is NEFECON®, an oral formulation that releases budesonide.

In an embodiment, the antibody molecule is administered with valsartan and/or probucol. In an embodiment, valsartan is administered at a dose between 50 mg/day and 200 mg/day, e.g., between 80 mg/day and 160 mg/day. In an embodiment, probucol is administered at a dose between 500 mg/day and 1000 mg/day, e.g., between 700 mg/day and 800 mg/day.

In an embodiment, the antibody molecule is administered in combination with OPL-CCL2-LPM. OPL-CCL2-LPM is a recombinant fusion protein comprised of the human CCL2 (monocyte chemoattractant protein-1) chemokine fused to a truncated form of the enzymatically active A1 domain of *Shigella dysenteriae* holotoxin (SA1). In an embodiment, OPL-CCL2-LPM is administered at a dose between 0.001 mg/kg and 1 mg/kg, e.g., between 0.01 mg/kg and 0.5 mg/kg or 0.05 mg/kg and 0.1 mg/kg, e.g., intravenously.

In an embodiment, the antibody molecule is administered in combination with methylprednisolone. In an embodiment, methylprednisolone is administered at a dose between 0.1 mg/kg and 2 mg/kg/day, e.g., between 0.2 mg/kg/day and 1.5 mg/kg/day or 0.5 mg/kg/day and 1 mg/kg/day, e.g., orally.

In an embodiment, the antibody molecule is administered in combination with sirolimus. Sirolimus, also known as rapamycin, can inhibit IL-2 and other cytokines receptor-dependent signal transduction mechanisms, via action on mTOR, and thereby block activation of T and B cells. In an embodiment, sirolimus is administered at dose between 0.2 mg/day and 2 mg/day, e.g., between 0.5 mg/day and 1 mg/day.

In an embodiment, the antibody molecule is administered in combination with a renin-angiotensin system (RAS) blocker. For example, the RAS blocker can be an angiotensin-converting enzyme (ACE) inhibitor or an AT1 receptor blocker (ARB). Exemplary ACE inhibitors that can be used in combination with the antibody molecule described herein include, e.g., benazepril (LOTENSIN®), captopril, enalapril (VASOTEC®), fosinopril, lisinopril (ZESTRIL®), moexipril (UNIVASC®), perindopril (ACEON®), quinapril (ACCUPRIL®), ramipril (ALTACE®), or trandolapril (MAVIK®). Exemplary AT1 receptor blockers that can be used in combination with the antibody molecule described herein include, e.g., candesartan (ATACAND®), eprosartan (TEVETEN®), irbesartan (AVAPRO®), losartan (COZAAR®), olmesartan (BENICAR®), telmisartan (MICARDIS®), or valsartan (DIOVAN®).

In an embodiment, the antibody molecule is administered in combination with fostamatinib. Fostamatinib is a prodrug of the active compound tamatinib (R-406), which is an inhibitor of the enzyme spleen tyrosine kinase (Syk). In an embodiment, fostamatinib is administered at a dose between about 50 mg and 200 mg, e.g., between 100 mg and 150 mg, e.g., orally, e.g., every day.

In an embodiment, the antibody molecule is administered in combination with paricalcitol. In an embodiment, paricalcitol is administered at a dose between about 0.2 mg and 2 mg, e.g., between 0.5 mg and 1 mg, e.g., every day.

In an embodiment, the antibody molecule is administered in combination with ramipril. In an embodiment, ramipril is administered at a dose between about 0.5 mg and 5 mg, e.g., between 1 mg and 4 mg or between 2 mg and 3 mg, e.g., every day.

In an embodiment, the antibody molecule is administered in combination with an angiotensin-converting-enzyme (ACE) inhibitor. In an embodiment, the ACE inhibitor is enalapril (VASOTEC®).

In an embodiment, the antibody molecule is administered in combination with an immunosuppressant. In an embodiment, the immunosuppressant is tacrolimus. Tacrolimus, also known as FK-506 or fujimycin, is a macrolide calcineurin inhibitor.

In an embodiment, the antibody molecule is administered in combination with omega-3 fatty acids.

In an embodiment, the antibody molecule is administered in combination with CCX168. CCX168 is an orally administered C5aR inhibitor.

Exemplary therapies that can be used in combination with an antibody molecule or composition described herein to treat or prevent other disorders are also described in the section of "Methods of Treating or Preventing Disorders" herein.

Methods of Diagnosis

In some aspects, the present disclosure provides a diagnostic method for detecting the presence of APRIL in vitro (e.g., in a biological sample, such as a biopsy or blood sample) or in vivo (e.g., in vivo imaging in a subject). The method includes: (i) contacting the sample with an antibody molecule described herein, or administering to the subject, the antibody molecule; (optionally) (ii) contacting a reference sample, e.g., a control sample (e.g., a control biological sample, such as a biopsy or blood sample) or a control subject with an antibody molecule described herein; and (iii) detecting formation of a complex between the antibody molecule and APRIL in the sample or subject, or the control sample or subject, wherein a change, e.g., a statistically significant change, in the formation of the complex in the sample or subject relative to the control sample or subject is indicative of the presence of APRIL in the sample. The antibody molecule can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting a polypeptide (e.g., APRIL) or a nucleic acid encoding the polypeptide includes, but is not limited to, cells, cell lysates, proteins or membrane extracts of cells, body fluids such as blood, or tissue samples such as biopsies.

Complex formation between the antibody molecule, and APRIL, can be detected by measuring or visualizing either the antibody molecule bound to APRIL or unbound antibody molecule. Any suitable detection assays can be used, and conventional detection assays include an enzyme-linked immunosorbent assays (ELISA), a radioimmunoassay (RIA) or tissue immunohistochemistry. Alternative to labeling the antibody molecule, the presence of APRIL can be assayed in a sample by a competition immunoassay utilizing standards labeled with a detectable substance and an unlabeled antibody molecule. In this assay, the biological sample, the labeled standards and the antibody molecule are combined and the amount of labeled standard bound to the unlabeled binding molecule is determined. The amount of APRIL in the sample is inversely proportional to the amount of labeled standard bound to the antibody molecule.

The antibody molecules described herein can be used to diagnose disorders that can be treated or prevented by the antibody molecules described herein. The detection or diagnostic methods described herein can be used in combination with other methods described herein to treat or prevent a disorder described herein.

EXAMPLES

Example 1: Immunization and Selection of Anti-APRIL Antibodies

CD-1 IGS (outbred stock) mice (Charles River Laboratories), female (20-25 g weight), 7-8 weeks old were immunized intraperitoneally (i.p.) with 10 µg of recombinant, oligomeric FLAG-ACRP30headless APRIL herein referred to as FLAG-ACR-APRIL. For purposes of potentially generating a species cross reactive (mouse and human) anti-APRIL antibody response, both autologous and heterologous immunizations were carried out and comprised the use of human and/or mouse APRIL as immunogens. FLAG-tagged APRIL immunogens were formulated in a 200 µl volume consisting of 100 µl sterile PBS and 100 µl emulsified RIBI adjuvant system (Sigma Aldrich) comprised of a defined mixture of Monophosphoryl Lipid A (MPL, isolated from *Salmonella minnesota*) and synthetic trehalose dicorynomycolate (TDM, an analogue of trehalose dimycolate from the cord factor of the tubercle *bacillus*). 3 mice per arm were immunized twice weekly for up to four weeks. Serum titers of anti-APRIL antibodies were detected subsequently by indirect ELISA using FLAG-GCN4 APRIL, R&D Systems. In brief, 50 ng FLAG-GCN4 hAPRIL (105-250) or FLAG-GCN4 mAPRIL (96-241) in PBS were coated on Maxisorp 96-well flat bottom plates (NUNC #439454), overnight at 4° C. Coated plates were blocked in 1× blocking buffer containing 5% BLOTTO™ in PBS and 0.05% Tween- 20 (PBST) for 1 hour at room temperature. All subsequent incubation steps were followed out with an intervening 3× wash step in PBST. Anti-APRIL antibody titers were determined from a fold-dilution of mouse sera (in PBS) initially starting at 1:1000 and followed by incubation of a 1:5000 HRP conjugated rabbit anti-mouse IgG secondary antibody (Jackson Immunoresearch Laboratories) for 1 hour at room temperature. Anti-APRIL immunoglobulin reactivity was visualized using 100 µl/well of freshly prepared TMB substrate (KPL). Colorimetric development was carried out for up to 10 minutes at room temperature before quenching enzymatic reaction by the addition of 100 µl of 1N sulfuric acid and quantification by absorbance at 450 nm. Mice with strong seropositive titers against primary immunogen (human or mouse APRIL) were boosted by tail vein injection three days prior to sacrifice, removal of spleen and isolation of splenoctye fusions. Mice with preferable species cross-reactivity from serum profiling were noted.

P3X63Ag8.653 plasmacytomas (ATCC #CRL-1580), herein referred to as P3X cells were used as source of fusion partner myelomas. Splenically-derived B cell clones were immortalized using published methods with modification. In brief, P3X cells were cultured at least 1 week prior to use and maintained in log phase to achieve a target cell density of between $6 \times 10^5$ and $1.2 \times 10^6$ cells/mL and 95% viability the day prior to subsequently performing the splenic fusion. Spleen cells were isolated from 2-3 mice per immunization arm following euthanization and cardiac puncture and collected into DMEM+1% antibiotic (penicillin/streptomycin), followed by gently washing centrifugation (2×) to pellet tissue debris and clarify suspended splenocytes. Splenocytes were then pelleted by centrifugation for 10 min at 400×g at 4° C., and red blood cells lysed at room temperature for 5 minutes following gentle resuspension of cell pellet in 1× red blood cell lysis buffer. Splenocytes were collected by centrifugation (2×) following dilution with ice cold DMEM. P3X cells were also washed 3× in DMEM prior to fusion.

Mouse splenocytes were fused with P3X cells in fusion medium (50% PEG 1450, Sigma Aldrich)) at a 3:1 ratio in accordance with established methods. In brief, pre-warmed PEG was added gradually to pelleted mixture of splenocytes and P3X cells (37° C., with gentle resuspension) followed by gradual addition of pre-warmed DMEM. Fused cells were collected by low speed centrifugation and resuspended in hybridoma selective media (hypoxanthine-aminopterin-thymidine, Sigma Aldrich) followed by incubation at 37° C. for 30 minutes. Fused cells sere plated in a 96 well plate at a density of approximately $2.0 \times 10^6$ spleen cells per plate (20,000 cells per well).

Hybridoma supernatants were screened by ELISA on day 14 post-fusion as described (Example 2). In brief, supernatants from conditioned media were quantified for total IgG by bioinferometry using AMC anti mouse IgG quantification kit (Pall Biosciences). Supernatants from hybridoma conditioned media were normalized to 10 µg/mL when possible and assayed for APRIL reactivity to both FLAG-GCN4-hAPRIL and FLAG GCN4-mAPRIL as described. A counter screen using non-APRIL FLAG-tagged protein (FLAG-ACR30-myc-his) was also included to exclude clones with a strong immunoreactivity to either FLAG or ACRP30 specific epitopes (non-relevant epitopes present in original immunogen). APRIL positive hybridomas (human APRIL or mouse) were screened for receptor blocking activity by ELISA as described in Example 3. In brief, recombinant TACI-Fc was coated on to Maxisorp 96-well flat bottom plates at 100 ng/well in 0.1 M Carbonate-Bicarbonate Buffer (pH 9.6), overnight at 4° C. Plates were blocked with 1% BSA in 1×PBS for 1 hour at 37° C. followed by 3× washing in 1×PBST (with 0.025% Tween). Recombinant FLAG-tagged APRIL (mouse or human) at a concentration of 50 ng/mL was premixed in binding buffer with supernatant from hybridoma media normalized when possible to 10 µg/mL IgG concentration. Antibody-APRIL preincubation was carried out for 1 hour at 30° C. with mixing prior to adding to TACI-Fc coated plates, followed by a 1-hour incubation, likewise at 30° C. Detection of FLAG-APRIL bound to TACI-Fc was quantified using anti-FLAG M2 antibody conjugated with HRP (Sigma Aldrich) used at 1:10000 dilution as described in Example 3. APRIL immunoreactive Hybridomas which also exhibited at least 10% inhibition to either human APRIL or mouse APRIL were isolated, subcloned by limited dilution, and reassessed for APRIL binding and blocking activity and IgG titer by ELISA as described. Hybridomas with positive activity but low IgG titers were further isotyped for determination of potential IgM-producing clones. Positive hybridomas were selected for culture scale up, antibody purification and further characterization as described in Example 2.

Example 2: Purification and Characterization of Anti-APRIL Antibodies Derived from Mouse Hybridomas Thirteen hybridoma clones from Example 1 were cultured at sequentially higher scale from 96 well plates to 24 well plates and subsequently to T150 flasks (20 mL culture volume). Prior to purification, cells were transferred out of HAT selective media into pre-defined, low Ig media. Supernatants were harvested 3-5 days after media transfer and clarified by centrifugation, followed by sterile filtration through a 0.22 µm PES membranes (Corning). IgG titers were confirmed by Bioinferometry as described. Supernatants were diluted 1:1 with 2× Protein G binding buffer (1M glycine, 2M NaCl, pH 9.0). Antibodies were purified by Protein G affinity chromatography using 1 mL Protein G HiTrap columns (GE Health Care) at a flow rate of 1 ml/min and as per the manufacturer's recommendations. IgG was eluted from the protein G column by lowering pH using 0.1M glycine buffer, pH 2.8 followed by immediate neutralization using 2M TRIS, pH 8.5. Purified antibodies were reformulated by dialysis in 1×PBS, pH 7.4 followed by concentration by ultrafiltration using an Ultra-30 AMICON 30 kD MWCO filtration unit. Final antibody concentration was determined spectrophotometrically by NanoDrop using a generalized extinction coefficient for murine antibodies (IgG1). Antibody purity and integrity was confirmed by SDS-PAGE under both reducing and non-reducing conditions. Antibody isotype was determined using the Rapid ELISA Mouse mAb isotyping kit (Pierce/Thermofisher Scientific) in conjunction with preliminary sequence analysis (see Example 3). All purified antibodies were determined to be predominantly a distribution of IgG1 and G2a; light chains were all determined to be of kappa class. A relatively smaller subset of APRIL immunoreactive antibodies derived from mice B-002/B-003 (e.g., 02-009, 02-016, 046, FIGS. 1A-1B) were determined to be IgMs and not carried forward for purification.

Purified antibodies were further characterized for APRIL binding, APRIL species cross reactivity (human APRIL vs. mouse APRIL), and receptor blocking activity using TACI-Fc. For binding, an APRIL-based indirect ELISA was used to determine by first approximation the relative affinity of purified anti-APRIL antibodies to either human APRIL or mouse APRIL. ELISA method was as generally described above. In brief, HA-GCN4 hAPRIL (amino acid residues 105-250) and HA-GCN4 mAPRIL (amino acid residues 96-241) were coated at a density of 50 ng/well. Blocking and wash steps were completed as described. Binding of anti-APRIL antibodies to APRIL was quantified using an 8 point dilution of test antibody that spanned over a four log scale. Antibody binding to APRIL was detected using a rabbit anti-mouse IgG (H+L)-HRP conjugate (Jackson ImmunoResearch Laboratories). Antibody binding data was analyzed by non-linear regression analysis using a 3 parameter fit to determine max binding and apparent $EC_{50}$ values. The results are shown in FIG. 3. Human specific, anti-APRIL monoclonal antibodies h01A (described, e.g., in Guadagnoli, M. et al. *Blood* 117, 6856-6865 (2011)), herein described as mAb 1313, and A019C11 (described, e.g., in Jagessar, S. et al. *J Neuroimmune Pharmacol* 7:557-570 (2012)), herein referred to as mAb 0201, were used as positive controls for binding to human APRIL and for comparative purposes. Mouse specific antibody Apry-1-1 (Adipogen) was likewise used for quantification of antibody binding to mouse APRIL.

Receptor blocking activity of anti-APRIL antibodies was likewise measured by ELISA using recombinant TACI or BCMA (extracellular domain(s) expressed and purified as Fc fusion proteins in a binding competition-based experiment. For this experiment, recombinant TACI-Fc or BCMA-Fc were produced in HEK 293 cells following transient transfection of these cells using the Fc expression vector pc-tPA-Fc. In brief, this vector was constructed from parental mammalian expression vector pcDNA3.1 (Life Technologies) using standard molecular cloning techniques. Vector was designed to include a 5' Kozak translation initiation consensus sequence followed by an N-terminal tPA signal sequence for processing and optimized secretion of recombinant protein into the media as a soluble protein. The c-termini of the extracellular APRIL binding domains of human TACI or human BCMA were fused in frame to the Fc portion of human IgG1 beginning at position E98 in CH1. DNA sequences were synthesized following codon optimization for mammalian expression and initially cloned into pcDNA3.1 typically as a Bam H1-Xba cassette. Receptor variants were cloned into resultant vector as Asc1-Bbs1 or Asc1-Not 1 DNA fragments depending on design and cloning strategy. TACI-Fc comprises human TACI sequences 29-110 that includes both CRD1 and CRD2 domains and generally corresponds to the TACI-Fc based receptor decoy atacicept. This sequence is herein described as HuTACI-Fc-001 (or more commonly as TACI-Fc unless otherwise noted). A variant of TACI, likewise expressed as an Fc fusion protein only includes CRD2. TACI may include the C-terminal region (or so-called "stalk") from amino acids 110 to approximately 166 that immediately precede the transmembrane domain. BCMA-Fc comprises the extracellular cytokine binding domain (amino acid residues 1-54) and herein described as HuBCMA-Fc-001 (or more commonly as BCMA-Fc unless otherwise noted).

Figure 2B:
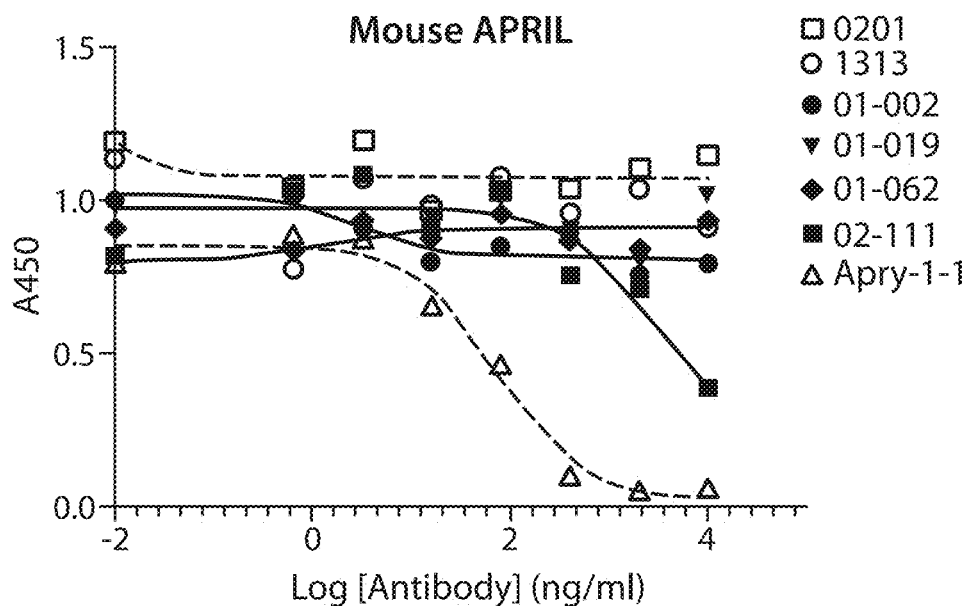

Recombinant TACI-Fc or BCMA-Fc was coated on 96 well plates in 0.1 M carbonate-bicarbonate buffer (pH 9.6), overnight at 4° C. Plates were washed three times with 1×PBST (PBS+0.025% Tween 20) followed by blocking with 1% BSA in 1×PBS, 37° C. for 1 hour. All subsequent wash steps were carried out with 1×PBST. To assess antibody blocking, either 15 ng/mL or 50 ng/mL HA-GCN4-huAPRIL was preincubated with varying antibody concentrations ranging from 0.03-30 µg/mL in binding buffer comprised of 1% BSA and 0.025% Tween-20 in 1×PBS. Preincubation was carried out at 30° C. for 1 hour with mixing. Antibody-APRIL premix with 50 ng/mL APRIL or 15 ng/mL APRIL was then added to TACI-Fc coated or BCMA-Fc coated plates, respectively, and incubated for an additional hour at 30° C. HA-tagged APRIL binding to either receptor was quantified using a goat polyclonal anti-HA tag-HRP antibody (Abcam) added at a 1:10000 dilution followed by colorimetric development using 100 µl/well of freshly prepared TMB substrate (KPL) carried out for up to 30 minutes at room temperature before quenching enzymatic reaction by the addition of 1N sulfuric acid. ELISA signal was quantified by absorbance at 450 nm. The results are shown in FIGS. 2A-2B and FIG. 3. ELISA data was analyzed by non-linear regression. $IC_{50}$ values were calculated based on a 4 parameter fit of antibody titration curves. Where appropriate, % inhibition is calculated based on normalization of data to no antibody control (0% inhibition) vs. background (no APRIL), set as 100% inhibition. Anti-human mAb 1313 and mAb 0201 were used as positive controls and for comparative purposes. Non-blocking antibodies Aprly-1 or Aprly-5 (Enzo Biosciences) were used as negative controls. Mouse specific, blocking antibody aprily-1-1 (Adipogen) was generally used as a positive control in experiments using mouse APRIL (HA-GCN4-mAPRIL).

The functional activity of anti-APRIL antibodies was also evaluated using a cell-based receptor signaling transduction assay. In this assay, binding of APRIL to either TACI or BCMA results in receptor activation leading, in turn, to downstream activation of NF-κB, a transcription factor that ultimately mediates programmed changes in B cell gene expression and phenotype. The use of established NF-κB reporter cell lines for this purpose has been described in the literature. The use of heterologous (non-lymphoid) cell lines lacking TACI or BCMA expression but wherein TACI or BCMA can be introduced exogenously through transfection allows for controlled, receptor defined analysis of APRIL signaling and inhibition of this signal by anti-APRIL antibodies. For this purpose, the commercial 293TN-derived NF-κB reporter cell line NF-κB/293/GFP-Luc™ (System Biosciences) was chosen. These cells are stably transfected with the genes for both GFP and firefly luciferase placed in tandem under the transcriptional control of a minimal CMV promoter (mCMV) and multiple copies of the NF-κB recognition element.

NF-κB/293/GFP-Luc™ cells were maintained and grown in 293TN Cell growth medium (DMEM base medium supplemented with GlutaMAX and FBS) as per manufacturer's instruction. cDNA Expression plasmids pcMV6-XL4/TACI and pcMV6-XL4/BCMA (Origene) were used for transfections. These plasmids encode full-length human TACI (TNFRSF13B, accession number NM_012452) or BCMA (TNFRSF17, accession number NM_001192) 293TN reporter cells were transfected at a density of approximately 6×10⁵ cells/mL (>90% viability) using PEI-MAX as follows: For pcMV6-XL4/TACI, 10.4 ng/mL (~1 ng/well); for pcMV6-XL4/BCMA 83 ng/mL cell culture (~8 ng/well). Total plasmid concentration was held constant at 1.67 µg/mL culture volume (167 ng/well) using empty vector pcMV6-XL4 as needed to maintain constant plasmid amounts for each transfection. Transfections were scaled appropriately based on number of plates needed. 100 µl of transfection mix was transferred to each well. Plates were transferred to 37° C. incubator with 5% $CO_2$ for 20-24 hours.

Figure 4:
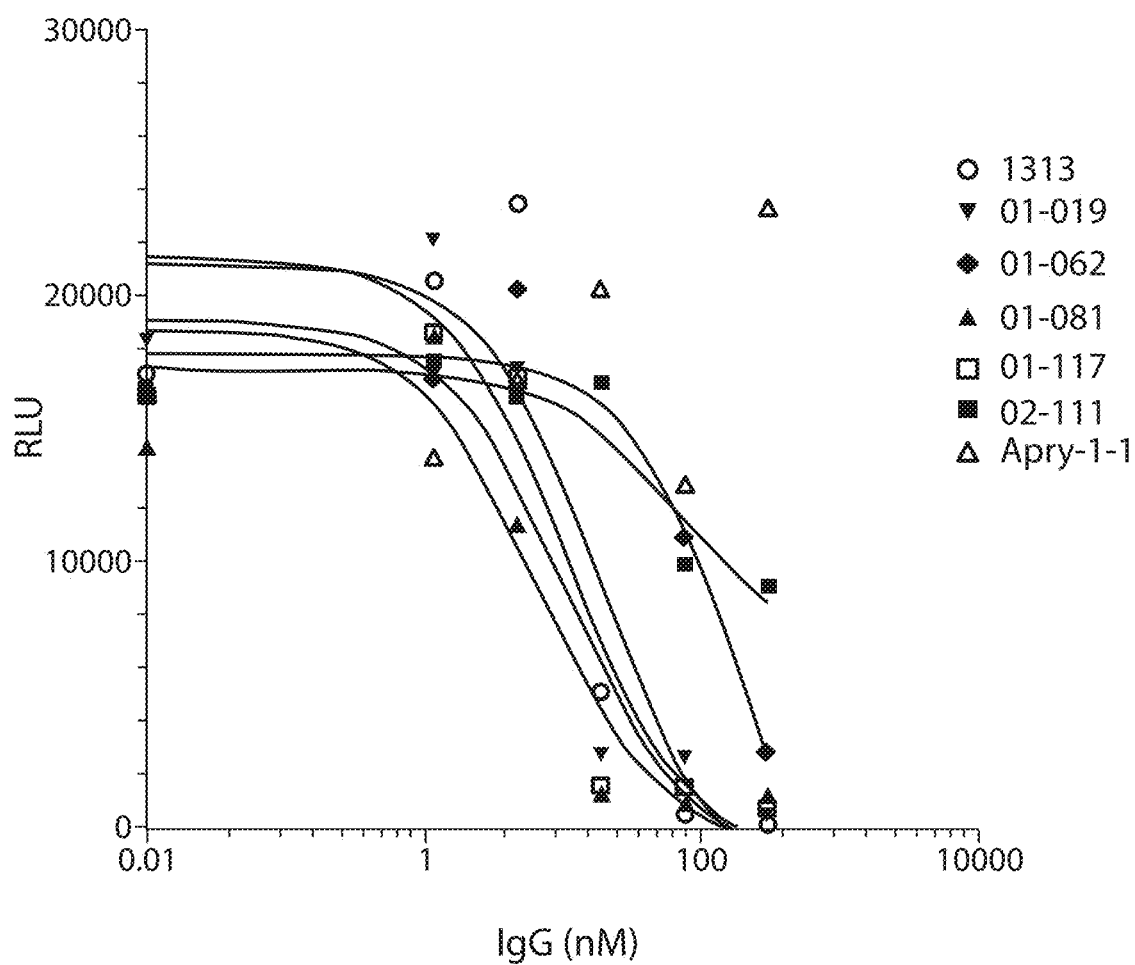
FIG. 4 depicts the inhibition of APRIL-mediated TACI signaling in HEK 293 cells. Functional inhibition of human APRIL-mediated receptor activation was assessed using a 293-derived cell line with stably transfected NF-κB reporter and transiently transfected, human APRIL receptor TACI. HA-tagged GCN4 human APRIL (R&D Systems) was used as source of APRIL. Pre-existing mAb 1313 (human specific, with pre-established blocking activity) was used as a positive control; mouse specific anti-APRIL antibody Apry-1-1 was used as a negative control. Data is illustrative of an orthogonal, biologically relevant assay to assess anti-APRIL activity of mouse derived antibodies.

On day 2, recombinant APRIL (HA-GCN4-APRIL) was preincubated with serially diluted antibody in complete 293TN culture media prior to addition to cells. In brief, for APRIL-mediated activation of TACI signal transduction, 40 ng/mL APRIL (2× target concentration) was mixed 1:1 with serially diluted antibody (likewise diluted in cell culture media) in a 96 well plate; for APRIL-mediated activation of BCMA signal transduction, 200 ng/mL APRIL (2× target concentration) was likewise mixed 1:1. Antibody-APRIL mix was incubated for 1 hour at 37° C. with shaking. 40 µl of preincubation was added to transfected cell culture following removal of spent cell culture media. Cells were incubated at 37° C. as above for an additional 20-24 hours. NF-κB-driven luciferase activity was subsequently quantified using ONE-Glo™ Luciferase kit (Promega) generally in accordance with manufacturer protocol, but with minor modifications. Relative fluorescent units (RLUs) were measured in Opaque white 96-well plates using a luminometer plate reader. The results are shown in FIG. 4. Data was normalized to no Ab control after correcting for assay signal background (no APRIL). $IC_{50}$ values were derived from a non-linear regression analysis of antibody titration curves fit to a four fit parameter. Antibodies 1313 and 0201 typically were used as positive controls. In the case of using recombinant mouse APRIL, apry1-1, was used as a positive control. Non-neutralizing antibodies anti human APRIL antibodies Aprily-1 or Aprily-5 were typically used as negative controls.

Example 3: Determination and Molecular Cloning of Anti-APRIL Immunoglobulin Sequences VH and VL gene sequences of mouse antibodies derived from hybridoma screening were initially determined by reverse transcriptase PCR of B cell RNA using a pool of pre-defined set of mouse Ig sequence-specific primers of varying degeneracy. 5' Primer design for VH sequencing was based on a comprehensive analysis of the mouse immunoglobulin database with corresponding alignment to variable leader sequences. From this analysis, VH leader sequences were clustered (or binned based on sequence relatedness and representation of germline "families"); a unique set of primers, each predicted to anneal more specifically to these binned VH sequence families were designed and used as a cocktail in the RT-PCR reaction. 3' primers were designed to anneal in the constant region of the heavy chain. This primer set was naturally less complex and corresponded to unique sequences in CH1 that define the four known mouse IgG constant regions (IgG1, IgG2a, IgG2b and IgG3). IgM related VH sequences were amplified as above but with substitution of an IgM isotype 3' primer. Similarly, a so-called "pooled primer" RT-PCR approach was used to amplify the corresponding VL sequences from mouse hybridoma RNA. A systematic query of all known mouse VL leader sequences was likewise performed. As kappa and lambda light chains share neither the constant region nor variable region sequences, separate primer sets (kappa vs. lambda specific) were designed. 3' primers were designed based on isotype specific light chain constant region sequence (kappa vs. lambda) in a manner analogous to the one described above for heavy chain sequences. RT-PCR amplification of hybridoma gene sequences from B cell RNA was completed using otherwise established methods. In brief, RNA was extracted from $0.5-2 \times 10^6$ cells using the RNeasy kit (Life Technologies) as per manufacturer's instructions. Cell lysis was facilitated using Qiashredder or related method for initial nucleic acid extraction. Purified RNA was quantified by UV absorbance. cDNA synthesis and subsequent PCR amplification (using Platinum Taq polymerase and primer mixes described above) were completed in tandem using Superscript III One Step RT-PCR kit (Life Technologies). PCR amplicons were purified using Qiaquick PCR clean up kit (Life Technologies) and quantified by UV absorbance at 260 and 280 nm using a Nanodrop spectrophotometer. PCR products were also analyzed by agarose gel electrophoresis to confirm predicted size and gel purified as needed. VH and VL gene sequences were determined by directly sequencing of PCR products using nested primers. Ambiguous sequence data was followed by re-amplification of cell RNA by RT PCR as described above but with modification to protocol and using a subset of smaller pooled primer sets; if necessary PCR products were cloned by TA cloning into an intermediate vector) and transformed into chemically competent TOP10 (Life Technologies) or DH5a (New England Biolabs) as per the manufacturers protocols. DNA sequence data was analyzed using publically available databases (e.g., International Immunogenetics Information system (IMGT), VBase, or NCBI Ig-Blast) to evaluate germline usage, identify CDR sequences and assign putative isotype when possible. In general, this sequencing strategy led to the identification of unique VH sequences for each hybridoma of interest; several clones resulted in the identification of multiple light chains.

Productive VH and VL Ig sequences were amplified by PCR and cloned separately into mammalian Ig expression vectors o-pcMG2 and o-pcMK2, respectively, for recombinant production in HEK293 cells as paired mouse IgG2 (HC) and kappa (LC) isotyped antibodies. Gene-specific primers were designed based on VH and VL sequences identified as described above. Primer design included 18-23 overlapping nucleotides complementary to the corresponding framework regions of the variable gene sequences in addition to vector complementary sequences designed to enable recombination based cloning by modified Gibson assembly fused in frame to variable region sequences through DNA ligation as described below. Primer design was assisted through the use of NEB Builder (New England Biolabs) or Primer3 software. Additional Primer design included the incorporation of restriction endonuclease recognition sequences on respective 5' ends for subcloning as needed. In the case of ambiguous variable sequences, primer design incorporated the use of modestly degenerate nucleotide sequences (at 1-2 positions) or surrogate ("best guess") codons guided by the knowledge of the predicted germline framework identified in the original VH and VL sequence analysis.

For molecular cloning by RT PCR, RNA was extracted from hybridomas generally as described. cDNA first strand was synthesized using Superscript III First Strand Synthesis Supermix (Life Technologies) as per the manufacturer's protocol. 2.5 µl of cDNA template DNA was amplified by PCR using Q5 high fidelity DNA polymerase (New England BioLabs). Amplification included a total of 35 cycles by "touch-up" PCR" using initially a three step amplification for 10 cycles followed by 25 cycles involving 2 step amplification (annealing and extension both at 72° C.). PCR amplicons were evaluated by agarose gel electrophoresis to confirm purity, correct size, and approximate amounts. Gel purification of PCR products was carried when necessary using Qiaquick gel purification kit (Qiagen). HC and LC Ig expression vectors were linearized and prepared for cloning by restriction endonuclease double digestion. 5' ends of digested vectors were subsequently dephosphorylated with shrimp alkaline phosphatase followed by heat inactivation of enzymes. PCR products were ligated into 50 ng linearized vector (gel purified) using NEB Builder (New England Biolabs) at a 2:1 mole ratio of insert:vector. 2 µl of ligation reaction was transformed into chemically competent *E. coli*

(DH5α, New England Biolabs) and plated on LB with antibiotic. Recombinant clones were selected by colony DNA sequencing followed by plasmid purification of positive clones at 200 mL E. coli scale using low endotoxin Purelink Maxiprep kits (Life Technologies) as per the manufacturer's protocols.

For recombinant antibody production, approximately 225 µg each of purified Ig expression vectors (HC and LC) were used to transiently transfect HEK 293F cells. About $2 \times 10^6$ cells/mL cells were transfected using PEI-Max-based transfection reagent and cultured in Freestyle 293 cell media for a total of 5-7 days. Antibody titer was quantified by bioinferometry using Protein A-immobilized biosensors (Pall Biosensors).

Figure 5:
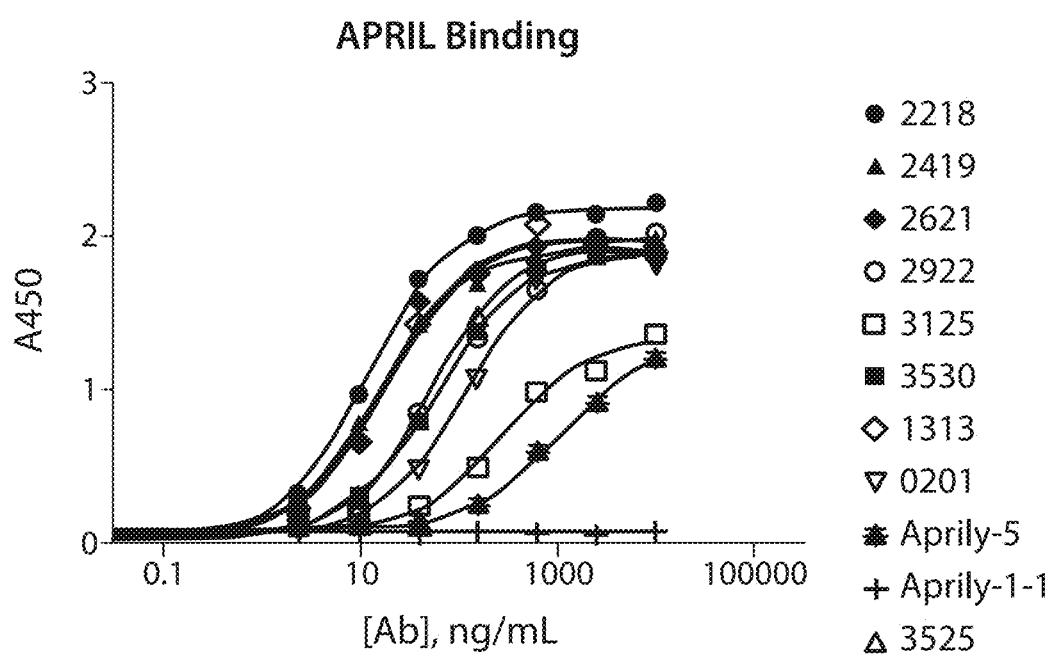
FIG. 5 depicts the binding of anti-APRIL antibodies to human APRIL. Relative binding of select anti-APRIL antibodies was measured by indirect ELISA. Select antibodies based on prior hybridoma screening were recombinantly produced (based on immunoglobin VH and VL gene sequencing) as described. HA-tagged GCN4 human APRIL R&D Systems was used as source of APRIL. Binding data was analyzed by non-linear regression using a three parameter fit. MAbs 1313, 0201, and Aprily-5 were included for comparative purposes; Apry-1-1 was used as a negative control. Extrapolated $EC_{50}$ values are summarized in FIG. 6.
Figure 7:
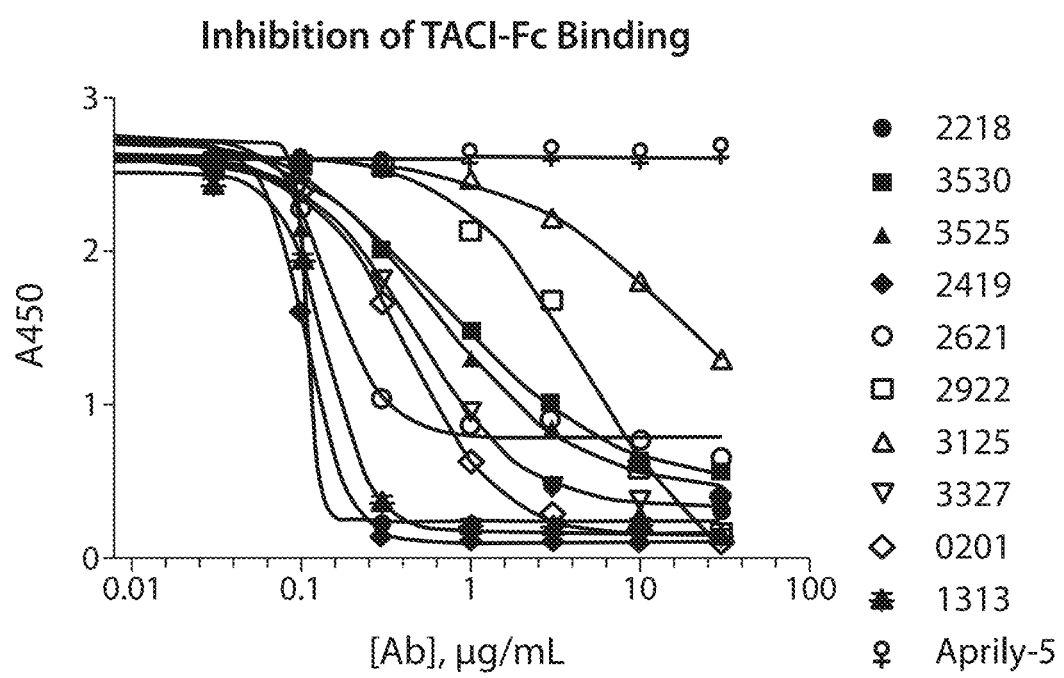
FIG. 7 depicts the antibody inhibition of APRIL binding to TACI. Assay is based on blocking ELISA using recombinant human APRIL (R&D Systems) and Human TACI-Fc. Inhibition was analyzed by non-linear regression using a four parameter fit. MAbs 1313 and 0201 were used as controls and for comparative purposes. Non-neutralizing anti-APRIL mAb Aprily-5 was used as a negative control.
Figure 8:
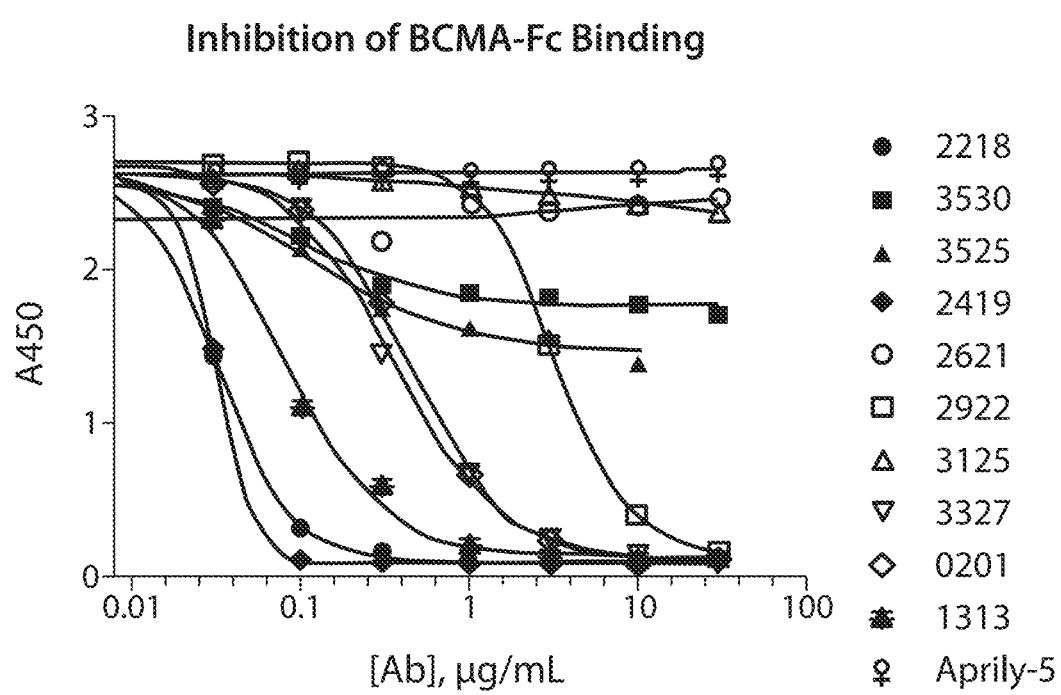
FIG. 8 depicts the antibody inhibition of APRIL binding to BCMA. Assay is based on blocking ELISA using recombinant human APRIL and Human BCMA-Fc. See the description of FIG. 7 for details.

Recombinant antibodies were purified from culture supernatant following clarification by low speed centrifugation and sterile filtration through 0.22 µm PES membranes followed by addition of a protease inhibitor cocktail (Cocktail III, Thermofisher) to mitigate against proteolysis. Antibodies were purified by Protein A affinity chromatography using a 1 mL Protein A Hitrap column (GE Healthcare) with low pH elution as described followed by neutralization by TRIS, pH 8.5. Antibodies were reformulated and concentrated in 1×PBS, pH 7.4 by tandem dialysis and ultrafiltration using Amicon-Ultra 30 centrifugation concentrating units Example 4: In Vitro Binding and Receptor Blocking Activities of Anti-APRIL Antibodies Recombinant anti-APRIL antibodies were characterized with respect to both APRIL binding and receptor blocking activities using both ELISA-based and cell-signaling methods as described. As shown in FIGS. 5-6, first-pass antibody binding to human APRIL by indirect ELISA indicated several antibodies with low and subnanomolar binding affinities to the cytokine target based on $EC_{50}$ values extrapolated from nonlinear regression analyses of antibody titration curves. Antibodies 2218, 2419, and 2621 in particular bound human APRIL with apparent target binding affinities of less than 0.2 nM; antibodies 3530 and 2922 bound human APRIL with apparent target binding affinities between 0.2 nM and 1 nM. 3125 bound human APRIL with an apparently lower affinity (>1 nM). Similar analysis of monoclonal antibody binding to mouse APRIL homologue indicated only mAb 3530 having appreciable cross-species binding to target (data not shown). Functional analysis of antibody blocking activity was evaluated by competition ELISA using receptor-Fc as the APRIL capture ligand in a 96 well based format as described. This analysis included the use of both biologically relevant APRIL TNFR-related receptors (human TACI and human BCMA) for purposes of evaluating any selectivity with respect to the antibody-mediated antagonism of APRIL-receptor interactions. As shown in FIG. 9, antibody $IC_{50}$ values were calculated from a non-linear analysis of antibody titration curves. Anti-human blocking antibodies 1313 and 0201 were used as positive controls and for comparative purposes. Non-neutralizing antibody Aprly-5 (Enzo Biosciences) was used as a negative control. Based on this in vitro data, all of the recombinant antibodies demonstrated at least partial blocking of human APRIL to human TACI-Fc. As shown in FIG. 7, monoclonal antibodies 2218, 2419, 2621, 3327, and 3530 blocked APRIL-TACI binding with corresponding $IC_{50}$ values in the low or sub-nanomolar range. MAbs 3125 and 2922 would appear to block with somewhat lower potency, with $IC_{50}$ values greater than 10 nM. As shown in FIG. 8, a similar evaluation of receptor blocking using BCMA-Fc indicates antibodies 2218, 2419, and 3327 are likewise able to block BCMA binding with low or subnanomolar potency. MAb 3530 would appear to be relatively selective with respect to blocking APRIL binding to TACI-Fc in comparison to BCMA-Fc; as such this antibody may be viewed as being "TACI selective." MAb 2621 did not appear to block APRIL binding to BCMA-Fc as evaluated in this assay; as such, mAb 2621 may be viewed as being a potentially "TACI-specific" antibody.

Figure 11A:
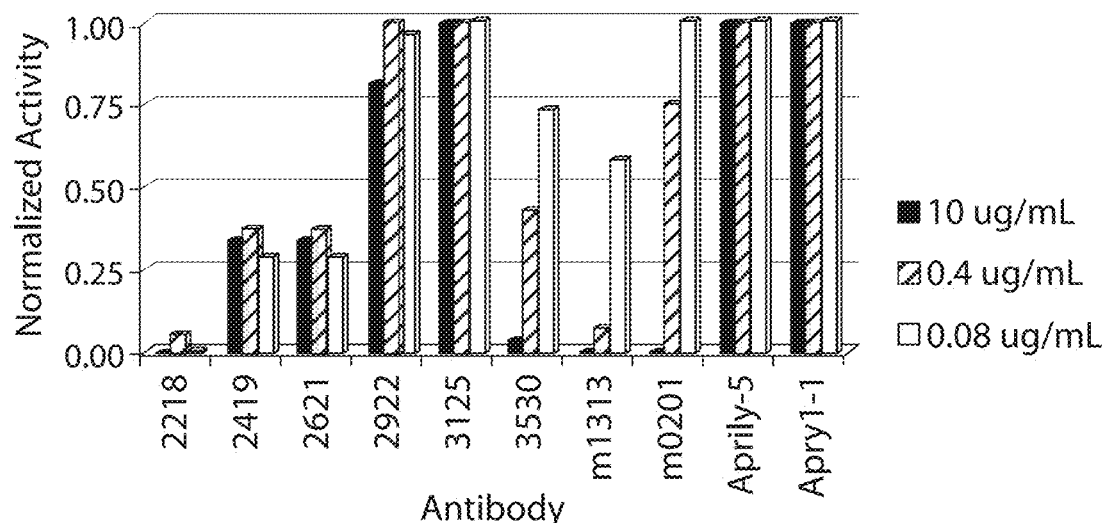
FIGS. 11A-11B depict antibody Inhibition of APRIL-mediated receptor signaling. Inhibition of APRIL-receptor mediated NF-κB intracellular signaling was evaluated using the HEK 293 NF-κB reporter cell line following transient transfection of either full-length human TNF family receptors TACI or BCMA full-length cDNA expression vectors. Data are normalized to activity vs. no antibody treatment. Scale of Y axis displayed ranges from 0 to 1. Inhibition of APRIL-mediated receptor signaling was measured at three different antibody concentrations (0.08 µg/mL, 0.4 µg/mL, and 10 µg/mL).
Figure 11B:
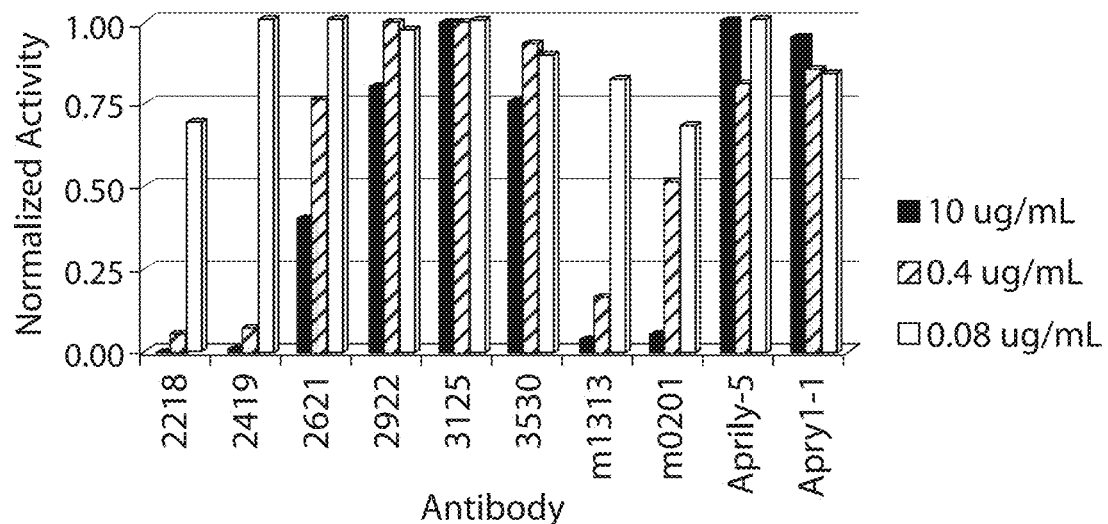

Functional (receptor antagonism) activity of anti-APRIL antibodies was further evaluated using an orthogonal, cell-based NF-κB transcriptional reporter assay to assess inhibition of APRIL-mediated receptor signal activation. This assay involved the heterologous expression of full-length (transmembrane) TACI or BCMA by transient plasmid transfection in and engineered HEK293 cell line possessing a stably transfected NF-kB—transcriptionally activated luciferase reporter gene. Assay was generally carried out as described using recombinant Hu APRIL as the exogenous source of receptor activating cytokine. Data was normalized to the minus antibody control after subtraction of signal background (no APRIL or Ab). The data are summarized in FIGS. 11A-11B. Based on these data, the potent receptor blocking activities of monoclonal antibodies 2218 and 2419 were further confirmed in an antibody-dose dependent manner. These activities included blocking of both BCMA and TACI receptors. Monoclonal antibodies 2922 and 3125 qualitatively exhibited lesser activity, consistent with their relatively lower activities in the Receptor-Fc blocking ELISA (i.e., in comparison to mAbs 2218 and 2419). Apparent discrepancies between these two assays may be attributed to differential receptor expression levels, protein turnover, or other biological factors not present in the less complex ELISA based binding assays. Nevertheless, these data, taken collectively, demonstrate clear functional activity of the recombinant anti-APRIL antibodies with respect to antagonism of APRIL activity described herein.

Figure 16:
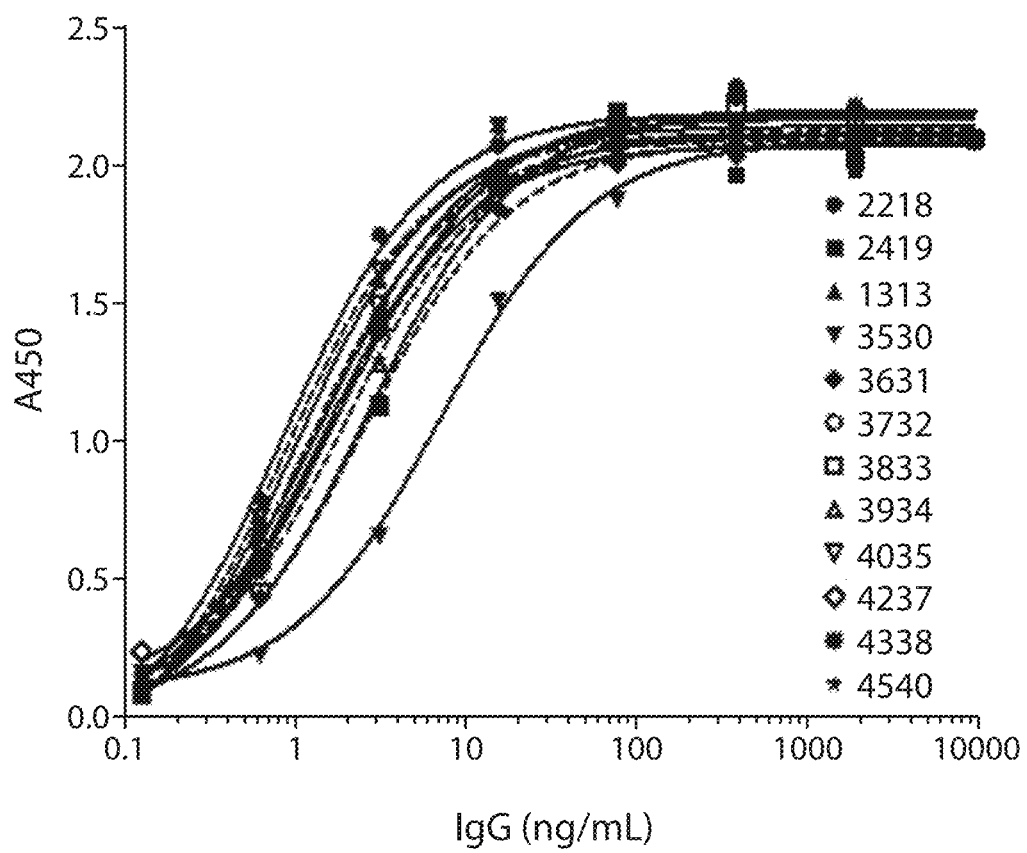
FIG. 16 depicts the binding of exemplary anti-APRIL antibodies to human APRIL. Relative binding of exemplary anti-APRIL antibodies was measured by indirect ELISA. Extrapolated $EC_{50}$ values are summarized in FIG. 17.
Figure 18A:
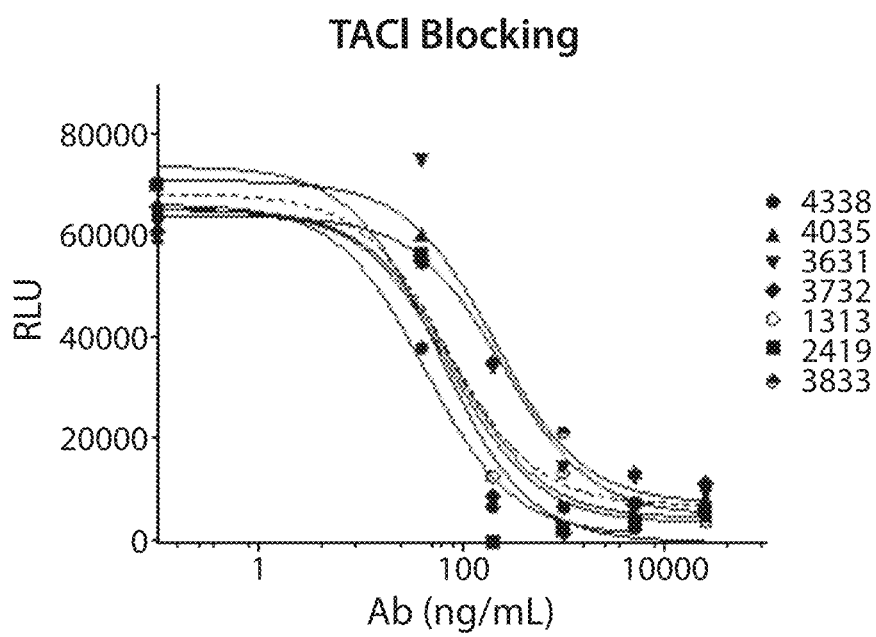
FIGS. 18A-18B depict the antibody inhibition of APRIL-mediated receptor signaling. Inhibition of APRIL-receptor mediated NFκB intracellular signaling was evaluated using the HEK 293 NFκB reporter cell line following transient transfection of either full-length human TNF family receptors TACI (FIG. 18A) or BCMA (FIG. 18B) full-length cDNA expression vectors. Exemplary antibodies were shown for illustrative purposes.
Figure 18B:
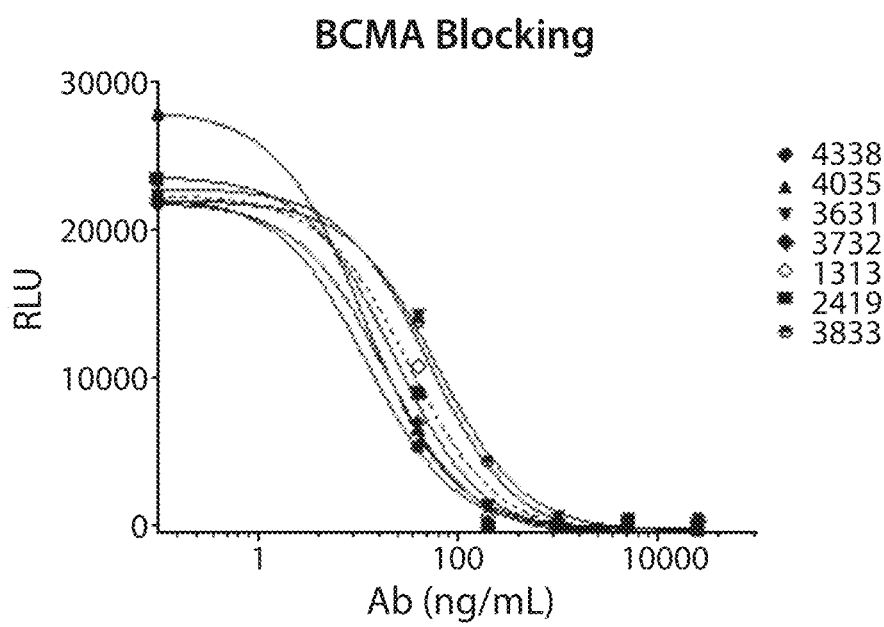
Figure 19A:
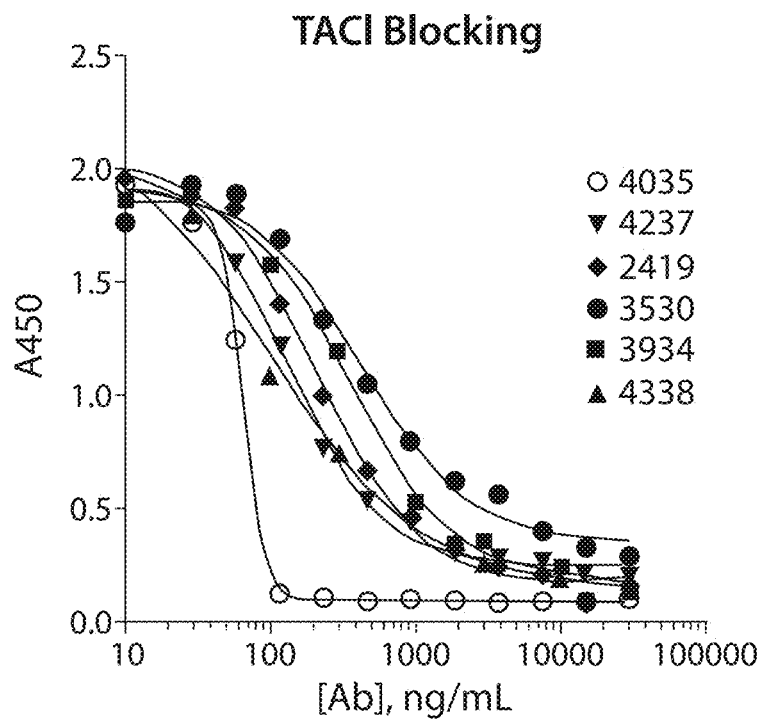
FIGS. 19A-19B depict the antibody inhibition of APRIL binding to TNFSF receptors TACI (FIG. 19A) and BCMA (FIG. 19B). Assay is based on blocking ELISA using recombinant human APRIL (R&D Systems) and Human TACI-Fc. Inhibition was analyzed by non-linear regression using a four parameter fit. $IC_{50}$ values are summarized in FIG. 20.
Figure 19B:
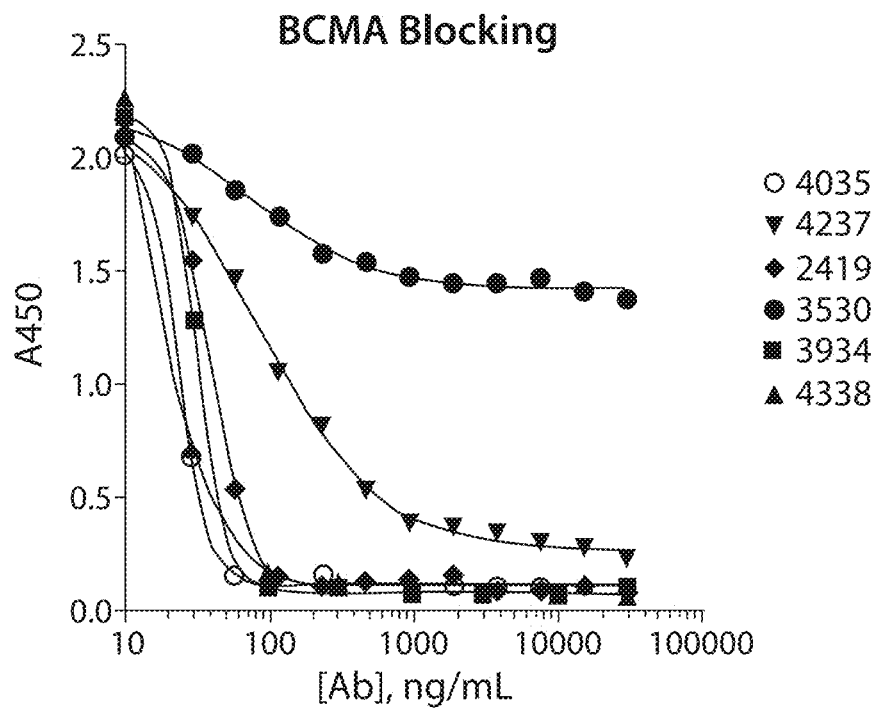

Additional experimental data include, for example, the following. Binding of exemplary anti-APRIL antibodies to human APRIL is shown in FIG. 16. Relative binding affinities of exemplary anti-APRIL antibodies are shown in FIG. 17. Antibody inhibition of APRIL-mediated receptor signaling is shown in FIGS. 18A-18B. Antibody inhibition of APRIL binding to TNFSF receptors TACI and BCMA is shown in FIGS. 19A-19B. Antibody inhibition of APRIL binding to both human TACI-Fc and human BCMA-Fc is summarized in the table in FIG. 20.

Example 5: Species Cross-Reactivity of Anti-APRIL Antibodies

Figure 10A:
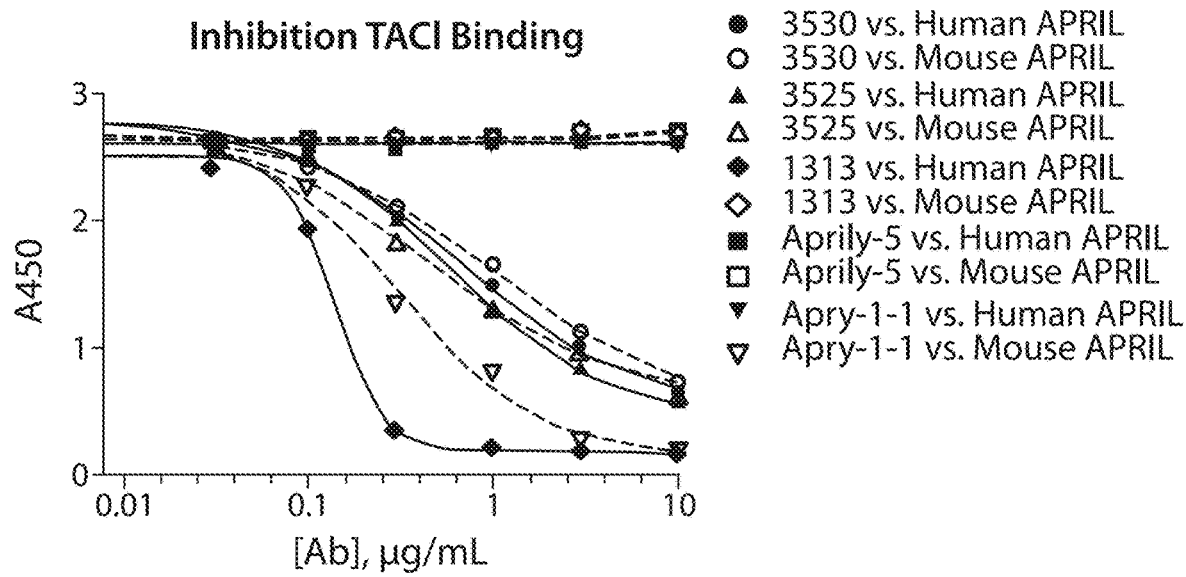
FIGS. 10A-10B depict APRIL species cross reactivity of anti-APRIL antibodies. Anti-APRIL antibodies with blocking activity (summarized in FIG. 9) were assessed for ability to block both human and mouse APRIL binding to human TACI-Fc and BCMA-Fc. Recombinant mouse and human APRIL with otherwise identical HA-tagged GCN4 N-terminal fusions (R&D Systems) were used as receptor ligands. Select data is included for illustrative purposes. Antibodies 3530 and 3525 demonstrated any cross-species activity with respect to TACI-Fc receptor blocking (FIG. 10A). Analogous cross-neutralization with respect to APRIL binding to BCMA-Fc was only partially achieved (FIG. 10B). Neutralizing Antibody 1313 (human specific) and antibody Apry-1-1 (mouse specific) were used as controls. Closed symbols, human APRIL; open symbols, mouse APRIL.
Figure 10B:
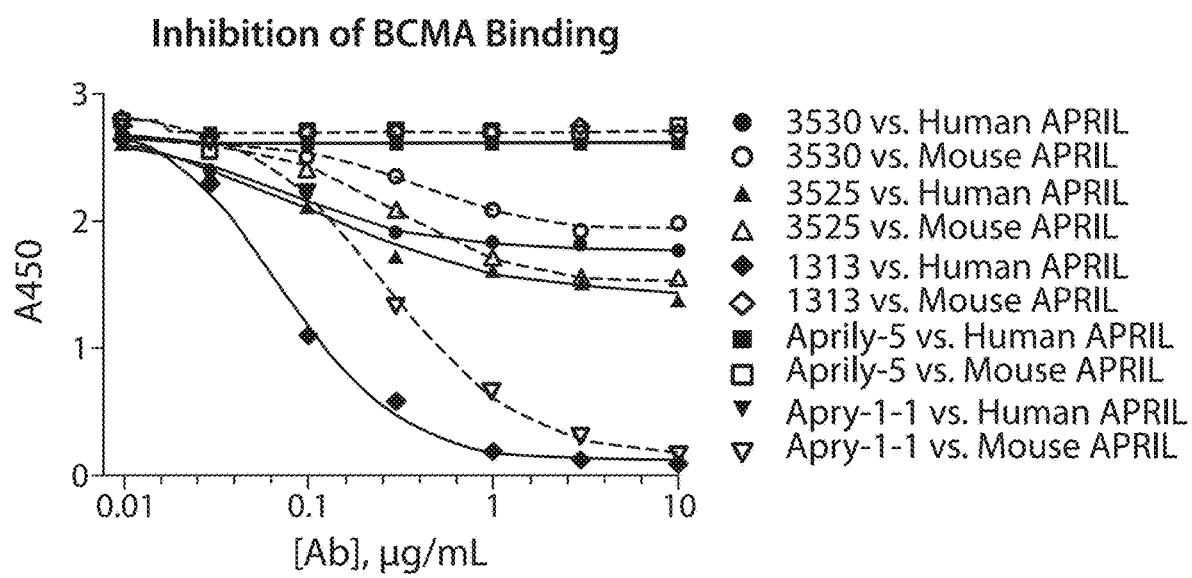

In addition to demonstrating the functional activity of several anti-APRIL antibodies, the cross-reactivity of these antibodies with respect to binding and blocking both mouse and human APRIL was also evaluated. This characterization employed the same set of in vitro assays as described but with the inclusion of analogously HA-tagged mouse APRIL (R&D Systems). For illustrative purposes, a subset of data from the receptor-Fc based blocking ELISA (both TACI-Fc and BCMA-Fc) is included. In this analysis, mAb 3530 was compared to antibodies 1313 (human specific anti-APRIL blocking antibody), Apry-1-1 (mouse specific anti-APRIL blocking antibody) and non-neutralizing antibody Aprly-5 (negative control). Antibody-titered receptor blocking activity data are summarized in FIGS. 10A-10B for blocking APRIL binding to human TACI-Fc and human BCMA-Fc, respectively. Consistent with other data, mAb 3530 would appear to be a "TACI-selective" antibody based on its relative neutralization profile (TACI vs. BCMA). Moreover, this antibody was able to apparently block both mouse and APRIL binding to TACI-Fc with comparable potency (apparent $IC_{50}$ values). To our knowledge, this the first example of a species cross reactive anti-APRIL antibody with both implications with respect to epitope specificity as well as use in preclinical development of this antibody using disease relevant (syngeneic) rodent models.

Figure 21A:
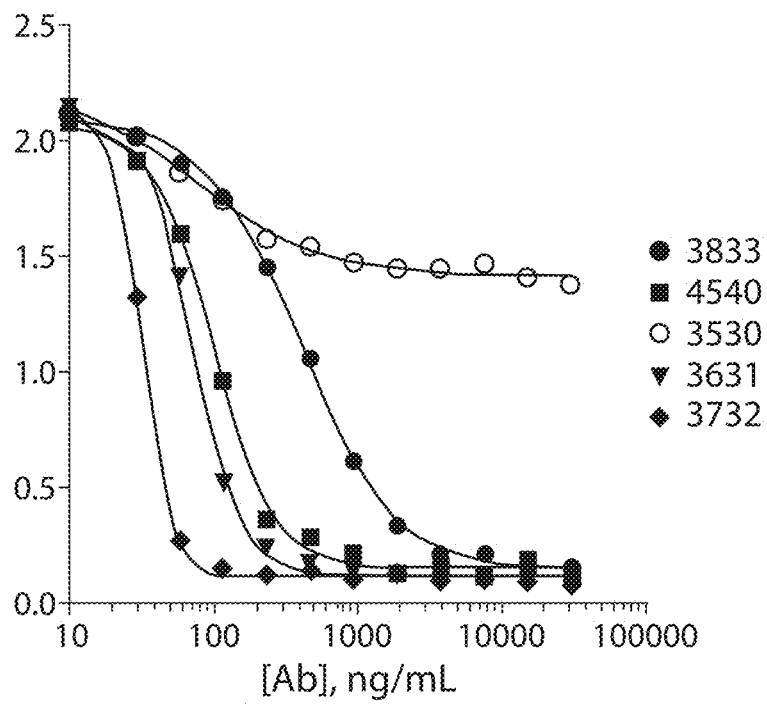
FIGS. 21A-21B depict APRIL species cross blocking activities of anti-APRIL antibodies. Ability of anti-APRIL antibodies to block binding of both human (FIG. 21A) and mouse (FIG. 21B) APRIL to BCMA was evaluated by ELISA. Respective blocking activities of exemplary antibodies (3833, 4540, 3530, 3631, and 3732) with previously determined cross-species (mouse and human) APRIL binding are shown.
Figure 21B:
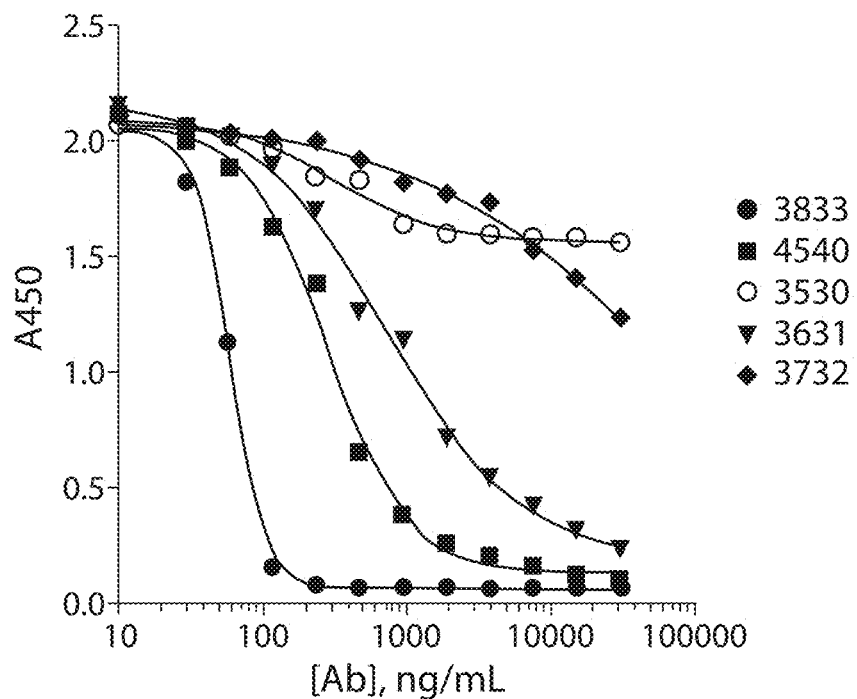

APRIL species cross blocking activities of anti-APRIL antibodies are also shown in FIGS. 21A-21B.

Figure 12A:
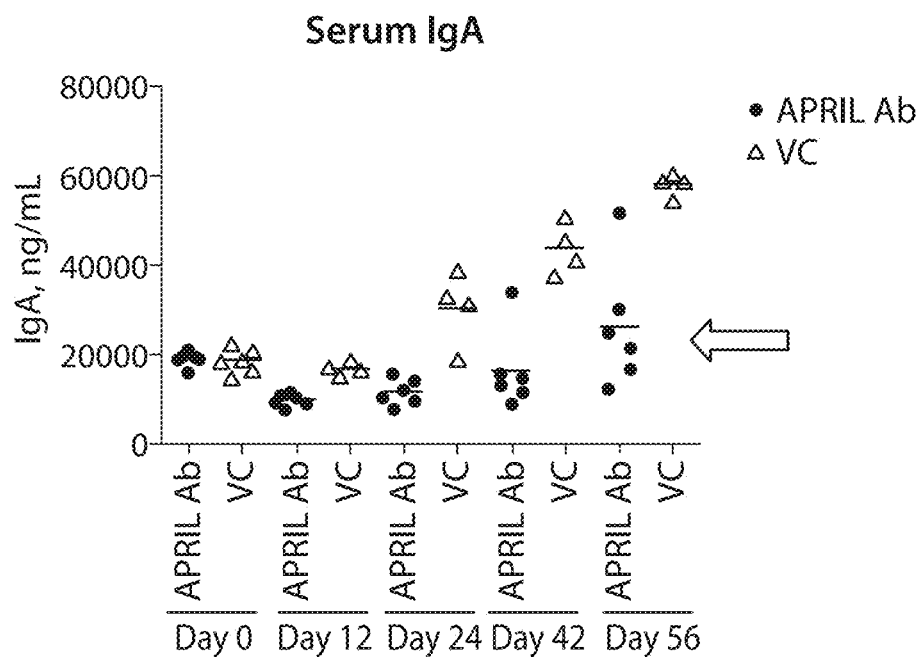
FIGS. 12A-12B depict in vivo potency of an anti-APRIL antibody in reducing serum IgA levels. The suitability of use of anti-APRIL antibody for modulating IgA production in vivo was evaluated based directly on a reduction of serum IgA levels following the administration of a neutralizing anti-APRIL antibody in a laboratory rodent model. For this purpose mouse-APRIL specific, blocking antibody Apry-1-1 (Adipogen) hitherto used as a control for assessing anti-APRIL antibody activity in vitro was also used as a test antibody to demonstrate proof-of-concept. Age-matched male B6C3F1 mice (6-10 weeks old) were dosed with 20 mg/kg antibody two times a week via i.p. injection for a total of 8 weeks. Saline for injection was used as the negative (vehicle) control (VC). Serum isotype specific immunoglobulin levels (IgG, IgM, and IgA) were monitored individually by ELISA approximately every 12 days.
Figure 12B:
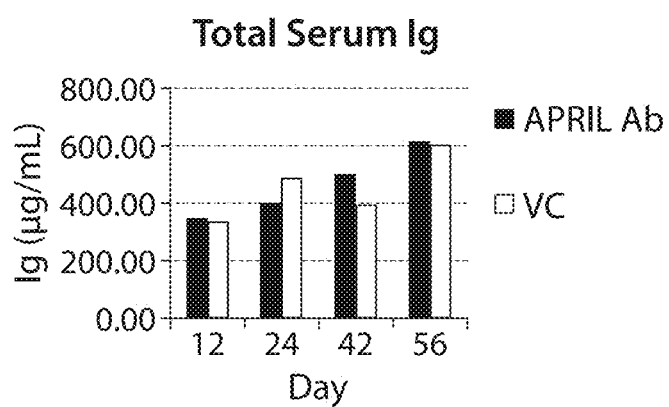

Example 6: Functional Activity of Anti-APRIL Antibody for Reduction of Serum IgA In Vivo In addition to its role in promotion of tumor growth, the cytokine APRIL plays several critical roles in the regulation of adaptive and mucosal immunity vis-à-vis the modulation of B and T cell function. This immunological activity includes induction of IgA production in B cells through receptor-mediated induction of Ig class switching, B cell proliferation, and survival of IgA+ related plasma cells. This central role of APRIL in IgA production leads to its potential as a therapeutic target for diseases involving the dysregulated production of IgA and/or formation of IgA-containing immune complexes. Such diseases would include but not limited to IgA nephropathy, IgA-related vasculitis (e.g., Henoch-Schodein purpura), SLE, IgA-related monoclonal gammopathies, alcoholic liver disease, etc. The biological potency of anti-APRIL therapeutic antibody can therefore be evaluated in vivo based directly on a reduction of serum IgA levels following the administration of such an antibody in a laboratory rodent model. Toward this end, the mouse-APRIL specific, blocking antibody Apry-1-1 (Adipogen) used as described herein as a control for assessing anti-APRIL antibody activity in vitro was also used as a test article. Age-matched male B6C3F1 mice (6-10 weeks old) were dosed with 20 mg/kg antibody two times a week via IP injection. 12 for 8 weeks. Saline for injection was used as the negative (vehicle) control. Serum Isotype specific immunoglobulin levels (IgG, IgM, and IgA) were monitored individually by ELISA approximately every 12 days. Body weights were monitored 3× weekly, hematology and serum chemistries, and general health of the animals was monitored on a regular basis. Blood was drawn prior to dosing (day 0, pre-bleeds). Survival bleeds occurred at the end of 2 weeks (end of phase I) at 4 weeks, and 6 weeks. Terminal bleeds occurred at the end of 8 weeks. The results are shown in FIGS. 12A-12B.

In this study, chronic administration of a functional anti-APRIL antibody with in vitro validated blocking activity led to a reduction in serum IgA levels below 50%. Reduction was observed by day 24 and was sustained over the course of antibody treatment. Treatment with the mouse anti-APRIL antibody had no statistically differential effects on total Ig serum levels relative to the control; hematology and blood chemistry likewise were not affected.

Example 7: Epitope Mapping

Figure 22:
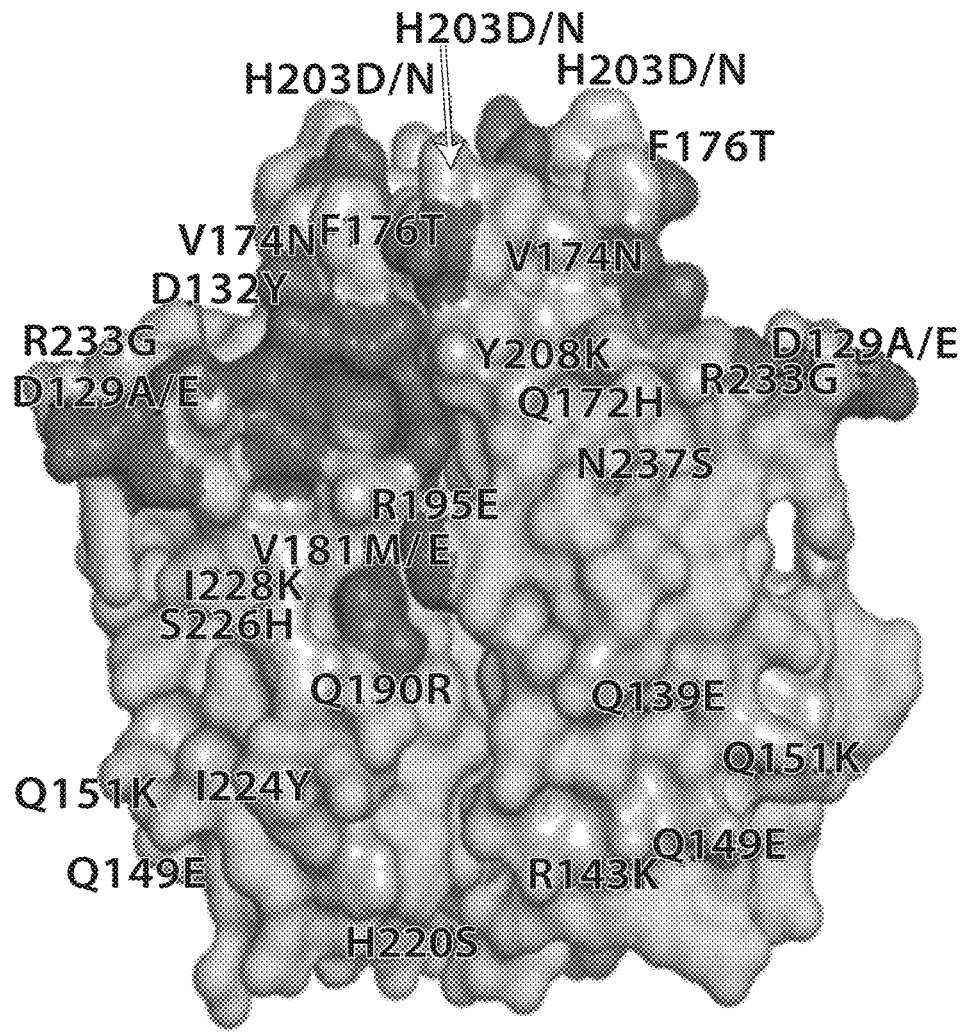
FIG. 22 depicts human APRIL site-directed variants used for epitope mapping. APRIL is depicted as a trimer. Typical epitope containing CRD2 high affinity receptor binding site is depicted in dark gray. Positions of amino acid changes are noted with wildtype amino acid preceding number and mutation following (e.g., R233G represents mutation of arginine at position 233 to glycine).
Figure 23A:
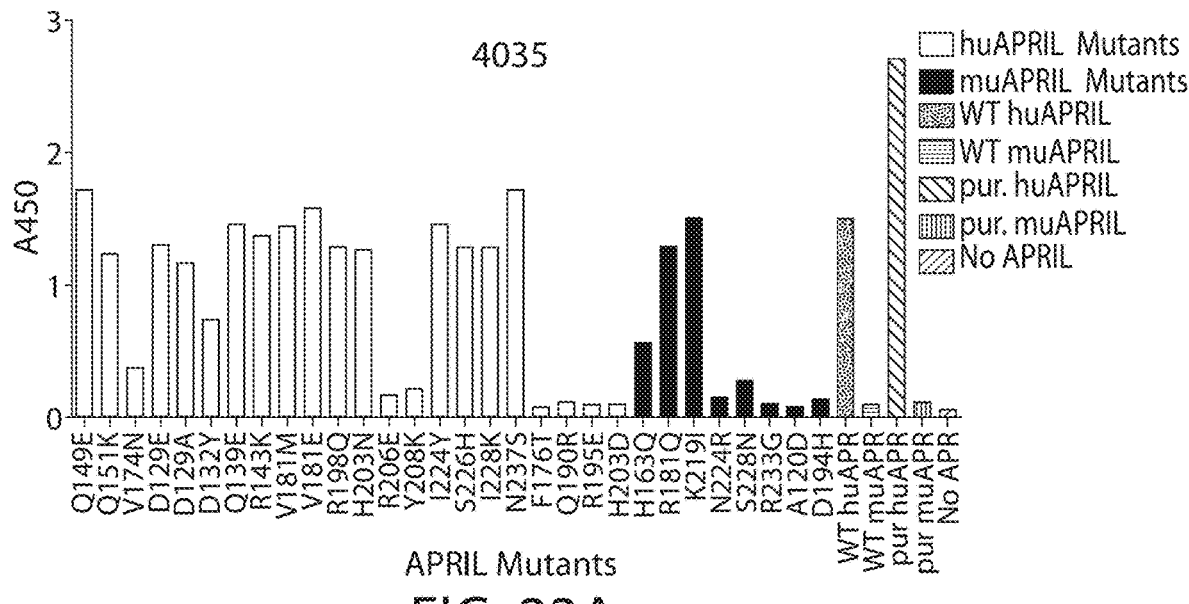
FIGS. 23A-23B depict epitope mapping of antibody 4035 (FIG. 23A) (comparison is made to reference antibody 1313; see FIG. 23B). Antibody binding to human and mouse variants was assessed by ELISA. FLAG-tagged APRIL was captured from cell culture media using anti-FLAG antibody. Human APRIL variants are depicted as open bars; mouse APRIL variants are depicted as solid bars.
Figure 23B:
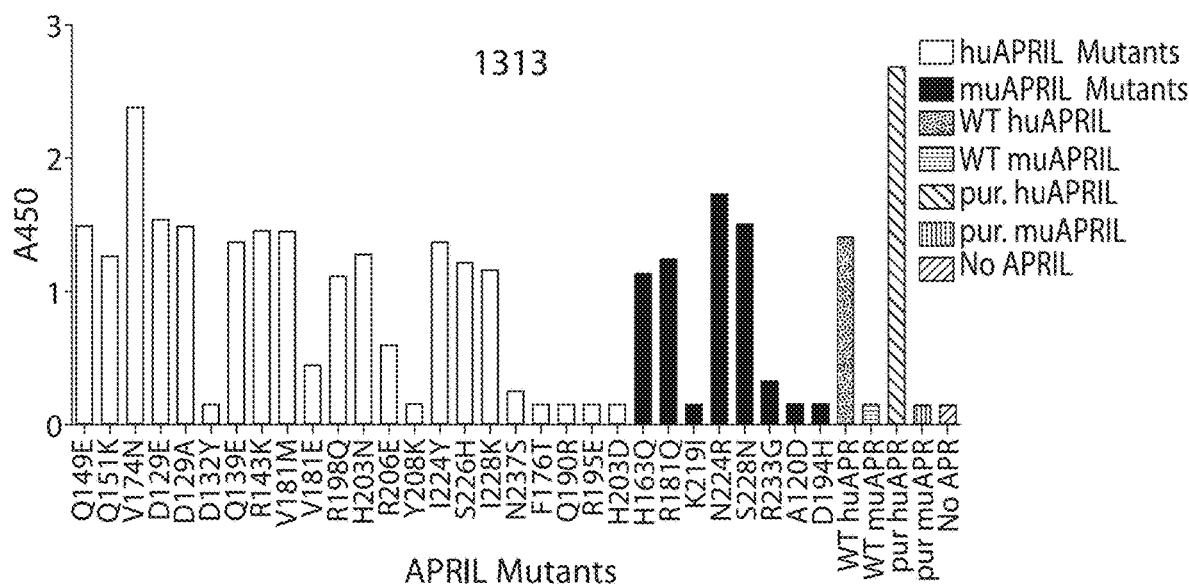
Figure 24A:
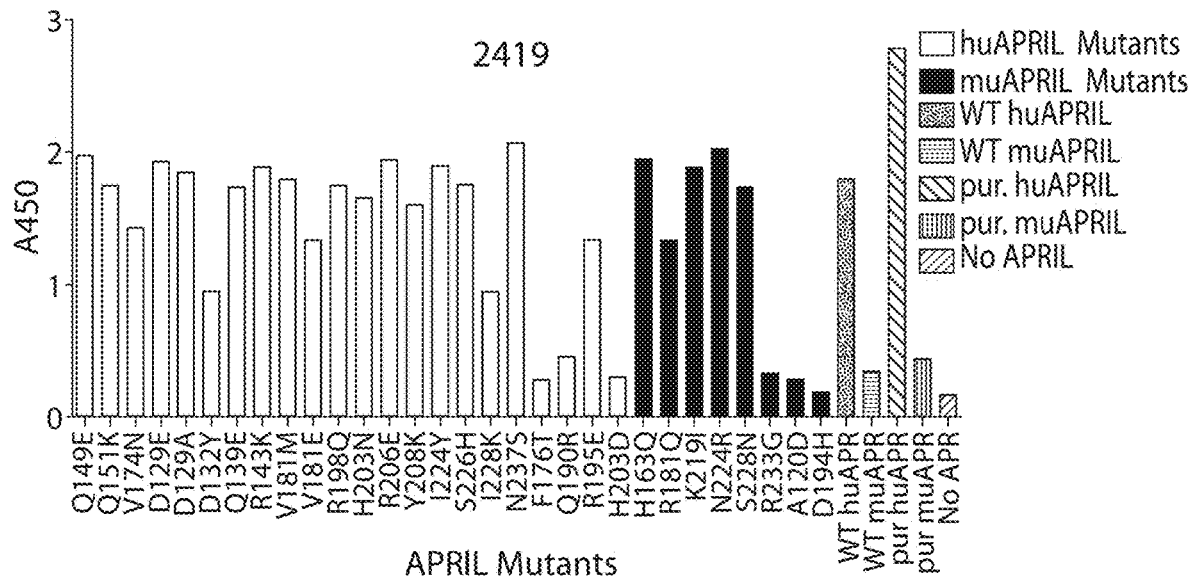
FIGS. 24A-24B depict epitope mapping of antibody 2419 (FIG. 24A) (comparison is made to reference antibody 1313; see FIG. 24B). Antibody binding to human and mouse variants was assessed by ELISA. Human APRIL variants are depicted as open bars; mouse APRIL variants are depicted as solid bars.
Figure 24B:
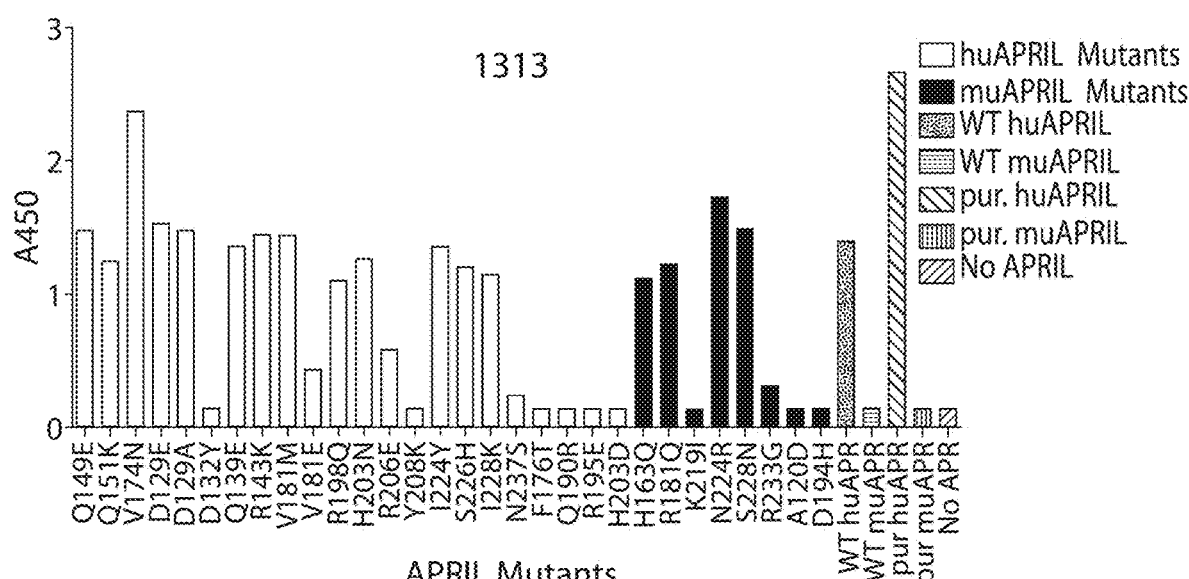
Figure 25A:
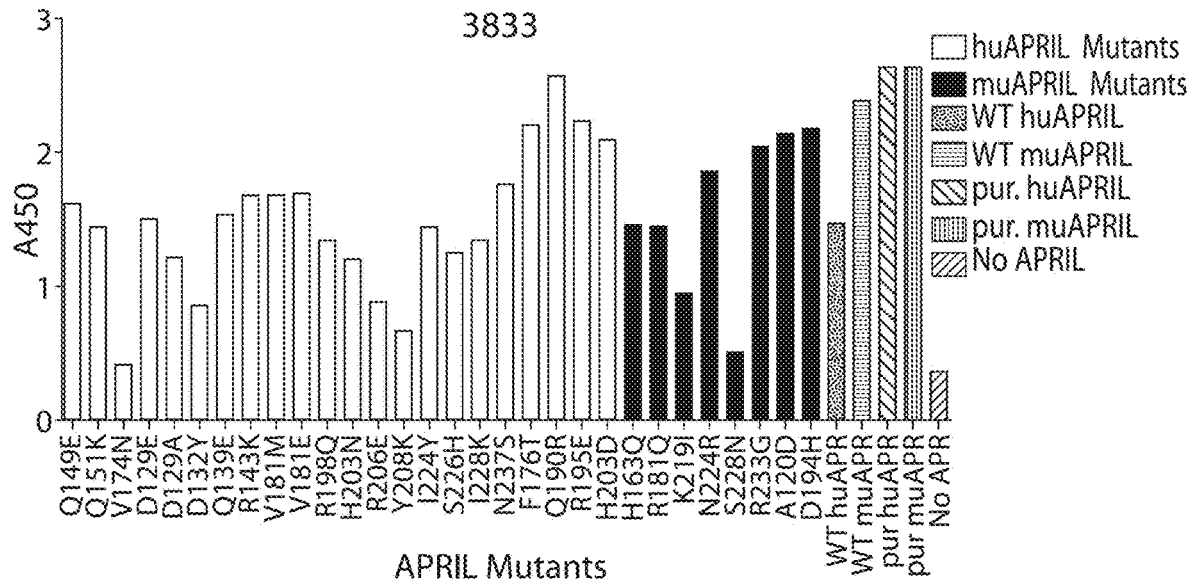
FIGS. 25A-25B depict epitope mapping of antibody 3833 (FIG. 25A) (comparison is made to reference antibody 1313; see FIG. 25B). Antibody binding to human and mouse variants was assessed by ELISA. FLAG-tagged APRIL was captured from cell culture media using anti-FLAG antibody. Human APRIL variants are depicted as open bars; mouse APRIL variants are depicted as solid bars.
Figure 25B:
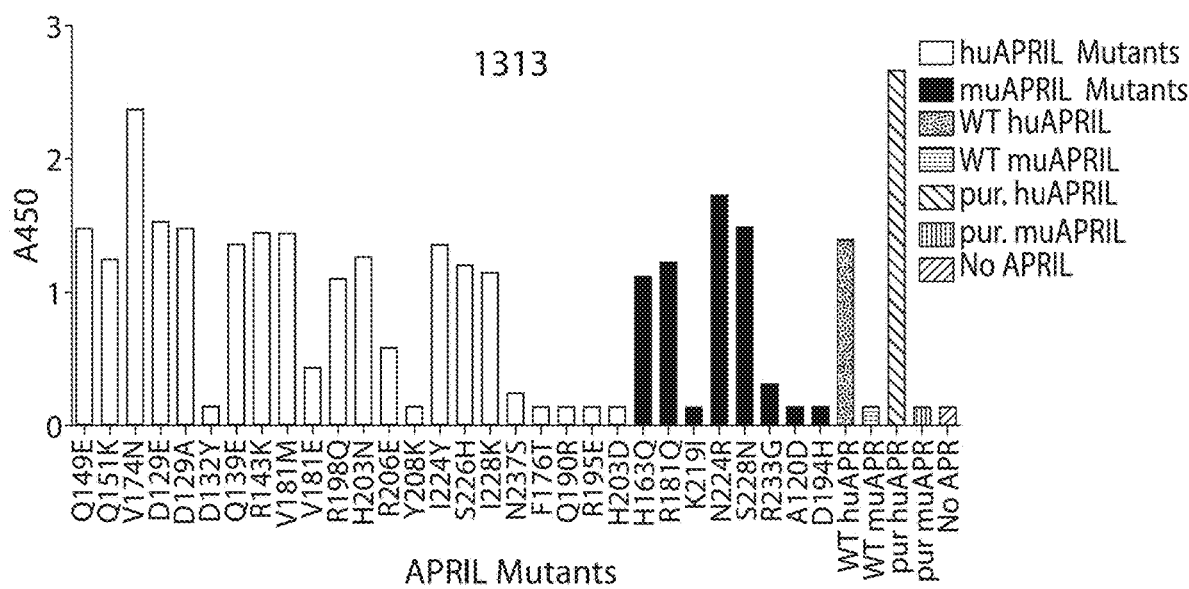

Human APRIL site-directed variants were used for epitope mapping. As shown in FIG. 22, APRIL is depicted as a trimer (cyan, green, and magenta). Typical epitope containing CRD2 high affinity receptor binding site is depicted in dark blue. Positions of amino acid changes are noted with wildtype amino acid preceding number and mutation following (e.g., R233G represents mutation of arginine at position 233 to glycine).

Figure 26:
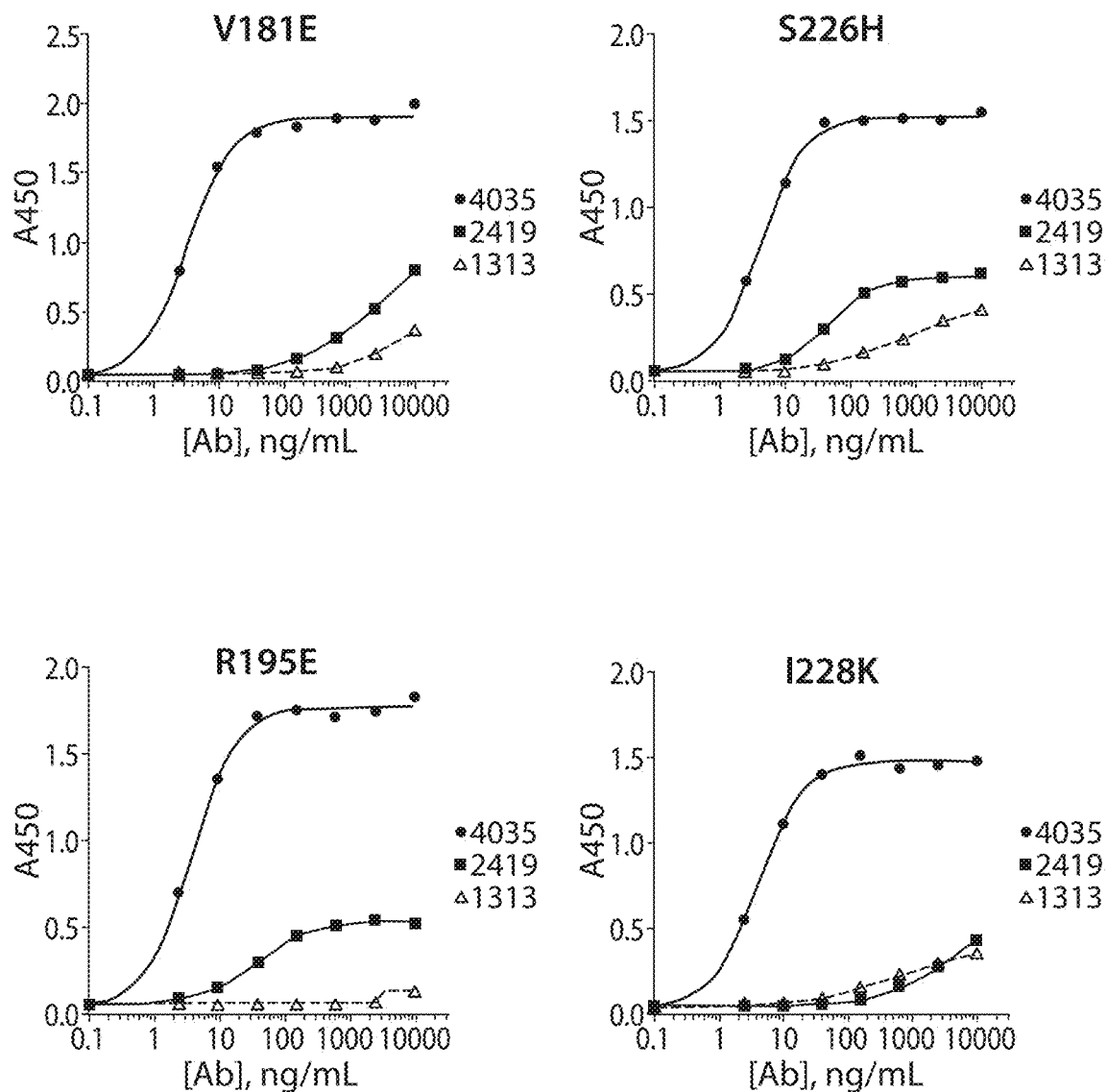
FIG. 26 depicts differentiated epitope mapping of anti-APRIL antibodies by site directed mutagenesis. Primary characterization of human APRIL binding site was carried out by site-directed mutagenesis of select amino acid positions within APRIL followed by evaluation of antibody binding to these variants by ELISA. Exemplary data for three anti-APRIL antibodies 4035 (solid circles), 2419 (solid squares), and 1313 (open triangles) are shown for illustrative purposes.

Epitope mapping of exemplary antibodies 4035, 2419, and 3833 was performed. Antibody binding to human and mouse variants was assessed by ELISA. Comparison is made to reference antibody 1313. FLAG-tagged APRIL was captured from cell culture media using anti-FLAG antibody. The results are shown in FIGS. 23A-23B, 24A-24B, and 25A-25B. Differentiated epitope mapping of exemplary anti-APRIL antibodies was performed by site directed mutagenesis. Primary characterization of human APRIL binding site was carried out by site-directed mutagenesis of select amino acid positions within APRIL followed by evaluation of antibody binding to these variants by ELISA. Exemplary data for three anti-APRIL antibodies 4035 (solid circles), 2419 (solid squares), and 1313 (open triangles) are shown in FIG. 26 for illustrative purposes.

Differential binding profiles of exemplary anti-APRIL antibodies are shown in Table 6. Exemplary amino acid residues that bind to the anti-APRIL antibody molecules described herein are listed. One or more of these residues form at least part of a binding region on APRIL. Exemplary residues within the binding region predicted to have an impact on binding (e.g., based on the site directed mutagenesis studies described herein) are noted by an "X". Exemplary residues predicted to have lesser or no impact on binding (e.g., based on the site directed mutagenesis studies described herein) are noted by an "N" for comparative purposes.

TABLE 6

Differential Binding Profiles of Exemplary Anti-APRIL Antibodies
(Table discloses SEQ ID NOS: 338-341, respectively, in order of appearance)

| AA position | AA | 1313 Impact | No impact | 4035 Impact | No impact | 3833 Impact | No impact | 2419 Impact | No impact |
|---|---|---|---|---|---|---|---|---|---|
| 129 | Asp | | | | | | | | |
| 130 | Asp | | | | | | | | |
| 131 | Ser | | | | | | | | |
| 132 | Asp | X | | | | | | | |
| 170 | Leu | | | | | | | | |
| 174 | Val | | N | X | | X | | | |
| 175 | Thr | | | | | | | | |
| 176 | Phe | X | | X | | | N | X | |
| 177 | Thr | | | | | | | | |
| 178 | Met | | | | | | | | |
| 179 | Gly | | | | | | | | |
| 180 | Gln | | | | | | | | |

TABLE 6-continued

Differential Binding Profiles of Exemplary Anti-APRIL Antibodies
(Table discloses SEQ ID NOS: 338-341, respectively, in order of appearance)

| AA position | AA | 1313 Impact | No impact | 4035 Impact | No impact | 3833 Impact | No impact | 2419 Impact | No impact |
|---|---|---|---|---|---|---|---|---|---|
| 181 | Val | X | | | | N | | N | X |
| 190 | Gln | X | | X | | | | N | X |
| 192 | Thr | | | | | | | | |
| 195 | Arg | X | | X | | | | | |
| 196 | Cys | | | | | | | | |
| 197 | Ile | | | | | | | | |
| 200 | Met | | | | | | | | |
| 201 | Pro | | | | | | | | |
| 202 | Ser | | | | | | | | |
| 203 | His | | | | | | | | |
| 205 | Asp | | | | | | | | |
| 206 | Arg | | N | X | | X | | | N |
| 208 | Tyr | X | | X | | X | | | N |
| 226 | Ser | | | | N | | | | |
| 228 | Ile | | N | | N | | | X | |
| 230 | Pro | | | | | | | | |
| 231 | Arg | | | | | | | | |
| 232 | Ala | | | | | | | | |
| 233 | Arg | | | | | | | | |
| 237 | Asn | X | | | N | | N | | N |
| 241 | His | | | | | | | | |

Example 8: Humanization of Mouse Derived Anti-APRIL Antibodies

Select anti-APRIL antibodies were derived from mouse immunization as described herein. The variable regions of select antibodies, namely 2419, 4035, and 4540 were subsequently humanized for purposes of potential therapeutic use and mitigation of immunogenicity. In brief, humanization was performed by identifying human germlines proximal to the mouse variable heavy (VH) and variable light (VL). Once identified, the complementarity determining regions (CDRs) from mAb2419 VH and VL were grafted on the human VH and VL germline templates respectively using structure-guided design. Additional mutations (including back mutations to the parental residue in the mouse mAb) were selectively introduced based on visual inspection of the structural model. The humanized antibody constructs were recombinantly produced in HEK293 cells following transient transfection of separate vectors for heavy and light chain expression. Recombinant antibodies were purified by Protein A affinity chromatography using standard methods. Humanized antibodies were subsequently tested for binding to APRIL, functional receptor blocking (TACI-APRIL and BCMA-APRIL interactions) and thermal stability using a differential scanning fluorescence protein unfolding assay. Relative activity and stability profiles were compared to parental, mouse antibodies upon which humanization was based.

Figure 27A:
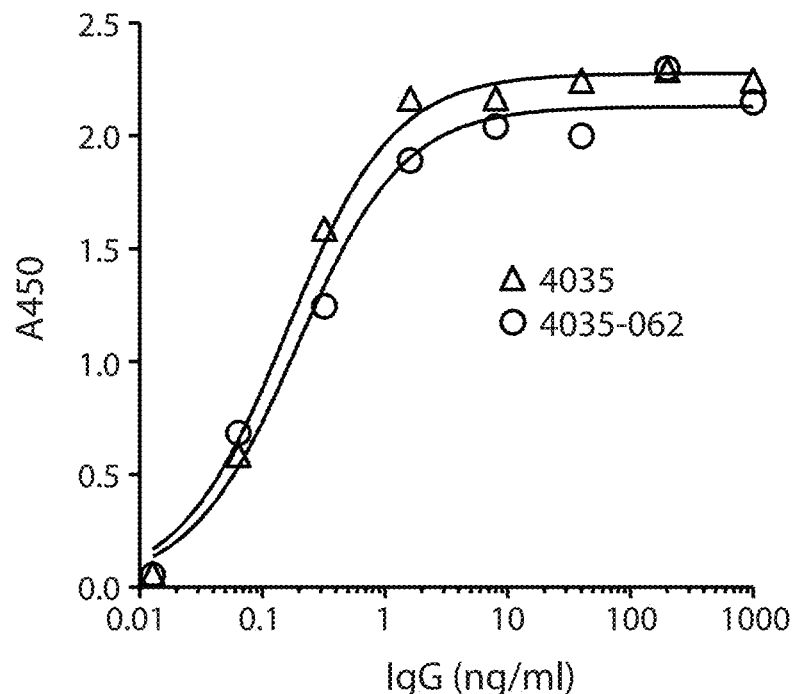
FIGS. 27A-27B depict the binding of exemplary anti-APRIL antibodies to human APRIL. Antibodies include humanized variants of mouse antibodies 4035 (FIG. 27A) and 2419 (FIG. 27B). Relative binding of exemplary anti-APRIL antibodies was measured by indirect ELISA. Comparison of humanized anti-APRIL antibodies to parental (non-humanized) mouse antibodies is made for comparative purposes. Extrapolated $EC_{50}$ values are summarized in FIG. 29A.
Figure 27B:
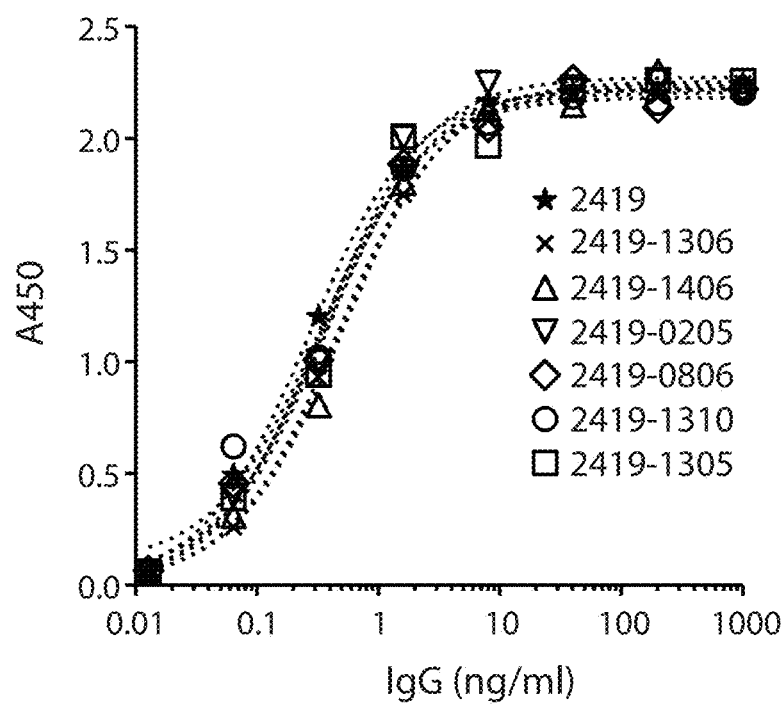
Figure 28A:
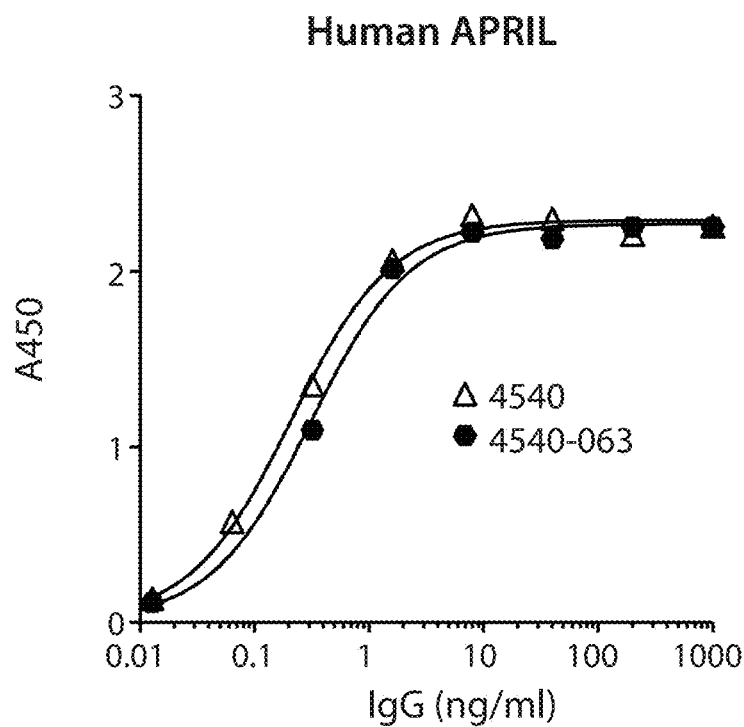
FIGS. 28A-28B depict the binding of humanized variant of human-mouse cross reactive antibody 4540-063 to both human APRIL (FIG. 28A) and mouse APRIL (FIG. 28B). Relative binding of exemplary anti-APRIL antibody was measured by indirect ELISA. Comparison of parental (non-humanized) antibody is made for comparative purposes. Extrapolated $EC_{50}$ values are summarized in FIG. 29B.
Figure 28B:
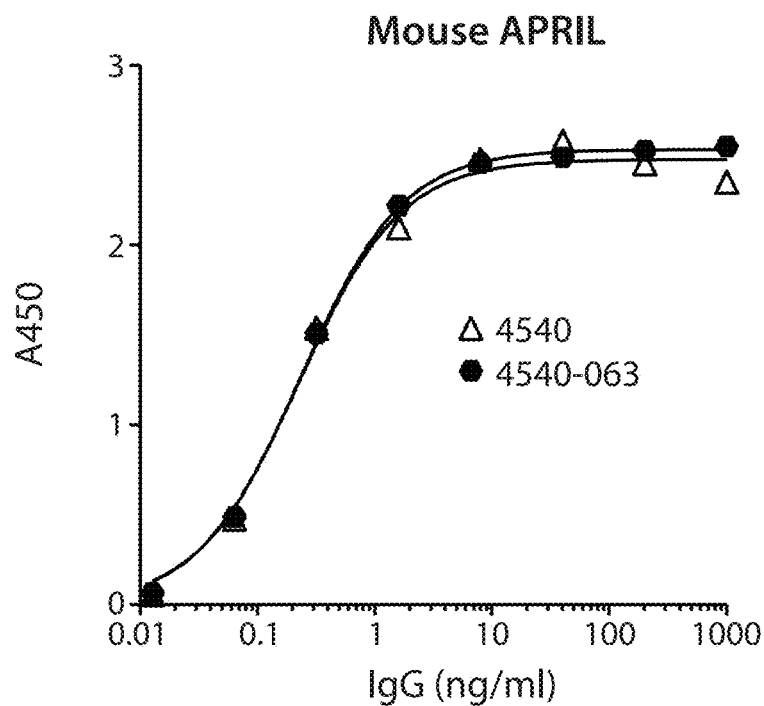

Example 9: In Vitro Binding and Receptor Blocking Activities of Humanized Anti-APRIL Antibodies Relative binding of exemplary anti-APRIL antibodies was measured by indirect ELISA. The binding of humanized variants of mouse antibodies 4035 and 2419 to human APRIL is shown in FIG. 27A-27B, respectively. The binding of a humanized variant of human-mouse cross-reactive antibody 4540-063 to both human APRIL and mouse APRIL is shown in FIGS. 28A-28B, respectively. Comparison of humanized anti-APRIL antibodies to parental (non-humanized) mouse antibodies is made for comparative purposes. Extrapolated $EC_{50}$ values are summarized in FIGS. 29A-29B. The exemplary antibody molecules bind to APRIL with picomolar affinity.

Figures 29C, 29D:
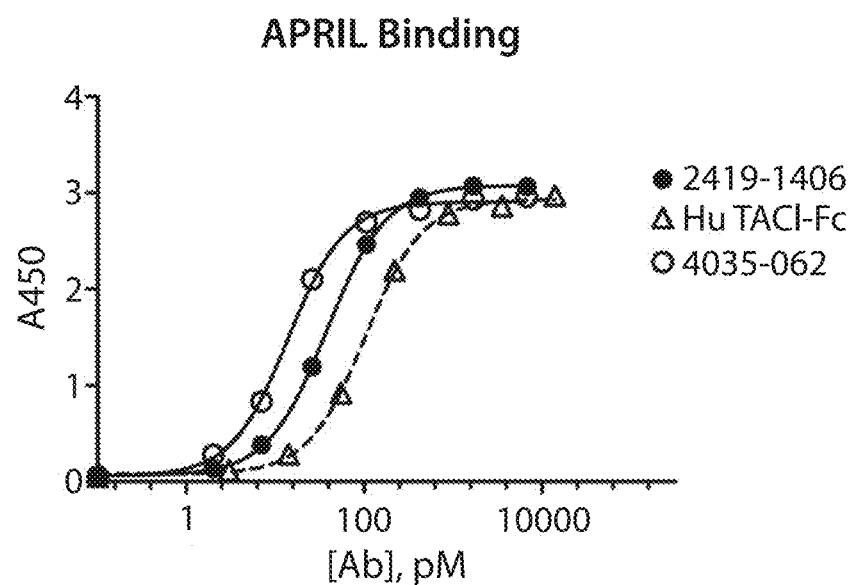
FIGS. 29C-29D depict the binding affinity of antibody 2419-1406 and 4035-062 to trimeric human APRIL measured by ELISA. Trimer was stabilized by N-terminal fusion of APRIL with isoleucine zipper (GCN4) domain Binding of APRIL to human TACI-Fc is shown for comparative purposes. The $EC_{50}$ values derived from the binding curves depicted in FIG. 29C are summarized in FIG. 29D.

The apparent binding affinities of antibodies 2419-1406 and 4035-062 to trimeric human APRIL were also measured by ELISA. APRIL trimer was stabilized by the N-terminal fusion of APRIL with an isoleucine zipper (GCN4) oligomerization domain Binding of APRIL to human TACI-Fc is shown for comparative purposes. The ELISA binding results are shown in FIG. 29C. Picomolar $EC_{50}$ values derived from the binding curves depicted in FIG. 29C are summarized in FIG. 29D. The antibody showed picomolar (pM) binding to trimeric human APRIL as measured by ELISA. Higher affinity binding of 2419-1406 and 4035-062 to APRIL relative to APRIL binding to its own receptor (TACI-Fc) was observed.

Figure 30A:
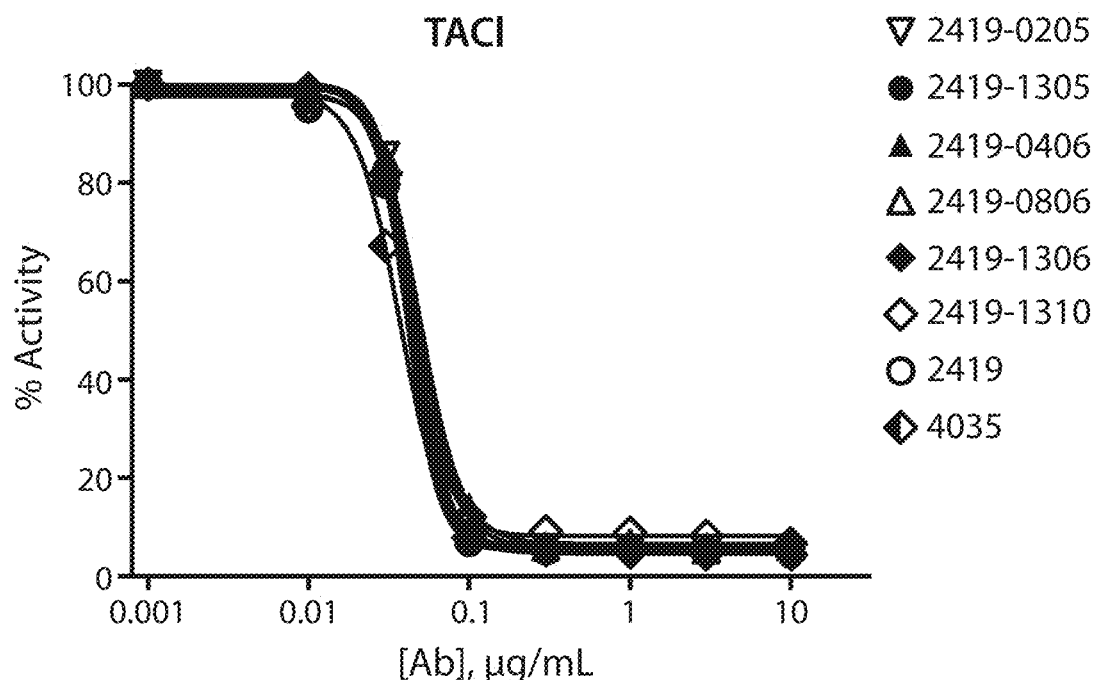
FIGS. 30A-30B depict antibody inhibition of APRIL binding to TNFSF receptors TACI and BCMA by humanized IgG2κ variants of parental, murine derived antibody 2419. Assay is based on receptor blocking ELISA using recombinant human APRIL (R&D Systems) and either human TACI-Fc (FIG. 30A) or BCMA-Fc (FIG. 30B). Parental, chimeric 2419 (mouse VH-VL grafted on to human IgG1κ constant regions) was included for comparative purposes as was chimeric anti-human APRIL antibody 4035. Inhibition was analyzed by non-linear regression using a four parameter curve fit following normalization to 100% activity (no antibody control). $IC_{50}$ values are summarized in FIG. 33.
Figure 30B:
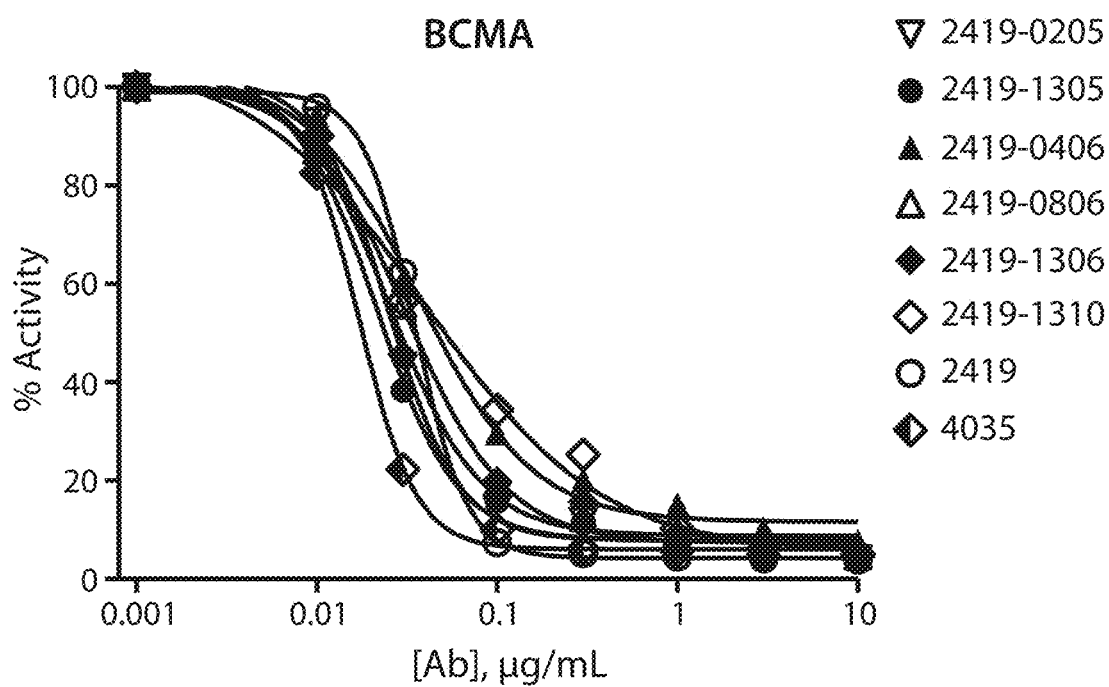

The inhibition of APRIL binding to TNFSF receptors TACI and BCMA by humanized IgG2κ variants of parental, murine derived antibody 2419 was measured. Assay is based on receptor blocking ELISA using recombinant human APRIL (R&D Systems) and either human TACI-Fc (FIG. 30A) or BCMA-Fc (FIG. 30B). Parental, chimeric 2419 (mouse VH-VL grafted on to human IgG1κ constant regions) is included for comparative purposes as is chimeric anti-human APRIL antibody 4035. Inhibition was analyzed by non-linear regression using a four parameter curve fit following normalization to 100% activity (no antibody control). $IC_{50}$ values are summarized in FIG. 33.

Figure 31A:
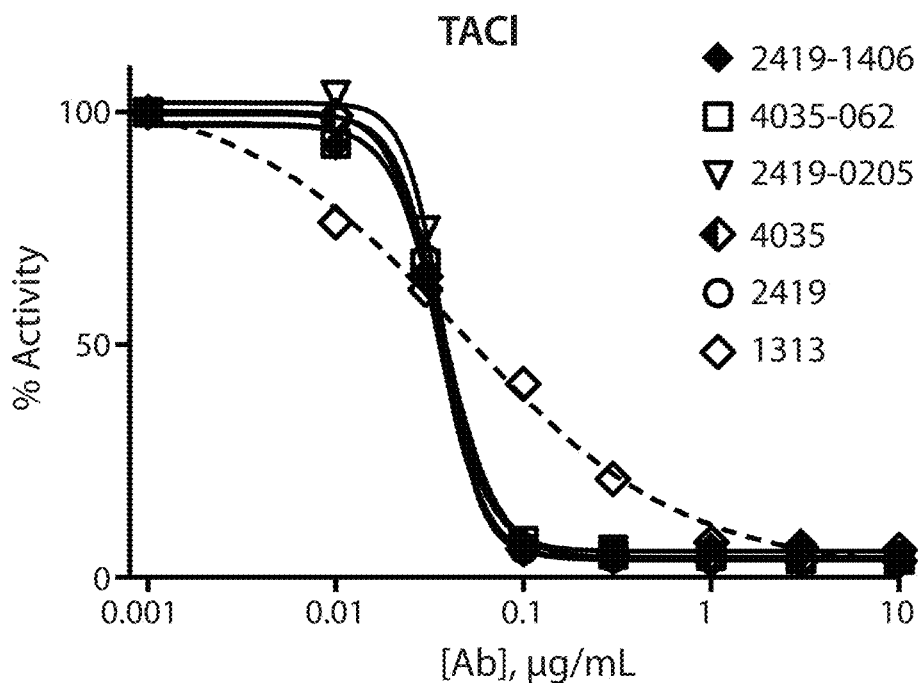
FIGS. 31A-31B depict the inhibition of APRIL binding to TNFSF receptors TACI (FIG. 31A) and BCMA (FIG. 31B) by additional humanized variants of 2419 (IgG2κ) 2419-0205 and 2419-1406 and humanized variant (4035-062) of parental antibody 4035. Humanized 4035-062 is of the IgG1κ subtype. Chimeric, non-humanized versions of mouse derived antibodies 4035 and 2419, and 1313 are included for comparative purposes. mAb1313 is a control anti-APRIL antibody. TACI-Fc and BCMA-Fc were used. $IC_{50}$ values are summarized in FIG. 33.
Figure 31B:
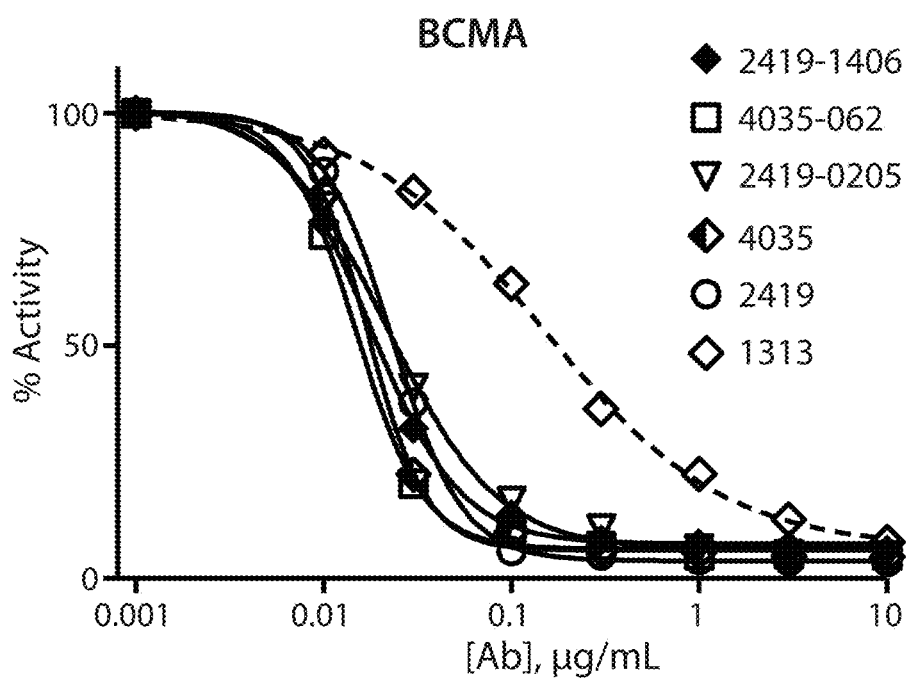

The inhibition of APRIL binding to TNFSF receptors TACI (FIG. 31A) and BCMA (FIG. 31B) by additional humanized variants of 2419 (IgG2κ) 2419-0205 and 2419-1406 and humanized variant (4035-062) of parental antibody 4035 was measured. Humanized 4035-062 is of the IgG1κ subtype. Chimeric, non-humanized versions of mouse derived antibodies 4035 and 2419, and 1313 are included for comparative purposes. mAb1313 is a control anti-APRIL antibody. TACI-Fc and BCMA-Fc were used. $IC_{50}$ values are summarized in FIG. 33.

Figure 32A:
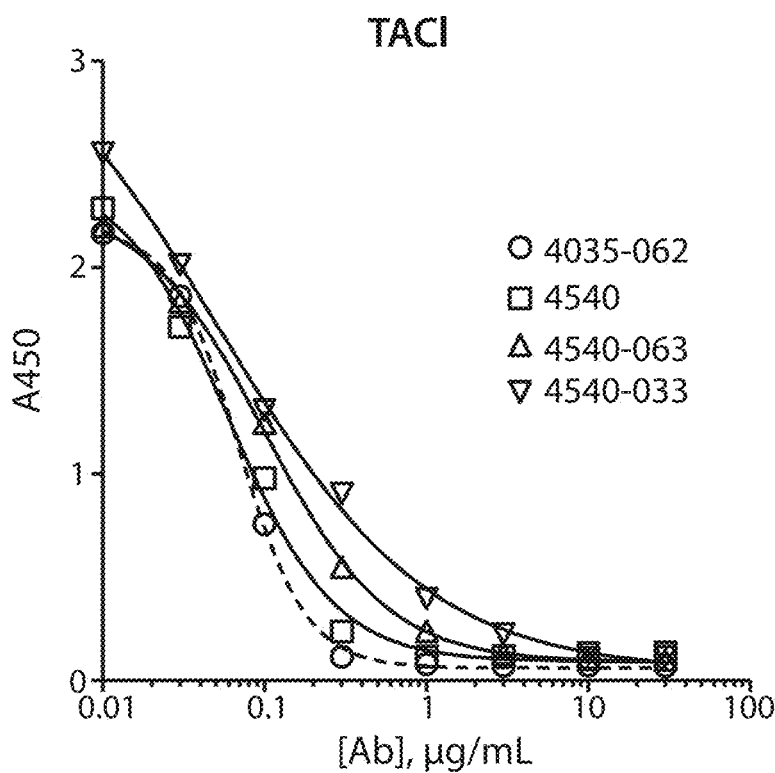
FIGS. 32A-32B depict the antibody inhibition of APRIL binding to TNFSF receptors TACI (FIG. 32A) and BCMA (FIG. 32B) by humanized variants of mouse/human APRIL cross neutralizing antibody 4540. Humanized antibody 4540 is of the IgG1κ subtype. Parental 4540 (non-humanized chimera) and humanized 4035-062 (FIGS. 30A-30B) are included for comparative purposes. Inhibition was analyzed by non-linear regression using a four parameter curve fit as described for FIGS. 29A-29B and FIGS. 30A-30B. $IC_{50}$ values are also summarized in FIG. 33.
Figure 32B:
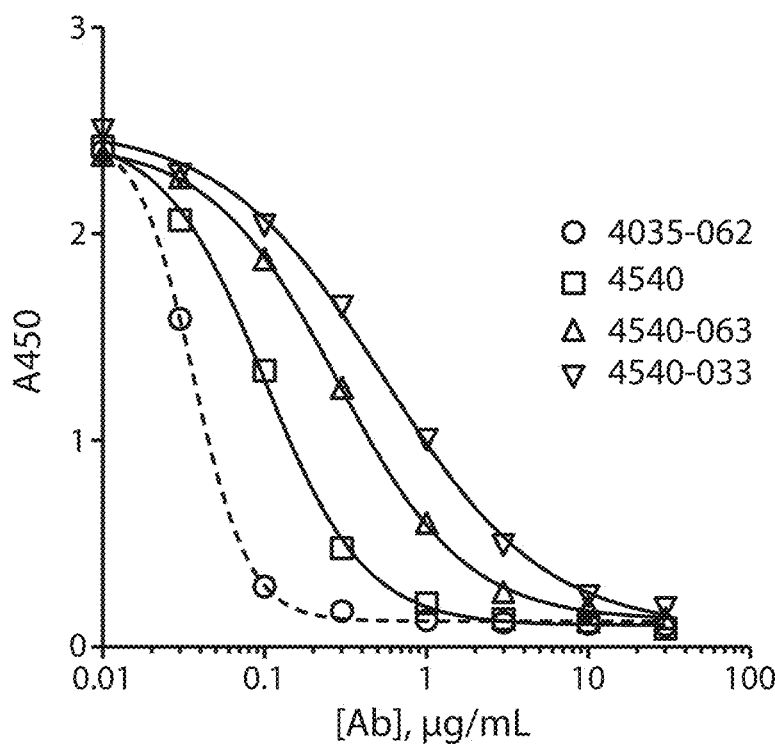

The inhibition of APRIL binding to TNFSF receptors TACI (FIG. 32A) and BCMA (FIG. 32B) by humanized variants of mouse/human APRIL cross-neutralizing antibody 4540 was measured. Humanized antibody 4540 is of the IgG1κ subtype. Parental 4540 (non-humanized chimera) and humanized 4035-062 (FIGS. 30A-30B) are included for comparative purposes. Inhibition was analyzed by non-linear regression using a four parameter curve fit as described for FIGS. 29A-29B and FIGS. 30A-30B. $IC_{50}$ values are also summarized in FIG. 33. Sub-nanomolar blocking of APRIL-receptor binding was observed for most of the tested antibodies.

These results indicate that humanization and reformatting (e.g., as IgG2) generally, if not always, leads to comparable retention of receptor blocking activities.

Figure 34A:
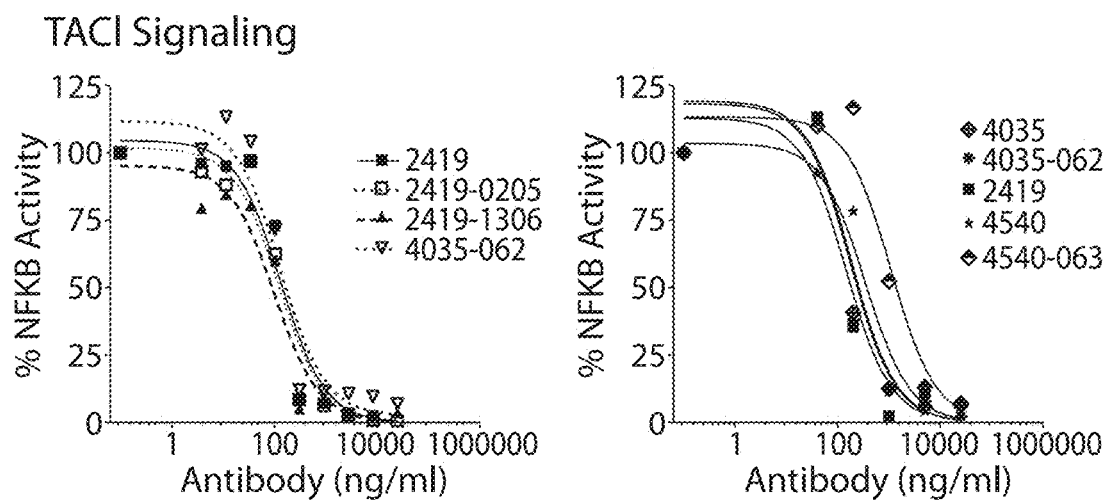
FIGS. 34A-34B depict the antibody inhibition of APRIL-mediated receptor signaling. Inhibition of APRIL-receptor mediated NFκB intracellular signaling was evaluated using the HEK 293 NFκB reporter cell line following transient transfection of either full-length human TNF family receptors TACI or BCMA cDNA expression vectors. Data are normalized to no antibody control (100%).
Figure 34B:
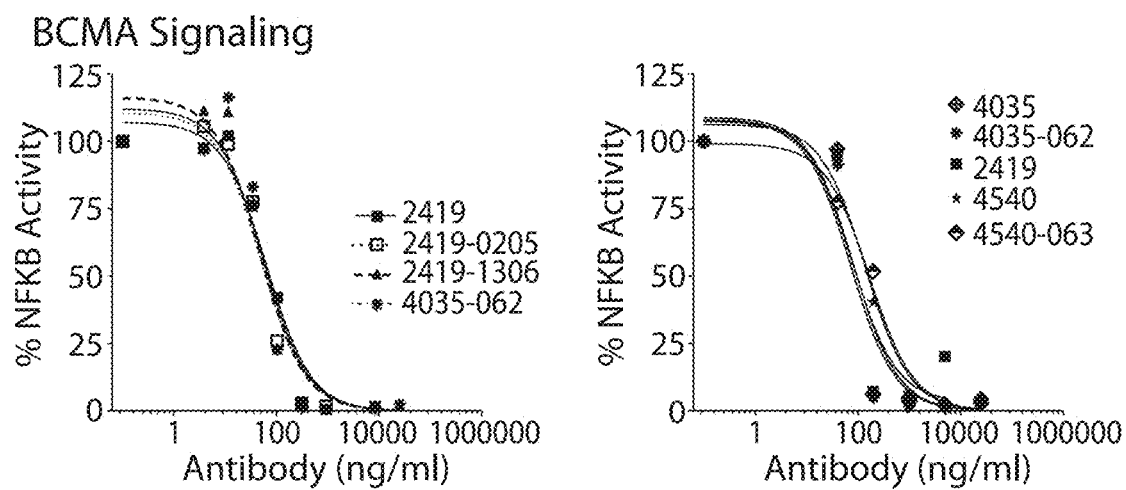

The antibody inhibition of APRIL-mediated receptor signaling was evaluated. Inhibition of APRIL-receptor mediated NFκB intracellular signaling was evaluated using the HEK 293 NFκB reporter cell line following transient transfection of either full-length human TNF family receptors TACI or BCMA cDNA expression vectors. Data are normalized to no antibody control (100%). The inhibition of TACI- and BCMA-mediated NFκB signaling is shown in FIGS. 34A-34B, respectively. FIG. 35 depicts the approximate $IC_{50}$ values of antibody inhibition of APRIL-mediated receptor signaling. Data are extrapolated from FIGS. 34A-34B based on a non-linear regression analysis using a variable slope, three parameter fit of antibody concentration vs. response. Negative antibody control (no APRIL binding) demonstrated no activity in this assay (data not shown). These results indicate potent inhibition of APRIL-mediated NFκB downstream signaling pathway (with low or sub-nM $IC_{50}$) by exemplary anti-APRIL antibody molecule. Blocking occurs with both TACI and BCMA receptors.

Example 10: Evaluation of Anti-APRIL Antibody Binding Specificity to APRIL

Selected anti-APRIL antibodies were evaluated for potential cross-reactivity with other members of the TNFa superfamily (TNFSF) family of cytokines, including: human TNFα (TNFSF2; Adipogen), human CD40 (TNFSF4, Adipogen), human FasL (TNFSF6, Adipogen), human TRAIL (TNFSF10, Adipogen), human RANKL (TNFSF11; Adipogen), human Tweak (TNFSF12; Abcam), human and mouse BAFF (TNFSF13B, AB Biosciences and Adipogen, respectively), and human LIGHT (TNFSF14, Adipogen). These cytokines share variable degree of sequence as well as higher order structural homologies. Among them, BAFF appears to be the most closely related to APRIL, with 29% identity and 53% amino acid sequence similarity.

Figure 36:
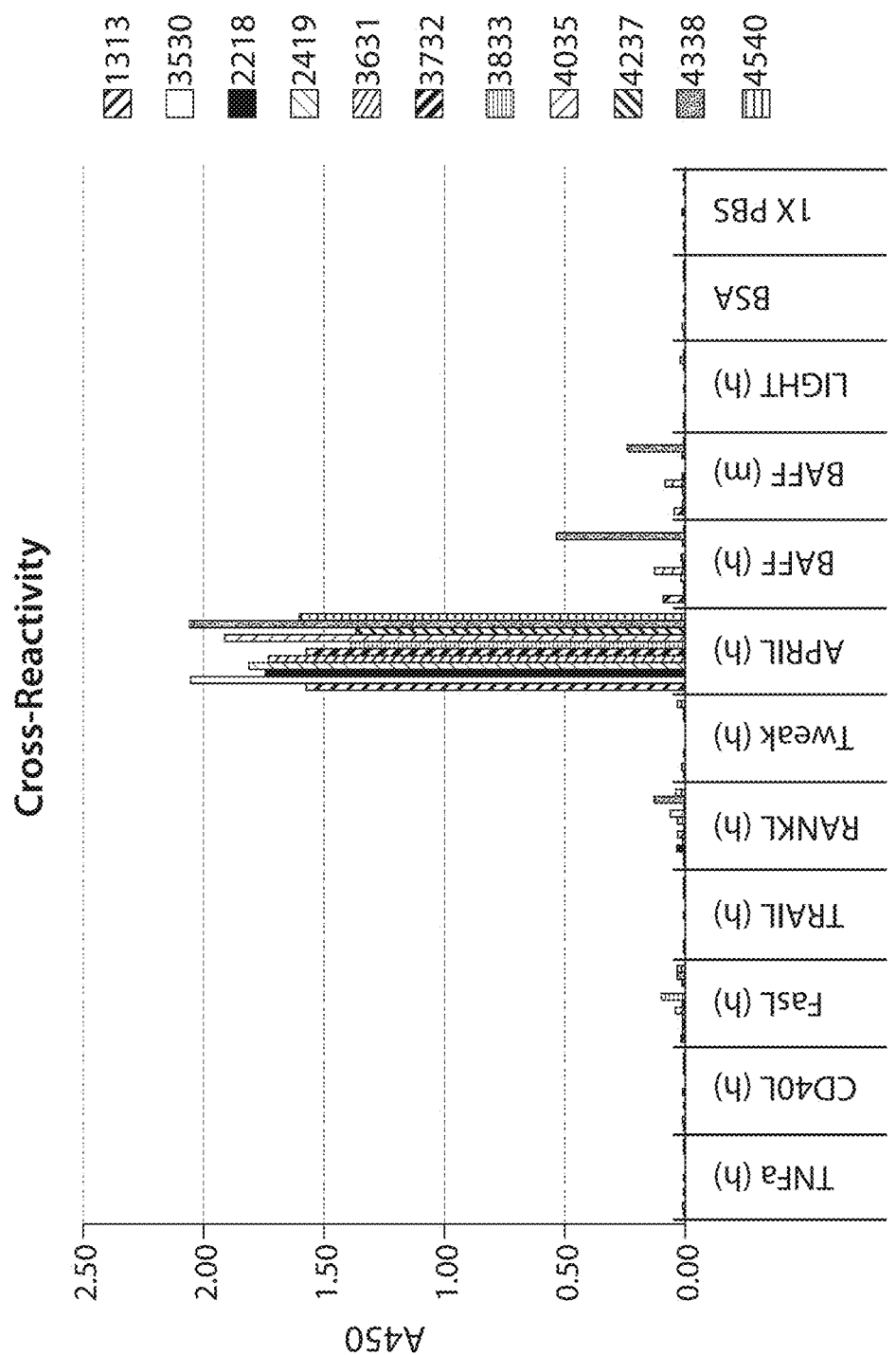
FIG. 36 depicts analysis of APRIL antibody binding reactivity to other members of the TNFSF13 family of cytokines. A select panel of recombinant TNFSF-related cytokines (Adipogen) was used to test for antibody cross-reactivity as measured by ELISA. Panel included human APRIL (specific target) and structurally related BAFF. Exemplary antibodies are included for illustrative purposes. As predicted, strong binding of anti-APRIL antibodies to human APRIL was detected. Cross-reactivity to BAFF and other members other than the target (human APRIL), however, was generally not substantially detected above assay background (measured here using BSA only and assay diluent, 1×PBS controls). Antibody 4338, a previously identified BAFF cross-reactive antibody, was used as a positive (BAFF-reactive) control. A control antibody, mAb1313, was also included.
Figures 37A, 37B, 37C:
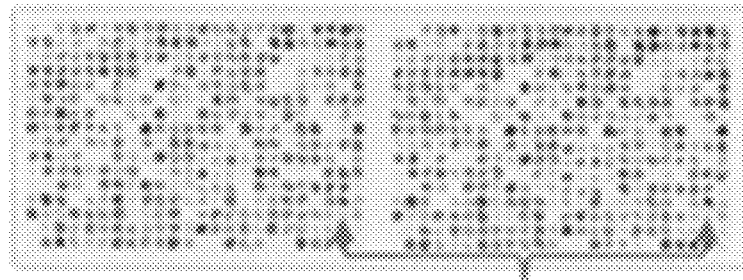
FIGS. 37A-37C depict the minimal protein cross-reactivity of mAb 2419-1406 and mAb 4035-062 in an extensive array of over 4500 heterologously expressed human membrane proteins in an HEK293-based assay and the confirmatory/secondary screen. An example of protein expression array design is shown in FIG. 37A.

Binding was evaluated by an indirect ELISA protocol using similar methods described for evaluation of APRIL binding; cytokines were immobilized to ELISA plate at 50 ng per well and then exposed to a solution of each of the test antibodies at a fixed concentration of 10 μg/ml Anti-human or anti-mouse Ig-HRP polyclonal antibody conjugates (Jackson Laboratories) were used for detection of antibody binding. The results presented in FIG. 36 indicated eleven of the twelve antibodies tested in this assay to specifically bind APRIL with no measurable cross-reactivity with the other TNFSF members substantially above assay background. Antibody 4338 demonstrated detectable binding to both the human and mouse versions of BAFF and was used as an assay control.

mAbs 2419-1406 and 4035-062 demonstrate minimal or no extraneous protein cross-reactivity in extensive array of over 4500 human membrane proteins (RETROGENIX™). An example of protein expression array design is shown in FIG. 37A. Confirmatory/secondary screen was performed on 12 proteins (FIGS. 37B-37C). Binding to Fc receptors was observed for both 2419-1406 and 4035-062 as predicted. Weaker binding to FcγR1 was observed for antibody 2419-1406 consistent with it having an IGg2 isotype. Negligible binding to PDGFR was also detected for 2419-1406. Binding to any other membrane targets except those described was not observed Antibody 4035-062

Example 11: Identification of Target Epitope for Maximal Anti-APRIL Antibody Potency The epitope of an exemplary anti-APRIL antibody molecule, mAb 2419, was mapped using a combination of empirical and computational tools and data. These methods and resultant data included 1) low resolution crystallography of mAb 2419 Fab in complex with human APRIL (amino acids 115-250) in tandem with 2) structural modeling (FIG. 38A), and 3) APRIL saturation mutagenesis at select positions within the surface of APRIL carried out in combination with APRIL surface display in yeast (FIG. 38B). As shown in both FIGS. 38A-38B, the antibody molecule targets a non-linear, quaternary epitope spanning two different monomers of APRIL within a larger trimeric complex. The epitope of 2419 also substantially overlaps with a region of APRIL corresponding to the high affinity receptor binding site (CRD2 site) critical for both TACI and BCMA receptor blocking (FIG. 38B). A secondary receptor binding site (CRD1 site) also overlaps with the 2419 epitope with implications for blocking TACI-APRIL interactions. Based on this analysis, positions within APRIL that define the epitope of 2419 include V133, V181, E185, Q187, G188, R189, Q190, E191, T192, R195, H218, L219, H220, S226, I228, P230 (located in monomer A); V121, I123, Q139, P140, A141, L142, N237, S239, P240, and H241 (located in monomer B).

A more focused analysis of this epitope by mutagenesis of select surface-accessible positions of APRIL point to a subset of positions within the larger epitope of 2419 (structurally depicted in FIG. 38A) that appear to particularly critical for antibody binding. These so-called "hotspot residues", i.e., those residues that are critical to the interaction between APRIL and mAb 2419, are empirically defined) using a combination of the methods described above) as those positions where mutation from the wildtype sequence to nearly any other amino residue resulted in a substantial loss of binding of 2419 to APRIL. Examples of such positions include V181, Q190, T192, and I228 on one monomer, and A141 and H241 on an adjacent monomer.

TABLE 8

Exemplary Human APRIL Amino Acid Residues that Bind to mAb 2419 (amino acid numbering based on SEQ ID NO: 85)

| Position Human | Monomer | Hotspot |
|---|---|---|
| V133 | A | |
| V181 | A | Y |
| E185 | A | |
| Q187 | A | |
| G188 | A | |
| R189 | A | |
| Q190 | A | Y |
| E191 | A | |
| T192 | A | Y |
| R195 | A | |
| H218 | A | |

TABLE 8-continued

Exemplary Human APRIL Amino Acid Residues that Bind
to mAb 2419 (amino acid numbering based on SEQ ID NO: 85)

| Position Human | Monomer | Hotspot |
|---|---|---|
| L219 | A | |
| H220 | A | |
| S226 | A | |
| I228 | A | Y |
| P230 | A | |
| V121 | B | |
| I123 | B | |
| Q139 | B | |
| P140 | B | |
| A141 | B | Y |
| L142 | B | |
| N237 | B | |
| S239 | B | |
| P240 | B | |
| H241 | B | Y |

In summary, the epitope overlaps predicted regions for maximal receptor blocking, and targets a non-linear, quaternary epitope spanning two different monomers of APRIL, implications for neutralizing biologically most active form of APRIL (trimer).

Example 12: Pharmaceutical Properties of Anti-APRIL Antibodies

Figures 39A, 39B:
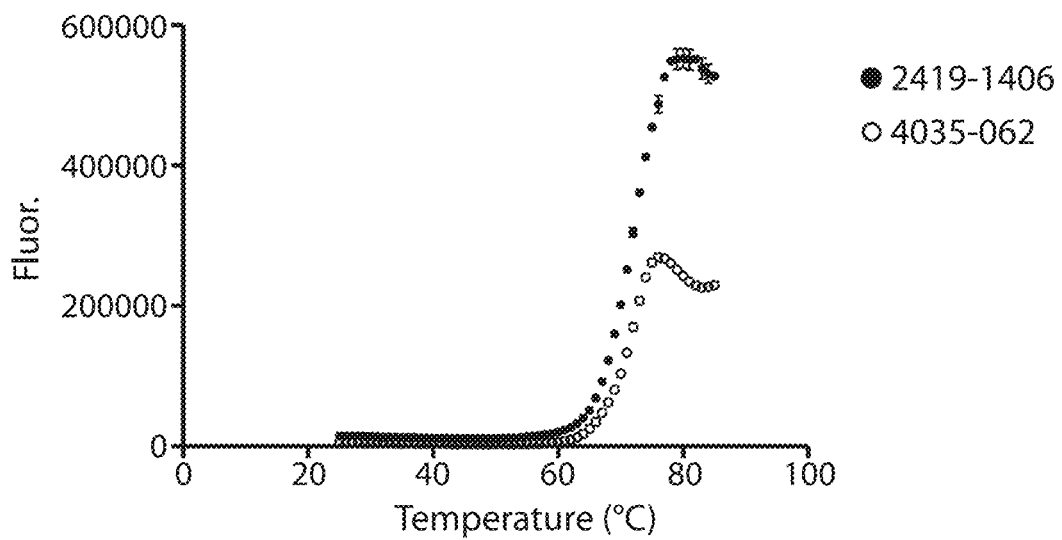
FIGS. 39A-39B depict the thermal stability of antibodies mAb 2419-1406 and 4035-062 as measured using SYPRO-ORANGE® fluorescence scanning assay. The thermal melting temperatures (Tm values) for both 2419-1406 and 4035-062 are listed in FIG. 39B.

Thermal stability of exemplary anti-APRIL molecules, 2419-1406 and 4035-062, were measured using SYPRO-ORANGE® fluorescence scanning assay (FIG. 39A). The thermal melting temperatures (Tm values) for both 2419-1406 and 4035-062 are listed in FIG. 39B. mAb 2419-1406 and mAb 4035-062 exhibit high thermal stability.

Figures 40A, 40B:
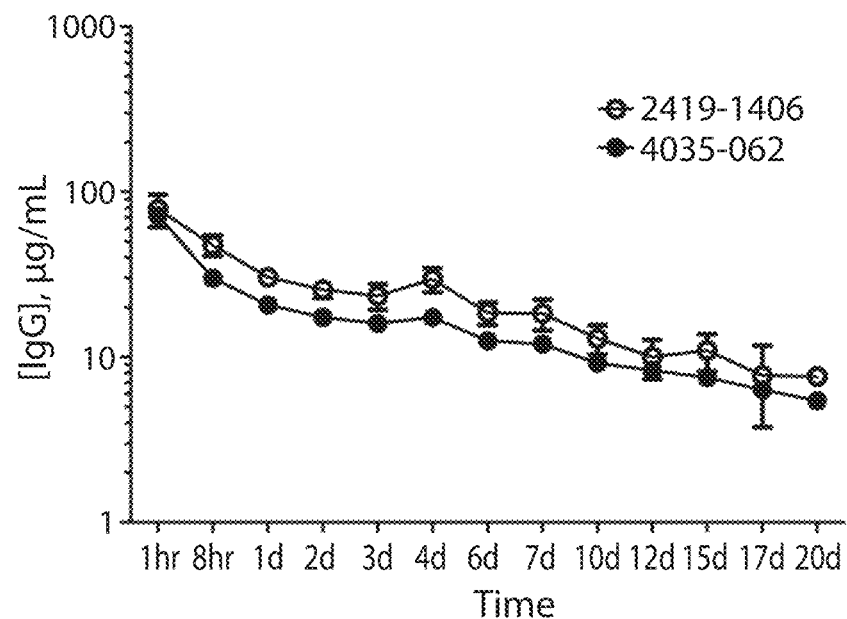
FIGS. 40A-40B depict the PK profiles of mAb 2419-1406 and 4035-062 in humanized FcRn transgenic mouse strain tg32. Tg32 mice were administered a single 5 mg/kg dose of mAb 2419-1406 or mAb 4035-062 by intravenous injection. Antibody levels in sera were determined by ELISA following timepoints taken out to 20 days. PK values are listed in FIG. 40B.

The tg32 mouse model was used as a surrogate for predicting the PK of antibody pharmacokinetics (PK) in humans. PK of control antibody (IgG1) with pre-established PK of approximately 25 days (in humans) was also evaluated in this study for comparative purposes. As shown in FIGS. 40A-40B, favorable PK profile of an exemplary anti-APRIL antibody molecule, 2419-1406 and 4035-062, in humanized FcRn transgenic mouse strain tg32 was observed.

Figure 41:
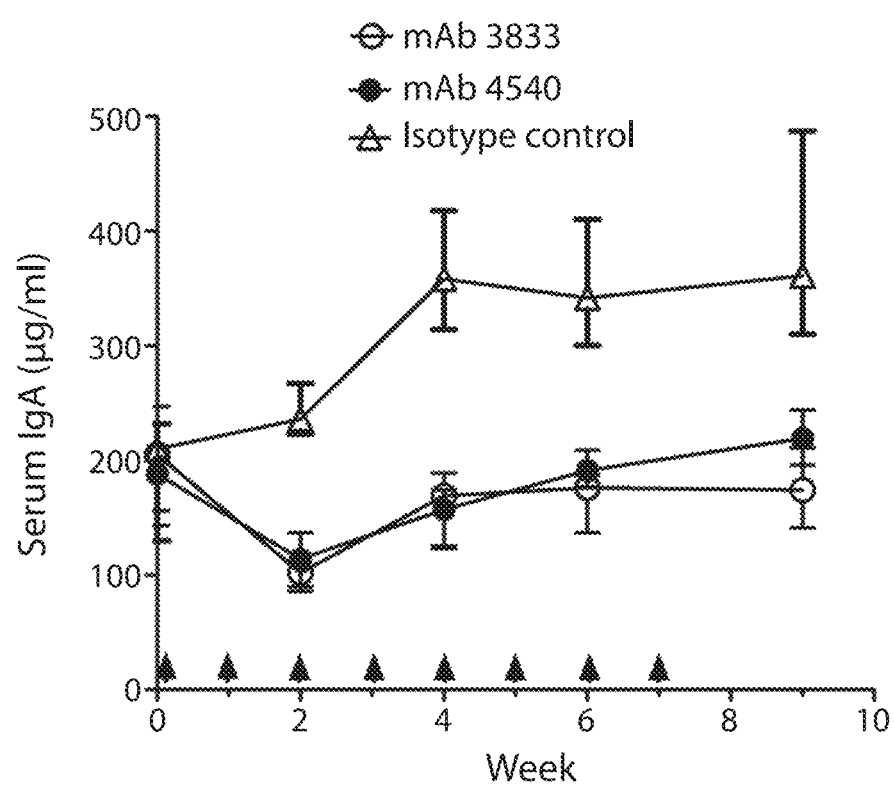
FIG. 41 depicts the reduction of basal serum IgA levels in mice treated with mAb 4540 and mAb 3833. 11 week old C57/BL6 mice were sub-chronically dosed (1× weekly by i.p injection) with 20 mg/kg of mAb 4540 or isotype control antibody for seven weeks. Basal serum levels of total IgA were quantified by ELISA. Median IgA levels graphed; N=5 mice per group.

Example 13: Species Cross-Reactive Anti-APRIL Antibodies Effectively Reduce Serum IgA Levels in Mice Mouse mAb 4540 is a cross-species reactive (mouse and human) anti-APRIL with receptor neutralizing activity. mAb 4540 targets an overlapping APRIL epitope to mAb 2419-1406. mAb4540 was used as a surrogate to evaluate the effect of anti-APRIL mAb treatment on a reduction of serum IgA levels in C57/BL6 mice. 11 week old mice were sub-chronically dosed (1× weekly by i.p injection) with 20 mg/kg of mAb 4540, mAb 3833, or isotype control antibody for seven weeks. Basal serum levels of total IgA were quantified by ELISA. As shown in FIG. 41, treatment of mAb 4540 or mAb 3833 reduced serum IgA levels in C57/BL6 mice.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of treating IgA nephropathy, the method comprising administering to a subject in need thereof an effective amount of an anti-A PRoliferation Inducing Ligand (APRIL) antibody molecule,
wherein the antibody molecule comprises a heavy chain variable region (VH) comprising three heavy chain complementarity determining regions (HCDR1, HCDR2, and HCDR3) and a light chain variable region (VL) comprising three light chain complementarity determining regions (LCDR1, LCDR2, and LCDR3),
wherein the VH comprises an HCDR1 comprising the amino acid sequence of SEQ ID NO: 11; an HCDR2 comprising the amino acid sequence of SEQ ID NO: 12, and an HCDR3 comprising the amino acid sequence of SEQ ID NO: 13; and the VL comprises an LCDR1 comprising the amino acid sequence of SEQ ID NO: 280; an LCDR2 comprising the amino acid sequence of SEQ ID NO: 285, and an LCDR3 comprising the amino acid sequence of SEQ ID NO: 16; or
wherein the VH comprises an HCDR1 comprising the amino acid sequence of SEQ ID NO: 17; an HCDR2 comprising the amino acid sequence of SEQ ID NO: 282, and an HCDR3 comprising the amino acid sequence of SEQ ID NO: 13; and the VL comprises an LCDR1 comprising the amino acid sequence of SEQ ID NO: 280; an LCDR2 comprising the amino acid sequence of SEQ ID NO: 285, and an LCDR3 comprising the amino acid sequence of SEQ ID NO: 16,
thereby treating IgA nephropathy.

2. The method of claim 1, wherein the VH comprises an HCDR1 comprising the amino acid sequence of SEQ ID NO: 11; an HCDR2 comprising the amino acid sequence of SEQ ID NO: 12, and an HCDR3 comprising the amino acid sequence of SEQ ID NO: 13; and the VL comprises an LCDR1 comprising the amino acid sequence of SEQ ID NO: 280; an LCDR2 comprising the amino acid sequence of SEQ ID NO: 285, and an LCDR3 comprising the amino acid sequence of SEQ ID NO: 16.

3. The method of claim 1, wherein the VH comprises an HCDR1 comprising the amino acid sequence of SEQ ID NO: 17; an HCDR2 comprising the amino acid sequence of SEQ ID NO: 282, and an HCDR3 comprising the amino acid sequence of SEQ ID NO: 13; and the VL comprises an LCDR1 comprising the amino acid sequence of SEQ ID NO: 280; an LCDR2 comprising the amino acid sequence of SEQ ID NO: 285, and an LCDR3 comprising the amino acid sequence of SEQ ID NO: 16.

4. The method of claim 1, wherein the VH comprises the amino acid sequence of SEQ ID NO: 296, or an amino acid sequence that is at least 85% identical thereto.

5. The method of claim 1, wherein the VH comprises the amino acid sequence of SEQ ID NO: 296.

6. The method of claim 1, wherein the VL comprises the amino acid sequence of SEQ ID NO: 286, or an amino acid sequence that is at least 85% identical thereto.

7. The method of claim 1, wherein the VL comprises the amino acid sequence of SEQ ID NO: 286.

8. The method of claim 1, wherein the VH comprises the amino acid sequence of SEQ ID NO: 296, and wherein the VL comprises the amino acid sequence of SEQ ID NO: 286.

9. The method of claim 1, wherein the VH comprises the amino acid sequence of any of SEQ ID NOs: 19, 283, 288, 289, 291, 292, 294, 296, or 317.

10. The method of claim 9, wherein the VL comprises the amino acid sequence of SEQ ID NO: 286.

11. The method of claim 1, wherein the antibody molecule is a synthetic antibody molecule, an isolated antibody molecule, or a humanized antibody molecule.

12. The method of claim 1, wherein the antibody molecule comprises a heavy chain constant region of IgG1, IgG2, IgG3, or IgG4.

13. The method of claim 1, wherein the antibody molecule comprises a heavy chain constant region of IgG2.

14. The method of claim 1, wherein the antibody molecule comprises a light chain constant region of kappa or lambda light chain.

15. The method of claim 1, wherein the antibody molecule comprises an Fc region.

16. The method of claim 1, wherein the antibody molecule comprises:
   (i) a Fab, F(ab')2, Fv, or single chain Fv (scFv) fragment; or
   (ii) two VHs and two VLs.

17. The method of claim 1, wherein the VH is encoded by a nucleic acid molecule comprising the nucleotide sequence of SEQ ID NO: 313.

18. The method of claim 1, wherein the VL is encoded by a nucleic acid molecule comprising the nucleotide sequence of SEQ ID NO: 306.

19. The method of claim 1, wherein the antibody molecule is administered to the subject
   (i) intravenously or subcutaneously;
   (ii) at a dose between 0.1 mg/kg and 50 mg/kg; and/or
   (iii) once a week, twice a week, once every two weeks, or once every four weeks.

20. The method of claim 1, wherein administration of the antibody molecule reduces (a) the level of IgA in a peripheral tissue chosen from serum, mucosal tissue, or bone marrow; (b) the level of a variant of IgA chosen from IgA1, IgA1 in polymeric form (pIgA1), or IgA1 with an O-linked glycosylation variant; or (c) both (a) and (b).

21. The method of claim 1, further comprising:
   (i) determining the level of IgA in a peripheral tissue sample, wherein the peripheral tissue is serum, mucosal tissue, or bone marrow; and/or
   (ii) administering to the subject a second therapy for IgA nephropathy.

22. The method of claim 21, wherein the second therapy is chosen from an angiotensin-converting enzyme (ACE) inhibitor, an angiotensin receptor blocker (ARB), omega-3 fatty acids, an immunosuppressant, a statin, mycophenolate mofetil, or any combination thereof.

23. The method of claim 1, wherein the antibody molecule is administered to the subject at a dose between 0.5 mg/kg and 10 mg/kg.

24. The method of claim 1, wherein the antibody molecule is administered to the subject at a dose of 1 mg/kg, 2 mg/kg, 4 mg/kg, or 8 mg/kg.

25. The method of claim 1, wherein the antibody molecule is administered to the subject once a month, once every two months, or once every three months.

26. The method of claim 1, wherein the antibody molecule is administered to the subject intravenously.

27. The method of claim 1, wherein the antibody molecule is administered to the subject subcutaneously.

28. The method of claim 1, wherein the antibody molecule is administered to the subject at a dose between 0.5 mg/kg and 2 mg/kg.

29. The method of claim 1, wherein the antibody molecule is administered to the subject at a dose between 1 mg/kg and 3 mg/kg.

30. The method of claim 1, wherein the antibody molecule is administered to the subject at a dose between 1 mg/kg and 5 mg/kg.

31. The method of claim 1, wherein the antibody molecule is administered to the subject at a dose between 1 mg/kg and 10 mg/kg.

32. A method of treating IgA nephropathy, the method comprising:
   administering to a subject in need thereof an effective amount of an anti-APRIL antibody molecule,
   wherein the antibody molecule comprises a VH and a VL, wherein the VH comprises the amino acid sequence of SEQ ID NO: 296, and wherein the VL comprises the amino acid sequence of SEQ ID NO: 286.

33. The method of claim 32, wherein the antibody molecule comprises a heavy chain constant region of IgG2.

34. The method of claim 32, wherein the antibody molecule is administered intravenously or subcutaneously.

35. The method of claim 32, wherein the antibody molecule is administered to the subject at a dose between 0.1 mg/kg and 50 mg/kg.

36. The method of claim 32, wherein the antibody molecule is administered to the subject once a month, once every two months, or once every three months.

37. The method of claim 32, wherein the antibody molecule is administered to the subject at a dose between 1 mg/kg and 10 mg/kg.

38. The method of claim 32, wherein the antibody molecule is administered to the subject at a dose of 1 mg/kg, 2 mg/kg, 4 mg/kg, or 8 mg/kg.

* * * * *